US011713453B2

(12) United States Patent
Van Geel et al.

(10) Patent No.: US 11,713,453 B2
(45) Date of Patent: *Aug. 1, 2023

(54) ENZYMES FOR TRIMMING OF GLYCOPROTEINS

(71) Applicant: Synaffix B.V., Oss (NL)

(72) Inventors: Remon Van Geel, Lithoijen (NL); Maria Antonia Wijdeven, Wijchen (NL); Inge Catharina Josephina Hurkmans, Liessel (NL); Floris Louis Van Delft, Nijmegen (NL); Sander Sebastiaan Van Berkel, Wijchen (NL)

(73) Assignee: SYNAFFIX B.V., Oss (NL)

( * ) Notice: Subject to any disclaimer, the term of this patent is extended or adjusted under 35 U.S.C. 154(b) by 278 days.

This patent is subject to a terminal disclaimer.

(21) Appl. No.: 17/113,975

(22) Filed: Dec. 7, 2020

(65) Prior Publication Data

US 2021/0332342 A1  Oct. 28, 2021

Related U.S. Application Data

(63) Continuation of application No. 16/076,319, filed as application No. PCT/EP2017/052792 on Feb. 8, 2017, now Pat. No. 10,858,641.

(30) Foreign Application Priority Data

| Feb. 8, 2016 | (EP) | 16154712 |
| Feb. 8, 2016 | (EP) | 16154739 |
| Jun. 8, 2016 | (EP) | 16173595 |
| Jun. 8, 2016 | (EP) | 16173599 |
| Dec. 23, 2016 | (EP) | 16206867 |

(51) Int. Cl.

| C12N 9/24 | (2006.01) |
| A61K 47/54 | (2017.01) |
| C07K 1/13 | (2006.01) |
| C07K 16/18 | (2006.01) |
| C12N 15/52 | (2006.01) |
| C12N 15/62 | (2006.01) |
| C12N 15/66 | (2006.01) |
| C12P 21/00 | (2006.01) |

(52) U.S. Cl.
CPC .......... *C12N 9/2497* (2013.01); *A61K 47/549* (2017.08); *C07K 1/13* (2013.01); *C07K 16/18* (2013.01); *C12N 9/24* (2013.01); *C12N 15/52* (2013.01); *C12N 15/62* (2013.01); *C12N 15/66* (2013.01); *C12P 21/005* (2013.01); *C12Y 302/01096* (2013.01); *C07K 2319/00* (2013.01)

(58) Field of Classification Search
None
See application file for complete search history.

(56) References Cited

U.S. PATENT DOCUMENTS

| 9,550,834 B2 | 1/2017 | Shirai et al. |
| 2012/0196310 A1 | 8/2012 | Jaeger et al. |

FOREIGN PATENT DOCUMENTS

| EP | 0 769 550 A2 | 4/1997 |
| WO | WO-2009/141599 A1 | 11/2009 |

OTHER PUBLICATIONS

Chen et al., "Fusion Protein Linkers: Property, Design and Functionality", Adv. Drug. Deliv. Rev., Author Manuscript, NIH Public Access, vol. 65, No. 10, pp. 1357-1369, Oct. 15, 2013 (32 pages).
Du, Yi et al., "Detection and Quantitation of Afucosylated N-Linked Oligosaccharides in Recombinant Monoclonal Antibodies Using Enzymatic Digestion and LC-MS" J. Am. Soc. Mass Spectrom., (2012) 23:1241-1249 (9 pages).
Elleuche, Skander, "Bringing functions together with fusion enzymes—from nature's inventions to biotechnological applications", Appl Microbiol Biotechnol, 2015, vol. 99, pp. 1545-1556 (12 pages).
Freeze et al., "Endoglycosidase and Glycoamidase Release of N-Linked Glycans," Curr. Protoc. Mol. Biol., Author Manuscript, Jan. 2010, vol. 17, pp. 1-33 (33 pages).
Gala et al., "V Region Carbohydrate and Antibody Expression", The Journal of Immunology, vol. 172, pp. 5489-5494, 2004 (6 pages).
Goetze et al., "High-mannose glycans on the Fc region of therapeutic IgG antibodies increase serum clearance in humans", Glycobiology, vol. 21, No. 7, pp. 949-959, 2001 (11 pages).
Gorovits et al., "Proposed mechanism of off-target toxicity for antibody-drug conjugates driven by mannose receptor uptake", Cancer Immunol Immunother, vol. 62, pp. 217-223, 2013 (7 pages).
Huang, Wei et al.,"Chemoenzymatic Glycoengineering of Intact IgG Antibodies for Gain of Functions" J. Am. Chem. Soc. (2012) 134:12308-12318 (11 pages).
International Search Report issued on PCT Application PCT/EP2017/052792, dated Jul. 24, 2017 (7 pages).
Kwan et al., "N-Glycosidase-carbohydrate-binding module fusion proteins as immobilized enzymes for protein deglycosylation", Protein Engineering, Design & Selection, vol. 18. No. 10, pp. 497-501, 2005 (5 pages).

(Continued)

*Primary Examiner* — Suzanne M Noakes
*Assistant Examiner* — Jae W Lee
(74) *Attorney, Agent, or Firm* — Sunit Talapatra; Foley & Lardner LLP

(57) ABSTRACT

The invention concerns fusion proteins, wherein two endoglycosidases are fused, possibly via a linker. The fusion enzymes according to the invention have structure (1): EndoX-(L)$_p$-EndoY (1), wherein EndoX is an endoglycosidase, EndoY is an endoglycosidase distinct from EndoX, L is a linker and p is 0 or 1. Such fusion enzymes capable of trimming glycoproteins comprising at least two distinct glycoforms in a single step. The invention further concerns the use of the fusion enzyme according to the invention for trimming glycoproteins. In another aspect, the invention relates to the process of production of the fusion enzyme. In a further aspect, the inventions concerns a process for trimming glycoproteins, comprising trimming the glycoprotein with a fusion enzyme according to the invention, to obtain a trimmed glycoprotein.

18 Claims, 5 Drawing Sheets

Specification includes a Sequence Listing.

(56) References Cited

OTHER PUBLICATIONS

Lu et al., "Construction and characterization of a bifunctional fusion enzyme of Bacillus-sourced beta-glucanase and xylanase expressed in *Escherichia coli*," FEMS Microbiology Letters, vol. 261, pp. 224-230, 2006 (7 pages).
QA-Bio Endo F Multi Kit Specifications—Protocol (catalog No. KE-EFX3)(2 pages).
Reusch et al., "Fc glycans of therapeutic antibodies as critical quality attributes", Glycobiology, vol. 25, No. 12, pp. 1325-1334, Aug. 11, 2015 (10 pages).
Sun et al., "Construction and characterization of a fusion [beta]-1,3-1,4-glucanase to improve hydrolytic activity and thermostability", Biotechnology Letters, vol. 33, pp. 2193-2199, 2011 (7 pages).
Trimble, Robert B. et al., "Identification of Distinct Endoglycosidase (Endo) Activities in Flavobacterium meningosepticum: Endo F1, Endo F2, and Endo F3" J. Biol. Chem. (1991) 266(3):1646-1651 (6 pages).
Van De Bovenkamp et al., "The Emerging Importance of IgG Fab Glycosylation in Immunity", The Journal of Immunology, vol. 196, pp. 1435-1441, 2016 (7 pages).
Van Geel et al., "Chemoenzymatic Conjugation of Toxic Payloads to the Globally Conserved N-Glycan of Native mAbs Provides Homogeneous and Highly Efficacious Antibody-Drug Conjugates", Bioconjugate Chemistry, vol. 26, pp. 2233-2242, 2015 (10 pages).
Yamamoto et al., "Mutational studies on endo-[beta]-N-acetylglucosaminidase D which hydrolyzes core portion of asparagine-linked complex type oligosaccharides", Glycoconjugate Journal, vol. 22, pp. 35-42, 2005 (8 pages).

Mannosylated

M3 (paucimannose)    M5    M9

Complex

G1    G1F    G0F $S_yG1F_x$
(x = 0-1, y = 0-1)

Bisected    Triantennary    Tetraantennary

Hybrid

M5G0    M5G1F

- ■ GlcNAc
- ● Man
- ▽ Fuc
- ○ Gal
- ◇ NeuAc

ENZYMES FOR TRIMMING OF GLYCOPROTEINS

CROSS-REFERENCE TO RELATED APPLICATIONS

This application is a continuation of U.S. application Ser. No. 16/076,319 filed Aug. 7, 2018, which is the National Phase of International Patent Application No. PCT/EP2017/052792, filed Feb. 8, 2017, published on Aug. 17, 2017 as WO 2017/137459 A1, which claims priority to European Patent Application No. 16154712.0, filed Feb. 8, 2016, and claims priority to European Patent Application No. 16154739.3, filed Feb. 8, 2016, and claims priority to European Patent Application No. 16173595.6 filed Jun. 8, 2016, and claims priority to European Patent Application No. 16173599.8 filed Jun. 8, 2016, and claims priority to European Patent Application No. 16206867.0 filed Dec. 23, 2016. The contents of these applications are herein incorporated by reference in their entirety.

SEQUENCE LISTING

The instant application contains a Sequence Listing which has been submitted in ASCII format via EFS-WEB and is hereby incorporated by reference in its entirety. The ASCII copy, created on Aug. 7, 2018, is named 069818-4031_Sequence_Listing.txt and is 157 KB.

FIELD OF THE INVENTION

The present invention is in the field of enzymatic hydrolysis of oligosaccharides, more in particular to the trimming of glycoproteins. The invention relates to improved enzymes for such trimming to liberate the core GlcNAc and to a process for trimming of glycoproteins using the enzymes according to the invention.

BACKGROUND OF THE INVENTION

Glycoproteins exist in many glycosylated variants, or glycoforms, which can differ substantially in their biochemical properties and (biological) functions. Glycans are structurally diverse, incorporating a wide range of monosaccharide residues and glycosidic linkages.

Many therapeutic proteins are glycoproteins, and although some are purified from natural sources, the majority are recombinantly expressed. The choice of expression system heavily influences the glycosylation. There have been notable efforts in controlling the glycosylation of glycoprotein production systems motivated by the impact on in vivo functionality. For example, monoclonal antibodies with engineered glycosylation display enhanced pharmacokinetics and effector function. Glycopeptides offer intriguing possibilities in the development of anticancer vaccines given their ability to stimulate both humoral and cellular immunity. Additionally, the HIV glycan shield is an effective target for antibody neutralization and an emerging target for vaccine design.

On the other hand, removal of N-glycans from glycoproteins provides complementary therapeutic opportunities. Deglycosylation of IgG significantly decreases binding of antibodies to Fc-gamma receptors, thereby avoiding a specific uptake of antibodies by e.g. macrophages or megakaryocytes, which may lead to thrombocytopenia. The latter biological phenomenon is responsible for the dose-limiting toxicity (DLT) of Kadcyla®, an antibody-drug-conjugate to treat HER2-upregulated breast cancer. Selective deglycosylation of antibodies in vivo affords opportunities to treat patients with antibody-mediated autoimmunity. Removal of high-mannose glycoform in a recombinant therapeutic glycoprotein may be beneficial, since high-mannose glycoforms are known to compromise therapeutic efficacy by a specific uptake by endogenous mannose receptors and leading to rapid clearance, as for example described by Gorovits and Krinos-Fiorotti, Cancer *Immunol. Immunother.* 2013, 62, 217-223 and Goetze et al, *Glycobiology* 2011, 21, 949-959 (both incorporated by reference). In addition, Van de Bovenkamp et al, *J. Immunol.* 2016, 196, 1435-1441 (incorporated by reference) describe how high-mannose glycans can influence immunity. It was described by Reusch and Tejada, *Glycobiology* 2015, 25, 1325-1334 (incorporated by reference), that inappropriate glycosylation in monoclonal antibodies could contribute to ineffective production from expressed Ig genes. In some cases, a carbohydrate addition sequence generated by either V region rearrangement or somatic hypermutation may result in an antibody that cannot be properly folded and secreted, as described by Gala and Morrison, J. Immunol. 2004, 172, 5489-5494 (incorporated by reference).

An additional advantage of deglycosylated therapeutic proteins is the much facilitated batch-to-batch consistency and significantly improved homogeneity, which is highly advantageous for regulatory approval.

A highly useful and straightforward approach to obtain deglycosylated recombinant proteins, thereby offering a route to improving the efficacy of therapeutic antibodies and other N-glycoproteins, is by enzymatic removal of glycans. Fortuitously, endoglycosidases have been discovered that are able to cleave N-glycans, which offers the possibility of selective removal from a recombinant glycoprotein. Endoglycosidases have further found use in the preparation of conjugates from glycoproteins, by selectively liberating the core GlcNAc moieties upon trimming, followed by bioconjugation. Another field of use of endoglycosidases is mass spectrometry, one of the key analytical tools for characterizing (therapeutic) proteins, including glycoproteins and monoclonal antibodies in particular. By enzymatic cleavage of the complex and heterogeneous glycan from the protein, mass spectrometric analysis is significantly facilitated.

Bioconjugation is the process of linking two or more molecules, of which at least one is a biomolecule and the other molecule(s) may be referred to as "target molecule" or "molecule of interest". Many different compounds have been found useful to be conjugated to glycoproteins. For example, the modulation of protein structure and function by covalent modification with a chemical probe for detection and/or isolation has evolved as a powerful tool in proteome-based research and biomedical applications. Fluorescent or affinity tagging of proteins is key to studying the trafficking of proteins in their native habitat, and vaccines based on protein-carbohydrate conjugates have gained prominence in the fight against HIV, cancer, malaria and pathogenic bacteria. PEGylation of proteins or attachment of a protein to serum albumin are useful strategies to enhance the pharmacokinetic profile by reducing clearance rates, whereas functionalization of a carrier protein such as a monoclonal antibody with a toxic payload is a promising strategy in the targeted treatment of disease (in particular cancer).

In general, two strategic concepts can be recognized in the field of bioconjugation: (a) conjugation based on a native functional group (in other words: a functional group already present in the biomolecule of interest, such as for example a thiol, an amine, an alcohol or a hydroxyphenol unit) or (b)

a two-stage process involving engineering of one (or more) unique reactive groups into a biomolecule prior to the actual conjugation process.

The first approach typically involves a reactive amino acid side-chain in a protein (e.g. cysteine or lysine), or a functional group in a glycan (e.g. amine, aldehyde) or nucleic acid (e.g. purine or pyrimidine functionality or alcohol). As summarized inter alia in G. T. Hermanson, "*Bioconjugate Techniques*", Elsevier, 3$^{rd}$ Ed. 2013, incorporated by reference. Most prominently, cysteine-maleimide conjugation stands out for protein conjugation by virtue of its high reaction rate and chemoselectivity. However, when no free cysteine is available for conjugation, as in many proteins, other methods are often required, each suffering from its own shortcomings especially in terms of site-specificity. Moreover, a general disadvantage of protein conjugates obtained via alkylation with maleimides is that in general the resulting succinimide conjugates can be unstable due to the reverse of alkylation, i.e. a retro-Michael reaction.

An elegant and broadly applicable solution for bioconjugation involves the two-stage approach. Although more laborious, two-stage conjugation via engineered functionality typically leads to higher selectivity (site-specificity) than conjugation on a natural functionality. Besides that, full stability can be achieved by proper choice of construct. Typical examples of a functional group that may be imparted onto the biomolecule include (strained) alkyne, (strained) alkene, norbornene, tetrazine, azide, phosphine, nitrile oxide, nitrone, nitrile imine, diazo compound, carbonyl compound, (O-alkyl)hydroxylamine and hydrazine, which may be achieved by either chemical or molecular biology approach. Each of the above functional groups is known to have at least one reaction partner, in many cases involving complete mutual reactivity. For example, cyclooctynes react selectively and exclusively with 1,3-dipoles, strained alkenes with tetrazines and phosphines with azides, leading to fully stable covalent bonds.

An efficient route towards the introduction of engineered functionalities such as azides into specifically glycoproteins is via selective functionalization of the glycans present on the glycoprotein. All recombinant antibodies, generated in mammalian host systems, contain the conserved N-glycosylation site on the asparagine residue at or close to position 297. These glycans are always formed as a complex mixture of isoforms, see e.g. FIGS. 1 and 2, consisting of a highly heterogeneous mixture of complex, hybrid and high-mannose glycans. Trimming of these glycans by an endoglycosidase leaves only the core GlcNAc moiety (attached to N297), optionally fucosylated at the 6-OH group. The liberated core GlcNAc provides a suitable anchor point for target molecules, providing a product with a much higher homogeneity in comparison to products obtained by conjugation to terminal sugar moieties present in the original glycan structure. A downside of this approach, however, is that different glycans may require different endoglycosidases, each with their own optimal conditions, such that multiple enzymatic treatments may be required for proper and complete trimming of the glycoprotein. For example, EndoH is known to trim high-mannose and hybrid glycoforms, but not complex type glycans, while EndoS is able to trim complex type glycans and to some extent hybrid glycan, but not high-mannose forms. EndoF2 is able to trim complex glycans (but not hybrid), while endoF3 can only trim complex glycans that are also 1,6-fucosylated. Another endoglycosidase, EndoD is able to hydrolyze Man5 (M5) glycan only. An overview of specific activities of different endoglycosidases is disclosed in Freeze et al. in *Curr. Protoc. Mol. Biol.*, 2010, 89:17.13A.1-17, incorporated by reference herein.

Yamamoto et al. disclose in Glycoconjugate J. 2005, 22, 35-42, incorporated by reference herein, a chimeric construct of EndoD and EndoBH, which was completely inactive. The chimeric construct was designed to investigate the homology of both endoglycosidases in trimming of glycans. In the context of glycoprotein conjugation, WO 2007/095506 and WO 2008/029281 disclose that trimming of the glycan can take place with EndoH, thereby hydrolysing a GlcNAc-GlcNAc glycosidic bond and liberating a GlcNAc for enzymatic introduction of GalNAz. Van Geel et al. disclose in *Bioconjugate Chem.* 2015, 26, 2233, incorporated by reference herein, that transfer of a range of azido-modified galactose moieties to the core GlcNAc residue of a monoclonal antibodies, obtained by trimming with an endoglycosidase, followed by attachment of a toxic payload by means of copper-free click chemistry, is an efficient method to obtain antibody-drug conjugates with a demonstrated improved efficacy and safety profile versus marketed drug Kadcyla®.

As a product of recombinant DNA technology, fusion proteins have been developed as a class of novel biomolecules with multi-functional properties. By genetically fusing two or more proteins or protein domains together, a fusion protein product is generated that may display similar or distinctly different functions as those of the component moieties. Fusion proteins have found applications in purification strategies, immobilization, imaging, and biopharmaceuticals. For example, many protein drugs are fused to Fc domains of antibodies, such as Fc-immunoglobulin G1 (Fc-IgG1), or to carrier proteins such as human serum albumin (HSA) or transferrin (Tf) to extend their plasma half-lives and to achieve enhanced therapeutic effects. Several fusion proteins drugs including Enbrel® (tumour necrosis factor/Fc-IgG1), Ontak® (interleukin-2/diphtheria toxin), Orencia® (cytotoxic T-lymphocyte antigen-4/Fc-IgG1), Amevive® (leukocyte function antigen-3/Fc-IgG1), Arcalyst® (interleukin-1 receptor extracellular domain/Fc-IgG1), and Nplate® (thrombopoietin/Fc-IgG1) have been approved by the FDA for therapeutic application. One relevant example of a fusion protein of an endoglycosidase can be found in Warren et al., *Prot. Eng. Design Select.* 2005, 18, 497-501 (incorporated by reference), disclosing a fusion of carbohydrate binding domain (CBM) to EndoF1 or PNGaseF.

The successful construction of a recombinant fusion protein requires the component proteins, but also the linkers may play an important role. Linkers may be short or long, flexible or rigid, and of cleavable or non-cleavable nature. In some cases, the linker may increase stability or folding, improve expression or biological activity, or alter pharmacokinetics. Typical nature of linkers known in the art are oligomers of glycine, e.g. $G_8$, oligomers of GGGGS, oligomers of EAAAK and variants thereof. A recent overview of linkers for fusion proteins can be found in Chen et al., *Adv. Drug Deliv. Rev.* 2013, 65, 1357-1369, incorporated herein by reference.

SUMMARY OF THE INVENTION

The invention concerns fusion proteins, wherein two endoglycosidases are fused, possibly via a linker. The fusion enzymes according to the invention are conveniently capable of trimming glycoproteins comprising at least two distinct glycoforms in a single step. All glycans of glycoproteins, which cannot be removed by a single conventional enzyme, are completely trimmed to liberate the core GlcNAc by the fusion enzyme according to the invention. Surprisingly, both activities of the fusion enzyme function smoothly at the optimal pH of one of the endoglycosidases, while the other endoglycosidase may normally require a different pH to operate optimally. Moreover, it was found that the activity of a particular endoglycosidase in a fusion protein can display a higher trimming efficiency compared to the same endoglycosidase as a single enzyme. The invention further concerns the use of the fusion enzyme according to the invention for trimming glycoproteins. In another aspect, the invention relates to the process of production of the fusion enzyme. In a further aspect, the inventions concerns a process for trimming glycoproteins, comprising trimming the glycoprotein with a fusion enzyme according to the invention, to obtain a trimmed glycoprotein.

DETAILED DESCRIPTION OF THE INVENTION

Definitions

Figure 1:
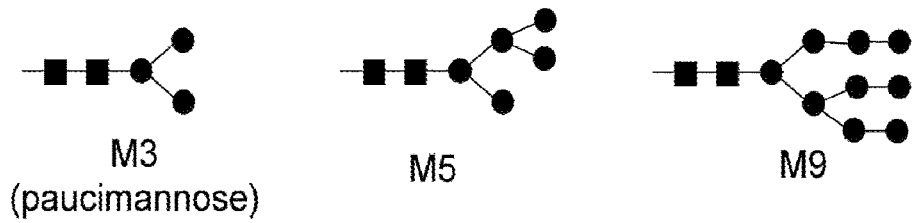
FIG. 1 shows exemplary glycans of high-mannose type (Mans (M3), Mans (M5) and Mans (M9)), complex type (biantennary), bisected type, triantennary and tetraantennary type.
Figure 1:
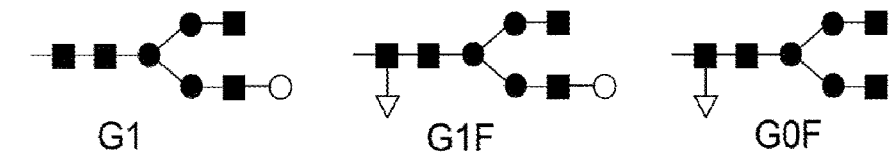
Figure 1:
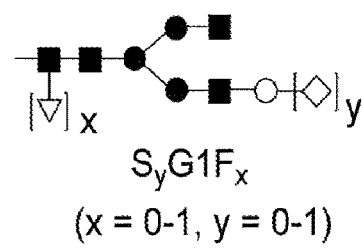
Figure 1:
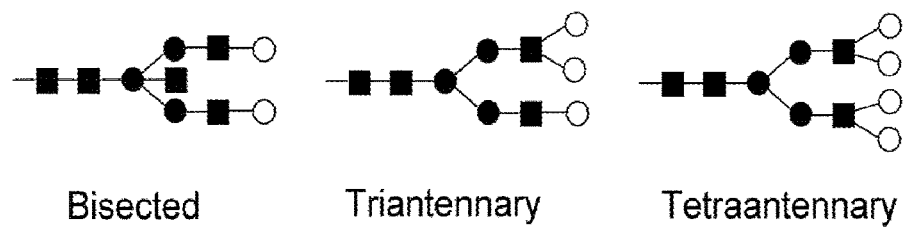
Figure 1:
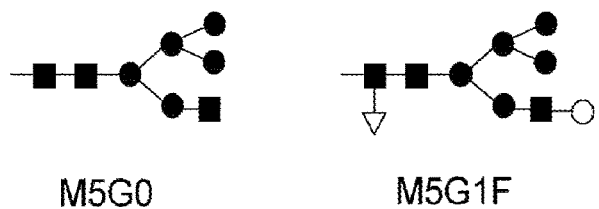

The verb "to comprise", and its conjugations, as used in this description and in the claims is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there is one and only one of the elements. The indefinite article "a" or "an" thus usually means "at least one".

The general term "sugar" is herein used to indicate a monosaccharide, for example glucose (Glc), galactose (Gal), mannose (Man) and fucose (Fuc). The term "sugar derivative" is herein used to indicate a derivative of a monosaccharide sugar, i.e. a monosaccharide sugar comprising substituents and/or functional groups. Examples of a sugar derivative include amino sugars and sugar acids, e.g. glucosamine ($GlcNH_2$), galactosamine ($GalNH_2$)N-acetylglucosamine (GlcNAc), N-acetylgalactosamine (GalNAc), sialic acid (Sia) which is also referred to as N-acetylneuraminic acid (NeuNAc), and N-acetylmuramic acid (MurNAc), glucuronic acid (GlcA) and iduronic acid (IdoA).

The term "nucleotide" is herein used in its normal scientific meaning. The term "nucleotide" refers to a molecule that is composed of a nucleobase, a five-carbon sugar (either ribose or 2-deoxyribose), and one, two or three phosphate groups. Without the phosphate group, the nucleobase and sugar compose a nucleoside. A nucleotide can thus also be called a nucleoside monophosphate, a nucleoside diphosphate or a nucleoside triphosphate. The nucleobase may be adenine, guanine, cytosine, uracil or thymine. Examples of a nucleotide include uridine diphosphate (UDP), guanosine diphosphate (GDP), thymidine diphosphate (TDP), cytidine diphosphate (CDP) and cytidine monophosphate (CMP).

The term "protein" is herein used in its normal scientific meaning. Herein, polypeptides comprising about 10 or more amino acids are considered proteins. A protein may comprise natural, but also unnatural amino acids.

Proteins and enzyme included mutants thereof. For example, "endoglycosidase" includes both native (wild-type) endoglycosidases and mutant endoglycosidases, as long as the endoglycosidase activity is substantially maintained. A domain having an amino acid sequence that is different from a wild-type amino acid sequence is herein referred to as a mutant domain. The mutation may e.g. comprise a single amino acid change (a point mutation), but also multiple amino acid changes (e.g. of 1 to 10, preferably of 1 to 6, more preferably of 1, 2, 3 or 4, even more preferably of 1 or 2 amino acids), or a deletion or insertion of one or more (e.g. of 1 to 10, preferably of 1 to 6, such as 1, 2, 3 or 4, preferably of 1 or 2) amino acids. Alternatively, larger deletions or insertions can be applied to the enzyme. For example, truncated endoglycosidase D (deletion of 599 amino acids from its C-terminal portion) has been found to retain its endoglycosidase activity (Yamamoto et al. in Glycoconjugate J. 2005, 22, 35-42). The skilled person is aware of the possibilities in this respect, and as long as the endoglycosidase activity is substantially retained the enzyme can contain any type of mutation.

The term "glycoprotein" is herein used in its normal scientific meaning and refers to a protein comprising one or more monosaccharide or oligosaccharide chains ("glycans") covalently bonded to the protein. A glycan may be attached to a hydroxyl group on the protein (O-linked-glycan), e.g. to the hydroxyl group of serine, threonine, tyrosine, hydroxylysine or hydroxyproline, or to an amide function on the protein (N-glycoprotein), e.g. asparagine or arginine, or to a carbon on the protein (C-glycoprotein), e.g. tryptophan. A glycoprotein may comprise more than one glycan, may comprise a combination of one or more monosaccharide and one or more oligosaccharide glycans, and may comprise a combination of N-linked, O-linked and C-linked glycans. It is estimated that more than 50% of all proteins have some form of glycosylation and therefore qualify as glycoprotein. Examples of glycoproteins include PSMA (prostate-specific membrane antigen), CAL (*candida* antartica lipase), gp41, gp120, EPO (erythropoietin), antifreeze protein and antibodies.

The term "glycan" is herein used in its normal scientific meaning and refers to a monosaccharide or oligosaccharide chain that is linked to a protein. The term glycan thus refers to the carbohydrate-part of a glycoprotein. The glycan is attached to a protein via the C-1 carbon of one sugar, which may be without further substitution (monosaccharide) or may be further substituted at one or more of its hydroxyl groups (oligosaccharide). A naturally occurring glycan typically comprises 1 to about 10 saccharide moieties. However, when a longer saccharide chain is linked to a protein, said saccharide chain is herein also considered a glycan. A glycan of a glycoprotein may be a monosaccharide. Typically, a monosaccharide glycan of a glycoprotein consists of a single N-acetylglucosamine (GlcNAc), glucose (Glc), mannose (Man) or fucose (Fuc) covalently attached to the protein. A glycan may also be an oligosaccharide. An oligosaccharide chain of a glycoprotein may be linear or branched. In an oligosaccharide, the sugar that is directly attached to the protein is called the core sugar. In an oligosaccharide, a sugar that is not directly attached to the protein and is attached to at least two other sugars is called an internal sugar. In an oligosaccharide, a sugar that is not directly attached to the protein but to a single other sugar, i.e. carrying no further sugar substituents at one or more of its other hydroxyl groups, is called the terminal sugar. For the avoidance of doubt, there may exist multiple terminal sugars in an oligosaccharide of a glycoprotein, but only one core sugar. The end of an oligosaccharide that is directly attached to the protein is called the reducing end of a glycan. The other end of the oligosaccharide is called the non-reducing end of a glycan. A glycan may be an O-linked glycan, an N-linked glycan or a C-linked glycan.

In an O-linked glycan a monosaccharide or oligosaccharide glycan is bonded to an O-atom in an amino acid of the protein, typically via a hydroxyl group of serine (Ser) or threonine (Thr). For 0-linked glycans, a wide diversity of chains exist. Naturally occurring O-linked glycans typically feature a serine or threonine-linked α-O-GalNAc moiety, further substituted with galactose, sialic acid and/or fucose. The hydroxylated amino acid that carries the glycan substitution may be part of any amino acid sequence in the protein.

In an N-linked glycan a monosaccharide or oligosaccharide glycan is bonded to the protein via an N-atom in an amino acid of the protein, typically via an amide nitrogen in the side chain of asparagine (Asn) or arginine (Arg). For N-linked glycans, a wide diversity of glycans exist. Naturally occurring N-linked glycans feature an asparagine-linked β-N-GlcNAc moiety, in turn further substituted at its 4-OH with β-GlcNAc, in turn further substituted at its 4-OH with β-Man, in turn further substituted at its 3-OH and 6-OH with α-Man, leading to the glycan pentasaccharide $Man_3GlcNAc_2$. The core GlcNAc moiety may be further substituted at its 6-OH by α-Fuc. The pentasaccharide $Man_3GlcNAc_2$ is the common oligosaccharide scaffold of nearly all N-linked glycoproteins and may carry a wide variety of other substituents, including but not limited to Man, GlcNAc, Gal and sialic acid. The asparagine that is substituted with the glycan on its side-chain is typically part of the sequence Asn-X-Y, with X being any amino acid but proline and Y being either serine or threonine.

In a C-linked glycan a monosaccharide or oligosaccharide glycan is bonded to a C-atom in an amino acid of the protein, typically to a C-atom of tryptophan (Trp).

The term "antibody" is herein used in its normal scientific meaning. An antibody is a protein generated by the immune system that is capable of recognizing and binding to a specific antigen. An antibody is an example of a glycoprotein. The term antibody herein is used in its broadest sense and specifically includes monoclonal antibodies, polyclonal antibodies, dimers, multimers, multispecific antibodies (e.g. bispecific antibodies), antibody fragments, and double and single chain antibodies. The term "antibody" is herein also meant to include human antibodies, humanized antibodies, chimeric antibodies and antibodies specifically binding cancer antigen. The term "antibody" is meant to include whole antibodies, but also antigen-binding fragments of an antibody, for example an antibody Fab fragment, F(ab')2, Fv fragment or Fc fragment from a cleaved antibody, a scFv-Fc fragment, a minibody, a diabody or a scFv. Furthermore, the term includes genetically engineered antibodies and derivatives of an antibody. Antibodies, fragments of antibodies and genetically engineered antibodies may be obtained by methods that are known in the art. Typical examples of antibodies include, amongst others, abciximab, rituximab, basiliximab, palivizumab, infliximab, trastuzumab, alemtuzumab, adalimumab, tositumomab-1131, cetuximab, ibrituximab tiuxetan, omalizumab, bevacizumab, natalizumab, ranibizumab, panitumumab, eculizumab, certolizumab pegol, golimumab, canakinumab, catumaxomab, ustekinumab, tocilizumab, ofatumumab, denosumab, belimumab, ipilimumab and brentuximab.

A "linker" is herein defined as a moiety that connects two or more elements of a compound. For example, the fusion enzyme according to the invention may contain a linker that connects the two endoglycosidase units. In the context of the fusion enzymes according to the present invention, linkers typically contain at least one amino acid and most preferably consist of one or more amino acids.

A "bioconjugate" is herein defined as a compound wherein a biomolecule is covalently connected to a target molecule via a linker. A bioconjugate comprises one or more biomolecules and/or one or more target molecules. The linker may comprise one or more spacer moieties. A target molecule may be an active substance, a reporter molecule, a polymer, a solid surface, a hydrogel, a nanoparticle, a microparticle or a biomolecule.

The term "fusion enzyme" herein refers to an enzyme wherein the amino acid sequences of two or more enzymes that originally belonged to separate enzymes are joined together, optionally via a linker. Fusion enzymes are known in the art and may be created by the joining of two or more genes that originally code for separate enzymes. Translation of this gene results in a single polypeptide with functional properties derived from each of the original enzymes.

Fusion Enzyme

In a first aspect, the invention concerns a fusion enzyme comprising two endoglycosidases, optionally connected via a linker. The fusion enzyme according to the invention may be represented by structure (1):

$$EndoX\text{-}(L)_p\text{-}EndoY \qquad (1)$$

Herein, EndoX and EndoY are both individually an endoglycosidase, L is a linker and p is 0 or 1. In the context of the present invention, "fusion enzyme" may also be referred to as "fusion protein". The fusion enzyme according to the invention is preferably an end-to-end fusion, either direct or via a linker L.

Endoglycosidase

Endoglycosidase are known in the art as enzymes that cleave oligosaccharides between two glycosidic bonds, as such releasing them from either glycoproteins, glycopeptides or glycolipids. Such oligosaccharides are typically referred to as glycans. In the context of the present invention, "Endo" refers to endoglycosidase. Endoglycosidases hydrolyse the bond between two sugar units in an oligosaccharide or polysaccharide, but not between the core sugar unit, which is directly bound to the peptide part of a glycoprotein, and the amino acid it is connected to. Endoglycosidases typically hydrolyse the bond between the two core N-acetylglucosamine (GlcNAc) residues in N-linked glycans, thus leaving the core GlcNAc residue connected to the peptide part of the glycoprotein.

In the context of the present invention, the term endoglycosidase encompasses all members of the family of endoglycosidase that releases oligosaccharides from glycoproteins, glycopeptides or glycolipids. Endoglycosidase may also cleave polysaccharide chains between residues that are not the terminal residue, although releasing oligosaccharides from conjugated protein and lipid molecules is more common.

In the context of the present invention, the term endoglycosidase encompasses both the native endoglycosidases or truncated endoglycosidases and mutants thereof, as long as the endoglycosidase activity is substantially retained. In other words, the amino acid sequence of EndoX and EndoY may comprise a different amino acids sequence compared to the native endoglycosidase. In one embodiment, the amino acid sequence of EndoX and EndoY comprise a mutant. In one embodiment, the amino acid sequence of EndoX and EndoY do not comprise a mutant. In one embodiment, the amino acid sequence of EndoX and EndoY comprise a truncated sequence. In one embodiment, the amino acid sequence of EndoX and EndoY do not comprise a truncated sequence. When looking at the sequence of EndoX and EndoY individually, it is preferred that each of EndoX and EndoY has at least 80% sequence identity with the corresponding native amino acid sequence of the catalytic domain of the endoglycosidase, such as at least 81%, 82%, 83%, 84%, 85%, 86%, 87%, 88%, 89%, 90%, 91%, 92%, 93%, 94%, 95%, 96%, 97%, 98% or 99% sequence identity with the corresponding native amino acid sequence. Most preferably, each of EndoX and EndoY has 100% sequence identity with the corresponding amino acid sequence of the catalytic domain of the endoglycosidase. Alternatively or additionally, it is preferred that each of EndoX and EndoY has at least 80% sequence similarity with the corresponding native amino acid sequence, such as at least 81%, 82%, 83%, 84%, 85%, 86%, 87%, 88%, 89%, 90%, 91%, 92%, 93%, 94%, 95%, 96%, 97%, 98% or 99% sequence similarity with the corresponding native amino acid sequence of the catalytic domain of the endoglycosidase. Most preferably, each of EndoX and EndoY has 100% sequence similarity with the corresponding native amino acid sequence of the catalytic domain of the endoglycosidase.

Sequence identity and similarities can be readily calculated by known methods and/or computer program methods known in the art such as BLASTP publicly available from NCBI and other sources (BLAST Manual, Altschul, S., et al., NCBI NLM NIH Bethesda, Md. 20894; Altschul, S., et al., *J. Mol. Biol.* 215:403-410 (1990), incorporated by reference.

Glycans that can be cleaved by glycosidases exist in various glycoforms, which are generally grouped in three types: high-mannose, complex and hybrid. All three types have a ☐1,4-N,N'-diacetylchitobiose (GlcNAc$_2$) core, connected to a mannose trisaccharide (Man$_3$). The core GlcNAc may optionally be fucosylated, but this is not always the case. High-mannose glycans contain at least 2 further mannose residues, typically resulting in 5 to 9 mannose residues. Complex glycans have one or more sugar monomers, not being mannose, connected to two of the mannose residues of the central Man$_3$ unit. These further sugar monomers are typically selected from GlcNAc, galactose (Gal), and sialic acid (Neu5Ac). Complex glycans exist in bi-, tri- and tetraantennary forms, depending on the number of (oligo) saccharide(s) that are connected to the central Man$_3$ unit.

Figure 2:
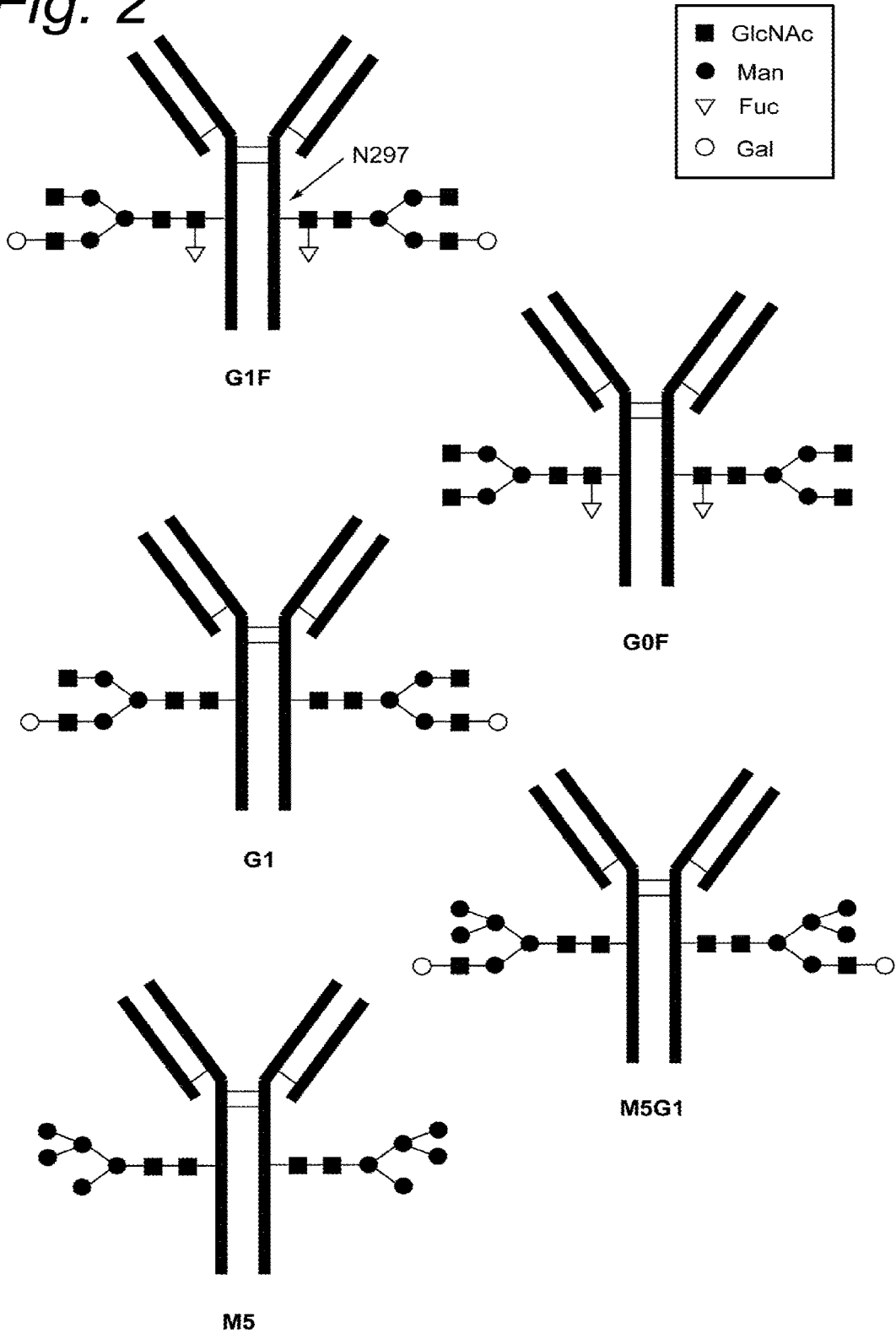
FIG. 2 shows an antibody comprising a glycan on each heavy chain. The most typical complex glycosylation patterns of a recombinant antibody are G1F, G0F and G1. Some mannose-type glycosylation may also be present (M5) and in some cases a hybrid type glycan (e.g. M5G1).

Hybrid glycans have high-mannose type oligosaccharide connected to one of the mannose residue of the central Man$_3$ unit, and a complex type oligosaccharide connected to the other mannose residue. An overview of the glycan types is given in FIG. 1. Even within a specific glycan type, many possibilities exist, increasing the heterogenicity of glycoproteins. For example, biantennary complex glycans attached to the N297 residue of antibodies may exists in several distinct glycoforms, including but not limited to G1, G1F, G0F and SG1F, as depicted in FIG. 2. Endo-β-N-acetylglucosaminidases (ENGases, also referred to endoglycosidases or Endos), typically hydrolyse the N-glycan of a glycoprotein at the β-1,4-glycosidic bond of the core chitobiose. These enzymes, found mainly in GH18 and GH85 in the CAZy classification (Lombard et al. in *Nucleic Acids Res.* 2014, 42, D490, incorporated by reference) are widely distributed from bacteria to animals and are involved in various biological functions such as glycan metabolism or bacterial pathogenesis (Karamanos, Adv. *Biochem.* 2013, 1, 81). Endoglycosidases are typically specific for hydrolysis of one or two glycan types. Some are specific for hydrolysis of high-mannose glycans (e.g. EndoA, EndoD, EndoT), while others in addition to high-mannose also cleave hybrid glycans (e.g. EndoF1, EndoH). Endoglycosidases specific for hydrolysis of complex glycans also exist in several variants. An overview of different activities is disclosed in Freeze et al. in *Cuff. Protoc. Mol. Biol.*, 2010, 89:17.13A.1-17, incorporated by reference herein. EndoS cleaves biantennary, triantennary and tetraantennary complex glycans, but its activity is nearly exclusively limited to antibodies, in particular the heavy chain of IgG.

EndoX and EndoY are two distinct endoglycosidases, which are preferably individually selected from the group consisting of EndoA, EndoBi, EndoBH, EndoBT, EndoCE, EndoD, EndoE, EfEndo18A, EndoF1, EndoF2, EndoF3, EndoH, EndoLL, EndoM, EndoOm, EndoS, and EndoT. These endoglycosidases and their amino acid sequences are known to the skilled person. Here below, some preferred amino acid sequences for specific endoglycosidases are given.

In a preferred embodiment, EndoS has at least 80%, preferably at least 90%, more preferably at least 95% sequence identity with SEQ ID No. 4 or SEQ ID No. 5, most preferably EndoS has 100% sequence identity with SEQ ID No. 4 or SEQ ID No. 5. In one embodiment, EndoS has SEQ ID No. 4 or SEQ ID No. 5. Preferably, EndoS has the indicated sequence identities with SEQ ID No. 4.

SEQ ID No. 4:
MPSIDSLHYLSENSKKEFKEELSKAGQESQKVKEILAKAQQADKQAQELA

KMKIPEKIPMKPLHGPLYGGYFRTWHDKTSDPTEKDKVNSMGELPKEVDL

AFIFHDWTKDYSLFWKELATKHVPKLNKQGTRVIRTIPWRFLAGGDNSGI

AEDTSKYPNTPEGNKALAKAIVDEYVYKYNLDGLDVDVEHDSIPKVDKKE

DTAGVERSIQVFEEIGKLIGPKGVDKSRLFIMDSTYMADKNPLIERGAPY

INLLLVQVYGSQGEKGGWEPVSNRPEKTMEERWQGYSKYIRPEQYMIGFS

FYEENAQEGNLWYDINSRKDEDKANGINTDITGTRAERYARWQPKTGGVK

GGIFSYAIDRDGVAHQPKKYAKQKEFKDATDNIFHSDYSVSKALKTVMLK

DKSYDLIDEKDFPDKALREAVMAQVGTRKGDLERFNGTLRLDNPAIQSLE

GLNKFKKLAQLDLIGLSRITKLDRSVLPANMKPGKDTLETVLETYKKDNK

```
EEPATIPPVSLKVSGLTGLKELDLSGFDRETLAGLDAATLTSLEKVDISG

NKLDLAPGTENRQIFDTMLSTISNHVGSNEQTVKFDKQKPTGHYPDTYGK

TSLRLPVANEKVDLQSQLLFGTVTNQGTLINSEADYKAYQNHKIAGRSFV

DSNYHYNNFKVSYENYTVKVTDSTLGTTTDKTLATDKEETYKVDFFSPAD

KTKAVHTAKVIVGDEKTMMVNLAEGATVIGGSADPVNARKVFDGQLGSET

DNISLGWDSKQSIIFKLKEDGLIKHWRFFNDSARNPETTNKPIQEASLQI

FNIKDYNLDNLLENPNKFDDEKYWITVDTYSAQGERATAFSNTLNNITSK

YWRVVFDTKGDRYSSPVVPELQILGYPLPNADTIMKTVTTAKELSQQKDK

ESQKMLDELKIKEMALETSLNSKIFDVTAINANAGVLKDCIEKRQLLKK

SEQ ID No. 5:
MGSSHHHHHHSSGLVPRGSHMPSIDSLHYLSENSKKEFKEELSKAGQESQ

KVKEILAKAQQADKQAQELAKMKIPEKIPMKPLHGPLYGGYFRTWHDKTS

DPTEKDKVNSMGELPKEVDLAFIFHDWTKDYSLFWKELATKHVPKLNKQG

TRVIRTIPWRFLAGGDNSGIAEDTSKYPNTPEGNKALAKAIVDEYVYKYN

LDGLDVDVEHDSIPKVDKKEDTAGVERSIQVFEEIGKLIGPKGVDKSRLF

IMDSTYMADKNPLIERGAPYINLLLVQVYGSQGEKGGWEPVSNRPEKTME

ERWQGYSKYIRPEQYMIGFSFYEENAQEGNLWYDINSRKDEDKANGINTD

ITGTRAERYARWQPKTGGVKGGIFSYAIDRDGVAHQPKKYAKQKEFKDAT

DNIFHSDYSVSKALKTVMLKDKSYDLIDEKDFPDKALREAVMAQVGTRKG

DLERFNGTLRLDNPAIQSLEGLNKFKKLAQLDLIGLSRITKLDRSVLPAN

MKPGKDTLETVLETYKKDNKEEPATIPPVSLKVSGLTGLKELDLSGFDRE

TLAGLDAATLTSLEKVDISGNKLDLAPGTENRQIFDTMLSTISNHVGSNE

QTVKFDKQKPTGHYPDTYGKTSLRLPVANEKVDLQSQLLFGTVTNQGTLI

NSEADYKAYQNHKIAGRSFVDSNYHYNNFKVSYENYTVKVTDSTLGTTTD

KTLATDKEETYKVDFFSPADKTKAVHTAKVIVGDEKTMMVNLAEGATVIG

GSADPVNARKVFDGQLGSETDNISLGWDSKQSIIFKLKEDGLIKHWRFFN

DSARNPETTNKPIQEASLQIFNIKDYNLDNLLENPNKFDDEKYWITVDTY

SAQGERATAFSNTLNNITSKYWRVVFDTKGDRYSSPVVPELQILGYPLPN

ADTIMKTVTTAKELSQQKDKFSQKMLDELKIKEMALETSLNSKIFDVTAI

NANAGVLKDCIEKRQLLKK
```

In a preferred embodiment, EndoH has at least 80%, preferably at least 90%, more preferably at least 95% sequence identity with SEQ ID No. 6, most preferably EndoH has 100% sequence identity with SEQ ID No. 6. In one embodiment, EndoH has SEQ ID No. 6.

```
SEQ ID No. 6:
APAPVKQGPTSVAYVEVNNNSMLNVGKYTLADGGGNAFDVAVIFAANINY

DTGTKTAYLHFNENVQRVLDNAVTQIRPLQQQGIKVLLSVLGNHQGAGFA

NFPSQQAASAFAKQLSDAVAKYGLDGVDFDDEYAEYGNNGTAQPNDSSFV

HLVTALRANMPDKIISLYNIGPAASRLSYGGVDVSDKFDYAWNPYYGTWQ

VPGIALPKAQLSPAAVEIGRTSRSTVADLARRTVDEGYGVYLTYNLDGGD

RTADVSAFTRELYGSEAVRTP
```

In a preferred embodiment, EndoF1 has at least 80%, preferably at least 90%, more preferably at least 95% sequence identity with SEQ ID No. 7, most preferably EndoF1 has 100% sequence identity with SEQ ID No. 7. In one embodiment, EndoF1 has SEQ ID No. 7.

```
SEQ ID No.7:
AVTGTTKANIKLFSFTEVNDTNPLNNLNFTLKNSGKPLVDMVVLFSANIN

YDAANDKVFVSNNPNVQHLLTNRAKYLKPLQDKGIKVILSILGNHDRSGI

ANLSTARAKAFAQELKNTCDLYNLDGVFFDDEYSAYQTPPPSGFVTPSNN

AAARLAYETKQAMPNKLVTVYVYSRTSSFPTAVDGVNAGSYVDYAIHDYG

GSYDLATNYPGLAKSGMVMSSQEFNQGRYATAQALRNIVTKGYGGHMIFA

MDPNRSNFTSGQLPALKLIAKELYGDELVYSNTPYSKDW
```

In a preferred embodiment, EndoF2 has at least 80%, preferably at least 90%, more preferably at least 95% sequence identity with SEQ ID No. 8, most preferably EndoF2 has 100% sequence identity with SEQ ID No. 8. In one embodiment, EndoF2 has SEQ ID No. 8.

```
SEQ ID No. 8:
MAVNLSNLIAYKNSDHQISAGYYRTWRDSATASGNLPSMRWLPDSLDMVM

VFPDYTPPENAYWNTLKTNYVPYLHKRGTKVIITLGDLNSATTTGGQDSI

GYSSWAKGIYDKWVGEYNLDGIDIDIESSPSGATLTKFVAATKALSKYFG

PKSGTGKTFVYDTNQNPTNFFIQTAPRYNYVFLQAYGRSTTNLTTVSGLY

APYISMKQFLPGFSFYEENGYPGNYWNDVRYPQNGTGRAYDYARWQPATG

KKGGVFSYAIERDAPLTSSNDNTLRAPNFRVTKDLIKIMNP
```

In a preferred embodiment, EndoF3 has at least 80%, preferably at least 90%, more preferably at least 95% sequence identity with SEQ ID No. 9, most preferably EndoF3 has 100% sequence identity with SEQ ID No. 9. In one embodiment, EndoF3 has SEQ ID No. 9.

```
SEQ ID No. 9:
MATALAGSNGVCIAYYITDGRNPTFKLKDIPDKVDMVILFGLKYWSLQDT

TKLPGGTGMMGSFKSYKDLDTQIRSLQSRGIKVLQNIDDDVSWQSSKPGG

FASAAAYGDAIKSIVIDKWKLDGISLDIEHSGAKPNPIPTFPGYAATGYN

GWYSGSMAATPAFLNVISELTKYFGTTAPNNKQLQIASGIDVYAWNKIME

NFRNNFNYIQLQSYGANVSRTQLMMNYATGTNKIPASKMVFGAYAEGGTN

QANDVEVAKWTPTQGAKGGMMIYTYNSNVSYANAVRDAVKN
```

In a preferred embodiment, EfEndo18A has at least 80%, preferably at least 90%, more preferably at least 95% sequence identity with SEQ ID No. 10, most preferably EfEndo18A has 100 sequence identity with SEQ ID No. 10. In one embodiment, EfEndo18A has SEQ ID No. 10.

```
SEQ ID No. 10:
ASTVTPKTVMYVEVNNHDFNNVGKYTLAGTNQPAFDMGIIFAANINYDTV

NKKPYLYLNERVQQTLNEAETQIRPVQARGTKVLLSILGNHEGAGFANFP

TYESADAFAAQLEQVVNTYHLDGIDFDDEYAEYGKNGTPQPNNSSFIWLL
```

-continued

QALRNRLGNDKLITFYNIGPAAANSSANPQMSSLIDYAWNPYYSTWNPPQ

IAGMPASRLGASAVEVGVNQNLAAQYAKRTKAEQYGIYLMYNLPGKDSSA

YISAATQELYGRKTNYSPTVPTP

These preferred sequences for the individual endoglycosidases also apply to the fusion enzyme according to the invention. Thus, for example in case EndoX is EndoS, it is preferred that the amino acid sequence of EndoS is as defined here above. The skilled person is capable of applying the sequences provided above to the fusion enzyme according to formula (1).

In one embodiment, the enzyme according to the invention comprises an amino acid sequence selected from SEQ ID NO:4-SEQ ID NO:10, connected via an amino acid sequence selected from SEQ ID NO:11 and SEQ ID NO:12 to another amino acid sequence selected from SEQ ID NO:4-SEQ ID NO:10, individually having at least 50% sequence identity, preferably at least 70%, more preferably at least 80% sequence identity with the individual SEQ IDs, such as at least 81%, 82%, 83%, 84%, 85%, 86%, 87%, 88%, 89%, 90%, 91%, 92%, 93%, 94%, 95%, 96%, 97%, 98% or 99% sequence identity with respect to each one of SEQ ID NO:4-SEQ ID NO:12. In a preferred embodiment, these sequence identities apply to the combination of SEQ IDs in the fusion enzyme according to the invention.

Preferably, the enzyme of the invention, having the above indicated sequence identities with respect to SEQ ID NO: 2, has EndoS and EndoH activity. Most preferably, the enzyme according to the invention has 100% sequence identity with SEQ ID NO: 2. In one embodiment, the enzyme according to the invention comprising SEQ ID NO:4 connected via SEQ ID NO:11 to SEQ ID NO:6, individually having at least 50% sequence identity, preferably at least 70%, more preferably at least 80% sequence identity with the individual SEQ IDs, such as at least 81%, 82%, 83%, 84%, 85%, 86%, 87%, 88%, 89%, 90%, 91%, 92%, 93%, 94%, 95%, 96%, 97%, 98% or 99% sequence identity with respect to SEQ ID NO:4, SEQ ID NO:11 and SEQ ID NO:6. In a preferred embodiment, these sequence identities apply to the combination of SEQ ID NO:4, SEQ ID NO:11 and SEQ ID NO:6.

Preferably, the enzyme of the invention, having the above indicated sequence identities with respect to SEQ ID NO: 1, has EndoS and EndoH activity. Most preferably, the enzyme according to the invention has 100% sequence identity with SEQ ID NO:1. In one embodiment, the enzyme according to the invention comprising SEQ ID NO:4 connected via SEQ ID NO:12 to SEQ ID NO:6, individually having at least 50% sequence identity, preferably at least 70%, more preferably at least 80% sequence identity with the individual SEQ IDs, such as at least 81%, 82%, 83%, 84%, 85%, 86%, 87%, 88%, 89%, 90%, 91%, 92%, 93%, 94%, 95%, 96%, 97%, 98% or 99% sequence identity with respect to SEQ ID NO:4, SEQ ID NO:12 and SEQ ID NO:6.

In a preferred embodiment, the fusion enzyme according to the invention has at least 50% sequence identity, preferably at least 70%, more preferably at least 80% sequence identity, such as at least 81%, 82%, 83%, 84%, 85%, 86%, 87%, 88%, 89%, 90%, 91%, 92%, 93%, 94%, 95%, 96%, 97%, 98% or 99%, or most preferably 100% sequence identity with respect to any one of SEQ ID NO:1, 2 and 13-21. Preferred sequence IDs are selected from SEQ ID NO:1, 2, 17, 19 and 21. Most preferred sequence IDs are selected from SEQ ID NO:1, 2 and 21.

In one embodiment, the fusion enzyme according to the invention has at least 50% sequence identity, preferably at least 70%, more preferably at least 80% sequence identity, such as at least 81%, 82%, 83%, 84%, 85%, 86%, 87%, 88%, 89%, 90%, 91%, 92%, 93%, 94%, 95%, 96%, 97%, 98% or 99%, or most preferably 100% sequence identity with respect to SEQ ID NO:1. In one embodiment, the fusion enzyme according to the invention has at least 50% sequence identity, preferably at least 70%, more preferably at least 80% sequence identity, such as at least 81%, 82%, 83%, 84%, 85%, 86%, 87%, 88%, 89%, 90%, 91%, 92%, 93%, 94%, 95%, 96%, 97%, 98% or 99%, or most preferably 100% sequence identity with respect to SEQ ID NO:2. In one embodiment, the fusion enzyme according to the invention has at least 50% sequence identity, preferably at least 70%, more preferably at least 80% sequence identity, such as at least 81%, 82%, 83%, 84%, 85%, 86%, 87%, 88%, 89%, 90%, 91%, 92%, 93%, 94%, 95%, 96%, 97%, 98% or 99%, or most preferably 100% sequence identity with respect to SEQ ID NO:13. In one embodiment, the fusion enzyme according to the invention has at least 50% sequence identity, preferably at least 70%, more preferably at least 80% sequence identity, such as at least 81%, 82%, 83%, 84%, 85%, 86%, 87%, 88%, 89%, 90%, 91%, 92%, 93%, 94%, 95%, 96%, 97%, 98% or 99%, or most preferably 100% sequence identity with respect to SEQ ID NO:14. In one embodiment, the fusion enzyme according to the invention has at least 50% sequence identity, preferably at least 70%, more preferably at least 80% sequence identity, such as at least 81%, 82%, 83%, 84%, 85%, 86%, 87%, 88%, 89%, 90%, 91%, 92%, 93%, 94%, 95%, 96%, 97%, 98% or 99%, or most preferably 100% sequence identity with respect to SEQ ID NO:15. In one embodiment, the fusion enzyme according to the invention has at least 50% sequence identity, preferably at least 70%, more preferably at least 80% sequence identity, such as at least 81%, 82%, 83%, 84%, 85%, 86%, 87%, 88%, 89%, 90%, 91%, 92%, 93%, 94%, 95%, 96%, 97%, 98% or 99%, or most preferably 100% sequence identity with respect to SEQ ID NO:16. In one embodiment, the fusion enzyme according to the invention has at least 50% sequence identity, preferably at least 70%, more preferably at least 80% sequence identity, such as at least 81%, 82%, 83%, 84%, 85%, 86%, 87%, 88%, 89%, 90%, 91%, 92%, 93%, 94%, 95%, 96%, 97%, 98% or 99%, or most preferably 100% sequence identity with respect to SEQ ID NO:17. In one embodiment, the fusion enzyme according to the invention has at least 50% sequence identity, preferably at least 70%, more preferably at least 80% sequence identity, such as at least 81%, 82%, 83%, 84%, 85%, 86%, 87%, 88%, 89%, 90%, 91%, 92%, 93%, 94%, 95%, 96%, 97%, 98% or 99%, or most preferably 100% sequence identity with respect to SEQ ID NO:18. In one embodiment, the fusion enzyme according to the invention has at least 50% sequence identity, preferably at least 70%, more preferably at least 80% sequence identity, such as at least 81%, 82%, 83%, 84%, 85%, 86%, 87%, 88%, 89%, 90%, 91%, 92%, 93%, 94%, 95%, 96%, 97%, 98% or 99%, or most preferably 100% sequence identity with respect to SEQ ID NO:19. In one embodiment, the fusion enzyme according to the invention has at least 50% sequence identity, preferably at least 70%, more preferably at least 80% sequence identity, such as at least 81%, 82%, 83%, 84%, 85%, 86%, 87%, 88%, 89%, 90%, 91%, 92%, 93%, 94%, 95%, 96%, 97%, 98% or 99%, or most preferably 100% sequence identity with respect to SEQ ID NO:20. In one embodiment, the fusion enzyme according to the invention has at least 50% sequence identity, preferably at least 70%, more preferably at least 80% sequence identity, such as at least 81%, 82%, 83%, 84%, 85%, 86%, 87%, 88%, 89%, 90%, 91%, 92%, 93%, 94%, 95%, 96%, 97%, 98% or 99%, or most preferably 100% sequence identity with respect to SEQ ID NO:21.

In one embodiment, EndoX and EndoY are two distinct endoglycosidases and both are selected from the group consisting of EndoA, EndoBi, EndoBH, EndoBT, EndoCE, EndoD, EndoE, EfEndo18A, EndoF1, EndoF2, EndoF3, EndoH, EndoLL, EndoM, EndoOm, EndoS, and EndoT. A preferred group of endoglycosidases to be used as EndoX and EndoY consists of EndoE, EfEndo18A, EndoF1, EndoF2, EndoF3, EndoH, EndoS and EndoT, more preferably of EndoF1, EndoF2, EndoF3, EfEndo18A, EndoH and EndoS. In one embodiment, at least one of EndoX and EndoY, preferably EndoX, is selected from the group consisting of EndoF2, EndoF3 and EndoS. In one embodiment, at least one of EndoX and EndoY, preferably EndoY, is selected from the group consisting of EfEndo18A EndoF1 and EndoH.

In one embodiment, one of EndoX and EndoY is an endoglycosidase capable of cleaving a glycan of the high-mannose type, such as EndoA, EndoE, EfEndo18A, EndoF1, EndoH, EndoM, or EndoT. Preferably, the endoglycosidase capable of cleaving a glycan of the high-mannose type is selected from the group consisting of EndoE, EfEndo18A, EndoF1, EndoH and EndoT, more preferably selected from the group consisting of EfEndo18A, EndoF1 and EndoH. Most preferably, the endoglycosidase capable of cleaving a glycan of the high-mannose type is EndoH. Preferably, the other of EndoX and EndoY is an endoglycosidase having a different activity, preferably an endoglycosidase capable of cleaving a glycan of the complex type.

In one embodiment, one of EndoX and EndoY is an endoglycosidase capable of cleaving a glycan of the complex type, such as EndoE, EndoF2, EndoF3 and EndoS. Preferably, the endoglycosidase capable of cleaving a glycan of the complex type is selected from the group consisting of EndoF2, EndoF3, and EndoS, more preferably selected from the group consisting of EndoF3 and EndoS. Most preferably, the endoglycosidase capable of cleaving a glycan of the complex type is EndoS. Preferably, the other of EndoX and EndoY is an endoglycosidase having a different activity, preferably an endoglycosidase capable of cleaving a glycan of the high-mannose type.

It is especially preferred that the fusion enzyme according to the invention contains two distinct endoglycosidases which differ in endoglycosidase activity, as two distinct endoglycosidase activities can as such be combined in a single enzyme. Thus, EndoX and EndoY preferably each have a distinct endoglycosidase activity selected from the capacity of hydrolysing high-mannose glycans, the capacity of hydrolysing complex glycans and the capacity of hydrolysing hybrid glycans, more preferably selected from the capacity of hydrolysing high-mannose glycans and the capacity of hydrolysing complex glycans. Preferably, one of EndoX and EndoY is an endoglycosidase that capable of hydrolysing high-mannose glycans, and the other endoglycosidase is capable of hydrolysing complex glycans. Preferably, the endoglycosidase that is capable of hydrolysing high-mannose glycans is also capable of hydrolysing hybrid glycans. Preferably, the endoglycosidase that is capable of hydrolysing complex glycans is capable of hydrolysing biantennary and/or triantennary complex glycans, most preferably all complex glycans.

For example, when EndoX is EndoS and EndoY is EndoH, the resulting fusion enzyme exhibits both EndoS and EndoH activity, and is capable of trimming complex glycans on glycoproteins (such as antibodies) at the core GlcNAc unit, leaving only the core GlcNAc residue on the glycoprotein (EndoS activity) as well as well as trimming (splitting off) high-mannose glycans (EndoH activity). Surprisingly, both activities of the fusion enzyme function smoothly at a pH around 7-8, while monomeric EndoH requires a pH in the range of 5-6, or even a pH of 6 to operate optimally. In one embodiment, EndoX and EndoY are two distinct endoglycosidases that differ in optimal pH of at least 1 pH units, preferably at least 1.5 pH unit, most preferably at least 2 pH units. The skilled person is aware of the pH optimum that belongs to specific endoglycosidases. Such fusion enzymes may be active at a specific pH, which is not the optimal pH of at least one of EndoX and EndoY.

In a preferred embodiment, one of EndoX and EndoY is selected from EndoF2, EndoF3 or EndoS, and the other of EndoX and EndoY is selected from EndoD, EndoH, EndoE, EfEndo18A, EndoT or EndoF1. Preferably, EndoX is selected from EndoF2, EndoF3 or EndoS, and EndoY is selected from EndoD, EndoH, EndoE, EfEndo18A, EndoT or EndoF1. A such, the fusion enzyme is capable of hydrolysing complex glycans (EndoF2, EndoF3 and EndoS activity) as well as hydrolysing high-mannose glycans (EndoD, EndoF1, EndoH, EndoE, EfEndo18A, EndoT or EndoF1 activity). In one embodiment, EndoX is EndoS, and EndoY is preferably EndoD, EndoF1, EndoH, EndoE, EfEndo18A, EndoT or EndoF1, more preferably EndoY is EndoF1, EndoH or EfEndo18A, most preferably EndoY is EndoH. Most preferably, EndoX is EndoS and EndoY is EndoH. Alternatively, EndoX is EndoF2 and EndoY is preferably EndoD, EndoH, EndoE, EfEndo18A, EndoT or EndoF1, more preferable EndoY is EndoF1, EndoH or EfEndo18A, most preferably EndoY is EndoF1. Most preferably, EndoX is EndoF2 and EndoY is EndoF1. Alternatively, EndoX is EndoF3 and EndoY is preferably EndoD, EndoH, EndoE, EfEndo18A, EndoT or EndoF1, more preferably EndoY is EndoF1, EndoH or EfEndo18A, most preferably EndoY is EndoH. Most preferably, EndoX is EndoF3 and EndoY is EndoH.

In one embodiment, Endo X and EndoY are both individually selected from EndoF1, EndoF2, EndoF3, EfEndo18A, EndoS and EndoH. Preferably, EndoX is selected from EndoF2, EndoF3 and EndoS and EndoY is selected from EndoF1, EfEndo18A and EndoH.

In one embodiment, one of EndoX and EndoY is EndoS or EndoF3, and the other one of EndoX and EndoY is EndoF1 or EndoH. Preferably, EndoX is EndoS or EndoF3, and EndoY is EndoF1 or EndoH.

In a preferred embodiment, the fusion enzyme according to the invention is selected from the group consisting of enzymes of structure (1), wherein EndoX=EndoF3 and EndoY=EndoH; EndoX=EndoF3 and EndoY=EndoE; EndoX=EndoF3 and EndoY=EfEndo18A; EndoX=EndoF3 and EndoY=EndoT; EndoX=EndoF3 and EndoY=EndoF1; EndoX=EndoS and EndoY=EndoH; EndoX=EndoS and EndoY=EndoE; EndoX=EndoS and EndoY=EfEndo18A; EndoX=EndoS and EndoY=EndoT; EndoX=EndoS and EndoY=EndoF1; EndoX=EndoF2 and EndoY=EndoH; EndoX=EndoF2 and EndoY=EndoE; EndoX=EndoF2 and EndoY=EfEndo18A; EndoX=EndoF2 and EndoY=EndoT; and EndoX=EndoF2 and EndoY=EndoF1. More preferably, the fusion enzymes according to the invention is selected from the group consisting of enzymes of structure (1), wherein EndoX=EndoF3 and EndoY=EndoH;

EndoX=EndoF3 and EndoY=EfEndo18A; EndoX=EndoF3 and EndoY=EndoF1; EndoX=EndoS and EndoY=EndoH; EndoX=EndoS and EndoY=EfEndo18A; EndoX=EndoS and EndoY=EndoF1; EndoX=EndoF2 and EndoY=EndoH; EndoX=EndoF2 and EndoY=EfEndo18A; and EndoX=EndoF2 and EndoY=EndoF1. Even more preferably, the fusion enzymes according to the invention is selected from the group consisting of enzymes of structure (1), wherein EndoX=EndoF3 and EndoY=EndoH; EndoX=EndoS and EndoY=EndoH; EndoX=EndoS and EndoY=EfEndo18A; EndoX=EndoS and EndoY=EndoF1; and EndoX=EndoF2 and EndoY=EndoF1. Most preferably, the fusion enzymes according to the invention is an enzyme of structure (1), wherein EndoX=EndoS and EndoY=EndoH.

Linker

In the enzyme according to the invention, EndoX and EndoY are preferably linked by a linker. In case a linker is present, p=1. In case no linker is present, p=0. Preferably, p=1. Linkers for fusion enzymes are known in the art, and any suitable linker may be used, including flexible and rigid linkers. Further guidance can be found in Chen et al., *Adv. Drug Deliv. Rev.* 2013, 65, 1357-1369 and *Fusion Protein Technologies for Biopharmaceuticals: Application and Challenges*, Chapter 4: *Fusion Protein Linkers: Effects on Production, Bioactivity, and Pharmacokinetics*, 2013, John Wiley & Sons, Inc, both of which are incorporated herein in their entirety. Preferably, said linker is a flexible linker allowing the adjacent protein to move relative freely.

In one embodiment, the linker, preferably the flexible linker, is composed of amino residues and has a length of 1 to 100 amino acid residues, preferably 3 to 59, 10 to 45 or 15 to 40 amino acid residues, such as 15, 16, 17, 18, 19, 20, 21, 22, 23, 24, 25, 26, 27, 28, 29, 30, 31, 32, 33, 34, 35, 36, 37, 38, 39 or 40 amino acid residues.

In one embodiment, the linker, preferably the flexible linker, is composed of amino residues like glycine, serine, histidine and/or alanine and has a length of 3 to 59 amino acid residues, preferably 10 to 45 or 15 to 40 amino acid residues, such as 15, 16, 17, 18, 19, 20, 21, 22, 23, 24, 25, 26, 27, 28, 29, 30, 31, 32, 33, 34, 35, 36, 37, 38, 39 or 40 amino acid residues.

The linker preferably comprises one or more flexible domains, that provide flexibility to the linker. Preferably, one or two, most preferably two of such flexible domains are comprised in the linker. Such flexible domains are known in the art and are typically composed of glycine, serine and/or threonine. In one embodiment, the linker comprises at least one glycine, serine and/or threonine residue. Preferably, at least 40% of the amino acids of the linker are selected from glycine, serine and threonine, more preferably 50-90%, most preferably 70-85% of the amino acids of the linker are selected from glycine, serine and threonine. In one embodiment, the linker does not comprise threonine and the above ranges apply to glycine and serine.

Specific suitable flexible domains include GS-domains (such as $(G4S)_n$, wherein n is an integer in the range 1-10, preferably 1-6, most preferably 2-4), poly-G (such as $G_m$, wherein m is an integer in the range 1-30, preferably 3-20, most preferably 5-10), GSAGSAAGSGEF, EGKSSGSGS-ESKST, PAS linkers (Pro, Ala, Ser based linkers; see Schlapschy et al., *Protein Eng Des Sel.* 2013, 26, 489-501, incorporated by reference) and extended recombinant polypeptide (XTEN) linkers (see Podust et al., *Protein Eng Des Sel.* 2013, 26, 743-753, incorporated by reference). GS-domains, consisting of stretches of glycine and serine residues, are most preferred. So, in one embodiment, the linker comprises one or more $(G4S)_n$ domains, preferably one or two, most preferably two domains.

Alternatively or additionally, the linker may comprise one or more rigid domains, such as □-helix forming domains, such as $(EAAAK)_o$ or $A(EAAAK)_oA$ (wherein o is an integer in the range 1-10, preferably 2-5, most preferably 3 or 4), and proline-rich domains, such as $(XP)_q$ (wherein X is any amino acid, preferably selected from alanine, lysine and glutamine, and q is an integer in the range 2-25, preferably 5-17).

Optionally, the linker comprises a tag for ease of purification and/or detection as known in the art, such as an Fc-tag, FLAG-tag, poly(His)-tag, $(RP)_6R$-tag, HA-tag and Myc-tag. Such a tag may also be present elsewhere in the linker according to the invention. Thus, in one embodiment, the fusion enzyme according to the invention comprises a tag for ease of purification and/or detection, such as an Fc-tag, FLAG-tag, poly(His)-tag, $(RP)_6R$-tag, HA-tag and Myc-tag, most preferably a poly(His)-tag. In one embodiment, the fusion enzyme according to the invention comprises a linker, i.e. p=1, and the linker comprises a tag for ease of purification and/or detection, such as an Fc-tag, FLAG-tag, poly(His)-tag, $(RP)_6R$-tag, HA-tag and Myc-tag, most preferably a poly(His)-tag. The tag may be located at the C-terminus of the linker, at the N-terminus of the linker or may be embedded in the linker with further amino acid(s) at either side of the tag. The latter conformation is preferred, especially when flexible domains are located at either side of the tag, as it brings optimal accessibility of the tag for binding to an affinity matrix.

In one embodiment, the linker has the structure $(G4S)_{n1}(H)_r(EF)_s(G4S)_{n2}$, wherein n1 and n2 individually are integers in the range 1-10, preferably 1-6, even more preferably 2-4, most preferably 3, and r is an integer in the range of 2-10, preferably 4-8, most preferably 6, and s=0 or 1. In one embodiment, the linker has the structure $(G4S)_3(H)_6(G4S)_3$, i.e. wherein n1=3, n2=3, r=6 and s=0 (amino acids 950 to 985 of SEQ ID No. 2). In one embodiment, the linker has the structure $(G4S)_3(H)_6EF(G4S)_3$, i.e. wherein n1=3, n2=3, r=6 and s=1 (amino acids 950 to 987 of SEQ ID No. 1).

In a preferred embodiment, the linker has at least 80%, preferably at least 90%, more preferably at least 95% sequence identity with SEQ ID No. 11 or 12, most preferably the linker has 100 sequence identity with SEQ ID No. 11 or SEQ ID No. 12. In one embodiment, the linker has SEQ ID No. 11. In one embodiment, the linker has SEQ ID No. 12.

```
SEQ ID No. 11:
GGGGSGGGGSGGGGSHHHHHHEFGGGGSGGGGSGGGGS

SEQ ID No. 12:
GGGGSGGGGSGGGGSHHHHHHGGGGSGGGGSGGGGS
```

The fusion enzyme according to the invention can be prepared by routine techniques known in the art, such as introducing an expression vector (e.g. plasmid) comprising the enzyme coding sequence into a host cell (e.g. *E. coli*) for expression, from which the enzyme can be isolated. Alternatively, the enzyme is produced by transient expression in CHO. A possible approach for the preparation and purification of the fusion enzyme according to the invention is given in examples 1-4 and 16-24, and its functioning is demonstrated in examples 5, 6, 8, 13-15 and 25-37, wherein various glycoproteins, including trastuzumab and high-mannose trastuzumab, are efficiently trimmed in a single step.

Preferred Fusion Enzyme

In an especially preferred embodiment, the invention concerns a fusion enzyme comprising the two endoglycosidases EndoS and EndoH. In a particular example the two endoglycosidases EndoS and EndoH are connected via a linker, preferably a -(Gly$_4$Ser)$_3$-(His)$_6$-(Gly$_4$Ser)$_3$- linker. The fusion enzyme according to the invention as also referred to as EndoSH. In one embodiment, the enzyme according to the invention has at least 50% sequence identity with SEQ ID NO: 1, preferably at least 70%, more preferably at least 80% sequence identity with SEQ ID NO: 1, such as at least 81%, 82%, 83%, 84%, 85%, 86%, 87%, 88%, 89%, 90%, 91%, 92%, 93%, 94%, 95%, 96%, 97%, 98% or 99% sequence identity with SEQ ID NO: 1. Preferably, the enzyme of the invention, having the above indicated sequence identity to SEQ ID NO: 1, has EndoS and EndoH activity. Most preferably, the enzyme according to the invention has 100% sequence identity with SEQ ID NO: 1. In one embodiment, the enzyme according to the invention has at least 50% sequence identity with SEQ ID NO: 2, preferably at least 70%, more preferably at least 80% sequence identity with SEQ ID NO: 2, such as at least 81%, 82%, 83%, 84%, 85%, 86%, 87%, 88%, 89%, 90%, 91%, 92%, 93%, 94%, 95%, 96%, 97%, 98% or 99% sequence identity with SEQ ID NO: 2. Preferably, the enzyme of the invention, having the above indicated sequence identity to SEQ ID NO: 2, has EndoS and EndoH activity. Most preferably, the enzyme according to the invention has 100% sequence identity with SEQ ID NO: 2.

Also encompassed are fusion enzymes of EndoS and EndoH, wherein the linker is replaced by another suitable linker known in the art, wherein said linker may be rigid or flexible. Preferably, said linker is a flexible linker allowing the adjacent protein domains to move relative freely to one another. Preferably, said flexible linker is composed of amino residues like glycine, serine, histidine and/or alanine and has a length of 3 to 59 amino acid residues, preferably 10 to 45 or 15 to 40 amino acid residues, such as 15, 16, 17, 18, 19, 20, 21, 22, 23, 24, 25, 26, 27, 28, 29, 30, 31, 32, 33, 34, 35, 36, 37, 38, 39 or 40 amino acid residues, or 20 to 38, 25 to 37 or 30 to 36 amino acid residues. Optionally, the fusion enzyme is covalently linked to, or comprises, a tag for ease of purification and or detection as known in the art, such as an Fc-tag, FLAG-tag, poly(His)-tag, HA-tag and Myc-tag. Trimming of glycoproteins is known in the art, from e.g. Yamamoto, *Biotechnol. Lett.* 2013, 35, 1733, WO 2007/133855 or WO 2014/065661, which are incorporated herein in their entirety. The enzyme according to this embodiment exhibits both EndoS and EndoH activity, and is capable of trimming glycans on glycoproteins (such as antibodies) at the core GlcNAc unit, leaving only the core GlcNAc residue on the glycoprotein (EndoS activity) as well as well as high-mannose glycans (EndoH activity). Surprisingly, both activities of the fusion enzyme function smoothly at a pH around 7-8, while monomeric EndoH requires a pH of 6 to operate optimally.

Use

A further aspect of the invention concerns the use of the fusion enzyme according to the invention for trimming glycoproteins, preferably for trimming antibodies. Trimming may also be referred to as deglycosylation and is further defined here below, in the context of the process according to the invention. The use according to this aspect may occur in vitro or in vivo.

Process for Trimming of Glycoproteins

The fusion enzyme according to the invention is particularly suited for trimming of glycoproteins. Thus, in a further aspect, the invention concerns a process for the trimming of glycoproteins. The process according to this aspect may occur in vitro or in vivo. Trimming of glycoproteins is known in the art, from e.g. Yamamoto, *Biotechnol. Lett.* 2013, 35, 1733, WO 2007/133855 or WO 2014/065661, which are incorporated herein in their entirety. Glycoproteins, such as antibodies, typically contain different glycoforms, which require different endoglycosidases to remove. The fusion enzymes of the invention are especially suitable to deglycosylate in a single step a glycoprotein having two different glycan chains. Thus, in one embodiment, the glycoprotein that is subjected to the process according to the invention comprises at least two distinct glycans, preferably two distinct glycans. Preferably, the glycoprotein comprises at least one high-mannose glycan and at least one complex glycan, more preferably the glycoprotein comprises at least one high-mannose glycan, at least one hybrid glycan and at least one complex glycan. The complex glycan may be a bi-, tri-, or tetraantennary glycan.

In an especially preferred embodiment, the glycoprotein is an antibody.

The process according to the present aspect may also be referred to as a process for modifying a glycoprotein. The process comprised contacting the glycoprotein with a fusion enzyme according to the invention, to obtain a trimmed glycoprotein. The process may also be referred to as a process for trimming a glycoprotein or deglycosylation of a glycoprotein. Trimming or deglycosylation of a glycoprotein refers to the removal of a glycan from said glycoprotein. The exact structure of the glycan that is removed may vary depending on the exact nature of the endoglycosidases that are present in the fusion enzyme, but the core GlcNAc residue is retained on the glycoprotein at all times. The skilled person will appreciate which fusion enzyme, i.e. which combination of endoglycosidases, is suitable for trimming of which glycosylation pattern of the glycoprotein.

With conventional endoglycosidases, glycoproteins containing a combination of a high-mannose glycan and a complex bi-, tri- or tetraantennary glycan would require two distinct enzymes for trimming, often requiring different buffer conditions and pH ranges. These glycoproteins can now efficiently be trimmed in a single step, without the need to apply buffer exchange to achieve the optimal pH, with the fusion enzyme according to the invention. Thus, in one embodiment, the glycoprotein, preferably the antibody, comprises at least one high-mannose glycan and at least one complex bi-, tri- or tetraantennary glycan, more preferably at least one high-mannose glycan, at least one hybrid and/or complex bi-, tri- or tetraantennary glycan. For example, the fusion enzyme wherein one of EndoX and EndoY is selected from EndoF2, EndoF3 or EndoS, and the other of EndoX and EndoY is selected from EndoH, EndoE, EfEndo18A, EndoT or EndoF1, is suitable for trimming a glycoprotein comprising a complex N-linked complex glycan and a high-mannose glycan, to obtain a trimmed glycoprotein comprising only the optionally fucosylated core N-acetylglucosamine substituent(s).

The skilled person is aware of suitable conditions to perform the trimming of glycoproteins. For example, the process is carried out in a medium and at a temperature that is effective for trimming glycoproteins. Typically, the media and conditions that apply for one of the individual endoglycosidase enzymes are applicable. As the optimal pH of the individual endoglycosidases may differ, the process may in one embodiment be carried out at a pH which is 0.5-3 pH units, preferably 1-2 pH units, different from the optimal pH of one or both, preferably one of EndoX and EndoY. For example, in case one of EndoX and EndoY is EndoH, which has an optimal pH or 5-6, the process may be carried out at pH 7-8. In one embodiment, the trimming performed at a pH in the range of 4-9, preferably in the range of 6-8, most preferably in the range of 7-8. The inventors surprisingly found that the fusion enzyme according to the invention wherein EndoX=EndoS and EndoY=EndoH is fully operational at a pH above 7, whereas the functional pH range for EndoH is 5.0 to 6.0, with the optimum pH at 5.5.

Moreover, the inventors found that the activity of a particular endoglycosidase in a fusion protein can display a higher trimming efficiency compared to the same endoglycosidase as a single enzyme.

The trimming affords trimmed glycoproteins, wherein all glycan moieties present in the original glycoprotein, irrespective of their type and glycoform, are trimmed and only the optionally fucosylated core N-acetylglucosamine substituent(s) remain. Said optionally fucosylated core N-acetylglucosamine substituent is typically bonded via an N-glycosidic bond to the amide nitrogen atom in the side chain of an asparagine amino acid of the glycoprotein, such as N297 when the glycoprotein is an antibody.

The thus obtained trimmed glycoprotein can be used as deemed fit. For example, when the glycoprotein is the product of interest, the trimmed glycoprotein according to the invention is homogeneous with respect to glycosylation patterns. This can be particularly important when the glycoprotein is used as medicament, since the therapeutic efficacy and/or the toxicity may vary for different glycoforms of the glycoprotein. Such unpredictable variations in efficacy and toxicity are eradicated when the process according to the invention is utilized.

Alternatively, the trimmed glycoprotein can be used for further functionalization, such as by introduction of an optionally substituted sugar moiety is known in the art, from e.g. van Geel et. al, Bioconjugate Chem, 2015, 26, 2233, incorporated by reference. The trimmed glycoprotein may be contacted with a compound of the formula S-P, wherein S is an optionally substituted sugar moiety and P is a nucleotide, in the presence of a suitable catalyst, such as a glycosyltransferase or N-acetylglycosyltransferase. The thus obtained modified glycoprotein comprises sugar moiety S connected to the non-reducing end of the trimmed glycan. Using a substituted sugar moiety S, the possibilities for further modification or functionalization of the glycoprotein via said substituent are endless. Such a sequence of reaction steps finds particular use in the preparation of bioconjugates, such as antibody-drug conjugates. Such steps are known to the skilled person, e.g. from WO 2014/065661, incorporated by reference herein.

EXAMPLES

RP-HPLC analysis of reduced monoclonal antibodies: Prior to RP-HPLC analysis samples were reduced by incubating a solution of 10 μg (modified) IgG for 15 minutes at 37° C. with 10 mM DTT and 100 mM Tris pH 8.0 in a total volume of 50 μL. A solution of 49% ACN, 49% MQ and 2% formic acid (50 μL) was added to the reduced sample. Reverse phase HPLC was performed on a Agilent 1100 HPLC using a ZORBAX Poroshell 300SB-C8 1×75 mm, 5 μm (Agilent Technologies) column run at 1 ml/min at 70° C. using a 16.9 minute linear gradient from 25 to 50% buffer B (with buffer A=90% MQ, 10% ACN, 0.1% TFA and buffer B=90% ACN, 10% MQ, 0.1% TFA).

Mass spectral analysis of monoclonal antibodies: Prior to mass spectral analysis, IgGs were either treated with DTT, which allows analysis of both light and heavy chain, or treated with Fabricator™ (commercially available from Genovis, Lund, Sweden), which allows analysis of the Fc/2 fragment. For analysis of both light and heavy chain, a solution of 20 μg (modified) IgG was incubated for 5 minutes at 37° C. with 100 mM DTT in a total volume of 4 μL. If present, azide-functionalities are reduced to amines under these conditions. For analysis of the Fc/2 fragment, a solution of 20 μg (modified) IgG was incubated for 1 hour at 37° C. with Fabricator™ (1.25 U/μL) in phosphate-buffered saline (PBS) pH 6.6 in a total volume of 10 μL. After reduction or Fabricator-digestion the samples were washed trice with milliQ using an Amicon Ultra-0.5, Ultracel-10 Membrane (Millipore) resulting in a final sample volume of approximately 40 μL. Next, the samples were analyzed by electrospray ionization time-of-flight (ESI-TOF) on a JEOL AccuTOF. Deconvoluted spectra were obtained using Magtran software.

Example 1: Cloning of Fusion Protein EndoSH into (pET22B) Expression Vector

A pET22B-vector containing an EndoS-$(G_4S)_3$-$(His)_6$-EF-$(G_4S)_3$-EndoH (EndoSH) coding sequence (EndoSH being identified by SEQ ID NO: 1) between EcoRI-HindIII sites was obtained from Genscript. The DNA sequence for the EndoSH fusion protein consists of the encoding residues 48-995 of EndoS fused via an N-terminal linked glycine-serine (GS) linker to the coding residues 41-313 of EndoH. The glycine-serine (GS) linker comprises a -$(G_4S)_3$-$(His)_6$-EF-$(G_4S)_3$- format, allowing spacing of the two enzymes and at the same time introducing a IMAC-purification tag.

Example 2: *E. coli* Expression of Fusion Protein EndoSH

Expression of the EndoSH fusion protein (identified by SEQ ID NO: 1) starts with the transformation of the plasmid (pET22b-EndoSH) into BL21 cells. Next step is the inoculation of 500 mL culture (LB medium+Ampilicin) with BL21 cells. When the OD600 reached 0.7 the cultures were induced with 1 mM IPTG (500 μL of 1M stock solution).

Example 3: Purification of Fusion Protein EndoSH from *E. coli*

After overnight induction at 16° C. the culture were pelleted by centrifugation. The pellet was resuspended in 40 mL PBS and incubated on ice with 5 ml lysozyme (10 mg/mL) for 30 minutes. After half an hour 5 ml 10% Triton-X-100 was added and sonicated (10 minutes) on ice. After the sonification the cell debris was removed by centrifugation (10 minutes 8000×g) followed by filtration through a 0.22 μM-pore diameter filter. Alternatively, lysis of the pellet containing EndoSH can be performed by means of French press. Here the pellet is re-suspended in 10 mL PBS/gram of pellet. The cell suspension is lysed three times under pressure (20000-25000 psi) by French press using Emulsiflex C3, Avestin. After French press the cell debris was removed by centrifugation (20 minutes 10000×g). The soluble extract/fraction was loaded onto a HisTrap HP 5 mL column (GE Healthcare). The column was first washed with buffer A (20 mM Tris buffer, 20 mM imidazole, 500 mM NaCl, pH 7.5). Retained protein was eluted with buffer B (20 mM Tris, 500 mM NaCl, 250 mM imidazole, pH 7.5, 10 mL). Fractions were analyzed by SDS-PAGE on polyacrylamide gels (12%). The fractions that contained purified target protein were combined and the buffer was exchanged against 20 mM Tris pH 7.5 and 150 mM NaCl by dialysis performed overnight at 4° C. The purified protein was concentrated to at least 2 mg/mL using an Amicon Ultra-0.5, Ultracel-10 Membrane (Millipore). The product is stored at −80° C. prior to further use.

Example 4: CHO Expression and Purification of Fusion Protein EndoSH from CHO EndoSH (identified by SEQ ID NO: 2) was transiently expressed in CHO K1 cells by Evitria (Zurich, Switzerland) at 20 mL scale. The supernatant, containing fusion protein EndoSH, was diluted with elution buffer (2 mL, 20 mM Tris, 500 mM NaCl, 500 mM imidazole) and binding buffer (18 mL, 20 mM Tris, 500 mM NaCl, 5 mM imidazole, pH=7.4) to a final imidazole concentration of 10 mM. The mixture was loaded onto a Ni-NTA column (GE Healthcare) and the product was eluted following a standard elution protocol. The collected fractions (5 mL) were analysed on an SDS-PAGE (10%) gel. The faction containing product was partially concentrated (~2 mL) and dialyzed against TBS buffer. Protein concentration, determined by nanodrop analysis, was set at 0.5 mg/mL.

Example 5: Trimming of Trastuzumab by EndoSH

Trastuzumab (obtained from Epirus biopharma (Utrecht, The Netherlands); 14 mg/mL) in 25 mM Tris buffer pH 8, was trimmed using a concentration of either 0.1 or 1 w/w % EndoSH. The reactions, 350 μg trastuzumab (25 μL) and the appropriate amount of EndoSH, were stirred at 37° C. and analyzed by MS analysis over time, 1 to 3 hours. Samples were subjected to Fabricator treatment prior to analysis. Full conversions to the trimmed product, which is trimmed to the core GlcNAc sugar residue, was observed after 1 hour at 37° C. with 0.1 w/w % EndoSH.

Example 6: Trimming of High-Mannose Trastuzumab by Fusion Protein EndoSH

Trastuzumab having high-mannose glycans (obtained via transient expression in CHO K1 cells in the presence of kifunensine performed by Evitria (Zurich, Switzerland)) (14 mg/mL) in 25 mM Tris buffer pH 8, was trimmed using a concentration of either 0.1 or 1 w/w % EndoSH. The reactions, 350 μg high-mannose trastuzumab (25 μL) and the appropriate amount of EndoSH, were stirred at 37° C. and analyzed by MS analysis over time, 1-3 hours. Samples were subjected to Fabricator treatment prior to analysis. Full conversions to the trimmed product, which is trimmed to the core GlcNAc sugar residue, was observed after 3 hours at 37° C. with 1 w/w % EndoSH.

Example 7: Transient Expression and Purification of cAC10 cAC10 was transiently expressed in CHO K1 cells by Evitria (Zurich, Switzerland) at 5 L scale. The supernatant was purified using a XK 26/20 column packed with 50 mL protein A sepharose. In a single run 5 L supernatant was loaded onto the column followed by washing with at least 10 column volumes of 25 mM Tris pH 7.5, 150 mM NaCl. Retained protein was eluted with 0.1 M Glycine pH 2.7. The eluted cAC10 was immediately neutralized with 1.5 M Tris-HCl pH 8.8 and dialyzed against 25 mM Tris pH 8.0. Next the IgG was concentrated to approximately 20 mg/mL using a Vivaspin Turbo 15 ultrafiltration unit (Sartorius) and stored at −80° C. prior to further use.

Example 8: Trimming of cAC10 by EndoSH

Glycan trimming of cAC10 (obtained via transient expression in CHO K1 cells performed by Evitria (Zurich, Switzerland)) was performed with fusion protein EndoSH. Thus, cAC10 (14.5 mg/mL) was incubated with EndoSH (1 w/w %) in 25 mM Tris pH 7.5 with 150 mM NaCl for approximately 16 hours at 37° C. The trimmed IgG was dialyzed against 3×1 L of 25 mM Tris-HCl pH 8.0. Mass spectral analysis of a fabricator-digested sample showed three peaks of the Fc/2-fragment belonging to one major product (observed mass 24105 Da, approximately 80% of total Fc/2 fragment), corresponding to core GlcNAc(Fuc)-substituted cAC10, and two minor products (observed masses of 23959 and 24233 Da, approximately 5 and 15% of total Fc/2 fragment), corresponding to core GlcNAc-substituted cAC10 and core GlcNAc(Fuc)-substituted cAC10 with C-terminal lysine.

Examples 9-12: Preparation of cAC10 Bioconjugate

To demonstrate that the antibodies trimmed by the fusion enzyme according to the invention can be further modified, antibody-drug-conjugate 113 has been prepared from the trimmed antibody of Example 8. Compound 99 was prepared via activation of compound 58 as disclosed in and prepared according to Example 50 of WO 2016/053107 (PCT/NL2015/050697). In the second step the trimmed cAC10 was converted to the azido-modified mAb 13d through the action of His-TnGalNAcT in the presence of 6-N$_3$-GalNAc-UDP (commercially available from GlycoHub) as a substrate. The preparation of the cAC10 bioconjugates is schematically depicted here below:

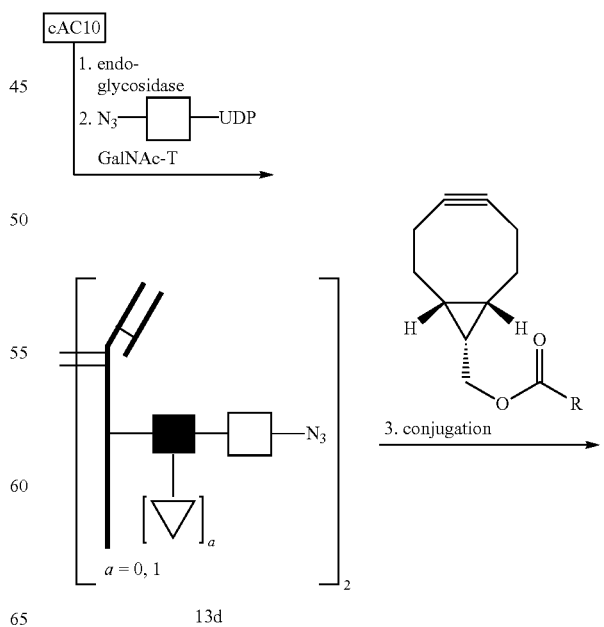

13d

25
-continued
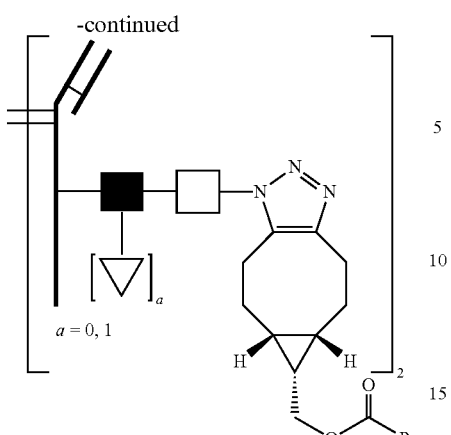
113
26
-continued
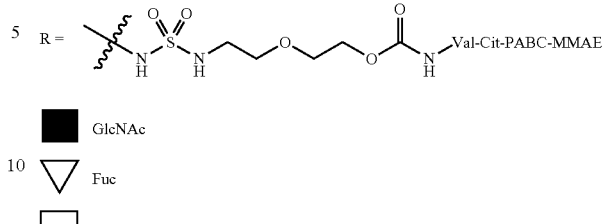
Example 9: Preparation of Compound 100
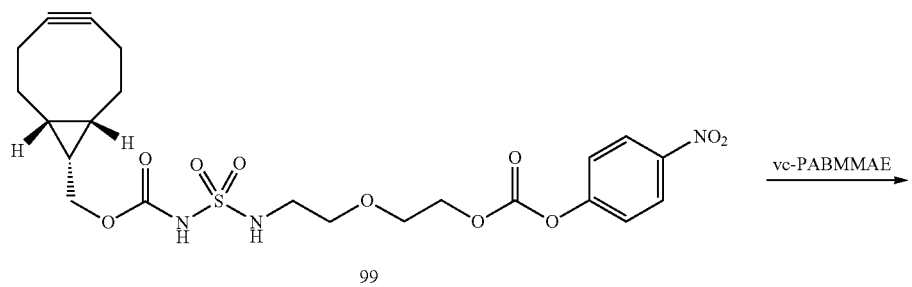
99
vc-PABMMAE →
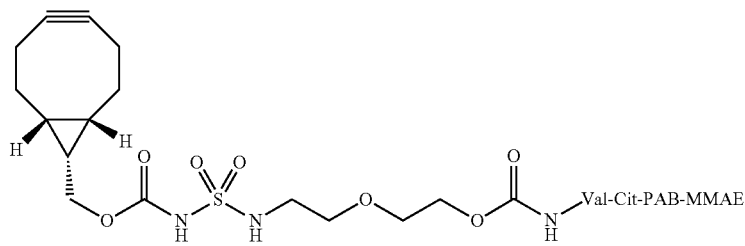
100
Val-Cit-PAB-MMAE =
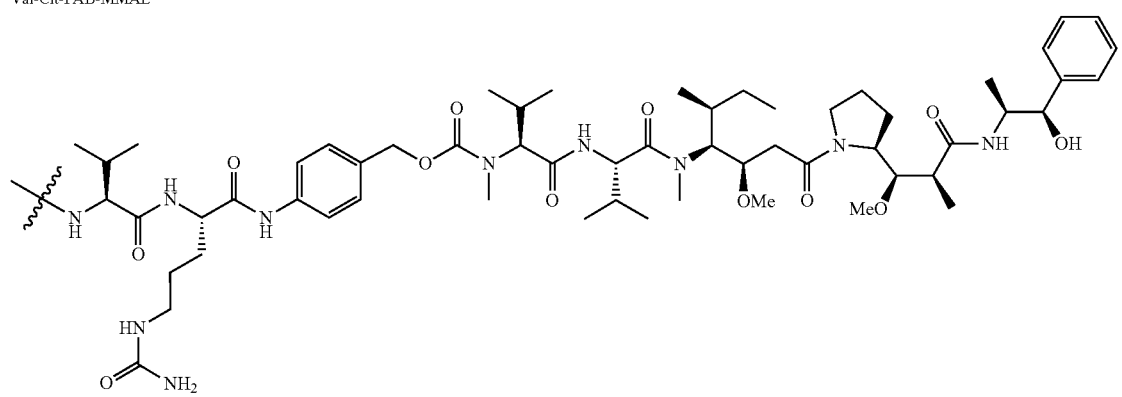

A solution of compound 99 (4.7 mg, 9.0 μmol) in DMF (200 μL) was added to solid Val-Cit-PABC-MMAE (vc-PABC-MMAE, 10 mg, 8.1 μmol) followed by addition of Et3N (3.7 μL, 2.7 mg, 27 μmol). After 23 h, 2'-(ethylene-dioxy)bis(ethylamine) (1.3 μL, 1.3 mg, 8.9 μmol) in DMF was added (13 μL of 10% solution in DMF). The mixture was left for 4 h and purified via reversed phase (C18) HPLC chromatography (30→90% MeCN (1% AcOH) in H$_2$O (1% AcOH). The product was obtained as a colourless film (10.7 mg, 7.1 μmol, 87%) LCMS (ESI$^+$) calculated for C$_{74}$H$_{117}$N$_{12}$O$_{19}$S$^+$ (M+H$^+$) 1509.83 found 1510.59.

Example 10: Transient Expression and Purification of his-TnGalNAcT(33-421)

His-TnGalNAcT(33-421) (identified by SEQ ID NO: 33) was codon optimized and transiently expressed in CHO K1 cells by Evitria (Zurich, Switzerland) at 5 L scale. The supernatant was purified using a XK 16/20 column packed with 25 mL Ni sepharose excel (GE Healthcare). Each run approximately 1.5 L supernatant was loaded onto the column followed by washing with at least 10 column volumes of buffer A (20 mM Tris buffer, 5 mM imidazole, 500 mM NaCl, pH 7.5). Retained protein was eluted with buffer B (20 mM Tris, 500 mM NaCl, 500 mM imidazole, pH 7.5). The buffer of the eluted fractions was exchanged to 25 mM Tris pH 8.0 using a HiPrep H26/10 desalting column (GE Healthcare). The purified protein was concentrated to at least 3 mg/mL using a Vivaspin Turbo 4 ultrafiltration unit (Sartorius) and stored at −80° C. prior to further use.

Example 11: Glycosyltransfer of the 6-N$_3$-GalNAc-UDP to Trimmed cAC10 Under the Action of TnGalNAcT Substrate 6-N$_3$-GalNAc-UDP (11d) is used for the preparation of the modified biomolecule cAC10-(6-N$_3$-GalNAc)$_2$ 13d. Trimmed cAC10 (10 mg/mL), obtained by EndoSH treatment of cAC10 as described above in Example 8, was incubated with the substrate 6-N$_3$-GalNAc-UDP (2.5 mM, commercially available from GlycoHub) and 0.5 mg/mL His-TnGalNAcT(33-421) (5 w/w %) in 10 mM MnCl$_2$ and 25 mM Tris-HCl pH 8.0 at 30° C. After 3 hours the amount of His-TnGalNAcT(33-421) was increased to a final concentration of 1 mg/mL (10 w/w %) and the reaction was incubated overnight at 30° C. Biomolecule 13d was purified from the reaction mixture on a HiTrap MabSelect SuRe 5 ml column (GE Healthcare) using an AKTA purifier-10 (GE Healthcare). The eluted IgG was immediately neutralized with 1.5 M Tris-HCl pH 8.8 and dialyzed against PBS pH 7.4. Next the IgG was concentrated using an Amicon Ultra-0.5, Ultracel-10 Membrane (Millipore) to a concentration of 23.38 mg/mL. Mass spectral analysis of a fabricator-digested sample showed three peaks of the Fc/2-fragment belonging to one major product (observed mass 24333 Da, approximately 80% of total Fc/2 fragment), corresponding to core 6-N$_3$-GalNAc-GlcNAc(Fuc)-substituted cAC10, and two minor products (observed masses of 24187 and 24461 Da, approximately 5 and 15% of total Fc/2 fragment), corresponding to core 6-N$_3$-GalNAc-GlcNAc-substituted cAC10 and core 6-N$_3$-GalNAc-GlcNAc(Fuc)-substituted cAC10 with C-terminal lysine.

Example 12: Conjugation of 13d with 100 to Obtain Conjugate 113

A bioconjugate according to the invention was prepared by conjugation of compound 100 as linker-conjugate to modified biomolecule 13d as biomolecule. To a solution of cAC10(azide)$_2$ (13d) (287 μL, 6.7 mg, 23.38 mg/ml in PBS pH 7.4) was added PBS pH 7.4 (133 μL) and compound 100 (27 μL, 10 mM solution in DMF). The reaction was incubated at rt overnight followed by purification on a Superdex200 10/300 GL (GE Healthcare) on an AKTA Purifier-10 (GE Healthcare). Mass spectral analysis of the fabricator-digested sample showed one major product (observed mass 25844 Da, approximately 80% of total Fc/2 fragment), corresponding to the conjugated Fc/2 fragment. RP-HPLC analysis of the reduced sample indicated an average DAR of 1.88.

Figure 3:
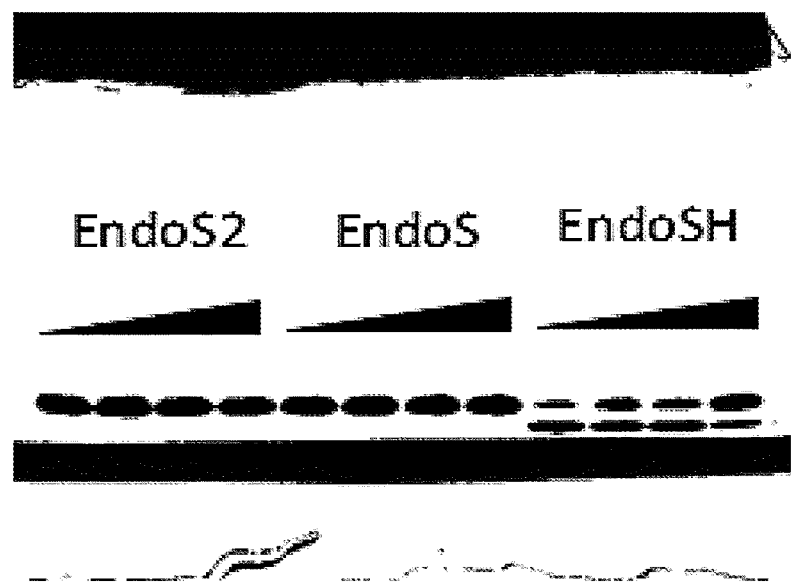
FIG. 3 shows the results of trimming of high-mannose glycoprotein RNAseB in Tris pH 7.5 by endoglycosidases EndoS, EndoS2 and EndoSH. Concentration series: 0.025, 0.125, 0.125 (duplo), and 0.25 mg/mL. Upper band=intact RNaseB, lower band=trimmed RNaseB.

Example 13: Comparison of Trimming Efficiency of EndoS, EndoS2 and EndoSH on RNaseB at Different Concentrations First, enzyme dilutions of the three enzymes (EndoS and EndoS2 from Genovis, Lund, Sweden; EndoSH as obtained in Example 3) are prepared to obtain stocks solutions with 0.25 mg/mL (dil 1), 0.125 mg/mL (dil 2) and 0.025 mg/mL (dil 3). Next, 12 vials were loaded with 2.5 μL RNase B (5 mg/mL) followed by 0.5 μL of dilution 1-3 (dil 2 in duplo) for each enzyme. The reactions were incubated for 30 minutes followed by addition of 36 μL water. Of these diluted solutions 6 μL was added to 6 μL sample buffer for SDS-page analysis. Twelve samples were loaded on SDS-page gel (4 per enzyme) and run for 70 min, stained in colloidal coomassie overnight, and finally de-stained in water (see FIG. 3 for resulting gel). Conversion percentages were calculated based on scanning of SDS-PAGE gel with regular flatbed scanner and quantification with a software tool (CLIQS v1.1).

TABLE 1

Percentages trimming (conversion) of RNaseB upon treatment with different endoglycosidases at different enzyme concentrations.

| [E] mg/mL | EndoS2 | EndoS | EndoSH |
|---|---|---|---|
| 0.25 | 0 | 0 | 45 |
| 0.125 | 0 | 0 | 53 |
| 0.125 | 0 | 0 | 50 |
| 0.025 | 0 | 0 | 66 |

Figure 4:
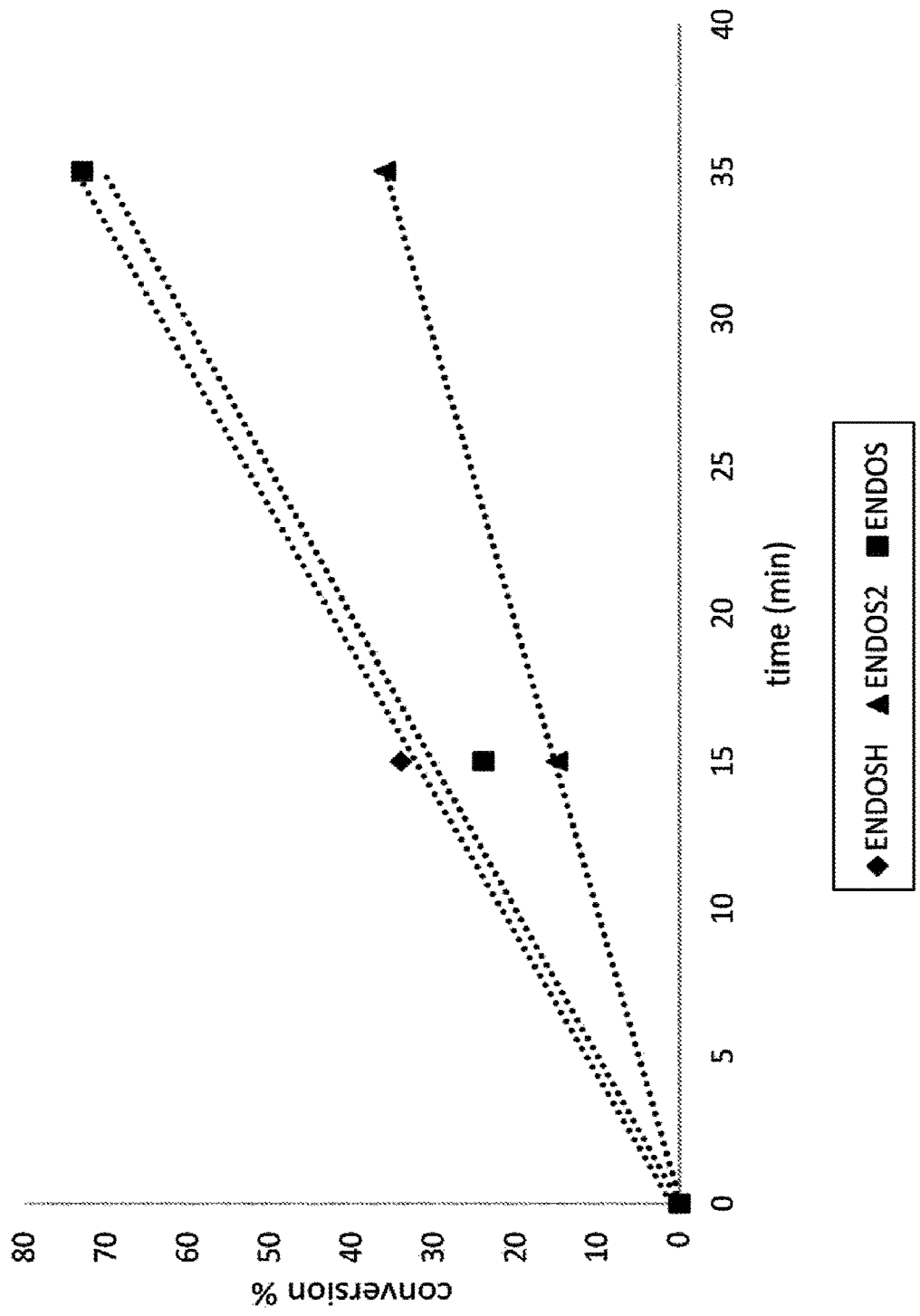
FIG. 4 shows a plot of percentage conversion (trimming) of cAC10 at pH 6 by endoglycosidases EndoS, EndoS2 and EndoSH as obtained in Example 14. Trendline for EndoSH: $y=2.0784x+1.027$ ($R^2=0.9982$). Trendline for EndoS: $y=2.0103x$ ($R^2=0.9838$). Trendline for EndoS2: $y=1.0297x-0.1622$ ($R^2=0.9998$).

Example 14: Comparison of Trimming Efficiency of EndoS, EndoS2 and EndoSH on cAC10 cAC10 (4 mg, 20 mg/mL in Tris pH 8.0) was treated with Fabricator™ (Genovis, Lund, Sweden, 4 μL, 66 U/μL) for 1 h at 37° C. Next, cleaved cAC10 was buffer exchanged to Tris pH 6.0 (50 mM, 3×) using an Amicon Ultra-0.5, Ultracel-10 Membrane (Merck Millipore) to a concentration of 20 mg/mL. Subsequent, three reactions containing each cAC10 (8.3 mg/mL) and an endoglycosidase (EndoS and EndoS2 from Genovis, Lund, Sweden; EndoSH as obtained in Example 3) at 0.83 μg/mL in Tris pH 6.0 50 mM were started. Samples of 2 μL were taken after 15 min and 35 min, diluted with 70 μL MiliQ and directly analysed by electrospray ionization time-of-flight (ESI-TOF) on a JEOL AccuTOF. Conversion percentages were calculated based the intensities of the trimmed and untrimmed mass peaks (see FIG. 4 for the plot).

TABLE 2

Percentages trimming (conversion) of cAC10 upon treatment with different endoglycosidases at different timepoints.

| Time | EndoS2 | EndoS | EndoSH |
|---|---|---|---|
| 0 min | 0 | 0 | 0 |
| 15 min | 15 | 24 | 34 |
| 35 min | 36 | 73 | 73 |

Figure 5:
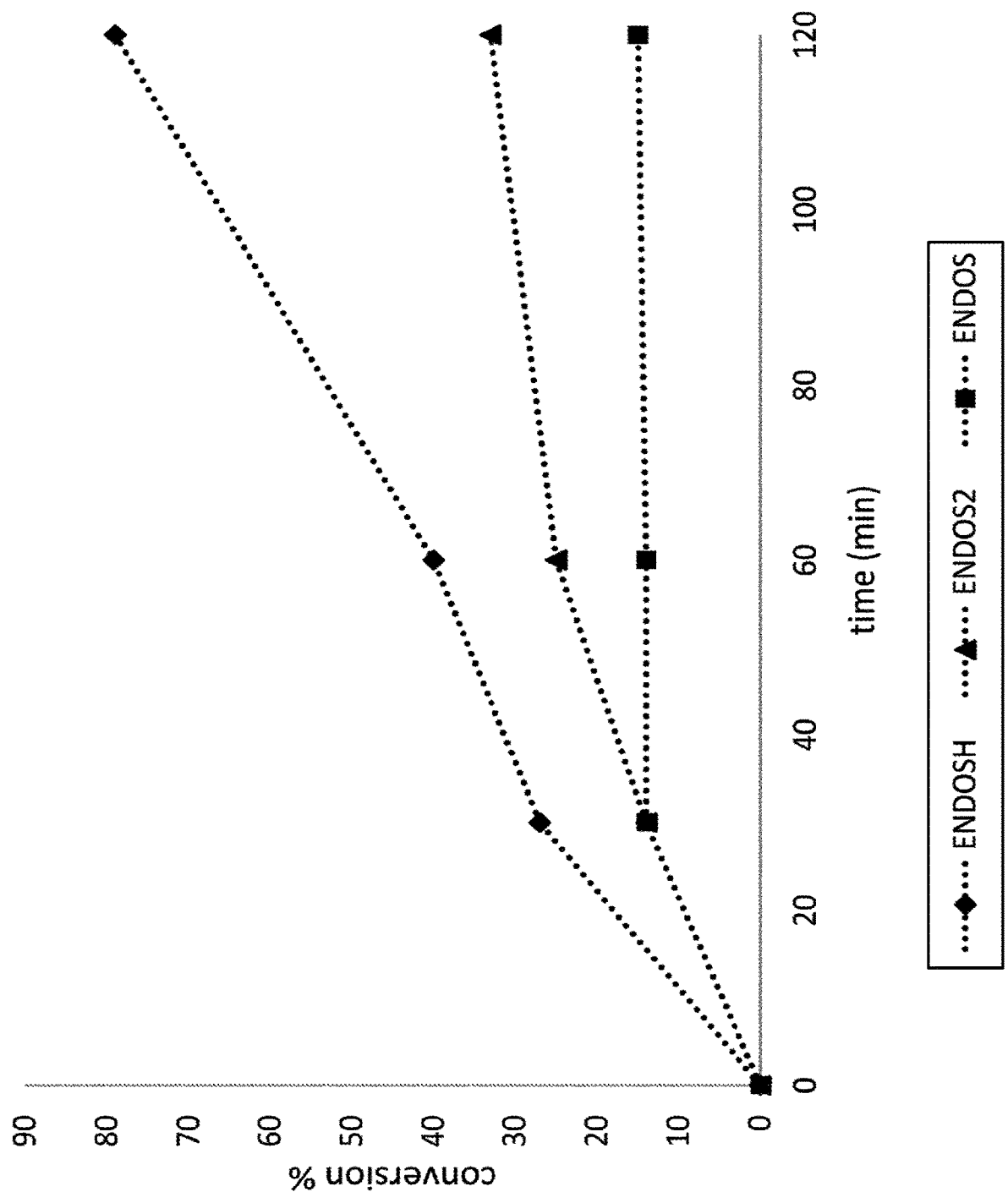
FIG. 5 shows a plot of percentage conversion (trimming) high-mannose trastuzumab at pH 6 by endoglycosidases EndoS, EndoS2 and EndoSH as obtained in Example 15.

Example 15: Comparison of Trimming Efficiency of EndoS, EndoS2 and EndoSH on High-Mannose Trastuzumab High-mannose trastuzumab (1.3 mg, 8.8 mg/mL in Tris pH 8.0), obtained through expression of trastuzumab in the presence of kifunensine, was treated with Fabricator™ (3 µL, 66 U/µL) for 1 h at 37° C. Next, cleaved high-mannose trastuzumab was buffer exchanged to Tris pH 6.0 (50 mM, 3×) using an Amicon Ultra-0.5, Ultracel-10 Membrane (Merck Millipore) to a concentration of 20 mg/mL. Three reactions were started containing each high-mannose-trastuzumab (10 mg/mL) and an endoglycosidase (EndoS and EndoS2 from Genovis, Lund, Sweden; EndoSH as obtained in Example 3) at 4.4 µg/mL in Tris pH 6.0 50 mM. Samples of 2 µL were taken after 30, 60 and 120 min, diluted with 70 µL MiliQ and directly analysed by electrospray ionization time-of-flight (ESI-TOF) on a JEOL AccuTOF. Conversion percentages were calculated based the intensities of the trimmed and untrimmed mass peaks (see FIG. 5 for the plot).

TABLE 3

Percentages trimming (conversion) of high-mannose trastuzumab upon treatment with different endoglycosidases at different timepoints.

| Time | EndoS2 | EndoS | EndoSH |
|---|---|---|---|
| 0 min | 0 | 0 | 0 |
| 30 min | 14 | 14 | 27 |
| 60 min | 25 | 14 | 40 |
| 120 min | 33 | 15 | 79 |

These experiments show that EndoSH It is more efficient in trimming high-mannose trastuzumab and cAC10 then EdnoS2, and EndoSH allows from trimming of other glycoproteins (e.g. RNAseB) which is not possible with EndoS2 since the activity is restricted to the N297 site. Thus, if an antibody, e.g. a monoclonal antibody, has some undesirable high-mannose on a different N-glycosylation site, EndoSH would be able to trim this whereas EndoS2 cannot.

Example 16: Cloning of Fusion Proteins into Expression Vector

A pET22B-vector containing either EndoF3-(G4S)$_3$-(His)$_6$-EF-(G4S)$_3$-EfEndo18A (EndoF3-EfEndo18A), coding sequence EndoF3-EfEndo18A being identified by SEQ ID NO: 13; or EndoF2-(G$_4$S)$_3$-His6-EF-(G$_4$S)$_3$-EfEndo18A (EndoF2-EfEndo18A), coding sequence EndoF2-EfEndo18A being identified by SEQ ID NO: 14; or EndoS-(G$_4$S)$_3$-His6-EF-(G$_4$S)$_3$-EfEndo18A (EndoS-EfEndo18A), coding sequence EndoS-EfEndo18A being identified by SEQ ID NO: 15; or EndoF3-(G$_4$S)$_3$-His6-EF-(G$_4$S)$_3$-EndoF1 (EndoF3-EndoF1), coding sequence EndoF3-EndoF1 being identified by SEQ ID NO: 16; or EndoF2-(G$_4$S)$_3$-His6-EF-(G$_4$S)$_3$-EndoF1 (EndoF2-EndoF1), coding sequence EndoF2-EndoF1 being identified by SEQ ID NO: 17; or EndoS-(G$_4$S)$_3$-His6-EF-(G$_4$S)$_3$-EndoF1 (EndoS-EndoF1), coding sequence EndoS-EndoF1 being identified by SEQ ID NO: 18; or EndoF3-(G$_4$S)$_3$-His6-EF-(G$_4$S)$_3$-EndoH (EndoF3-EndoH), coding sequence EndoF3-EndoH being identified by SEQ ID NO: 19; or EndoF2-(G$_4$S)$_3$-His6-EF-(G$_4$S)$_3$-EndoH (EndoF2-EndoH), coding sequence EndoF2-EndoH being identified by SEQ ID NO: 20, between the NdeI-HindIII sites was obtained from Genscript, Piscataway, USA.

The DNA sequence for the EndoF3-EfEndo18A fusion protein consists of the encoding residues 40-329 of EndoF3 fused via an N-terminal linked glycine-serine (GS) linker to the coding residues 42-314 of EfEndo18A. The DNA sequence is identified by SEQ ID NO: 22. The glycine-serine (GS) linker comprises a -(G$_4$S)$_3$-(His)$_6$-EF-(G$_4$S)$_3$- format, allowing spacing of the two enzymes and at the same time introducing a IMAC-purification tag.

The DNA sequence for the EndoF2-EfEndo18A fusion protein consists of the encoding residues 46-335 of EndoF2 fused via an N-terminal linked glycine-serine (GS) linker to coding residues 42-314 of EfEndo18A. The DNA sequence is identified by SEQ ID NO: 23. The glycine-serine (GS) linker comprises a -(G$_4$S)$_3$-(His)$_6$-EF-(G$_4$S)$_3$- format, allowing spacing of the two enzymes and at the same time introducing a IMAC-purification tag.

The DNA sequence for the EndoS-EfEndo18A fusion protein consists of the encoding residues 48-995 of EndoS fused via an N-terminal linked glycine-serine (GS) linker to the coding residues 42-314 of EfEndo18A. The DNA sequence is identified by SEQ ID NO: 24. The glycine-serine (GS) linker comprises a -(G$_4$S)$_3$-(His)$_6$-EF-(G$_4$S)$_3$- format, allowing spacing of the two enzymes and at the same time introducing a IMAC-purification tag.

The DNA sequence for the EndoF3-EndoF1 fusion protein consists of the encoding residues 40-329 of EndoF3 fused via an N-terminal linked glycine-serine (GS) linker to the coding residues 51-339 of EndoF1. The DNA sequence is identified by SEQ ID NO: 25. The glycine-serine (GS) linker comprises a -(G$_4$S)$_3$-(His)$_6$-EF-(G$_4$S)$_3$- format, allowing spacing of the two enzymes and at the same time introducing a IMAC-purification tag.

The DNA sequence for the EndoF2-EndoF1 fusion protein consists of the encoding residues 46-335 of EndoF2 fused via an N-terminal linked glycine-serine (GS) linker to the coding residues 51-339 of EndoF1. The DNA sequence is identified by SEQ ID NO: 26. The glycine-serine (GS) linker comprises a -(G$_4$S)$_3$-(His)$_6$-EF-(G$_4$S)$_3$- format, allowing spacing of the two enzymes and at the same time introducing a IMAC-purification tag.

The DNA sequence for the EndoS-EndoF1 fusion protein consists of the encoding residues 48-995 of EndoS fused via an N-terminal linked glycine-serine (GS) linker to the coding residues 51-339 of EndoF1. The DNA sequence is identified by SEQ ID NO: 27. The glycine-serine (GS) linker comprises a -(G$_4$S)$_3$-(His)$_6$-EF-(G$_4$S)$_3$- format, allowing spacing of the two enzymes and at the same time introducing a IMAC-purification tag.

The DNA sequence for the EndoF3-EndoH fusion protein consists of the encoding residues 40-329 of EndoF3 fused via an N-terminal linked glycine-serine (GS) linker to the coding residues 41-313 of EndoH. The DNA sequence is identified by SEQ ID NO: 28. The glycine-serine (GS) linker comprises a -(G$_4$S)$_3$-(His)$_6$-EF-(G$_4$S)$_3$- format, allowing spacing of the two enzymes and at the same time introducing a IMAC-purification tag.

The DNA sequence for the EndoF2-EndoH fusion protein consists of the encoding residues 46-335 of EndoF2 fused via an N-terminal linked glycine-serine (GS) linker to the coding residues 41-313 of EndoH. The DNA sequence is identified by SEQ ID NO: 29. The glycine-serine (GS) linker comprises a -(G$_4$S)$_3$-(His)$_6$-EF-(G$_4$S)$_3$- format, allowing spacing of the two enzymes and at the same time introducing a IMAC-purification tag.

The DNA sequence for the EndoS-EndoH fusion protein consists of the encoding residues 48-995 of EndoS fused via an N-terminal linked glycine-serine (GS) linker to the coding residues 41-313 of EndoH. The DNA sequence is identified by SEQ ID NO: 30. The glycine-serine (GS) linker comprises a -(G$_4$S)$_3$-(His)$_6$-EF-(G$_4$S)$_3$- format, allowing spacing of the two enzymes and at the same time introducing a IMAC-purification tag.

The DNA sequence for the His6-EndoS-EndoH fusion protein consists of the encoding residues 48-995 of EndoS directly fused (i.e. no (GS) linker) to the coding residues 41-313 of EndoH. The DNA sequence is identified by SEQ ID NO: 31. The His6-tag allows for purification by means of IMAC-purification.

The DNA sequence for the encoding residues 33-421 of His6-TnGalNAcT with a N-terminal His6-Tag is identified by SEQ ID NO: 32. The His6-tag allows for purification by means of IMAC-purification.

Example 17: Small Scale *E. coli* Expression of Fusion Protein

Expression of the fusion proteins EndoF3-EndoF1 (SEQ ID NO: 16), EndoS-EndoF1 (SEQ ID NO:18), EndoF2-EndoH (SEQ ID NO:20) starts with the transformation of the plasmid into BL21(DE3) cells. Next step is the inoculation of 50 mL culture (LB medium+ampilicin; 100 µg/ml) with BL21(DE3) cells. In case of His6-EndoS-EndoH kanamycin (50 µg/mL) was used. When the OD$_{600}$ reached a value of 0.5-0.7 the cultures were induced with 1 mM IPTG (50 µL of 1M stock solution). Expressions of EndoF3-EndoF1 (SEQ ID NO:16) and EndoF2-EndoH (SEQ ID NO: 20) were repeated on large scale as described in Examples 19 and 21.

Example 18: Small Scale Purification of Fusion Protein from *E. coli* by NiNTA After overnight induction at 16° C. the cultures of expressions EndoF3-EndoF1 (SEQ ID NO: 16), EndoS-EndoF1 (SEQ ID NO: 18), EndoF2-EndoH (SEQ ID NO: 20) were pelleted by centrifugation. The pellets were re-suspended in 3-8 mL PBS and sonicated by Sonopuls Mini20, Bandelin (using microtip MS 2.5) at 70% (3×1 min) on ice. After the sonication the cell debris was removed by centrifugation (10 min 10000×g). The soluble extract was loaded onto a hand-made Ni sepharose column (obtained from ThermoFisher Scientific and Ni sepharose from GE Healthcare). The column was first washed with buffer A (20 mM Tris buffer, 5 mM imidazole, 500 mM NaCl, pH 7.5). Retained protein was eluted with buffer B (20 mM Tris, 500 mM NaCl, 250 mM imidazole, pH 7.5, 5 mL). Fractions were analyzed by SDS-PAGE on polyacrylamide gels (12%). The fractions that contained purified target protein were combined and the buffer was exchanged against TBS pH 7.5 by dialysis performed overnight at 4° C. The yields are shown in Table 4. The proteins were snap-frozen and stored at −80° C. prior to further use.

TABLE 4

Yields for the small-scale purifications of fusion proteins from *E. coli* by NiNTA.

| Protein | Yield (mg) |
| --- | --- |
| EndoF3-EndoF1 | 0.36 |
| EndoS-EndoF1 | 2.7 |
| EndoF2-EndoH | 0.39 |

Example 19: Large Scale *E. coli* Expression of Fusion Protein

Expression of the fusion proteins EndoF3-EndoF1 (SEQ ID NO:16), EndoF2-EndoH (SEQ ID NO: 20), EndoS-EfEndo18A (SEQ ID NO: 15), EndoF2-EndoF1 (SEQ ID NO: 17) and EndoF3-EndoH (SEQ ID NO: 19) started with the transformation of the plasmid into BL21(DE3) cells. Next step was the inoculation of 500 mL culture (LB medium+ampilicin; 100 µg/ml) with BL21(DE3) cells. When the OD$_{600}$ reached 0.5-0.7 the cultures were induced with 1 mM IPTG (500 µL of 1M stock solution).

Example 20: Large Scale Purification of Fusion Protein from *E. coli* by NiNTA After overnight induction at 16° C. the cultures of proteins EndoS-EfEndo18A (SEQ ID NO: 15), EndoF2-EndoF1 (SEQ ID NO: 17), EndoF3-EndoH (SEQ ID NO: 19), EndoF3-EndoF1 (SEQ ID NO:16) and EndoF2-EndoH (SEQ ID NO: 20) were pelleted by centrifugation. The pellets were re-suspended in 10 mL PBS/gram of pellet. The cell suspension is lysed three times under pressure (20000-25000 psi) by French press using Emulsiflex C3, Avestin. After French press the cell debris was removed by centrifugation (20 minutes 10000×g). The soluble extract was loaded onto a HisTrap HP 5 mL column (GE Healthcare). The column was first washed with buffer A (20 mM Tris buffer, 5 mM imidazole, 500 mM NaCl, pH 7.5). Retained protein was eluted with buffer B (20 mM Tris, 500 mM NaCl, 250 mM imidazole, pH 7.5, ~10 mL). Fractions were analysed by SDS-PAGE on polyacrylamide gels (12%). The fractions that contained purified target protein were combined and the buffer was exchanged against Tris pH 7.5 by dialysis performed overnight at 4° C. The yields are shown in the table 5 below. The proteins were snap-frozen and stored at −80° C. prior to further use.

TABLE 5

Yields for the large-scale purifications of fusion proteins from *E. coli* by NiNTA.

| Protein | Yield (mg) |
| --- | --- |
| EndoS-EfEndo18A | 55 |
| EndoF2-EndoF1 | 22.1 |
| EndoF3-EndoH | 28 |
| EndoF3-EndoF1 | 5.1 |
| EndoF2-EndoH | 3.5 |

Example 21: Purification of Fusion Protein from *E. coli* by SEC

For EndoF3-EndoF1 (SEQ ID NO:16), EndoF2-EndoF1 (SEQ ID NO: 17), EndoF3-EndoH (SEQ ID NO: 19) and EndoF2-EndoH (SEQ ID NO: 20) the NiNTA-purification, which is described in example 20, was followed by size-exclusion chromatography (SEC) to isolate the monomer. A Superdex 75 10/300 GL was installed on the Akta Purifier. The column was rinsed with MilliQ (20 mL) followed by equilibration with TBS pH 7.5 (25 mL, 0.8 mL/min). Approximately 1-3 mg of NiNTA-purified protein was loaded and run with 0.8 mL/min using TBS pH 7.5. The monomer protein was collected and fractions were analysed by SDS-PAGE on polyacrylamide gels (12%) or by mass on AccuTOF. The yields are shown below in table 6. The proteins were snap-frozen and stored at −80° C. prior to further use.

TABLE 6

Overview of the amount of NiNTA-purified endoglycosidase fusion protein which was loaded onto the SEC-column and the yields for the monomer fraction.

| Protein | Amount loaded (mg) | Yield (mg) |
| --- | --- | --- |
| EndoF2-EndoF1 | 1.75 | 0.10 |
| EndoF3-EndoH | 0.80 | 0.02 |
| EndoF3-EndoF1 | 2.30 | 0.79 |
| EndoF2-EndoH | 1.40 | 0.12 |

Example 22: Cloning of Fusion Protein Hiss-EndoS-EndoH (without GS-Linker) into pET28B Expression Vector A pET28B-vector containing His6-EndoS-EndoH (His6-EndoSH without GS-linker) coding sequence His6-EndoS-EndoH being identified by SEQ ID NO: 21, between the NcoI-HindIII sites was obtained from Genscript Piscataway, USA.

The DNA sequence for the His6-EndoSH fusion protein encodes a N-terminal linked IMAC-purification tag and a thrombin cleavage site fused to the coding residues 48-995 of EndoS fused to the coding residues 41-313 of EndoH.

Example 23: Small Scale E. coli Expression of Fusion Protein Hiss-EndoS-EndoH (without GS-Linker Expression of the fusion protein Hiss-EndoS-EndoH (SEQ ID NO: 21) starts with the transformation of the plasmid into BL21(DE3) cells. Next step is the inoculation of 50 mL culture (LB medium+kanamycin; 50 µg/ml) with BL21(DE3) cells. When the $OD_{600}$ reached a value of 0.5 the culture was induced with 1 mM IPTG (50 µL of 1M stock solution).

Example 24: Small Scale Purification of Fusion Protein from E. coli by NiNTA

After overnight induction at 16° C. the culture of the expression in Example 23 was pelleted by centrifugation. The pellet was re-suspended in 7 mL PBS and sonicated by Sonopuls Mini20, Bandelin (using microtip MS 2.5) at 70% (3×1 min) on ice. After the sonication the cell debris was removed by centrifugation (10 min 10000×g). The soluble extract was loaded onto a hand-made Ni sepharose column (obtained from ThermoFisher Scientific and Ni sepharose from GE Healthcare). The column was first washed with buffer A (20 mM Tris buffer, 5 mM imidazole, 500 mM NaCl, pH 7.5). Retained protein was eluted with buffer B (20 mM Tris, 500 mM NaCl, 250 mM imidazole, pH 7.5, 5 mL). Fractions were analysed by SDS-PAGE on polyacrylamide gels (12%). The fractions that contained purified target protein were combined and the buffer was exchanged against TBS pH 7.5 by dialysis performed overnight at 4° C. The yield after dialysis is 9 mg. The product was snap-frozen and stored at −80° C. prior to further use.

Example 25: Comparison of Trimming Efficiency of EndoSH, EndoF3-EndoH, EndoS-EfEndo18A and EndoF2-EndoF1 on High-Mannose Trastuzumab High-mannose trastuzumab (0.7 mL, 6.0 mg, 8.8 mg/mL in Tris pH 8.0), was treated with Fabricator™ (9 µL, 50 U/µL) for 1 h at 37° C. Next, Fabricator™-digested high-mannose trastuzumab was divided into three equal portions and buffer exchanged to 50 mM sodium citrate pH 4.5 with 150 mM NaCl, 50 mM Tris.HCl pH 6.0 with 150 mM NaCl and 50 mM Tris.HCl pH 7.5 with 150 mM NaCl, respectively. Buffer exchange was performed using an Amicon Ultra-0.5, Ultracel-10 Membrane (Merck Millipore) and samples were concentrated to a final concentration of 10 mg/mL. For EndoSH (identified by SEQ ID NO: 1), EndoF3-EndoH (identified by SEQ ID NO: 19), EndoS-EfEndo18A (identified by SEQ ID NO: 15) and EndoF2-EndoF1 (identified by SEQ ID NO: 17) dilution series of 10, 50 and 250 nM in each of the above-mentioned reaction buffers were prepared. The reactions were started by adding 2 µL of Fabricator™-digested high-mannose trastuzumab (10 mg/mL) to 2 µL of the diluted endoglycosidase fusion protein in the corresponding buffer, resulting in a final concentration of 5 mg/mL Fabricator™-digested IgG (67 µM Fc/2-fragment) with 5, 25 and 125 nM endoglycosidase. The reactions were incubated for 60 minutes at 37° C. Reactions were quenched by addition of 16 µL 1× Laemmli sample buffer without 2-mercaptoethanol followed by incubation for 5 minutes at 95° C. Samples (5 µL/sample) were loaded on SDS-page gel and run for 70 min (20 mA), stained in colloidal coomassie overnight, and finally de-stained in water. Conversion percentages were calculated based on scanning of SDS-PAGE gel with regular flatbed scanner and quantification with a software tool (CLIQS v1.1).

TABLE 7

Percentages trimming (conversion) of Fabricator ™-digested high-mannose trastuzumab upon treatment of various endoglycosidase fusion proteins at pH 4.5, 6.0 and 7.5.

| pH | Enzyme (nM) | EndoSH | EndoF3-EndoH | EndoS-EfEndo18A | EndoF2-EndoF1 |
| --- | --- | --- | --- | --- | --- |
| 4.5 | 5 | 23* | 26* | 26* | 26* |
|  | 25 | 35 | 31 | 38 | 26* |
|  | 125 | 60 | 60 | 61 | 83 |
| 6.0 | 5 | 27* | 25* | 27* | 28* |
|  | 25 | 36 | 37 | 31 | 32 |
|  | 125 | 64 | 57 | 69 | 61 |
| 7.5 | 5 | 24* | 26* | 24* | 26* |
|  | 25 | 29* | 31 | 31 | 30 |
|  | 125 | 61 | 53 | 58 | 58 |

Conversion was calculated using the following formula: conversion (%) = 100 × (Fc/2$_{trimmed}$)/(Fc/2$_{trimmed}$ + Fc/2$_{glysosylated}$).
*Note:
Results are difficult to interpret accurately due to background signal at the height of untreated Fabricator ™-digested high-mannose trastuzumab. No background correction was applied for conversion quantification.

Example 26: Comparison of Trimming Efficiency of EndoSH, EndoF3-EndoH, EndoS-EfEndo18A and EndoF2-EndoF1 on Trastuzumab Trastuzumab (obtained from Epirus biopharma (Utrecht, The Netherlands); 287 µL, 6.0 mg, 21 mg/mL in Tris pH 8.0), was treated with Fabricator™ (9 μL, 50 U/μL) for 1 h at 37° C. Next, Fabricator™-digested trastuzumab was divided into three equal portions and buffer exchanged to 50 mM sodium citrate pH 4.5 with 150 mM NaCl, 50 mM Tris.HCl pH 6.0 with 150 mM NaCl and 50 mM Tris.HCl pH 7.5 with 150 mM NaCl, respectively. Buffer exchange was performed using an Amicon Ultra-0.5, Ultracel-10 Membrane (Merck Millipore) and samples were concentrated to a final concentration of 10 mg/mL. For EndoSH (identified by SEQ ID NO: 1), EndoF3-EndoH (identified by SEQ ID NO: 19), EndoS-EfEndo18A (identified by SEQ ID NO: 15) and EndoF2-EndoF1 (identified by SEQ ID NO: 17) dilution of 50 and 250 nM in each of the above-mentioned buffers were prepared. The reactions were started by adding 5 μL of Fabricator™-digested trastuzumab (10 mg/mL) to 5 μL of the diluted endoglycosidase fusion protein in the corresponding buffer, resulting in a final concentration of 5 mg/mL Fabricator™-digested IgG (67 μM Fc/2-fragment) with 25 and 125 nM endoglycosidase. The reactions were incubated for 60 minutes at 37° C. For each reaction a sample (4 μL) was taken and added to 16 μL 1× Laemmli sample buffer without 2-mercaptoethanol and incubated for 5 minutes at 95° C. Samples (5 μL/sample) were loaded on SDS-page gel and run for 70 min (20 mA), stained in colloidal coomassie overnight, and finally de-stained in water. Conversion percentages were calculated based on scanning of SDS-PAGE gel with regular flatbed scanner and quantification with a software tool (CLIQS v1.1).

TABLE 8

Percentages trimming (conversion) of Fabricator ™-digested trastuzumab upon treatment of various endoglycosidase fusion proteins at pH 4.5, 6.0 and 7.5.

| pH | Enzyme (nM) | EndoSH | EndoF3-EndoH | EndoS-EfEndo18A | EndoF2-EndoF1 |
|---|---|---|---|---|---|
| 4.5 | 25 | 29* | 29* | 29* | 29* |
|  | 125 | 28* | 40 | 29* | 50 |
| 6.0 | 25 | 72 | 28* | 77 | 28* |
|  | 125 | 85 | 31 | 84 | 42 |
| 7.5 | 25 | 81 | 27* | 82 | 26* |
|  | 125 | 87 | 31 | 86 | 41 |

Conversion was calculated using the following formula: conversion (%) = 100 × (Fc/2$_{trimmed}$)/(Fc/2$_{trimmed}$ + Fc/2$_{glycosylated}$).
*Note:
Results are difficult to interpret accurately due to background signal at the height of untreated Fabricator ™-digested trastuzumab. No background correction was applied for conversion quantification.

Example 27: Trimming of Trastuzumab by EndoF3-EndoH

To demonstrate that complete conversion can be achieved for trimming of trastuzumab by EndoF3-EndoH (identified by SEQ ID NO: 19), Fabricator™-digested trastuzumab (4 μL, 40 μg, 10 mg/mL in 50 mM sodium citrate pH 4.5 with 150 mM NaCl) was incubated with 50 mM sodium citrate pH 4.5 with 150 mM NaCl (8.73 μL) and EndoF3-EndoH (7.27 μL, 4 μg, 0.55 mg/mL in 50 mM sodium citrate pH 4.5 with 150 mM NaCl) for 60 minutes at 37° C. Mass spectral analysis of a fabricator-digested sample showed one main peak of the Fc/2-fragment (observed mass 24139 Da, approximately 95% of total Fc/2 fragment), corresponding to core GlcNAc(Fuc)-substituted trastuzumab.

Example 28: Trimming of Trastuzumab by EndoF2-EndoF1

To demonstrate that complete conversion can be achieved for trimming of trastuzumab by EndoF2-EndoF1 (identified by SEQ ID NO: 17), Fabricator™-digested trastuzumab (4 μL, 40 μg, 10 mg/mL in 50 mM sodium citrate pH 4.5 with 150 mM NaCl) was incubated with 50 mM sodium citrate pH 4.5 with 150 mM NaCl (11.06 μL) and EndoF2-EndoF1 (4.94 μL, 4 μg, 0.81 mg/mL in 50 mM sodium citrate pH 4.5 with 150 mM NaCl) for 60 minutes at 37° C. Mass spectral analysis of a fabricator-digested sample showed one main peak of the Fc/2-fragment (observed mass 24139 Da, approximately 95% of total Fc/2 fragment), corresponding to core GlcNAc(Fuc)-substituted trastuzumab.

Example 29: Comparison of Trimming Efficiency of EndoSH, EndoF3-EndoF1, EndoS-EndoF1, EndoF2-EndoH on High-Mannose Trastuzumab High-mannose trastuzumab (0.7 mL, 6.0 mg, 8.8 mg/mL in Tris pH 8.0), was treated with Fabricator™ (9 μL, 50 U/μL) for 1 h at 37° C. Next, Fabricator™-digested high-mannose trastuzumab was divided into three equal portions and buffer exchanged to 50 mM sodium citrate pH 4.5 with 150 mM NaCl, 50 mM Tris.HCl pH 6.0 with 150 mM NaCl and 50 mM Tris.HCl pH 7.5 with 150 mM NaCl, respectively. Buffer exchange was performed using an Amicon Ultra-0.5, Ultracel-10 Membrane (Merck Millipore) and samples were concentrated to a final concentration of 10 mg/mL. EndoSH (identified by SEQ ID NO: 1), EndoF3-EndoF1 (identified by SEQ ID NO: 16), EndoS-EndoF1 (identified by SEQ ID NO: 18) and EndoF2-EndoH (identified by SEQ ID NO: 20) were diluted to a concentration of 250 nM in each of the above-mentioned reaction buffers. The reactions were started by adding 2 μL of Fabricator™-digested high-mannose trastuzumab (10 mg/mL) to 2 μL of the endoglycosidase fusion protein (250 nM) in the corresponding buffer, resulting in a final concentration of 5 mg/mL Fabricator™-digested IgG (67 μM Fc/2-fragment) with 125 nM endoglycosidase. The reactions were incubated for 60 minutes at 37° C. Reactions were quenched by addition of 16 μL 1× Laemmli sample buffer without 2-mercaptoethanol followed by incubation for 5 minutes at 95° C. Samples (5 μL/sample) were loaded on SDS-page gel and run for 70 min (20 mA), stained in colloidal coomassie overnight, and finally de-stained in water. Conversion percentages were calculated based on scanning of SDS-PAGE gel with regular flatbed scanner and quantification with a software tool (CLIQS v1.1).

TABLE 9

Percentages trimming (conversion) of Fabricator ™-digested high-mannose trastuzumab upon treatment of various endoglycosidase fusion proteins (125 nM) at pH 4.5, 6.0 and 7.5.

| pH | EndoSH | EndoF3-EndoF1 | EndoS-EndoF1 | EndoF2-EndoH |
|---|---|---|---|---|
| 4.5 | 61 | 23* | 60 | 33 |
| 6.0 | 69 | 19* | 73 | 28* |
| 7.5 | 67 | 17* | 72 | 25* |

Conversion was calculated using the following formula: conversion (%) = 100 × (Fc/2$_{trimmed}$)/(Fc/2$_{trimmed}$ + Fc/2$_{glycosylated}$).
*Note:
Results are difficult to interpret accurately due to background signal at the height of untreated Fabricator ™-digested high-mannose trastuzumab. No background correction was applied for conversion quantification.

Example 30: Comparison of Trimming Efficiency of EndoSH, EndoF3-EndoH and EndoS-EfEndo18A, EndoF2-EndoF1 on Trastuzumab Trastuzumab (obtained from Epirus biopharma (Utrecht, The Netherlands); 287 μL, 6.0 mg, 21 mg/mL in Tris pH 8.0), was treated with Fabricator™ (9 μL, 50 U/μL) for 1 h at 37° C. Next, Fabricator™-digested trastuzumab was divided into three equal portions and buffer exchanged to 50 mM sodium citrate pH 4.5 with 150 mM NaCl, 50 mM Tris.HCl pH 6.0 with 150 mM NaCl and 50 mM Tris.HCl pH 7.5 with 150 mM NaCl, respectively. Buffer exchange was performed using an Amicon Ultra-0.5, Ultracel-10 Membrane (Merck Millipore) and samples were concentrated to a final concentration of 10 mg/mL. EndoSH (identified by SEQ ID NO: 1), EndoF3-EndoF1 (identified by SEQ ID NO: 16), EndoS-EndoF1 (identified by SEQ ID NO: 18) and EndoF2-EndoH (identified by SEQ ID NO: 20) were diluted to a concentration of 250 nM in each of the above-mentioned reaction buffers. The reactions were started by adding 5 μL of Fabricator™-digested trastuzumab (10 mg/mL) to 5 μL of the endoglycosidase fusion protein (250 nM) in the corresponding buffer, resulting in a final concentration of 5 mg/mL Fabricator™-digested IgG (67 μM Fc/2-fragment) with 125 nM endoglycosidase. The reactions were incubated for 60 minutes at 37° C. For each reaction, a sample (4 μL) was taken and added to 16 μL 1× Laemmli sample buffer without 2-mercaptoethanol and incubated for 5 minutes at 95° C. Samples (5 μL/sample) were loaded on SDS-page gel and run for 70 min (20 mA), stained in colloidal coomassie overnight, and finally de-stained in water. Conversion percentages were calculated based on scanning of SDS-PAGE gel with regular flatbed scanner and quantification with a software tool (CLIQS v1.1).

TABLE 10

Percentages trimming (conversion) of trastuzumab upon treatment with different endoglycosidases (125 nM) at pH 4.5, 6.0 and 7.5.

| pH | EndoSH | EndoF3-EndoF1 | EndoS-EndoF1 | EndoF2-EndoH |
|---|---|---|---|---|
| 4.5 | 22* | 19* | 23* | 20* |
| 6.0 | 77 | 16* | 79 | 16* |
| 7.5 | 80 | 14* | 83 | 13* |

Conversion was calculated using the following formula: conversion (%) = 100 × (Fc/2$_{trimmed}$)/(Fc/2$_{trimmed}$ + Fc/2$_{glycosylated}$).
*Note:
Results are difficult to interpret accurately due to background signal at the height of untreated Fabricator™-digested trastuzumab. No background correction was applied for conversion quantification.

Example 31: Comparison of Trimming Efficiency of EndoS-EndoH Fusion Proteins with and without Linker on High-Mannose Trastuzumab High-mannose trastuzumab (0.7 mL, 6.0 mg, 8.8 mg/mL in Tris pH 8.0), was treated with Fabricator™ (9 μL, 50 U/μL) for 1 h at 37° C. Next, Fabricator™-digested high-mannose trastuzumab was divided into three equal portions and buffer exchanged to 50 mM sodium citrate pH 4.5 with 150 mM NaCl, 50 mM Tris.HCl pH 6.0 with 150 mM NaCl and 50 mM Tris.HCl pH 7.5 with 150 mM NaCl, respectively. Buffer exchange was performed using an Amicon Ultra-0.5, Ultracel-10 Membrane (Merck Millipore) and samples were concentrated to a final concentration of 10 mg/mL. For EndoSH (identified by SEQ ID NO: 1) and Hiss-EndoSH (His6-EndoS-EndoH without GS-linker; identified by SEQ ID NO: 21) dilution series of 10, 50 and 250 nM in each of the above-mentioned reaction buffers were prepared. The reactions were started by adding 2 μL of Fabricator™-digested high-mannose trastuzumab (10 mg/mL) to 2 μL of the diluted endoglycosidase fusion protein in the corresponding buffer, resulting in a final concentration of 5 mg/mL Fabricator™-digested IgG (67 μM Fc/2-fragment) with 5, 25 and 125 nM endoglycosidase. The reactions were incubated for 60 minutes at 37° C. Reactions were quenched by addition of 16 μL 1× Laemmli sample buffer without 2-mercaptoethanol followed by incubation for 5 minutes at 95° C. Samples (5 μL/sample) were loaded on SDS-page gel and run for 70 min (20 mA), stained in colloidal coomassie overnight, and finally de-stained in water. Conversion percentages were calculated based on scanning of SDS-PAGE gel with regular flatbed scanner and quantification with a software tool (CLIQS v1.1).

TABLE 11

Percentages trimming (conversion) of Fabricator™-digested high-mannose trastuzumab upon treatment with EndoS-EndoH fusion proteins with and without linker at pH 4.5, 6.0 and 7.5.

| pH | Enzyme (nM) | EndoSH (with GS-linker) | His$_6$-EndoSH (without GS-linker) |
|---|---|---|---|
| 4.5 | 5 | 23* | 23* |
|  | 25 | 35 | 31 |
|  | 125 | 60 | 63 |
| 6.0 | 5 | 27* | 28* |
|  | 25 | 36 | 42 |
|  | 125 | 64 | 66 |
| 7.5 | 5 | 24* | 28* |
|  | 25 | 29* | 38 |
|  | 125 | 61 | 63 |

Conversion was calculated using the following formula: conversion (%) = 100 × (Fc/2$_{trimmed}$)/(Fc/2$_{trimmed}$ + Fc/2$_{glycosylated}$).
*Note:
Results are difficult to interpret accurately due to background signal at the height of untreated Fabricator™-digested high-mannose trastuzumab. No background correction was applied for conversion quantification.

Example 32: Comparison of Trimming Efficiency of EndoS-EndoH Fusion Proteins with and without Linker on Trastuzumab Trastuzumab (obtained from Epirus biopharma (Utrecht, The Netherlands); 287 μL, 6.0 mg, 21 mg/mL in Tris pH 8.0), was treated with Fabricator™ (9 μL, 50 U/μL) for 1 h at 37° C. Next, Fabricator™-digested trastuzumab was divided into three equal portions and buffer exchanged to 50 mM sodium citrate pH 4.5 with 150 mM NaCl, 50 mM Tris.HCl pH 6.0 with 150 mM NaCl and 50 mM Tris.HCl pH 7.5 with 150 mM NaCl, respectively. Buffer exchange was performed using an Amicon Ultra-0.5, Ultracel-10 Membrane (Merck Millipore) and samples were concentrated to a final concentration of 10 mg/mL. For EndoSH (identified by SEQ ID NO: 1) and Hiss-EndoSH (EndoS-EndoH without GS-linker; identified by SEQ ID NO: 21) dilution series of 2, 10, 50 and 250 nM in each of the above-mentioned buffers were prepared. The reactions were started by adding 5 μL of Fabricator™-digested trastuzumab (10 mg/mL) to 5 μL of the diluted endoglycosidase fusion protein in the corresponding buffer, resulting in a final concentration of 5 mg/mL Fabricator™-digested IgG (67 μM Fc/2-fragment) with 1, 5, 25 and 125 nM endoglycosidase. The reactions were incubated for 60 minutes at 37° C. For each reaction, a sample (4 μL) was taken and added to 16 μL 1× Laemmli sample buffer without 2-mercaptoethanol and incubated for 5 minutes at 95° C. Samples (5 μL/sample) were loaded on SDS-page gel and run for 70 min (20 mA), stained in colloidal coomassie overnight, and finally de-stained in water. Conversion percentages were calculated based on scanning of SDS-PAGE gel with regular flatbed scanner and quantification with a software tool (CLIQS v1.1).

TABLE 12

Percentages trimming (conversion) of Fabricator ™-digested
trastuzumab upon treatment with EndoS-EndoH fusion proteins
with and without linker at pH 4.5, 6.0 and 7.5.

| pH | Enzyme (nM) | EndoSH | EndoSH, no linker |
|---|---|---|---|
| 4.5 | 1 | 30 | 28* |
|  | 5 | 29* | 29* |
|  | 25 | 29* | 29* |
|  | 125 | 28* | 29* |
| 6.0 | 1 | 36 | 35 |
|  | 5 | 45 | 46 |
|  | 25 | 72 | 73 |
|  | 125 | 85 | 83 |
| 7.5 | 1 | 34 | 40 |
|  | 5 | 47 | 51 |
|  | 25 | 81 | 80 |
|  | 125 | 87 | 84 |

Conversion was calculated using the following formula: conversion (%) = 100 × $(Fc/2_{trimmed})/(Fc/2_{trimmed} + Fc/2_{glycosylated})$.
*Note:
Results are difficult to interpret accurately due to background signal at the height of untreated Fabricator ™-digested trastuzumab. No background correction was applied for conversion quantification.

Example 33: Comparison of Trimming Efficiency of EndoSH, EndoF3-EndoH and EndoS-EfEndo18A, EndoF2-EndoF1 on cAC10 cAC10 (300 µL, 6.0 mg, 20.1 mg/mL in Tris pH 8.0), obtained by as described above in Example 7, was treated with Fabricator™ (9 µL, 50 U/µL) for 1 h at 37° C. Next, Fabricator™-digested cAC10 was divided into three equal portions and buffer exchanged to 50 mM sodium citrate pH 4.5 with 150 mM NaCl, 50 mM Tris.HCl pH 6.0 with 150 mM NaCl and 50 mM Tris.HCl pH 7.5 with 150 mM NaCl. Buffer exchange was performed using an Amicon Ultra-0.5, Ultracel-10 Membrane (Merck Millipore) and samples were concentrated to a final concentration of 10 mg/mL. Example 26 showed an optimal pH for the trimming of complex-type glycans of pH 7.5 for EndoSH (identified by SEQ ID NO: 1), pH 4.5 for EndoF3-EndoH (identified by SEQ ID NO: 19), pH 7.5 for EndoS-EfEndo18A (identified by SEQ ID NO: 15) and pH 4.5 for EndoF2-EndoF1 (identified by SEQ ID NO: 17). For each of the above mentioned fusion proteins a dilution series was prepared of 5, 50 and 500 nM in the reaction buffer with the optimal pH as mentioned above. The reactions were started by adding 5 µL of Fabricator™-digested cAC10 (10 mg/mL) to 5 µL of the diluted endoglycosidase fusion protein in the corresponding buffer, resulting in a final concentration of 5 mg/mL Fabricator™-digested IgG (67 µM Fc/2-fragment) with 2.5, 25 and 250 nM endoglycosidase fusion protein. The reactions were incubated for 60 minutes at 37° C. For each reaction, a sample (4 µL) was taken and added to 16 µL 1× Laemmli sample buffer without 2-mercaptoethanol and incubated for 5 minutes at 95° C. Samples (5 µL/sample) were loaded on SDS-page gel and run for 70 min (20 mA), stained in colloidal coomassie overnight, and finally de-stained in water. Conversion percentages were calculated based on scanning of SDS-PAGE gel with regular flatbed scanner and quantification with a software tool (CLIQS v1.1).

TABLE 13

Percentages trimming (conversion) of Fabricator ™-
digested cAC10 upon treatment of various endoglycosidase
fusion proteins at an optimal pH specific for each fusion protein.

| Enzyme concen- tration (nM) | EndoSH (at pH 7.5) | EndoF3- EndoH (at pH 4.5) | EndoS- EfEndo18A (at pH 7.5) | EndoF2- EndoF1 (at pH 4.5) |
|---|---|---|---|---|
| 2.5 | 27* | 70 | 26* | 71 |
| 25 | 100 | 71 | 100 | 71 |
| 250 | 100 | 70 | 100 | 73 |

Conversion was calculated using the following formula: conversion (%) = 100 × $(Fc/2_{trimmed})/(Fc/2_{trimmed} + Fc/2_{glycosylated})$.
*Note:
Results are difficult to interpret accurately due to background signal at the height of untreated Fabricator ™-digested cAC10. No background correction was applied for conversion quantification.

Example 34: Comparison of Trimming Efficiency of EndoSH, EndoF3-EndoH and EndoS-EfEndo18A, EndoF2-EndoF1 on RNAseB A stock solution of RNaseB (2 mg/mL) was prepared in 50 mM sodium citrate pH 4.5 with 150 mM NaCl and in 50 mM Tris.HCl pH 6.0 with 150 mM NaCl. Example 26 showed an optimal pH for the trimming of high-mannose glycans of pH 6.0 for EndoSH (identified by SEQ ID NO: 1), pH 6.0 for EndoF3-EndoH (identified by SEQ ID NO: 19), pH 6.0 for EndoS-EfEndo18A (identified by SEQ ID NO: 15) and pH 4.5 for EndoF2-EndoF1 (identified by SEQ ID NO: 17). For each of the above mentioned fusion proteins a dilution series was prepared of 10, 50 and 250 nM in the reaction buffer with the optimal pH as mentioned above. The reactions were started by adding 5 µL of RNase B (2 mg/mL in the corresponding buffer) to 5 µL of the diluted endoglycosidase fusion protein in the optimal reaction buffer as mentioned above. This results in a final concentration of 1 mg/mL RNase B with 5, 25 and 125 nM endoglycosidase fusion protein. The reactions were incubated for 60 minutes at 37° C. For each reaction, a sample (4 µL) was taken and added to 16 µL 1× Laemmli sample buffer without 2-mercaptoethanol and incubated for 5 minutes at 95° C. Samples (5 µL/sample) were loaded on SDS-page gel and run for 70 min (20 mA), stained in colloidal coomassie overnight, and finally de-stained in water. Conversion percentages were calculated based on scanning of SDS-PAGE gel with regular flatbed scanner and quantification with a software tool (CLIQS v1.1).

TABLE 14

Percentages trimming (conversion) of RNase B upon treatment
of various endoglycosidase fusion proteins at the optimal
pH value specific for each fusion protein.

| Enzyme concentration (nM) | EndoSH (at pH 6.0) | EndoF3- EndoH (at pH 6.0) | EndoS- EfEndo18A (at pH 6.0) | EndoF2- EndoF1 (at pH 4.5) |
|---|---|---|---|---|
| 5 | 34 | 37 | 52 | 43 |
| 25 | 100 | 100 | 100 | 100 |
| 125 | 100 | 100 | 100 | 100 |

Conversion was calculated using the following formula: conversion (%) = 100 × $(RNaseB_{trimmed})/(RNaSeB_{trimmed} + RNaseB_{glycosylated})$.

Example 35: Comparison of Trimming Efficiency of EndoSH, EndoF3-EndoH and EndoS-EfEndo18A, EndoF2-EndoF1 on Fibrinogen Fibrinogen from human plasma (commercially available from Sigma), which contains one glycosylation-site on the alpha-, beta- and gamma-chain, was dissolved to a final concentration of 10 mg/mL in 50 mM Tris.HCl pH 6.0 with 150 mM NaCl and in 50 mM Tris.HCl pH 7.5 with 150 mM NaCl by rotating at 300 rpm at 37° C. for 15 minutes. Fibrinogen could not be dissolved in 50 mM sodium citrate pH 4.5 with 150 mM NaCl using the above-mentioned procedure. Example 26 showed an optimal pH for the trimming of complex-type glycans of pH 7.5 for EndoSH (identified by SEQ ID NO: 1), pH 4.5 for EndoF3-EndoH (identified by SEQ ID NO: 19), pH 7.5 for EndoS-EfEndo18A (identified by SEQ ID NO: 15) and pH 4.5 for EndoF2-EndoF1 (identified by SEQ ID NO: 17). For EndoSH and EndoS-EfEndo18A a dilution series was prepared of 5, 50 and 500 nM in 50 mM Tris.HCl pH 7.5 with 150 mM NaCl, which is the optimal reaction buffer for these enzymes. For EndoF3-EndoH and EndoF2-EndoF1 a dilution series was prepared of 5, 50 and 500 nM in 50 mM Tris.HCl pH 6.0 with 150 mM NaCl, which is the most optimal pH in which fibrinogen can be solubilized. The reactions were started by adding 5 μL of fibrinogen (10 mg/mL) to 5 μL of the diluted endoglycosidase fusion protein in the corresponding buffer, resulting in a final concentration of 5 mg/mL fibrinogen with 2.5, 25 and 250 nM endoglycosidase fusion protein. The reactions were incubated for 60 minutes at 37° C. For each reaction, a sample (4 μL) was taken and added to 16 μL 1× Laemmli sample buffer with 2-mercaptoethanol and incubated for 5 minutes at 95° C. Samples (5 μL/sample) were loaded on SDS-page gel and run for approximately 120 min (20 mA), stained in colloidal coomassie overnight, and finally destained in water. Conversion percentages were calculated for the beta- and gamma-chain based on scanning of SDS-PAGE gel with regular flatbed scanner and quantification with a software tool (CLIQS v1.1).

Example 36: Comparison of Trimming Efficiency of Fusion Proteins EndoSH and EndoF3-EndoH with Individual Proteins EndoS, EndoF3 and EndoH on Trastuzumab Trastuzumab (obtained from Epirus biopharma (Utrecht, The Netherlands); 287 μL, 6.0 mg, 21 mg/mL in Tris pH 8.0), was treated with Fabricator™ (9 μL, 50 U/μL) for 1 h at 37° C. Next, Fabricator™-digested trastuzumab was divided into three equal portions and buffer exchanged to 50 mM sodium citrate pH 4.5 with 150 mM NaCl, 50 mM Tris.HCl pH 6.0 with 150 mM NaCl and 50 mM Tris.HCl pH 7.5 with 150 mM NaCl, respectively. Buffer exchange was performed using an Amicon Ultra-0.5, Ultracel-10 Membrane (Merck Millipore) and samples were concentrated to a final concentration of 10 mg/mL. EndoSH (identified by SEQ ID NO: 1), EndoF3-EndoH (identified by SEQ ID NO: 19), EndoS (commercially available from Genovis, Lund, Sweden), EndoF3 (commercially available from Sigma-Aldrich, EU) and EndoH (commercially available from New England Biolabs, Ipswich, USA) were diluted to 50 and 500 nM in each of the above-mentioned buffers. The reactions were started by adding 5 μL of Fabricator™-digested trastuzumab (10 mg/mL) to 5 μL of the diluted endoglycosidases in the corresponding buffer, resulting in a final concentration of 5 mg/mL Fabricator™-digested IgG (67 μM Fc/2-fragment) with 25 and 250 nM endoglycosidase. The reactions were incubated for 60 minutes at 37° C. For each reaction a sample (4 μL) was taken and added to 16 μL 1× Laemmli sample buffer without 2-mercaptoethanol and incubated for 5 minutes at 95° C. Samples (5 μL/sample) were loaded on SDS-page gel and run for 70 min (20 mA), stained in colloidal coomassie overnight, and finally destained in water. Conversion percentages were calculated based on scanning of SDS-PAGE gel with regular flatbed scanner and quantification with a software tool (CLIQS v1.1).

TABLE 15

Percentages trimming (conversion) of fibrinogen upon treatment of various endoglycosidase fusion proteins at the optimal pH value specific for each fusion protein.

| Fibrinogen chain | Enzyme concentration (nM) | EndoSH (at pH 7.5) | EndoF3-EndoH (at pH 6.0) | EndoS-EfEndo18A (at pH 7.5) | EndoF2-EndoF1 (at pH 6.0) |
|---|---|---|---|---|---|
| beta-chain | 2.5 | 9* | 10* | 1* | 23 |
| | 25 | 9* | 10* | 10* | 34 |
| | 250 | 8* | 8* | 7* | 54 |
| gamma-chain | 2.5 | 5* | 7* | 6* | 13 |
| | 25 | 5* | 4* | 5* | 25 |
| | 250 | 4* | 6* | 4* | 50 |

Conversion was calculated separately for the beta- and gamma-chain using the following formula: conversion (%) = 100 × (fibrinogen$_{trimmed}$)/(fibrinogen$_{trimmed}$ + fibrinogen$_{glycosylated}$).
*Note:
Results are difficult to interpret accurately due to background signals at the height of untreated fibrinogen. No background correction was applied for conversion quantification.

TABLE 16

Percentages trimming (conversion) of Fabricator™-digested trastuzumab upon treatment of various endoglycosidases and endoglycosidase fusion proteins at pH 4.5, 6.0 and 7.5.

| pH | Enzyme (nM) | EndoSH | EndoF3-EndoH | EndoS | EndoF3 | EndoH |
|---|---|---|---|---|---|---|
| 4.5 | 25 | 21* | 21* | 22* | 21* | 21* |
| | 250 | 27* | 50 | 29* | 21* | 19* |
| 6.0 | 25 | 68 | 23* | 76 | 24* | 21* |
| | 250 | 83 | 39 | 82 | 22* | 19* |
| 7.5 | 25 | 77 | 26* | 82 | 15* | 21* |
| | 250 | 100 | 36 | 100 | 12* | 20* |

Conversion was calculated using the following formula: conversion (%) = 100 × (Fc/2$_{trimmed}$)/(Fc/2$_{trimmed}$ + Fc/2$_{glycosylated}$).
*Note:
Results are difficult to interpret accurately due to background signal at the height of untreated Fabricator™-digested trastuzumab. No background correction was applied for conversion quantification.

Example 37: Comparison of Trimming Efficiency of Fusion Proteins EndoSH and EndoF3-EndoH with Individual Proteins EndoS, EndoF3 and EndoH on RNaseB A stock solution of RNaseB (2 mg/mL) was prepared in 50 mM sodium citrate pH 4.5 with 150 mM NaCl, in 50 mM Tris.HCl pH 6.0 with 150 mM NaCl and in 50 mM Tris.HCl pH 7.5 with 150 mM NaCl. EndoSH (identified by SEQ ID NO: 1), EndoF3-EndoH (identified by SEQ ID NO: 19), EndoS (commercially available from Genovis, Lund, Sweden), EndoF3 (commercially available from Sigma-Aldrich, EU) and EndoH (commercially available from New England Biolabs, Ipswich, USA) were diluted to a concentration of 50 nM in each of the above-mentioned buffers. The reactions were started by adding 5 μL of RNase B (2 mg/mL) to 5 μL of the diluted endoglycosidase fusion protein (50 nM) in the corresponding reaction buffer, resulting in a final concentration of 1 mg/mL RNase B and 25 nM endoglycosidase. The reactions were incubated for 60 minutes at 37° C. For each reaction, a sample (4 μL) was taken and added to 16 μL 1× Laemmli sample buffer without 2-mercaptoethanol and incubated for 5 minutes at 95° C. Samples (5 μL/sample) were loaded on SDS-page gel and run for 70 min (20 mA), stained in colloidal coomassie overnight, and finally de-stained in water. Conversion percentages were calculated based on scanning of SDS-PAGE gel with regular flatbed scanner and quantification with a software tool (CLIQS v1.1).

TABLE 17

Percentages trimming (conversion) of RNase B upon treatment of various endoglycosidases and endoglycosidase fusion proteins (25 nM) at pH 4.5, 6.0 and 7.5.

| pH | EndoSH | EndoF3-EndoH | EndoS | EndoF3 | EndoH |
|---|---|---|---|---|---|
| 4.5 | 74 | 75 | 0 | 0 | 30 |
| 6.0 | 70 | 100 | 0 | 0 | 39 |
| 7.5 | 42 | 48 | 0 | 0 | 33 |

Conversion was calculated using the following formula: conversion (%) = 100 × (RNaseB$_{trimmed}$)/(RNaSeB$_{trimmed}$ + RNaSeB$_{glycosylated}$).

```
Sequences
Sequence identification of fusion protein EndoS-EndoH (or EndoSH) as
expressed in E coli (SEQ. ID NO: 1):
    1 MPSIDSLHYL SENSKKEFKE ELSKAGQESQ KVKEILAKAQ QADKQAQELA

51 KMKIPEKIPM KPLHGPLYGG YFRTWHDKTS DPTEKDKVNS MGELPKEVDL

101 AFIFHDWTKD YSLFWKELAT KHVPKLNKQG TRVIRTIPWR FLAGGDNSGI

151 AEDTSKYPNT PEGNKALAKA IVDEYVYKYN LDGLDVDVEH DSIPKVDKKE

201 DTAGVERSIQ VFEEIGKLIG PKGVDKSRLF IMDSTYMADK NPLIERGAPY

251 INLLLVQVYG SQGEKGGWEP VSNRPEKTME ERWQGYSKYI RPEQYMIGFS

301 FYEENAQEGN LWYDINSRKD EDKANGINTD ITGTRAERYA RWQPKTGGVK

351 GGIFSYAIDR DGVAHQPKKY AKQKEFKDAT DNIFHSDYSV SKALKTVMLK

401 DKSYDLIDEK DFPDKALREA VMAQVGTRKG DLERFNGTLR LDNPAIQSLE

451 GLNKFKKLAQ LDLIGLSRIT KLDRSVLPAN MKPGKDTLET VLETYKKDNK

501 EEPATIPPVS LKVSGLTGLK ELDLSGFDRE TLAGLDAATL TSLEKVDISG

551 NKLDLAPGTE NRQIFDTMLS TISNHVGSNE QTVKFDKQKP TGHYPDTYGK

601 TSLRLPVANE KVDLQSQLLF GTVTNQGTLI NSEADYKAYQ NHKIAGRSFV

651 DSNYHYNNFK VSYENYTVKV TDSTLGTTTD KTLATDKEET YKVDFFSPAD

701 KTKAVHTAKV IVGDEKTMMV NLAEGATVIG GSADPVNARK VFDGQLGSET

751 DNISLGWDSK QSIIFKLKED GLIKHWRFFN DSARNPETTN KPIQEASLQI

801 FNIKDYNLDN LLENPNKFDD EKYWITVDTY SAQGERATAF SNTLNNITSK

851 YWRVVFDTKG DRYSSPVVPE LQILGYPLPN ADTIMKTVTT AKELSQQKDK

901 FSQKMLDELK IKEMALETSL NSKIFDVTAI NANAGVLKDC IEKRQLLKKG

951 GGGSGGGGSG GGGSHHHHHH EFGGGGSGGG GSGGGGSAPA PVKQGPTSVA

1001 YVEVNNNSML NVGKYTLADG GGNAFDVAVI FAANINYDTG TKTAYLHFNE

1051 NVQRVLDNAV TQIRPLQQQG IKVLLSVLGN HQGAGFANFP SQQAASAFAK

1101 QLSDAVAKYG LDGVDFDDEY AEYGNNGTAQ PNDSSFVHLV TALRANMPDK
```

-continued

```
1151 IISLYNIGPA ASRLSYGGVD VSDKFDYAWN PYYGTWQVPG IALPKAQLSP

1201 AAVEIGRTSR STVADLARRT VDEGYGVYLT YNLDGGDRTA DVSAFTRELY

1251 GSEAVRTP
```
(linker is underlined, EndoH sequence is denoted in italics)

Sequence identification of fusion protein EndoS-EndoH (or EndoSH) as expressed in CHO (SEQ. ID NO: 2):

```
   1 MPSIDSLHYL SENSKKEFKE ELSKAGQESQ KVKEILAKAQ QADKQAQELA

51 KMKIPEKIPM KPLHGPLYGG YFRTWHDKTS DPTEKDKVNS MGELPKEVDL

101 AFIFHDWTKD YSLFWKELAT KHVPKLNKQG TRVIRTIPWR FLAGGDNSGI

151 AEDTSKYPNT PEGNKALAKA IVDEYVYKYN LDGLDVDVEH DSIPKVDKKE

201 DTAGVERSIQ VFEEIGKLIG PKGVDKSRLF IMDSTYMADK NPLIERGAPY

251 INLLLVQVYG SQGEKGGWEP VSNRPEKTME ERWQGYSKYI RPEQYMIGFS

301 FYEENAQEGN LWYDINSRKD EDKANGINTD ITGTRAERYA RWQPKTGGVK

351 GGIFSYAIDR DGVAHQPKKY AKQKEFKDAT DNIFHSDYSV SKALKTVMLK

401 DKSYDLIDEK DFPDKALREA VMAQVGTRKG DLERFNGTLR LDNPAIQSLE

451 GLNKFKKLAQ LDLIGLSRIT KLDRSVLPAN MKPGKDTLET VLETYKKDNK

501 EEPATIPPVS LKVSGLTGLK ELDLSGFDRE TLAGLDAATL TSLEKVDISG

551 NKLDLAPGTE NRQIFDTMLS TISNHVGSNE QTVKFDKQKP TGHYPDTYGK

601 TSLRLPVANE KVDLQSQLLF GTVTNQGTLI NSEADYKAYQ NHKIAGRSFV

651 DSNYHYNNFK VSYENYTVKV TDSTLGTTTD KTLATDKEET YKVDFFSPAD

701 KTKAVHTAKV IVGDEKTMMV NLAEGATVIG GSADPVNARK VFDGQLGSET

751 DNISLGWDSK QSIIFKLKED GLIKHWRFFN DSARNPETTN KPIQEASLQI

801 FNIKDYNLDN LLENPNKFDD EKYWITVDTY SAQGERATAF SNTLNNITSK

851 YWRVVFDTKG DRYSSPVVPE LQILGYPLPN ADTIMKTVTT AKELSQQKDK

901 FSQKMLDELK IKEMALETSL NSKIFDVTAI NANAGVLKDC IEKRQLLKKG

951 GGGSGGGGSG GGGSHHHHHH GGGGSGGGGS GGGGSAPAPV KQGPTSVAYV

1001 EVNNNSMLNV GKYTLADGGG NAFDVAVIFA ANINYDTGTK TAYLHFNENV

1051 QRVLDNAVTQ IRPLQQQGIK VLLSVLGNHQ GAGFANFPSQ QAASAFAKQL

1101 SDAVAKYGLD GVDFDDEYAE YGNNGTAQPN DSSFVHLVTA LRANMPDKII

1151 SLYNIGPAAS RLSYGGVDVS DKFDYAWNPY YGTWQVPGIA LPKAQLSPAA

1201 VEIGRTSRST VADLARRTVD EGYGVYLTYN LDGGDRTADV SAFTRELYGS

1251 EAVRTP
```
(linker is underlined, EndoH sequence is denoted in italics)

Sequence of His$_6$-TnGalNAcT(33-421) as expressed in E coli (SEQ. ID NO: 3):

```
   1 MGSSHHHHHH SSGLVPRGSH MSPLRTYLYT PLYNATQPTL RNVERLAANW PKKIPSNYIE

61 DSEEYSIKNI SLSNHTTRAS VVHPPSSITE TASKLDKNMT IQDGAFAMIS PTPLLITKLM

121 DSIKSYVTTE DGVKKAEAVV TLPLCDSMPP DLGPITLNKT ELELEWVEKK FPEVEWGGRY

181 SPPNCTARHR VAIIVPYRDR QQHLAIFLNH MHPFLMKQQI EYGIFIVEQE GNKDFNRAKL

241 MNVGFVESQK LVAEGWQCFV FHDIDLLPLD TRNLYSCPRQ PRHMSASIDK LHFKLPYEDI

301 FGGVSAMTLE QFTRVNGFSN KYWGWGGEDD DMSYRLKKIN YHIARYKMSI ARYAMLDHKK

361 STPNPKRYQL LSQTSKTFQK DGLSTLEYEL VQVVQYHLYT HILVNIDERS
```

Sequence identification of fusion protein EndoF3-EfEndo18A as expressed in *E coli* (SEQ. ID NO: 13):

```
  1 MATALAGSNG VCIAYYITDG RNPTFKLKDI PDKVDMVILF GLKYWSLQDT

51 TKLPGGTGMM GSFKSYKDLD TQIRSLQSRG IKVLQNIDDD VSWQSSKPGG

101 FASAAAYGDA IKSIVIDKWK LDGISLDIEH SGAKPNPIPT FPGYAATGYN

151 GWYSGSMAAT PAFLNVISEL TKYFGTTAPN NKQLQIASGI DVYAWNKIME

201 NFRNNFNYIQ LQSYGANVSR TQLMMNYATG TNKIPASKMV FGAYAEGGTN

251 QANDVEVAKW TPTQGAKGGM MIYTYNSNVS YANAVRDAVK NGGGGSGGGG

301 SGGGGSHHHH HHEFGGGGSG GGGSGGGGSA STVTPKTVMY VEVNNHDFNN

351 VGKYTLAGTN QPAFDMGIIF AANINYDTVN KKPYLYLNER VQQTLNEAET

401 QIRPVQARGT KVLLSILGNH EGAGFANFPT YESADAFAAQ LEQVVNTYHL

451 DGIDFDDEYA EYGKNGTPQP NNSSFIWLLQ ALRNRLGNDK LITFYNIGPA

501 AANSSANPQM SSLIDYAWNP YYSTWNPPQI AGMPASRLGA SAVEVGVNQN

551 LAAQYAKRTK AEQYGIYLMY NLPGEDSSAY ISAATQELYG RKTNYSPTVP

601 TP
```
(linker is underlined, EfEndo18A sequence is denoted in italics)

Sequence identification of fusion protein EndoF2-EfEndo18A as expressed in *E coli* (SEQ. ID NO: 14):

```
  1 MAVNLSNLIA YKNSDHQISA GYYRTWRDSA TASGNLPSMR WLPDSLDMVM

51 VFPDYTPPEN AYWNTLKTNY VPYLHKRGTK VIITLGDLNS ATTTGGQDSI

101 GYSSWAKGIY DKWVGEYNLD GIDIDIESSP SGATLTKFVA ATKALSKYFG

151 PKSGTGKTFV YDTNQNPTNF FIQTAPRYNY VFLQAYGRST TNLTTVSGLY

201 APYISMKQFL PGFSFYEENG YPGNYWNDVR YPQNGTGRAY DYARWQPATG

251 KKGGVFSYAI ERDAPLTSSN DNTLRAPNFR VTKDLIKIMN PGGGGSGGGG

301 SGGGGSHHHH HHEFGGGGSG GGGSGGGGSA STVTPKTVMY VEVNNHDFNN

351 VGKYTLAGTN QPAFDMGIIF AANINYDTVN KKPYLYLNER VQQTLNEAET

401 QIRPVQARGT KVLLSILGNH EGAGFANFPT YESADAFAAQ LEQVVNTYHL

451 DGIDFDDEYA EYGKNGTPQP NNSSFIWLLQ ALRNRLGNDK LITFYNIGPA

501 AANSSANPQM SSLIDYAWNP YYSTWNPPQI AGMPASRLGA SAVEVGVNQN

551 LAAQYAKRTK AEQYGIYLMY NLPGKDSSAY ISAATQELYG RKTNYSPTVP

601 TP
```
(linker is underlined, EfEndo18A sequence is denoted in italics)

Sequence identification of fusion protein EndoS-EfEndo18A as expressed in *E coli* (SEQ. ID NO: 15):

```
  1 MPSIDSLHYL SENSKKEFKE ELSKAGQESQ KVKEILAKAQ QADKQAQELA

51 KMKIPEKIPM KPLHGPLYGG YFRTWHDKTS DPTEKDKVNS MGELPKEVDL

101 AFIFHDWTKD YSLFWKELAT KHVPKLNKQG TRVIRTIPWR FLAGGDNSGI

151 AEDTSKYPNT PEGNKALAKA IVDEYVYKYN LDGLDVDVEH DSIPKVDKKE

201 DTAGVERSIQ VFEEIGKLIG PKGVDKSRLF IMDSTYMADK NPLIERGAPY

251 INLLLVQVYG SQGEKGGWEP VSNRPEKTME ERWQGYSKYI RPEQYMIGFS

301 FYEENAQEGN LWYDINSRKD EDKANGINTD ITGTRAERYA RWQPKTGGVK

351 GGIFSYAIDR DGVAHQPKKY AKQKEFKDAT DNIFHSDYSV SKALKTVMLK

401 DKSYDLIDEK DFPDKALREA VMAQVGTRKG DLERFNGTLR LDNPAIQSLE

451 GLNKFKKLAQ LDLIGLSRIT KLDRSVLPAN MKPGKDTLET VLETYKKDNK
```

-continued

```
 501 EEPATIPPVS LKVSGLTGLK ELDLSGFDRE TLAGLDAATL TSLEKVDISG

551 NKLDLAPGTE NRQIFDTMLS TISNHVGSNE QTVKFDKQKP TGHYPDTYGK

601 TSLRLPVANE KVDLQSQLLF GTVTNQGTLI NSEADYKAYQ NHKIAGRSFV

651 DSNYHYNNFK VSYENYTVKV TDSTLGTTTD KTLATDKEET YKVDFFSPAD

701 KTKAVHTAKV IVGDEKTMMV NLAEGATVIG GSADPVNARK VFDGQLGSET

751 DNISLGWDSK QSIIFKLKED GLIKHWRFFN DSARNPETTN KPIQEASLQI

801 FNIKDYNLDN LLENPNKFDD EKYWITVDTY SAQGERATAF SNTLNNITSK

851 YWRVVFDTKG DRYSSPVVPE LQILGYPLPN ADTIMKTVTT AKELSQQKDK

901 FSQKMLDELK IKEMALETSL NSKIFDVTAI NANAGVLKDC IEKRQLLKKG

951 GGGSGGGGSG GGGSHHHHHH EFGGGGSGGG GSGGGGSAST VTRKTVMYVE

1001 VNNHDFNNVG KYTLAGTNQP AFDMGIIFAA NINYDTVNKK PYLYLNERVQ

1051 QTLNEAETQI RPVQARGTKV LLSILGNHEG AGFANFPTYE SADAFAAQLE

1101 QVVNTYHLDG IDFDDEYAEY GENGTPQPNN SSFIWLLQAL RNRLGNDKLI

1151 TFYNIGPAAA NSSANPQMSS LIDYAWNPYY STWNPPQIAG MPASRLGASA

1201 VEVGVNQNLA AQYAKRTKAE QYGIYLMYNL PGEDSSAYIS AATQELYGRK

1251 TNYSPTVPTP
```
(linker is underlined, EfEndo18A sequence is denoted in italics)

Sequence identification of fusion protein EndoF3-EndoF1 as expressed in *E coli* (SEQ. ID NO: 16):
```
   1 MATALAGSNG VCIAYYITDG RNPTFKLKDI PDKVDMVILF GLKYWSLQDT

51 TKLPGGTGMM GSFKSYKDLD TQIRSLQSRG IKVLQNIDDD VSWQSSKPGG

101 FASAAAYGDA IKSIVIDKWK LDGISLDIEH SGAKPNPIPT FPGYAATGYN

151 GWYSGSMAAT PAFLNVISEL TKYFGTTAPN NKQLQIASGI DVYAWNKIME

201 NFRNNFNYIQ LQSYGANVSR TQLMMNYATG TNKIPASKMV FGAYAEGGTN

251 QANDVEVAKW TPTQGAKGGM MIYTYNSNVS YANAVRDAVK NGGGGSGGGG

301 SGGGGSHHHH HHEFGGGGSG GGGSGGGGSA VTGTTKANIK LFSFTEVNDT

351 NPLNNLNFTL KNSGKPLVDM VVLFSANINY DAANDKVFVS NNPNVQHLLT

401 NRAKYLKPLQ DKGIKVILSI LGNHDRSGIA NLSTARAKAF AQELENTCDL

451 YNLDGVFFDD EYSAYQTPPP SGFVTPSNNA AARLAYETKQ AMPNKLVTVY

501 VYSRTSSFPT AVDGVNAGSY VDYAIHDYGG SYDLATNYPG LAKSGMVMSS

551 QEFNQGRYAT AQALRNIVTK GYGGHMIFAM DPNRSNFTSG QLPALKLIAK

601 ELYGDELVYS NTPYSKDW
```
(linker is underlined, EndoF1 sequence is denoted in italics)

Sequence identification of fusion protein EndoF2-EndoF1 as expressed in *E coli* (SEQ. ID NO: 17):
```
   1 MAVNLSNLIA YKNSDHQISA GYYRTWRDSA TASGNLPSMR WLPDSLDMVM

51 VFPDYTPPEN AYWNTLKTNY VPYLHKRGTK VIITLGDLNS ATTGGQDSI

101 GYSSWAKGIY DKWVGEYNLD GIDIDIESSP SGATLTKFVA ATKALSKYFG

151 PKSGTGKTFV YDTNQNPTNF FIQTAPRYNY VFLQAYGRST TNLTTVSGLY

201 APYISMKQFL PGFSFYEENG YPGNYWNDVR YPQNGTGRAY DYARWQPATG

251 KKGGVFSYAI ERDAPLTSSN DNTLRAPNFR VTKDLIKIMN PGGGGSGGGG

301 SGGGGSHHHH HHEFGGGGSG GGGSGGGGSA VTGTTKANIK LFSFTEVNDT

351 NPLNNLNFTL ENSGKPLVDM VVLFSANINY DAANDKVFVS NNPNVQHLLT

401 NRAKYLKPLQ DKGIKVILSI LGNHDRSGIA NLSTARAKAF AQELKNTCDL
```

```
    451 YNLDGVFFDD EYSAYQTPPP SGFVTPSNNA AARLAYETKQ AMPNKLVTVY

501 VYSRTSSFPT AVDGVNAGSY VDYAIHDYGG SYDLATNYPG LAKSGMVMSS

551 QEFNQGRYAT AQALRNIVTK GYGGHMIFAM DPNRSNFTSG QLPALKLIAK

601 ELYGDELVYS NTPYSKDW
(linker is underlined, EndoF1 sequence is denoted in italics)

Sequence identification of fusion protein EndoS-EndoF1 as expressed in
E coli (SEQ. ID NO: 18):
      1 MPSIDSLHYL SENSKKEFKE ELSKAGQESQ KVKEILAKAQ QADKQAQELA

51 KMKIPEKIPM KPLHGPLYGG YFRTWHDKTS DPTEKDKVNS MGELPKEVDL

101 AFIFHDWTKD YSLFWKELAT KHVPKLNKQG TRVIRTIPWR FLAGGDNSGI

151 AEDTSKYPNT PEGNKALAKA IVDEYVYKYN LDGLDVDVEH DSIPKVDKKE

201 DTAGVERSIQ VFEEIGKLIG PKGVDKSRLF IMDSTYMADK NPLIERGAPY

251 INLLLVQVYG SQGEKGGWEP VSNRPEKTME ERWQGYSKYI RPEQYMIGFS

301 FYEENAQEGN LWYDINSRKD EDKANGINTD ITGTRAERYA RWQPKTGGVK

351 GGIFSYAIDR DGVAHQPKKY AKQKEFKDAT DNIFHSDYSV SKALKTVMLK

401 DKSYDLIDEK DFPDKALREA VMAQVGTRKG DLERFNGTLR LDNPAIQSLE

451 GLNKFKKLAQ LDLIGLSRIT KLDRSVLPAN MKPGKDTLET VLETYKKDNK

501 EEPATIPPVS LKVSGLTGLK ELDLSGFDRE TLAGLDAATL TSLEKVDISG

551 NKLDLAPGTE NRQIFDTMLS TISNHVGSNE QTVKFDKQKP TGHYPDTYGK

601 TSLRLPVANE KVDLQSQLLF GTVTNQGTLI NSEADYKAYQ NHKIAGRSFV

651 DSNYHYNNFK VSYENYTVKV TDSTLGTTTD KTLATDKEET YKVDFFSPAD

701 KTKAVHTAKV IVGDEKTMMV NLAEGATVIG GSADPVNARK VFDGQLGSET

751 DNISLGWDSK QSIIFKLKED GLIKHWRFFN DSARNPETTN KPIQEASLQI

801 FNIKDYNLDN LLENPNKFDD EKYWITVDTY SAQGERATAF SNTLNNITSK

851 YWRVVFDTKG DRYSSPVVPE LQILGYPLPN ADTIMKTVTT AKELSQQKDK

901 FSQKMLDELK IKEMALETSL NSKIFDVTAI NANAGVLKDC IEKRQLLKK<u>G</u>

951 <u>GGGSGGGGSG GGGSHHHHHH EFGGGGSGGG GSGGGGS</u>AVT GTTKANIKLF

1001 SFTEVNDTNP LNNLNFTLKN SGKPLVDMVV LFSANINYDA ANDKVFVSNN

1051 PNVQHLLTNR AKYLKPLQDK GIKVILSILG NHDRSGIANL STARAKAFAQ

1101 ELKNTCDLYN LDGVFFDDEY SAYQTPPPSG FVTPSNNAAA RLAYETKQAM

1151 PNKLVTVYVY SRTSSFPTAV DGVNAGSYVD YAIHDYGGSY DLATNYPGLA

1201 KSGMVMSSQE FNQGRYATAQ ALRNIVTKGY GGHMIFAMDP NRSNFTSGQL

1251 PALKLIAKEL YGDELVYSNT PYSKDW
(linker is underlined, EndoF1 sequence is denoted in italics)

Sequence identification of fusion protein EndoF3-EndoH as expressed in
E coli (SEQ. ID NO: 19):
      1 MATALAGSNG VCIAYYITDG RNPTFKLKDI PDKVDMVILF GLKYWSLQDT

51 TKLPGGTGMM GSFKSYKDLD TQIRSLQSRG IKVLQNIDDD VSWQSSKPGG

101 FASAAAYGDA IKSIVIDKWK LDGISLDIEH SGAKPNPIPT FPGYAATGYN

151 GWYSGSMAAT PAFLNVISEL TKYFGTTAPN NKQLQIASGI DVYAWNKIME

201 NFRNNFNYIQ LQSYGANVSR TQLMMNYATG TNKIPASKMV FGAYAEGGTN

251 QANDVEVAKW TPTQGAKGGM MIYTYNSNVS YANAVRDAVK N<u>GGGGSGGGG</u>

301 <u>SGGGGSHHHH HHEFGGGGSG GGGSGGGGS</u>A PAPVKQGPTS VAYEVNNNS
```

-continued

```
    351 MLNVGKYTLA DGGGNAFDVA VIFAANINYD TGTKTAYLHF NENVQRVLDN

401 AVTQIRPLQQ QGIKVLLSVL GNHQGAGFAN FPSQQAASAF AKQLSDAVAK

451 YGLDGVDFDD EYAEYGNNGT AQPNDSSFVH LVTALRANMP DKIISLYNIG

501 PAASRLSYGG VDVSDKFDYA WNPYYGTWQV PGIALPKAQL SPAAVEIGRT

551 SRSTVADLAR RTVDEGYGVY LTYNLDGGDR TADVSAFTRE LYGSEAVRTP
```
(linker is underlined, EndoH sequence is denoted in italics)

Sequence identification of fusion protein EndoF2-EndoH as expressed in *E coli* (SEQ. ID NO: 20):

```
      1 MAVNLSNLIA YKNSDHQISA GYYRTWRDSA TASGNLPSMR WLPDSLDMVM

51 VFPDYTPPEN AYWNTLKTNY VPYLHKRGTK VIITLGDLNS ATTTGGQDSI

101 GYSSWAKGIY DKWVGEYNLD GIDIDIESSP SGATLTKFVA ATKALSKYFG

151 PKSGTGKTFV YDTNQNPTNF FIQTAPRYNY VFLQAYGRST TNLTTVSGLY

201 APYISMKQFL PGFSFYEENG YPGNYWNDVR YPQNGTGRAY DYARWQPATG

251 KKGGVFSYAI ERDAPLTSSN DNTLRAPNFR VTKDLIKIMN PGGGGSGGGG

301 SGGGGSHHHH HHEFGGGGSG GGGSGGGGSA PAPVKQGPTS VAYVEVNNNS

351 MLNVGKYTLA DGGGNAFDVA VIFAANINYD TGTKTAYLHF NENVQRVLDN

401 AVTQIRPLQQ QGIKVLLSVL GNHQGAGFAN FPSQQAASAF AKQLSDAVAK

451 YGLDGVDFDD EYAEYGNNGT AQPNDSSFVH LVTALRANMP DKIISLYNIG

501 PAASRLSYGG VDVSDKFDYA WNPYYGTWQV PGIALPKAQL SPAAVEIGRT

551 SRSTVADLAR RTVDEGYGVY LTYNLDGGDR TADVSAFTRE LYGSEAVRTP
```
(linker is underlined, EndoH sequence is denoted in italics)

Sequence identification of fusion protein His$_6$-EndoS-EndoH (EndoS-EndoH without GS-linker) as expressed in *E coli* (SEQ. ID NO: 21):

```
      1 MGSSHHHHHH SSGLVPRGSH MPSIDSLHYL SENSKKEFKE ELSKAGQESQ

51 KVKEILAKAQ QADKQAQELA KMKIPEKIPM KPLHGPLYGG YFRTWHDKTS

101 DPTEKDKVNS MGELPKEVDL AFIFHDWTKD YSLFWKELAT KHVPKLNKQG

151 TRVIRTIPWR FLAGGDNSGI AEDTSKYPNT PEGNKALAKA IVDEYVYKYN

201 LDGLDVDVEH DSIPKVDKKE DTAGVERSIQ VFEEIGKLIG PKGVDKSRLF

251 IMDSTYMADK NPLIERGAPY INLLLVQVYG SQGEKGGWEP VSNRPEKTME

301 ERWQGYSKYI RPEQYMIGFS FYEENAQEGN LWYDINSRKD EDKANGINTD

351 ITGTRAERYA RWQPKTGGVK GGIFSYAIDR DGVAHQPKKY AKQKEFKDAT

401 DNIFHSDYSV SKALKTVMLK DKSYDLIDEK DFPDKALREA VMAQVGTRKG

451 DLERFNGTLR LDNPAIQSLE GLNKFKKLAQ LDLIGLSRIT KLDRSVLPAN

501 MKPGKDTLET VLETYKKDNK EEPATIPPVS LKVSGLTGLK ELDLSGFDRE

551 TLAGLDAATL TSLEKVDISG NKLDLAPGTE NRQIFDTMLS TISNHVGSNE

601 QTVKFDKQKP TGHYPDTYGK TSLRLPVANE KVDLQSQLLF GTVTNQGTLI

651 NSEADYKAYQ NHKIAGRSFV DSNYHYNNFK VSYENYTVKV TDSTLGTTTD

701 KTLATDKEET YKVDFFSPAD KTKAVHTAKV IVGDEKTMMV NLAEGATVIG

751 GSADPVNARK VFDGQLGSET DNISLGWDSK QSIIFKLKED GLIKHWRFFN

801 DSARNPETTN KPIQEASLQI FNIKDYNLDN LLENPNKFDD EKYWITVDTY

851 SAQGERATAF SNTLNNITSK YWRVVFDTKG DRYSSPVVPE LQILGYPLPN

901 ADTIMKTVTT AKELSQQKDK FSQKMLDELK IKEMALETSL NSKIFDVTAI

951 NANAGVLKDC IEKRQLLKKA PAPVKQGPTS VAYVEVNNNS MLNVGKYTLA

1001 DGGGNAFDVA VIFAANINYD TGTKTAYLHF NENVQRVLDN AVTQIRPLQQ
```

1051 *QGIKVLLSVL GNHQGAGFAN FPSQQAASAF AKQLSDAVAK YGLDGVDFDD*

1101 *EYAEYGNNGT AQPNDSSFVH LVTALRANMP DKIISLYNIG PAASRLSYGG*

1151 *VDVSDKFDYA WNPYYGTWQV PGIALPKAQL SPAAVEIGRT SRSTVADLAR*

1201 *RTVDEGYGVY LTYNLDGGDR TADVSAFTRE LYGSEAVRTP*
(N-terminal sequence including His-tag and thrombin cleavage site is underlined, EndoH sequence is in italics)

Sequence identification of DNA encoding for fusion protein EndoF3-EfEndo18A as expressed in *E coli* (SEQ. ID NO: 22):
ATGGCTACAGCGCTGGCTGGTTCTAACGGGGTCTGCATCGCGTATTACATCACCGATGGGCGTAATCCGACG

TTCAAATTGAAAGACATCCCGGATAAAGTAGACATGGTAATTCTTTTTGGTCTTAAGTATTGGTCATTGCAG

GATACAACCAAATTGCCAGGGGGTACTGGTATGATGGGTTCGTTTAAATCCTACAAGGACCTGGACACCCAG

ATTCGTAGTCTTCAAAGCCGTGGAATCAAAGTGTTGCAGAACATTGACGACGACGTCTCATGGCAGTCCTCG

AAGCCGGGTGGGTTCGCTTCCGCCGCTGCTTACGGGGATGCTATTAAGAGTATCGTAATTGATAAGTGGAAG

CTGGACGGGATTAGCTTGGATATTGAGCATTCGGGGCTAAACCCAACCCTATCCCAACTTTTCCTGGATAT

GCCGCGACAGGATATAATGGCTGGTATTCAGGATCTATGGCAGCCACGCCTGCCTTTCTTAATGTTATCTCA

GAGCTTACTAAATACTTTGGTACAACGGCACCGAATAATAAGCAACTTCAGATTGCTTCGGGTATTGACGTA

TATGCCTGGAATAAAATCATGGAGAACTTTCGTAATAACTTCAACTACATCCAATTACAGTCATACGGAGCT

AATGTCTCTCGTACTCAACTTATGATGAATTACGCAACGGGAACTAATAAAATTCCCGCCTCTAAAATGGTT

TTCGGCGCCTACGCAGAGGGTGGCACTAACCAGGCAAATGACGTGGAGGTCGCCAAGTGGACACCTACGCAG

GGCGCAAAGGGCGGTATGATGATCTATACTTACAATTCGAACGTGAGCTATGCAAATGCGGTTCGCGACGCA

GTGAAAAATGGCGGCGGCGGCTCTGGCGGCGGCGGCTCTGGCGGCGGCGGCTCTCACCACCACCACCACCAC

GAATTCGGCGGCGGCGGCTCTGGCGGCGGCGGCTCTGGCGGCGGCGGCTCTGCTTCAACCGTAACCCCTAAA

ACGGTTATGTACGTAGAAGTAAATAACCACGATTTCAACAATGTCGGGAAATACACTCTTGCCGGTACTAAT

CAGCCGGCGTTCGATATGGGTATTATTTTTGCCGCCAACATCAATTATGACACCGTCAATAAGAAACCATAC

CTGTACTTGAACGAGCGCGTACAGCAAACACTGAATGAAGCGGAGACGCAGATCCGTCCGGTCCAGGCACGT

GGAACGAAGGTTTTGCTTTCCATCTTGGGTAATCACGAAGGCGCAGGATTTGCCAATTTTCCTACGTATGAG

TCGGCGGACGCTTTCGCCGCGCAACTTGAGCAGGTTGTCAATACGTACCATTTAGACGGGATTGATTTCGAT

GATGAGTACGCCGAGTACGGAAAAAACGGGACCCCTCAGCCGAACAACTCATCCTTCATCTGGTTACTGCAA

GCTCTTCGCAACCGTCTGGGAAATGATAAACTTATCACTTTCTACAACATTGGCCCGGCAGCCGCTAACAGC

AGCGCAAACCCTCAAATGTCATCTTTGATTGACTATGCCTGGAATCCCTATTATTCGACATGGAACCCCCCA

CAAATTGCAGGTATGCCTGCCTCCCGCCTGGGGGCTTCTGCGGTTGAAGTGGGCGTTAACCAGAATCTTGCA

GCACAGTATGCCAAGCGTACTAAGGCTGAGCAGTATGGAATCTATCTGATGTACAATCTGCCAGGAAAAGAT

TCTAGCGCTTATATCTCAGCAGCGACTCAGGAGCTGTATGGGCGCAAGACGAACTATAGCCCCACGGTCCCG

ACTCCGTGATAA

Sequence identification of DNA encoding for fusion protein EndoF2-EfEndo18A as expressed in *E coli* (SEQ. ID NO: 23):
ATGGCGGTAAACCTTAGTAATCTTATCGCTTATAAAAATAGTGACCATCAGATCAGTGCGGGATATTACGT

ACATGGCGTGACAGCGCCACAGCCAGTGGTAATCTTCCTAGTATGCGTTGGTTGCCAGACTCATTGGACATG

GTAATGGTATTCCCAGACTATACTCCTCCGGAAAATGCGTATTGGAACACACTGAAGACTAACTACGTACCA

TACCTGCATAAGCGTGGCACGAAAGTTATTATCACATTGGGGGACCTTAACTCTGCAACGACCACGGGAGGG

CAAGATTCTATTGGGTATTCATCGTGGGCCAAAGGAATCTATGATAAATGGGTGGGCGAGTATAATCTTGAT

GGAATCGATATTGACATCGAATCGTCACCGTCCGGTGCGACCTTAACGAAGTTTGTTGCGGCAACAAAAGCG

TTGTCAAAGTATTTTGGACCAAAGAGTGGGACAGGCAAGACCTTTGTATACGATACCAATCAGAATCCGACT

-continued

AATTTCTTTATCCAAACTGCCCCACGCTACAACTACGTATTTCTTCAAGCATACGGGCGCTCGACCACTAAT

CTGACGACGGTCTCTGGATTATACGCCCCCTATATTTCAATGAAACAATTTCTGCCCGGCTTCTCTTTTTAC

GAAGAAAACGGTTACCCAGGTAATTATTGGAATGATGTGCGTTACCCCCAGAACGGTACAGGCCGTGCCTAC

GACTACGCGCGCTGGCAGCCCGCCACGGGAAAAAAGGAGGGGTGTTCAGTTATGCCATCGAGCGCGACGCC

CCTCTTACATCGTCAAACGACAATACCCTGCGTGCGCCTAACTTTCGTGTAACGAAGGACTTAATCAAAATT

ATGAATCCTGGCGGCGGCGGCTCTGGCGGCGGCGGCTCTGGCGGCGGCGGCTCTCACCACCACCACCACCAC

GAATTCGGCGGCGGCGGCTCTGGCGGCGGCGGCTCTGGCGGCGGCGGCTCTGCTTCAACCGTAACCCCTAAA

ACGGTTATGTACGTAGAAGTAAATAACCACGATTTCAACAATGTCGGGAAATACACTCTTGCCGGTACTAAT

CAGCCGGCGTTCGATATGGGTATTATTTTTGCCGCCAACATCAATTATGACACCGTCAATAAGAAACCATAC

CTGTACTTGAACGAGCGCGTACAGCAAACACTGAATGAAGCGGAGACGCAGATCCGTCCGGTCCAGGCACGT

GGAACGAAGGTTTTGCTTTCCATCTTGGGTAATCACGAAGGCGCAGGATTTGCCAATTTTCCTACGTATGAG

TCGGCGGACGCTTTCGCCGCGCAACTTGAGCAGGTTGTCAATACGTACCATTTAGACGGGATTGATTTCGAT

GATGAGTACGCCGAGTACGGAAAAAACGGGACCCCTCAGCCGAACAACTCATCCTTCATCGGTTACTGCAA

GCTCTTCGCAACCGTCTGGGAAATGATAAACTTATCACTTTCTACAACATTGGCCCGGCAGCCGCTAACAGC

AGCGCAAACCCTCAAATGTCATCTTTGATTGACTATGCCTGGAATCCCTATTATTCGACATGGAACCCCCCA

CAAATTGCAGGTATGCCTGCCTCCCGCCTGGGGGCTTCTGCGGTTGAAGTGGGCGTTAACCAGAATCTTGCA

GCACAGTATGCCAAGCGTACTAAGGCTGAGCAGTATGGAATCTATCTGATGTACAATCTGCCAGGAAAAGAT

TCTAGCGCTTATATCTCAGCAGCGACTCAGGAGCTGTATGGGCGCAAGACGAACTATAGCCCCACGGTCCCG

ACTCCGTGATAA

Sequence identification of DNA encoding for fusion protein EndoS-EfEndo18A
as expressed in *E coli* (SEQ. ID NO: 24):
ATGCCGTCAATCGATTCGCTGCATTATCTGAGCGAAAACTCTAAAAAAGAATTTAAAGAAGAACTGAGCAAA

GCGGGCCAGGAATCTCAAAAAGTTAAAGAAATCCTGGCAAAAGCTCAGCAAGCCGATAAACAGGCACAAGAA

CTGGCTAAAATGAAAATTCCGGAAAAAATCCCGATGAAACCGCTGCATGGTCCGCTGTACGCGGTTATTTC

CGTACCTGGCACGATAAAACGTCAGACCCGACCGAAAAAGACAAAGTCAACTCGATGGGCGAACTGCCGAAA

GAAGTGGATCTGGCTTTTATTTTCCATGATTGGACCAAAGACTACTCTCTGTTTTGGAAAGAACTGGCAACG

AAACACGTTCCGAAACTGAACAAACAGGGTACGCGTGTCATTCGTACCATTCCGTGGCGCTTCCTGGCTGGC

GGTGATAATTCAGGCATCGCGGAAGACACCTCGAAATATCCGAACACGCCGGAAGGTAATAAAGCGCTGGCC

AAAGCAATCGTCGATGAATACGTGTACAAATACAATCTGGACGGCCTGGATGTGGACGTTGAACATGATTCA

ATTCCGAAAGTGGATAAAAAAGAAGACACCGCCGGCGTGGAACGTTCGATCCAGGTTTTTGAAGAAATTGGT

AAACTGATCGGCCCGAAAGGTGTTGATAAAAGCCGTCTGTTCATCATGGATTCTACCTATATGGCCGACAAA

AATCCGCTGATTGAACGCGGTGCACCGTACATCAACCTGCTGCTGGTCCAGGTGTATGGCAGCCAAGGTGAA

AAAGGCGGTTGGGAACCGGTGTCTAACCGTCCGGAAAAAACCATGGAAGAACGCTGGCAGGGCTACTCAAAA

TATATTCGTCCGGAACAATACATGATCGGCTTTTCGTTCTATGAAGAAAACGCGCAGGAAGGTAATCTGTGG

TACGATATTAATAGTCGCAAAGATGAAGACAAAGCCAACGGCATTAATACCGATATCACGGGTACCCGTGCG

GAACGCTATGCCCGTTGGCAGCCGAAAAACCGGCGGTGTTAAAGGCGGTATTTTTAGCTACGCGATCGATCGT

GACGGTGTCGCCCATCAGCCGAAAAAATACGCAAACAAAAAGAGTTCAAAGATGCTACCGACAACATCTTC

CACAGCGATTACAGTGTCTCCAAAGCGCTGAAAACCGTGATGCTGAAAGATAAATCTTACGATCTGATCGAC

GAAAAGATTTTCCGGACAAAGCGCTGCGCGAAGCCGTTATGGCACAGGTCGGCACCCGCAAAGGTGACCTG

GAACGTTTTAATGGCACGCTGCGCCTGGATAACCCGGCCATTCAGAGCCTGGAAGGTCTGAATAAATTCAAA

AAACTGGCACAACTGGACCTGATTGGCCTGAGCCGTATCACCAAACTGGATCGCTCTGTGCTGCCGGCCAAC

ATGAAACCGGGTAAAGACACGCTGGAAACCGTTCTGGAAACCTACAAAAAAGATAACAAAGAAGAACCGGCA

-continued

ACGATCCCGCCGGTGTCTCTGAAAGTTTCCGGCCTGACCGGTCTGAAAGAACTGGATCTGAGCGGCTTTGAC

CGTGAAACGCTGGCAGGTCTGGATGCGGCCACGCTGACCAGTCTGGAAAAAGTTGATATTTCCGGCAATAAA

CTGGACCTGGCGCCGGGTACCGAAAACCGCCAGATTTTTGATACGATGCTGAGTACCATCTCCAACCATGTT

GGCAGCAATGAACAGACCGTCAAATTCGACAAACAAAAACCGACGGGCCACTACCCGGATACGTATGGTAAA

ACCAGCCTGCGTCTGCCGGTCGCCAACGAAAAGTGGATCTGCAGTCTCAACTGCTGTTTGGCACGGTTACC

AATCAGGGTACCCTGATTAACAGCGAAGCAGATTACAAGGCTTACCAAAACCATAAAATCGCGGGTCGCTCA

TTTGTGGATTCGAACTACCACTACAACAACTTCAAAGTTAGTTACGAAAACTACACCGTTAAAGTCACGGAT

TCCACCCTGGGCACCACGACCGATAAAACGCTGGCCACCGACAAAGAAGAAACCTACAAAGTCGATTTCTTT

AGCCCGGCAGACAAAACGAAAGCGGTGCATACCGCCAAAGTGATTGTTGGCGATGAAAAAACCATGATGGTG

AACCTGGCTGAAGGTGCGACGGTTATCGGCGGTTCCGCAGACCCGGTTAACGCTCGCAAAGTCTTTGATGGC

CAGCTGGGTAGTGAAACCGATAATATTTCCCTGGGTTGGGACTCAAAACAGTCGATTATCTTCAAACTGAAA

GAAGACGGCCTGATCAAACACTGGCGTTTCTTTAACGATAGTGCCCGCAATCCGGAAACGACCAACAAACCG

ATTCAGGAAGCATCCCTGCAAATCTTCAACATCAAAGATTACAACCTGGACAATCTGCTGGAAAACCCGAAT

AAATTCGATGACGAAAAATACTGGATCACGGTGGATACCTATAGCGCGCAGGGCGAACGTGCTACGGCGTTT

AGTAACACCCTGAACAATATTACGTCCAAATACTGGCGTGTGGTTTTCGATACCAAAGGTGACCGCTATAGC

TCTCCGGTCGTGCCGGAACTGCAGATTCTGGGCTATCCGCTGCCGAATGCTGATACGATCATGAAAACCGTG

ACGACCGCGAAAGAACTGTCACAGCAAAAAGATAAATTCTCGCAGAAAATGCTGGACGAACTGAAAATTAAA

GAAATGGCTCTGGAAACCAGCCTGAACAGTAAAATTTTCGATGTTACGGCGATCAATGCTAACGCTGGTGTG

CTGAAAGACTGTATTGAAAAACGCCAACTGCTGAAAAAAGGCGGCGGCGGCTCTGGCGGCGGCGGCTCTGGC

GGCGGCGGCTCTCACCACCACCACCACCACGAATTCGGCGGCGGCGGCTCTGGCGGCGGCGGCTCTGGCGGC

GGCGGCTCTGCTTCAACCGTAACCCCTAAAACGGTTATGTACGTAGAAGTAAATAACCACGATTTCAACAAT

GTCGGGAAATACACTCTTGCCGGTACTAATCAGCCGGCGTTCGATATGGGTATTATTTTGCCGCCAACATC

AATTATGACACCGTCAATAAGAAACCATACCTGTACTTGAACGAGCGCGTACAGCAAACACTGAATGAAGCG

GAGACGCAGATCCGTCCGGTCCAGGCACGTGGAACGAAGGTTTTGCTTTCCATCTTGGGTAATCACGAAGGC

GCAGGATTTGCCAATTTTCCTACGTATGAGTCGGCGGACGCTTTCGCCGCGCAACTTGAGCAGGTTGTCAAT

ACGTACCATTTAGACGGGATTGATTTCGATGATGAGTACGCCGAGTACGGAAAAAACGGGACCCCTCAGCCG

AACAACTCATCCTTCATCTGGTTACTGCAAGCTCTTCGCAACCGTCTGGGAAATGATAAACTTATCACTTTC

TACAACATTGGCCCGGCAGCCGCTAACAGCAGCGCAAACCCTCAAATGTCATCTTTGATTGACTATGCCTGG

AATCCCTATTATTCGACATGGAACCCCCCACAAATTGCAGGTATGCCTGCCTCCCGCCTGGGGGCTTCTGCG

GTTGAAGTGGGCGTTAACCAGAATCTTGCAGCACAGTATGCCAAGCGTACTAAGGCTGAGCAGTATGGAATC

TATCTGATGTACAATCTGCCAGGAAAAGATTCTAGCGCTTATATCTCAGCAGCGACTCAGGAGCTGTATGGG

CGCAAGACGAACTATAGCCCCACGGTCCCGACTCCGTGATAA

Sequence identification of DNA encoding for fusion protein EndoF3-EndoF1 as
expressed in *E coli* (SEQ. ID NO: 25):
ATGGCTACAGCGCTGGCT -continued GAGCTTACTAAATACTTTGGTACAACGGCACCGAATAATAAGCAACTTCAGATTGCTTCGGGTATTGACGTA
TATGCCTGGAATAAAATCATGGAGAACTTTCGTAATAACTTCAACTACATCCAATTACAGTCATACGGAGCT
AATGTCTCTCGTACTCAACTTATGATGAATTACGCAACGGGAACTAATAAAATTCCCGCCTCTAAAATGGTT
TTCGGCGCCTACGCAGAGGGTGGCACTAACCAGGCAAATGACGTGGAGGTCGCCAAGTGGACACCTACGCAG
GGCGCAAAGGGCGGTATGATGATCTATACTTACAATTCGAACGTGAGCTATGCAAATGCGGTTCGCGACGCA
GTGAAAAATGGCGGCGGCGGCTCTGGCGGCGGCGGCTCTGGCGGCGGCGGCTCTCACCACCACCACCACCAC
GAATTCGGCGGCGGCGGCTCTGGCGGCGGCGGCTCTGGCGGCGGCGGCTCTGCGGTAACCGGGACAACGAAG
GCTAACATCAAACTTTTTAGTTTTACAGAGGTAAACGACACTAATCCGTTGAACAATCTGAACTTTACCTTA
AAAAACTCGGGAAAACCCTTAGTAGATATGGTAGTGTTATTTTCCGCGAACATTAACTATGACGCGGCCAAC
GATAAGGTCTTCGTATCGAATAATCCGAACGTACAGCATCTTTTGACCAATCGTGCGAAGTACCTTAAGCCG
TTACAAGACAAGGGGATCAAGGTGATTTTGTCAATCTTAGGGAACCATGATCGCTCCGGGATCGCCAATTTG
AGTACGGCTCGTGCGAAGGCATTTGCTCAGGAACTGAAGAATACTTGCGATTTGTATAATTTAGACGGGGTA
TTCTTTGATGATGAGTACTCTGCTTACCAAACGCCACCGCCGAGCGGCTTCGTGACACCCAGTAATAACGCC
GCAGCTCGCCTTGCTTATGAAACAAAGCAGGCTATGCCAAACAAGCTGGTCACGGTGTACGTCTATTCCCGC
ACTTCGAGTTTTCCCACAGCGGTAGACGGGGTCAACGCCGGGTCCTACGTAGACTATGCGATTCATGACTAC
GGTGGCTCATACGACTTGGCTACTAATTATCCGGGGTTGGCTAAGTCTGGGATGGTGATGTCTAGTCAGGAG
TTTAACCAGGGCCGTTACGCGACTGCACAAGCATTGCGCAACATTGTGACCAAGGGCTATGGAGGCCACATG
ATCTTTGCCATGGACCCCAATCGTTCTAATTTCACGTCAGGGCAACTGCCCGCACTGAAGCTGATTGCCAAG
GAGCTTTACGGGGATGAGCTTGTGTACAGCAACACTCCTTACAGTAAGGATTGGTGATAA Sequence identification of DNA encoding for fusion protein EndoF2-EndoF1 as expressed in *E coli* (SEQ. ID NO: 26):
ATGGCGGTAAACCTTAGTAATCTTATCGCTTATAAAAATAGTGACCATCAGATCAGTGCGGGATATTACCGT

ACATGGCGTGACAGCGCCACAGCCAGTGGTAATCTTCCTAGTATGCGTTGGTTGCCAGACTCATTGGACATG

GTAATGGTATTCCCAGACTATACTCCTCCGGAAAATGCGTATTGGAACACACTGAAGACTAACTACGTACCA

TACCTGCATAAGCGTGGCACGAAAGTTATTATCACATTGGGGGACCTTAACTCTGCAACGACCACGGGAGGG

CAAGATTCTATTGGGTATTCATCGTGGGCCAAAGGAATCTATGATAAATGGGTGGGCGAGTATAATCTTGAT

GGAATCGATATTGACATCGAATCGTCACCGTCCGGTGCGACCTTAACGAAGTTTGTTGCGGCAACAAAAGCG

TTGTCAAAGTATTTTGGACCAAAGAGTGGGACAGGCAAGACCTTTGTATACGATACCAATCAGAATCCGACT

AATTTCTTTATCCAAACTGCCCCACGCTACAACTACGTATTTCTTCAAGCATACGGGCGCTCGACCACTAAT

CTGACGACGGTCTCTGGATTATACGCCCCCTATATTTCAATGAAACAATTTCTGCCCGGCTTCTCTTTTTAC

GAAGAAAACGGTTACCCAGGTAATTATTGGAATGATGTGCGTTACCCCCAGAACGGTACAGGCCGTGCCTAC

GACTACGCGCGCTGGCAGCCCGCCACGGGAAAAAAAGGAGGGGTGTTCAGTTATGCCATCGAGCGCGACGCC

CCTCTTACATCGTCAAACGACAATACCCTGCGTGCGCCTAACTTTCGTGTAACGAAGGACTTAATCAAAATT

ATGAATCCTGGCGGCGGCGGCTCTGGCGGCGGCGGCTCTGGCGGCGGCGGCTCTCACCACCACCACCACCAC

GAATTCGGCGGCGGCGGCTCTGGCGGCGGCGGCTCTGGCGGCGGCGGCTCTGCGGTAACCGGGACAACGAAG

GCTAACATCAAACTTTTTAGTTTTACAGAGGTAAACGACACTAATCCGTTGAACAATCTGAACTTTACCTTA

AAAAACTCGGGAAAACCCTTAGTAGATATGGTAGTGTTATTTTCCGCGAACATTAACTATGACGCGGCCAAC

GATAAGGTCTTCGTATCGAATAATCCGAACGTACAGCATCTTTTGACCAATCGTGCGAAGTACCTTAAGCCG

TTACAAGACAAGGGGATCAAGGTGATTTTGTCAATCTTAGGGAACCATGATCGCTCCGGGATCGCCAATTTG

AGTACGGCTCGTGCGAAGGCATTTGCTCAGGAACTGAAGAATACTTGCGATTTGTATAATTTAGACGGGGTA

TTCTTTGATGATGAGTACTCTGCTTACCAAACGCCACCGCCGAGCGGCTTCGTGACACCCAGTAATAACGCC

GCAGCTCGCCTTGCTTATGAAACAAAGCAGGCTATGCCAAACAAGCTGGTCACGGTGTACGTCTATTCCCGC

-continued

ACTTCGAGTTTTCCCACAGCGGTAGACGGGGTCAACGCCGGGTCCTACGTAGACTATGCGATTCATGACTAC

GGTGGCTCATACGACTTGGCTACTAATTATCCGGGGTTGGCTAAGTCTGGGATGGTGATGTCTAGTCAGGAG

TTTAACCAGGGCCGTTACGCGACTGCACAAGCATTGCGCAACATTGTGACCAAGGGCTATGGAGGCCACATG

ATCTTTGCCATGGACCCCAATCGTTCTAATTTCACGTCAGGGCAACTGCCCGCACTGAAGCTGATTGCCAAG

GAGCTTTACGGGGATGAGCTTGTGTACAGCAACACTCCTTACAGTAAGGATTGGTGATAA

Sequence identification of DNA encoding for fusion protein EndoS-EndoF1 as expressed in E coli (SEQ. ID NO: 27):
ATGCCGTCAATCGATTCGCTGCATTATCTGAGCGAAAACTCTAAAAAAGAATTTAAAGAAGAACTGAGCAAA

GCGGGCCAGGAATCTCAAAAAGTTAAAGAAATCCTGGCAAAAGCTCAGCAAGCCGATAAACAGGCACAAGAA

CTGGCTAAAATGAAAATTCCGGAAAAAATCCCGATGAAACCGCTGCATGGTCCGCTGTACGGCGGTTATTTC

CGTACCTGGCACGATAAAAACGTCAGACCCGACCGAAAAAGACAAAGTCAACTCGATGGGCGAACTGCCGAAA

GAAGTGGATCTGGCTTTTATTTTCCATGATTGGACCAAAGACTACTCTCTGTTTTGGAAAGAACTGGCAACG

AAACACGTTCCGAAACTGAACAAACAGGGTACGCGTGTCATTCGTACCATTCCGTGGCGCTTCCTGGCTGGC

GGTGATAATTCAGGCATCGCGGAAGACACCTCGAAATATCCGAACACGCCGGAAGGTAATAAAGCGCTGGCC

AAAGCAATCGTCGATGAATACGTGTACAAATACAATCTGGACGGCCTGGATGTGGACGTTGAACATGATTCA

ATTCCGAAAGTGGATAAAAAAGAAGACACCGCCGGCGTGAACGTTCGATCCAGGTTTTTGAAGAAATTGGT

AAACTGATCGGCCCGAAAGGTGTTGATAAAAGCCGTCTGTTCATCATGGATTCTACCTATATGGCCGACAAA

AATCCGCTGATTGAACGCGGTGCACCGTACATCAACCTGCTGCTGGTCCAGGTGTATGGCAGCCAAGGTGAA

AAAGGCGGTTGGGAACCGGTGTCTAACCGTCCGGAAAAAACCATGGAAGAACGCTGGCAGGGCTACTCAAAA

TATATTCGTCCGGAACAATACATGATCGGCTTTTCGTTCTATGAAGAAAACGCGCAGGAAGGTAATCTGTGG

TACGATATTAATAGTCGCAAAGATGAAGACAAAGCCAACGGCATTAATACCGATATCACGGGTACCCGTGCG

GAACGCTATGCCCGTTGGCAGCCGAAAACCGGCGGTGTTAAAGGCGGTATTTTTAGCTACGCGATCGATCGT

GACGGTGTCGCCCATCAGCCGAAAAAATACGCAAACAAAAAGAGTTCAAAGATGCTACCGACAACATCTTC

CACAGCGATTACAGTGTCTCCAAAGCGCTGAAAACCGTGATGCTGAAAGATAAATCTTACGATCTGATCGAC

GAAAAAGATTTTCCGGACAAAGCGCTGCGCGAAGCCGTTATGGCACAGGTCGGCACCCGCAAAGGTGACCTG

GAACGTTTTAATGGCACGCTGCGCCTGGATAACCCGGCCATTCAGAGCCTGGAAGGTCTGAATAAATTCAAA

AAACTGGCACAACTGGACCTGATTGGCCTGAGCCGTATCACCAAACTGGATCGCTCTGTGCTGCCGGCCAAC

ATGAAACCGGGTAAAGACACGCTGGAAACCGTTCTGGAAACCTACAAAAAAGATAACAAAGAAGAACCGGCA

ACGATCCCGCCGGTGTCTCTGAAAGTTTCCGGCCTGACCGGTCTGAAAGAACTGGATCTGAGCGGCTTTGAC

CGTGAAACGCTGGCAGGTCTGGATGCGGCCACGCTGACCAGTCTGGAAAAAGTTGATATTTCCGGCAATAAA

CTGGACCTGGCGCCGGGTACCGAAAACCGCCAGATTTTTGATACGATGCTGAGTACCATCTCCAACCATGTT

GGCAGCAATGAACAGACCGTCAAATTCGACAAACAAAAACCGACGGGCCACTACCCGGATACGTATGGTAAA

ACCAGCCTGCGTCTGCCGGTCGCCAACGAAAAAGTGGATCTGCAGTCTCAACTGCTGTTTGGCACGGTTACC

AATCAGGGTACCCTGATTAACAGCGAAGCAGATTACAAGGCTTACCAAAACCATAAAATCGCGGGTCGCTCA

TTTGTGGATTCGAACTACCACTACAACAACTTCAAAGTTAGTTACGAAAACTACACCGTTAAAGTCACGGAT

TCCACCCTGGGCACCACGACCGATAAAACGCTGGCCACCGACAAAGAAGAAACCTACAAAGTCGATTTCTTT

AGCCCGGCAGACAAAACGAAAGCGGTGCATACCGCCAAAGTGATTGTTGGCGATGAAAAAACCATGATGGTG

AACCTGGCTGAAGGTGCGACGGTTATCGGCGGTTCCGCAGACCCGGTTAACGCTCGCAAAGTCTTTGATGGC

CAGCTGGGTAGTGAAACCGATAATATTTCCCTGGGTTGGGACTCAAAACAGTCGATTATCTTCAAACTGAAA

GAAGACGGCCTGATCAAACACTGGCGTTTCTTTAACGATAGTGCCCGCAATCCGGAAACGACCAACAAACCG

ATTCAGGAAGCATCCCTGCAAATCTTCAACATCAAAGATTACAACCTGGACAATCTGCTGGAAAACCCGAAT

-continued

```
AAATTCGATGACGAAAAATACTGGATCACGGTGGATACCTATAGCGCGCAGGGCGAACGTGCTACGGCGTTT

AGTAACACCCTGAACAATATTACGTCCAAATACTGGCGTGTGGTTTTCGATACCAAAGGTGACCGCTATAGC

TCTCCGGTCGTGCCGGAACTGCAGATTCTGGGCTATCCGCTGCCGAATGCTGATACGATCATGAAAACCGTG

ACGACCGCGAAAGAACTGTCACAGCAAAAAGATAAATTCTCGCAGAAAATGCTGGACGAACTGAAAATTAAA

GAAATGGCTCTGGAAACCAGCCTGAACAGTAAAATTTTCGATGTTACGGCGATCAATGCTAACGCTGGTGTG

CTGAAAGACTGTATTGAAAAACGCCAACTGCTGAAAAAAGGCGGCGGCGGCTCTGGCGGCGGCGGCTCTGGC

GGCGGCGGCTCTCACCACCACCACCACCACGAATTCGGCGGCGGCGGCTCTGGCGGCGGCGGCTCTGGCGGC

GGCGGCTCTGCGGTAACCGGGACAACGAAGGCTAACATCAAACTTTTTAGTTTTACAGAGGTAAACGACACT

AATCCGTTGAACAATCTGAACTTTACCTTAAAAAACTCGGGAAAACCCTTAGTAGATATGGTAGTGTTATTT

TCCGCGAACATTAACTATGACGCGGCCAACGATAAGGTCTTCGTATCGAATAATCCGAACGTACAGCATCTT

TTGACCAATCGTGCGAAGTACCTTAAGCCGTTACAAGACAAGGGGATCAAGGTGATTTGTCAATCTTAGGG

AACCATGATCGCTCCGGGATCGCCAATTTGAGTACGGCTCGTGCGAAGGCATTTGCTCAGGAACTGAAGAAT

ACTTGCGATTTGTATAATTTAGACGGGGTATTCTTTGATGATGAGTACTCTGCTTACCAAACGCCACCGCCG

AGCGGCTTCGTGACACCCAGTAATAACGCCGCAGCTCGCCTTGCTTATGAAACAAAGCAGGCTATGCCAAAC

AAGCTGGTCACGGTGTACGTCTATTCCCGCACTTCGAGTTTTCCCACAGCGGTAGACGGGGTCAACGCCGGG

TCCTACGTAGACTATGCGATTCATGACTACGGTGGCTCATACGACTTGGCTACTAATTATCCGGGGTTGGCT

AAGTCTGGGATGGTGATGTCTAGTCAGGAGTTTAACCAGGGCCGTTACGCGACTGCACAAGCATTGCGCAAC

ATTGTGACCAAGGGCTATGGAGGCCACATGATCTTTGCCATGGACCCCAATCGTTCTAATTTCACGTCAGGG

CAACTGCCCGCACTGAAGCTGATTGCCAAGGAGCTTTACGGGGATGAGCTTGTGTACAGCAACACTCCTTAC

AGTAAGGATTGGTGATAA
```

Sequence identification of DNA encoding for fusion protein EndoF3-EndoH as expressed in *E coli* (SEQ. ID NO: 28):

```
ATGGCTACAGCGCTGGCTGGTTCTAACGGGGTCTGCATCGCGTATTACATCACCGATGGGCGTAATCCGACG

TTCAAATTGAAAGACATCCCGGATAAAGTAGACATGGTAATTCTTTTTGGTCTTAAGTATTGGTCATTGCAG

GATACAACCAAATTGCCAGGGGGTACTGGTATGATGGGTTCGTTTAAATCCTACAAGGACCTGGACACCCAG

ATTCGTAGTCTTCAAAGCCGTGGAATCAAAGTGTTGCAGAACATTGACGACGACGTCTCATGGCAGTCCTCG

AAGCCGGGTGGGTTCGCTTCCGCCGCTGCTTACGGGGATGCTATTAAGAGTATCGTAATTGATAAGTGGAAG

CTGGACGGGATTAGCTTGGATATTGAGCATTCGGGGCTAAACCCAACCCTATCCCAACTTTTCCTGGATAT

GCCGCGACAGGATATAATGGCTGGTATTCAGGATCTATGGCAGCCACGCCTGCCTTTCTTAATGTTATCTCA

GAGCTTACTAAATACTTTGGTACAACGGCACCGAATAATAAGCAACTTCAGATTGCTTGGGTATTGACGTA

TATGCCTGGAATAAAATCATGGAGAACTTTCGTAATAACTTCAACTACATCCAATTACAGTCATACGGAGCT

AATGTCTCTCGTACTCAACTTATGATGAATTACGCAACGGGAACTAATAAAATTCCCGCCTCTAAAATGGTT

TTCGGCGCCTACGCAGAGGGTGGCACTAACCAGGCAAATGACGTGGAGGTCGCCAAGTGGACACCTACGCAG

GGCGCAAAGGGCGGTATGATGATCTATACTTACAATTCGAACGTGAGCTATGCAAATGCGGTTCGCGACGCA

GTGAAAAATGGCGGCGGCGGCTCTGGCGGCGGCGGCTCTGGCGGCGGCGGCTCTCACCACCACCACCACCAC

GAATTCGGCGGCGGCGGCTCTGGCGGCGGCGGCTCTGGCGGCGGCGGCTCTGCCCCGGCCCCGGTGAAGCAG

GGGCCGACCTCGGTGGCCTACGTCGAGGTGAACAACAACAGCATGCTCAACGTCGGCAAGTACACCCTGGCG

GACGGAGGCGGCAACGCCTTCGACGTAGCCGTGATCTTCGCGGCGAACATCAACTACGACACCGGCACGAAG

ACGGCCTACCTGCACTTCAACGAGAACGTGCAGCGCGTCCTTGACAACGCTGTCACGCAGATACGGCCGTTG

CAGCAACAGGGCATCAAGGTCCTCCTCTCGGTGCTCGGCAACCACCAGGGCGCCGGGTTCGCGAACTTCCCC

TCACAGCAGGCGGCTTCGGCGTTCGCGAAGCAGCTCTCGGACGCCGTGGCGAAGTACGGCCTCGACGGCGTC

GACTTCGACGACGAATACGCCGAGTACGGCAACAACGGCACCGCGCAGCCCAACGACAGTTCGTTCGTGCAC
```

-continued

CTGGTGACGGCACTGCGCGCGAACATGCCCGACAAGATCATCAGCCTCTACAACATCGGCCCGGCCGCGTCC

CGCCTGTCGTACGGCGGTGTCGACGTCTCCGACAAGTTCGACTACGCCTGGAATCCCTACTACGGCACCTGG

CAGGTCCCCGGCATCGCACTGCCCAAGGCGCAGCTGTCGCCGGCGGCCGTCGAGATCGGCCGGACCTCACGG

AGCACCGTCGCCGACCTCGCCCGTCGCACCGTCGACGAGGGGTACGGCGTCTATCTGACGTACAACCTCGAC

GGCGGCGATCGCACCGCCGACGTCTCCGCGTTCACCAGGGAGCTGTACGGCAGCGAGGCGGTCCGGACGCCG

TGATAA

Sequence identification of DNA encoding for fusion protein EndoF2-EndoH as expressed in *E coli* (SEQ. ID NO: 29):
ATGGCGGTAAACCTTAGTAATCTTATCGCTTATAAAAATAGTGACCATCAGATCAGTGCGGGATATTACCGT

ACATGGCGTGACAGCGCCACAGCCAGTGGTAATCTTCCTAGTATGCGTTGGTTGCCAGACTCATTGGACATG

GTAATGGTATTCCCAGACTATACTCCTCCGGAAAATGCGTATTGGAACACACTGAAGACTAACTACGTACCA

TACCTGCATAAGCGTGGCACGAAAGTTATTATCACATTGGGGGACCTTAACTCTGCAACGACCACGGGAGGG

CAAGATTCTATTGGGTATTCATCGTGGGCAAAGGAATCTATGATAAATGGGTGGGCGAGTATAATCTTGAT

GGAATCGATATTGACATCGAATCGTCACCGTCCGGTGCGACCTTAACGAAGTTTGTTGCGGCAACAAAAGCG

TTGTCAAAGTATTTTGGACAAAGAGTGGGACAGGCAAGACCTTTGTATACGATACCAATCAGAATCCGACT

AATTTCTTTATCCAAACTGCCCCACGCTACAACTACGTATTTCTTCAAGCATACGGGCGCTCGACCACTAAT

CTGACGACGGTCTCTGGATTATACGCCCCCTATATTTCAATGAAACAATTTCTGCCCGGCTTCTCTTTTTAC

GAAGAAAACGGTTACCCAGGTAATTATTGGAATGATGTGCGTTACCCCCAGAACGGTACAGGCCGTGCCTAC

GACTACGCGCGCTGGCAGCCCGCCACGGGAAAAAAGGAGGGGTGTTCAGTTATGCCATCGAGCGCGACGCC

CCTCTTACATCGTCAAACGACAATACCCTGCGTGCGCCTAACTTTCGTGTAACGAAGGACTTAATCAAAATT

ATGAATCCTGGCGGCGGCGGCTCTGGCGGCGGCGGCTCTGGCGGCGGCGGCTCTCACCACCACCACCACCAC

GAATTCGGCGGCGGCGGCTCTGGCGGCGGCGGCTCTGGCGGCGGCGGCTCTGCCCCGGCCCCGGTGAAGCAG

GGGCCGACCTCGGTGGCCTACGTCGAGGTGAACAACAACAGCATGCTCAACGTCGGCAAGTACACCCTGGCG

GACGGAGGCGGCAACGCCTTCGACGTAGCCGTGATCTTCGCGGCGAACATCAACTACGACACCGGCACGAAG

ACGGCCTACCTGCACTTCAACGAGAACGTGCAGCGCGTCCTTGACAACGCTGTCACGCAGATACGGCCGTTG

CAGCAACAGGGCATCAAGGTCCTCCTCTCGGTGCTCGGCAACCACCAGGGCGCCGGGTTCGCGAACTTCCCC

TCACAGCAGGCGGCTTCGGCGTTCGCGAAGCAGCTCTCGGACGCCGTGGCGAAGTACGGCCTCGACGGCGTC

GACTTCGACGACGAATACGCCGAGTACGGCAACAACGGCACCGCGCAGCCCAACGACAGTTCGTTCGTGCAC

CTGGTGACGGCACTGCGCGCGAACATGCCCGACAAGATCATCAGCCTCTACAACATCGGCCCGGCCGCGTCC

CGCCTGTCGTACGGCGGTGTCGACGTCTCCGACAAGTTCGACTACGCCTGGAATCCCTACTACGGCACCTGG

CAGGTCCCCGGCATCGCACTGCCCAAGGCGCAGCTGTCGCCGGCGGCCGTCGAGATCGGCCGGACCTCACGG

AGCACCGTCGCCGACCTCGCCCGTCGCACCGTCGACGAGGGGTACGGCGTCTATCTGACGTACAACCTCGAC

GGCGGCGATCGCACCGCCGACGTCTCCGCGTTCACCAGGGAGCTGTACGGCAGCGAGGCGGTCCGGACGCCG

TGATAA

Sequence identification of DNA encoding for fusion protein EndoS-EndoH (or EndoSH) as expressed in *E coli* (SEQ. ID NO: 30):
ATGCCGTCAATCGATTCGCTGCATTATCTGAGCGAAAACTCTAAAAAAGAATTTAAAGAAGAACTGAGCAAA

GCGGGCCAGGAATCTCAAAAAGTTAAAGAAATCCTGGCAAAAGCTCAGCAAGCCGATAAACAGGCACAAGAA

CTGGCTAAAATGAAAATTCCGGAAAAAATCCCGATGAAACCGCTGCATGGTCCGCTGTACGCGGTTATTTC

CGTACCTGGCACGATAAAACGTCAGACCCGACCGAAAAAGACAAAGTCAACTCGATGGGCGAACTGCCGAAA

GAAGTGGATCTGGCTTTTATTTTCCATGATTGGACCAAAGACTACTCTCTGTTTTGGAAAGAACTGGCAACG

AAACACGTTCCGAAACTGAACAAACAGGGTACGCGTGTCATTCGTACCATTCCGTGGCGCTTCCTGGCTGGC

-continued

```
GGTGATAATTCAGGCATCGCGGAAGACACCTCGAAATATCCGAACACGCCGGAAGGTAATAAAGCGCTGGCC

AAAGCAATCGTCGATGAATACGTGTACAAATACAATCTGGACGGCCTGGATGTGGACGTTGAACATGATTCA

ATTCCGAAAGTGGATAAAAAAGAAGACACCGCCGGCGTGGAACGTTCGATCCAGGTTTTTGAAGAAATTGGT

AAACTGATCGGCCCGAAAGGTGTTGATAAAAGCCGTCTGTTCATCATGGATTCTACCTATATGGCCGACAAA

AATCCGCTGATTGAACGCGGTGCACCGTACATCAACCTGCTGCTGGTCCAGGTGTATGGCAGCCAAGGTGAA

AAAGGCGGTTGGGAACCGGTGTCTAACCGTCCGGAAAAAACCATGGAAGAACGCTGGCAGGGCTACTCAAAA

TATATTCGTCCGGAACAATACATGATCGGCTTTTCGTTCTATGAAGAAACGCGCAGGAAGGTAATCTGTGG

TACGATATTAATAGTCGCAAAGATGAAGACAAAGCCAACGGCATTAATACCGATATCACGGGTACCCGTGCG

GAACGCTATGCCCGTTGGCAGCCGAAAACCGGCGGTGTTAAAGGCGGTATTTTTAGCTACGCGATCGATCGT

GACGGTGTCGCCCATCAGCCGAAAAAATACGCAAAACAAAAAGAGTTCAAAGATGCTACCGACAACATCTTC

CACAGCGATTACAGTGTCTCCAAAGCGCTGAAAACCGTGATGCTGAAAGATAAATCTTACGATCTGATCGAC

GAAAAGATTTTCCGGACAAAGCGCTGCGCGAAGCCGTTATGGCACAGGTCGGCACCCGCAAAGGTGACCTG

GAACGTTTTAATGGCACGCTGCGCCTGGATAACCCGGCCATTCAGAGCCTGGAAGGTCTGAATAAATTCAAA

AAACTGGCACAACTGGACCTGATTGGCCTGAGCCGTATCACCAAACTGGATCGCTCTGTGCTGCCGGCCAAC

ATGAAACCGGGTAAAGACACGCTGGAAACCGTTCTGGAAACCTACAAAAAAGATAACAAAGAAGAACCGGCA

ACGATCCCGCCGGTGTCTCTGAAAGTTTCCGGCCTGACCGGTCTGAAAGAACTGGATCTGAGCGGCTTTGAC

CGTGAAACGCTGGCAGGTCTGGATGCGGCCACGCTGACCAGTCTGGAAAAAGTTGATATTTCCGGCAATAAA

CTGGACCTGGCGCCGGGTACCGAAAACCGCCAGATTTTTGATACGATGCTGAGTACCATCTCCAACCATGTT

GGCAGCAATGAACAGACCGTCAAATTCGACAAACAAAAACCGACGGGCCACTACCCGGATACGTATGGTAAA

ACCAGCCTGCGTCTGCCGGTCGCCAACGAAAAAGTGGATCTGCAGTCTCAACTGCTGTTTGGCACGGTTACC

AATCAGGGTACCCTGATTAACAGCGAAGCAGATTACAAGGCTTACCAAAACCATAAAATCGCGGGTCGCTCA

TTTGTGGATTCGAACTACCACTACAACAACTTCAAAGTTAGTTACGAAAACTACACCGTTAAAGTCACGGAT

TCCACCCTGGGCACCACGACCGATAAAACGCTGGCCACCGACAAAGAAGAAACCTACAAAGTCGATTTCTTT

AGCCCGGCAGACAAAACGAAAGCGGTGCATACCGCCAAAGTGATTGTTGGCGATGAAAAAACCATGATGGTG

AACCTGGCTGAAGGTGCGACGGTTATCGGCGGTTCCGCAGACCCGGTTAACGCTCGCAAAGTCTTTGATGGC

CAGCTGGGTAGTGAAACCGATAATATTTCCCTGGGTTGGGACTCAAAACAGTCGATTATCTTCAAACTGAAA

GAAGACGGCCTGATCAAACACTGGCGTTTCTTTAACGATAGTGCCCGCAATCCGGAAACGACCAACAAACCG

ATTCAGGAAGCATCCCTGCAAATCTTCAACATCAAAGATTACAACCTGGACAATCTGCTGGAAAACCCGAAT

AAATTCGATGACGAAAAATACTGGATCACGGTGGATACCTATAGCGCGCAGGGCGAACGTGCTACGGCGTTT

AGTAACACCCTGAACAATATTACGTCCAAATACTGGCGTGTGGTTTTCGATACCAAAGGTGACCGCTATAGC

TCTCCGGTCGTGCCGGAACTGCAGATTCTGGGCTATCCGCTGCCGAATGCTGATACGATCATGAAAACCGTG

ACGACCGCGAAAGAACTGTCACAGCAAAAAGATAAATTCTCGCAGAAAATGCTGGACGAACTGAAAATTAAA

GAAATGGCTCTGGAAACCAGCCTGAACAGTAAAATTTTCGATGTTACGGCGATCAATGCTAACGCTGGTGTG

CTGAAAGACTGTATTGAAAAACGCCAACTGCTGAAAAAAGGCGGCGGCGGCTCTGGCGGCGGCGGCTCTGGC

GGCGGCGGCTCTCACCACCACCACCACCACGAATTCGGCGGCGGCGGCTCTGGCGGCGGCGGCTCTGGCGGC

GGCGGCTCTGCCCCGGCCCCGGTGAAGCAGGGGCCGACCTCGGTGGCCTACGTCGAGGTGAACAACAACAGC

ATGCTCAACGTCGGCAAGTACACCCTGGCGGACGGAGGCGGCAACGCCTTCGACGTAGCCGTGATCTTCGCG

GCGAACATCAACTACGACACCGGCACGAAGACGGCCTACCTGCACTTCAACGAGAACGTGCAGCGCGTCCTT

GACAACGCTGTCACGCAGATACGGCCGTTGCAGCAACAGGGCATCAAGGTCCTCCTCTCGGTGCTCGGCAAC

CACCAGGGCGCCGGGTTCGCGAACTTCCCCTCACAGCAGGCGGCTTCGGCGTTCGCGAAGCAGCTCTCGGAC

GCCGTGGCGAAGTACGGCCTCGACGGCGTCGACTTCGACGACGAATACGCCGAGTACGGCAACAACGGCACC
```

-continued

```
GCGCAGCCCAACGACAGTTCGTTCGTGCACCTGGTGACGGCACTGCGCGCGAACATGCCCGACAAGATCATC
AGCCTCTACAACATCGGCCCGGCCGCGTCCCGCCTGTCGTACGGCGGTGTCGACGTCTCCGACAAGTTCGAC
TACGCCTGGAATCCCTACTACGGCACCTGGCAGGTCCCCGGCATCGCACTGCCCAAGGCGCAGCTGTCGCCG
GCGGCCGTCGAGATCGGCCGGACCTCACGGAGCACCGTCGCCGACCTCGCCCGTCGCACCGTCGACGAGGGG
TACGGCGTCTATCTGACGTACAACCTCGACGGCGGCGATCGCACCGCCGACGTCTCCGCGTTCACCAGGGAG
CTGTACGGCAGCGAGGCGGTCCGGACGCCGTGATAA
```

Sequence identification of DNA encoding for fusion protein His$_6$-EndoS-EndoH (EndoS-EndoH without GS-linker) as expressed in *E coli* (SEQ. ID NO: 31):

```
ATGGGCAGCAGCCATCATCATCATCATCACAGCAGCGGCCTGGTGCCGCGCGGCAGCCATATGCCGTCAATC
GATTCGCTGCATTATCTGAGCGAAAACTCTAAAAAAGAATTTAAAGAAGAACTGAGCAAAGCGGGCCAGGAA
TCTCAAAAAGTTAAAGAAATCCTGGCAAAAGCTCAGCAAGCCGATAAACAGGCACAAGAACTGGCTAAAATG
AAAATTCCGGAAAAAATCCCGATGAAACCGCTGCATGGTCCGCTGTACGGCGGTTATTTCCGTACCTGGCAC
GATAAAACGTCAGACCCGACCGAAAAAGACAAAGTCAACTCGATGGGCGAACTGCCGAAAGAAGTGGATCTG
GCTTTTATTTTCCATGATTGGACCAAAGACTACTCTCTGTTTTGGAAAGAACTGGCAACGAAACACGTTCCG
AAACTGAACAAACAGGGTACGCGTGTCATTCGTACCATTCCGTGGCGCTTCCTGGCTGGCGGTGATAATTCA
GGCATCGCGGAAGACACCTCGAAATATCCGAACACGCCGGAAGGTAATAAAGCGCTGGCCAAAGCAATCGTC
GATGAATACGTGTACAAATACAATCTGGACGGCCTGGATGTGGACGTTGAACATGATTCAATTCCGAAAGTG
GATAAAAAGAAGACACCGCCGGCGTGGAACGTTCGATCCAGGTTTTTGAAGAAATTGGTAAACTGATCGGC
CCGAAAGGTGTTGATAAAGCCGTCTGTTCATCATGGATTCTACCTATATGCCGACAAAAATCCGCTGATT
GAACGCGGTGCACCGTACATCAACCTGCTGCTGGTCCAGGTGTATGGCAGCCAAGGTGAAAAGGCGGTTGG
GAACCGGTGTCTAACCGTCCGGAAAAAACCATGGAAGAACGCTGGCAGGGCTACTCAAAATATATTCGTCCG
GAACAATACATGATCGGCTTTTCGTTCTATGAAGAAAACGCGCAGGAAGGTAATCTGTGGTACGATATTAAT
AGTCGCAAAGATGAAGACAAAGCCAACGGCATTAATACCGATATCACGGGTACCCGTGCGGAACGCTATGCC
CGTTGGCAGCCGAAAACCGGCGGTGTTAAAGGCGGTATTTTTAGCTACGCGATCGATCGTGACGGTGTCGCC
CATCAGCCGAAAAAATACGCAAAACAAAAAGAGTTCAAAGATGCTACCGACAACATCTTCCACAGCGATTAC
AGTGTCTCCAAAGCGCTGAAAACCGTGATGCTGAAAGATAAATCTTACGATCTGATCGACGAAAAAGATTTT
CCGGACAAAGCGCTGCGCGAAGCCGTTATGGCACAGGTCGGCACCCGCAAAGGTGACCTGGAACGTTTTAAT
GGCACGCTGCGCCTGGATAACCCGGCCATTCAGAGCCTGGAAGGTCTGAATAAATTCAAAAAACTGGCACAA
CTGGACCTGATTGGCCTGAGCCGTATCACCAAACTGGATCGCTCTGTGCTGCCGGCCAACATGAAACCGGGT
AAAGACACGCTGGAAACCGTTCTGGAAACCTACAAAAAAGATAACAAAGAAGAACCGGCAACGATCCCGCCG
GTGTCTCTGAAAGTTTCCGGCCTGACCGGTCTGAAAGAACTGGATCTGAGCGGCTTTGACCGTGAAACGCTG
GCAGGTCTGGATGCGGCACGCTGACCAGTCTGGAAAAAGTTGATATTTCCGGCAATAAACTGGACCTGGCG
CCGGGTACCGAAAACCGCCAGATTTTTGATACGATGCTGAGTACCATCTCCAACCATGTTGGCAGCAATGAA
CAGACCGTCAAATTCGACAAACAAAAACCGACGGGCCACTACCCGGATACGTATGGTAAAACCAGCCTGCGT
CTGCCGGTCGCCAACGAAAAAGTGGATCTGCAGTCTCAACTGCTGTTTGGCACGGTTACCAATCAGGGTACC
CTGATTAACAGCGAAGCAGATTACAAGGCTTACCAAAACCATAAATCGCGGGTCGCTCATTTGTGGATTCG
AACTACCACTACAACAACTTCAAAGTTAGTTACGAAAACTACACCGTTAAAGTCACGGATTCCACCCTGGGC
ACCACGACCGATAAAACGCTGGCCACCGACAAAGAAGAAACCTACAAAGTCGATTTCTTTAGCCCGGCAGAC
AAAACGAAAGCGGTGCATACCGCCAAAGTGATTGTTGGCGATGAAAAACCATGATGGTGAACCTGGCTGAA
GGTGCGACGGTTATCGGCGGTTCCGCAGACCCGGTTAACGCTCGCAAAGTCTTTGATGGCCAGCTGGGTAGT
GAAACCGATAATATTTCCCTGGGTTGGGACTCAAAACAGTCGATTATCTTCAAACTGAAAGAAGACGGCCTG
```

-continued

```
ATCAAACACTGGCGTTTCTTTAACGATAGTGCCCGCAATCCGGAAACGACCAACAAACCGATTCAGGAAGCA

TCCCTGCAAATCTTCAACATCAAAGATTACAACCTGGACAATCTGCTGGAAAACCCGAATAAATTCGATGAC

GAAAAATACTGGATCACGGTGGATACCTATAGCGCGCAGGGCGAACGTGCTACGGCGTTTAGTAACACCCTG

AACAATATTACGTCCAAATACTGGCGTGTGGTTTTCGATACCAAAGGTGACCGCTATAGCTCTCCGGTCGTG

CCGGAACTGCAGATTCTGGGCTATCCGCTGCCGAATGCTGATACGATCATGAAAACCGTGACGACCGCGAAA

GAACTGTCACAGCAAAAGATAAATTCTCGCAGAAAATGCTGGACGAACTGAAAATTAAAGAAATGGCTCTG

GAAACCAGCCTGAACAGTAAAATTTTCGATGTTACGGCGATCAATGCTAACGCTGGTGTGCTGAAAGACTGT

ATTGAAAAACGCCAACTGCTGAAAAAAGCCCCGGCCCCGGTGAAGCAGGGGCCGACCTCGGTGGCCTACGTC

GAGGTGAACAACAACAGCATGCTCAACGTCGGCAAGTACACCCTGGCGGACGGAGGCGGCAACGCCTTCGAC

GTAGCCGTGATCTTCGCGGCGAACATCAACTACGACACCGGCACGAAGACGGCCTACCTGCACTTCAACGAG

AACGTGCAGCGCGTCCTTGACAACGCTGTCACGCAGATACGGCCGTTGCAGCAACAGGGCATCAAGGTCCTC

CTCTCGGTGCTCGGCAACCACCAGGGCGCCGGGTTCGCGAACTTCCCCTCACAGCAGGCGGCTTCGGCGTTC

GCGAAGCAGCTCTCGGACGCCGTGGCGAAGTACGGCCTCGACGGCGTCGACTTCGACGACGAATACGCCGAG

TACGGCAACAACGGCACCGCGCAGCCCAACGACAGTTCGTTCGTGCACCTGGTGACGGCACTGCGCGCGAAC

ATGCCCGACAAGATCATCAGCCTCTACAACATCGGCCCGGCCGCGTCCCGCCTGTCGTACGGCGGTGTCGAC

GTCTCCGACAAGTTCGACTACGCCTGGAATCCCTACTACGGCACCTGGCAGGTCCCCGGCATCGCACTGCCC

AAGGCGCAGCTGTCGCCGGCGGCCGTCGAGATCGGCCGGACCTCACGGAGCACCGTCGCCGACCTCGCCCGT

CGCACCGTCGACGAGGGGTACGGCGTCTATCTGACGTACAACCTCGACGGCGGCGATCGCACCGCCGACGTC

TCCGCGTTCACCAGGGAGCTGTACGGCAGCGAGGCGGTCCGGACGCCGTGATAA
```

Sequence identification of DNA encoding for His₆-TnGalNAcT(33-421) as expressed in CHO (SEQ. ID NO: 32):

```
ATGAATTTTGGACTGAGGCTGATTTTCCTGGTGCTGACCCTGAAAGGCGTCCAGTGTCATCACCATCACCAT

CACTCCCCGCTTCGCACATATCTTTACACTCCATTATACAATGCCACCCAGCCCACACTCAGAAACGTCGAG

AGGCTGGCAGCTAACTGGCCAAAGAAGATCCCTAGTAATTATATAGAAGATAGCGAAGAGTATAGCATCAAG

AATATTTCTTTGAGCAACCACACAACTAGAGCATCTGTGGTACATCCTCCTTCCTCTATCACCGAAACGGCA

AGCAAACTGGATAAGAATATGACCATCCAAGACGGCGCCTTTGCTATGATTAGCCCGACGCCCTTGCTTATC

ACCAAATTGATGGATAGCATCAAATCTTATGTTACTACCGAGGATGGGGTTAAGAAAGCCGAAGCCGTCGTA

ACTCTCCCCCTCTGTGATAGCATGCCTCCTGACCTTGGTCCTATTACTCTTAACAAAACCGAGCTCGAGCTC

GAATGGGTTGAGAAAAAGTTCCCTGAGGTCGAGTGGGGTGGACGTTATAGTCCCCCCAACTGCACAGCTAGG

CATCGCGTAGCAATCATAGTCCCGTACCGAGACAGACAGCAACACCTGGCAATCTTCTTAAATCACATGCAC

CCCTTCCTGATGAAACAGCAGATCGAATATGGCATCTTTATCGTGGAGCAGGAAGGAAACAAGGACTTTAAC

CGTGCGAAACTTATGAACGTCGGCTTTGTTGAAAGTCAAAAACTCGTTGCCGAGGGATGGCAGTGTTTCGTT

TTTCATGACATAGACCTGCTCCCACTGGACACTAGAAACCTCTATAGCTGCCCGAGACAGCCACGCCACATG

AGCGCTTCCATTGACAAACTTCACTTTAAGCTGCCTTACGAAGACATCTTCGGTGGCGTGTCAGCCATGACT

CTGGAACAGTTCACCCGAGTGAATGGATTTTCAAATAAATACTGGGGATGGGGGGGAGAGGACGACGATATG

AGTTATCGGCTTAAGAAAATCAACTACCATATTGCAAGATATAAAATGTCCATCGCCCGATACGCCATGTTG

GACCACAAGAAGTCAACACCCAATCCTAAGCGGTACCAATTACTCTCACAGACCTCAAAGACATTCCAGAAA

GACGGGCTGAGCACCCTGGAATATGAGCTGGTGCAAGTCGTTCAATATCATCTGTATACTCACATCCTGGTT

AATATTGACGAGAGGTCCTGATAA
```

(signal sequence for secretion is underlined)

-continued

Sequence identification of His₆-TnGalNAcT(33-421) as expressed in CHO
(SEQ. ID NO: 33):
HHHHHHSPLRTYLYTPLYNATQPTLRNVERLAANWPKKIPSNYIEDSEEYSIKNISLSNHTTRASVVHPPSS

ITETASKLDKNMTIQDGAFAMISPTPLLITKLMDSIKSYVTTEDGVKKAEAVVTLPLCDSMPPDLGPITLNK

TELELEWVEKKFPEVEWGGRYSPPNCTARHRVAIIVPYRDRQQHLAIFLNHMHPFLMKQQIEYGIFIVEQEG

NKDFNRAKLMNVGFVESQKLVAEGWQCFVFHDIDLLPLDTRNLYSCPRQPRHMSASIDKLHFKLPYEDIFGG

VSAMTLEQFTRVNGFSNKYWGWGGEDDDMSYRLKKINYHIARYKMSIARYAMLDHKKSTPNPKRYQLLSQTS

KTFQKDGLSTLEYELVQVVQYHLYTHILVNIDERS

---

The invention claimed is:

1. A fusion enzyme of structure (1):

$$\text{EndoX-(L)}_p\text{-EndoY} \quad (1)$$

wherein
EndoX is an endoglycosidase,
EndoY is an endoglycosidase distinct from EndoX,
EndoX and EndoY are individually selected from the group consisting of EndoA, EndoBi, EndoBH, EndoBT, EndoCE, EndoD, EndoE, EfEndo18A, EndoF1, EndoF2, EndoF3, EndoH, EndoLL, EndoM, EndoOm, EndoS, and EndoT,
L is a linker, and
p is 0 or 1.

2. The fusion enzyme according to claim 1, wherein EndoX and EndoY are individually selected from the group consisting of EndoF1, EndoF2, EndoF3, EfEndo18A, EndoH and EndoS.

3. The fusion enzyme according to claim 1, wherein the endoglycosidases represented by EndoX and EndoY have distinct endoglycosidase activity.

4. The fusion enzyme according to claim 1, wherein EndoX is EndoF2, EndoF3 or EndoS.

5. The fusion enzyme according to claim 1, wherein EndoY is EndoF1, EndoD, EndoE, EndoH, EfEndo18A or EndoT.

6. The fusion enzyme according to claim 1, wherein EndoX and EndoY individually have at least 80% sequence identity with any one of SEQ ID NOs 4-10.

7. The fusion enzyme according to claim 1, having at least 50% sequence identity with any one of SEQ IDs No. 1, 2 or 13-21.

8. The fusion enzyme according to claim 1, wherein p=0.

9. The fusion enzyme according to claim 1, wherein p=1 and L is composed of amino residues and has a length of 1 to 100 amino acid residues.

10. The fusion enzyme according to claim 9, wherein the linker has the sequence $(G_4S)_{n1}(H)_r(EF)_s(G_4S)_{n2}$, wherein n1 and n2 individually are integers in the range 1-10, r is an integer in the range of 2-10 and s=0 or 1.

11. A process for trimming a glycoprotein comprising contacting the glycoprotein with the fusion enzyme according to claim 1.

12. The process according to claim 11, wherein the glycoprotein comprises at least one high-mannose glycan and at least one complex glycan.

13. The process according to claim 12, wherein the glycoprotein further comprises at least one hybrid glycan.

14. The process according to claim 11, wherein the glycoprotein is an antibody.

15. The process according to claim 11, wherein the contacting is performed at a pH which is 0.5-3 pH units different from the optimal pH of one or both of EndoX and EndoY.

16. The process according to claim 15, wherein the contacting is performed at a pH which is 1-2 pH units different from the optimal pH of one or both of EndoX and EndoY.

17. The enzyme according to claim 4, wherein EndoX in EndoS.

18. The enzyme according to claim 5, wherein EndoY in EndoH.

* * * * *

SEQUENCE LISTING

<160> NUMBER OF SEQ ID NOS: 33

<210> SEQ ID NO 1
<211> LENGTH: 1258
<212> TYPE: PRT
<213> ORGANISM: Artificial sequence
<220> FEATURE:
<223> OTHER INFORMATION: EndoS-EndoH

<400> SEQUENCE: 1

```
Met Pro Ser Ile Asp Ser Leu His Tyr Leu Ser Glu Asn Ser Lys Lys
1               5                   10                  15

Glu Phe Lys Glu Glu Leu Ser Lys Ala Gly Gln Glu Ser Gln Lys Val
            20                  25                  30

Lys Glu Ile Leu Ala Lys Ala Gln Gln Ala Asp Lys Gln Ala Gln Glu
        35                  40                  45

Leu Ala Lys Met Lys Ile Pro Glu Lys Ile Pro Met Lys Pro Leu His
    50                  55                  60

Gly Pro Leu Tyr Gly Gly Tyr Phe Arg Thr Trp His Asp Lys Thr Ser
65                  70                  75                  80

Asp Pro Thr Glu Lys Asp Lys Val Asn Ser Met Gly Glu Leu Pro Lys
                85                  90                  95

Glu Val Asp Leu Ala Phe Ile Phe His Asp Trp Thr Lys Asp Tyr Ser
            100                 105                 110

Leu Phe Trp Lys Glu Leu Ala Thr Lys His Val Pro Lys Leu Asn Lys
        115                 120                 125

Gln Gly Thr Arg Val Ile Arg Thr Ile Pro Trp Arg Phe Leu Ala Gly
    130                 135                 140

Gly Asp Asn Ser Gly Ile Ala Glu Asp Thr Ser Lys Tyr Pro Asn Thr
145                 150                 155                 160

Pro Glu Gly Asn Lys Ala Leu Ala Lys Ala Ile Val Asp Glu Tyr Val
                165                 170                 175

Tyr Lys Tyr Asn Leu Asp Gly Leu Asp Val Asp Val Glu His Asp Ser
            180                 185                 190

Ile Pro Lys Val Asp Lys Lys Glu Asp Thr Ala Gly Val Glu Arg Ser
        195                 200                 205

Ile Gln Val Phe Glu Glu Ile Gly Lys Leu Ile Gly Pro Lys Gly Val
    210                 215                 220

Asp Lys Ser Arg Leu Phe Ile Met Asp Ser Thr Tyr Met Ala Asp Lys
225                 230                 235                 240

Asn Pro Leu Ile Glu Arg Gly Ala Pro Tyr Ile Asn Leu Leu Leu Val
                245                 250                 255
```

-continued

```
Gln Val Tyr Gly Ser Gln Gly Glu Lys Gly Gly Trp Glu Pro Val Ser
            260                 265                 270

Asn Arg Pro Glu Lys Thr Met Glu Glu Arg Trp Gln Gly Tyr Ser Lys
            275                 280                 285

Tyr Ile Arg Pro Glu Gln Tyr Met Ile Gly Phe Ser Phe Tyr Glu Glu
            290                 295                 300

Asn Ala Gln Glu Gly Asn Leu Trp Tyr Asp Ile Asn Ser Arg Lys Asp
305                 310                 315                 320

Glu Asp Lys Ala Asn Gly Ile Asn Thr Asp Ile Thr Gly Thr Arg Ala
                325                 330                 335

Glu Arg Tyr Ala Arg Trp Gln Pro Lys Thr Gly Gly Val Lys Gly Gly
            340                 345                 350

Ile Phe Ser Tyr Ala Ile Asp Arg Asp Gly Val Ala His Gln Pro Lys
            355                 360                 365

Lys Tyr Ala Lys Gln Lys Glu Phe Lys Asp Ala Thr Asp Asn Ile Phe
    370                 375                 380

His Ser Asp Tyr Ser Val Ser Lys Ala Leu Lys Thr Val Met Leu Lys
385                 390                 395                 400

Asp Lys Ser Tyr Asp Leu Ile Asp Glu Lys Asp Phe Pro Asp Lys Ala
                405                 410                 415

Leu Arg Glu Ala Val Met Ala Gln Val Gly Thr Arg Lys Gly Asp Leu
            420                 425                 430

Glu Arg Phe Asn Gly Thr Leu Arg Leu Asp Asn Pro Ala Ile Gln Ser
            435                 440                 445

Leu Glu Gly Leu Asn Lys Phe Lys Leu Ala Gln Leu Asp Leu Ile
    450                 455                 460

Gly Leu Ser Arg Ile Thr Lys Leu Asp Arg Ser Val Leu Pro Ala Asn
465                 470                 475                 480

Met Lys Pro Gly Lys Asp Thr Leu Glu Thr Val Leu Glu Thr Tyr Lys
                485                 490                 495

Lys Asp Asn Lys Glu Glu Pro Ala Thr Ile Pro Pro Val Ser Leu Lys
            500                 505                 510

Val Ser Gly Leu Thr Gly Leu Lys Glu Leu Asp Leu Ser Gly Phe Asp
            515                 520                 525

Arg Glu Thr Leu Ala Gly Leu Asp Ala Ala Thr Leu Thr Ser Leu Glu
    530                 535                 540

Lys Val Asp Ile Ser Gly Asn Lys Leu Asp Leu Ala Pro Gly Thr Glu
545                 550                 555                 560

Asn Arg Gln Ile Phe Asp Thr Met Leu Ser Thr Ile Ser Asn His Val
                565                 570                 575

Gly Ser Asn Glu Gln Thr Val Lys Phe Asp Lys Gln Lys Pro Thr Gly
            580                 585                 590

His Tyr Pro Asp Thr Tyr Gly Lys Thr Ser Leu Arg Leu Pro Val Ala
        595                 600                 605

Asn Glu Lys Val Asp Leu Gln Ser Gln Leu Leu Phe Gly Thr Val Thr
    610                 615                 620

Asn Gln Gly Thr Leu Ile Asn Ser Glu Ala Asp Tyr Lys Ala Tyr Gln
625                 630                 635                 640

Asn His Lys Ile Ala Gly Arg Ser Phe Val Asp Ser Asn Tyr His Tyr
                645                 650                 655

Asn Asn Phe Lys Val Ser Tyr Glu Asn Tyr Thr Val Lys Val Thr Asp
            660                 665                 670
```

```
Ser Thr Leu Gly Thr Thr Thr Asp Lys Thr Leu Ala Thr Asp Lys Glu
            675                 680                 685

Glu Thr Tyr Lys Val Asp Phe Phe Ser Pro Ala Asp Lys Thr Lys Ala
        690                 695                 700

Val His Thr Ala Lys Val Ile Val Gly Asp Glu Lys Thr Met Met Val
705                 710                 715                 720

Asn Leu Ala Glu Gly Ala Thr Val Ile Gly Gly Ser Ala Asp Pro Val
                725                 730                 735

Asn Ala Arg Lys Val Phe Asp Gly Gln Leu Gly Ser Glu Thr Asp Asn
            740                 745                 750

Ile Ser Leu Gly Trp Asp Ser Lys Gln Ser Ile Ile Phe Lys Leu Lys
        755                 760                 765

Glu Asp Gly Leu Ile Lys His Trp Arg Phe Phe Asn Asp Ser Ala Arg
    770                 775                 780

Asn Pro Glu Thr Thr Asn Lys Pro Ile Gln Glu Ala Ser Leu Gln Ile
785                 790                 795                 800

Phe Asn Ile Lys Asp Tyr Asn Leu Asp Asn Leu Leu Glu Asn Pro Asn
                805                 810                 815

Lys Phe Asp Asp Glu Lys Tyr Trp Ile Thr Val Asp Thr Tyr Ser Ala
            820                 825                 830

Gln Gly Glu Arg Ala Thr Ala Phe Ser Asn Thr Leu Asn Asn Ile Thr
        835                 840                 845

Ser Lys Tyr Trp Arg Val Phe Asp Thr Lys Gly Asp Arg Tyr Ser
    850                 855                 860

Ser Pro Val Val Pro Glu Leu Gln Ile Leu Gly Tyr Pro Leu Pro Asn
865                 870                 875                 880

Ala Asp Thr Ile Met Lys Thr Val Thr Ala Lys Glu Leu Ser Gln
                885                 890                 895

Gln Lys Asp Lys Phe Ser Gln Lys Met Leu Asp Glu Leu Lys Ile Lys
            900                 905                 910

Glu Met Ala Leu Glu Thr Ser Leu Asn Ser Lys Ile Phe Asp Val Thr
        915                 920                 925

Ala Ile Asn Ala Asn Ala Gly Val Leu Lys Asp Cys Ile Glu Lys Arg
    930                 935                 940

Gln Leu Leu Lys Lys Gly Gly Gly Ser Gly Gly Gly Ser Gly
945                 950                 955                 960

Gly Gly Gly Ser His His His His His Glu Phe Gly Gly Gly
                965                 970                 975

Ser Gly Gly Gly Gly Ser Gly Gly Gly Ser Ala Pro Ala Pro Val
            980                 985                 990

Lys Gln Gly Pro Thr Ser Val Ala Tyr Val Glu Val Asn Asn Asn Ser
        995                 1000                1005

Met Leu Asn Val Gly Lys Tyr Thr Leu Ala Asp Gly Gly Gly Asn
1010                1015                1020

Ala Phe Asp Val Ala Val Ile Phe Ala Ala Asn Ile Asn Tyr Asp
    1025                1030                1035

Thr Gly Thr Lys Thr Ala Tyr Leu His Phe Asn Glu Asn Val Gln
    1040                1045                1050

Arg Val Leu Asp Asn Ala Val Thr Gln Ile Arg Pro Leu Gln Gln
    1055                1060                1065

Gln Gly Ile Lys Val Leu Leu Ser Val Leu Gly Asn His Gln Gly
    1070                1075                1080
```

```
Ala Gly Phe Ala Asn Phe Pro Ser Gln Gln Ala Ser Ala Phe
        1085                1090                1095

Ala Lys Gln Leu Ser Asp Ala Val Ala Lys Tyr Gly Leu Asp Gly
    1100                1105                1110

Val Asp Phe Asp Asp Glu Tyr Ala Glu Tyr Gly Asn Asn Gly Thr
    1115                1120                1125

Ala Gln Pro Asn Asp Ser Ser Phe Val His Leu Val Thr Ala Leu
    1130                1135                1140

Arg Ala Asn Met Pro Asp Lys Ile Ile Ser Leu Tyr Asn Ile Gly
    1145                1150                1155

Pro Ala Ala Ser Arg Leu Ser Tyr Gly Gly Val Asp Val Ser Asp
    1160                1165                1170

Lys Phe Asp Tyr Ala Trp Asn Pro Tyr Tyr Gly Thr Trp Gln Val
    1175                1180                1185

Pro Gly Ile Ala Leu Pro Lys Ala Gln Leu Ser Pro Ala Ala Val
    1190                1195                1200

Glu Ile Gly Arg Thr Ser Arg Ser Thr Val Ala Asp Leu Ala Arg
    1205                1210                1215

Arg Thr Val Asp Glu Gly Tyr Gly Val Tyr Leu Thr Tyr Asn Leu
    1220                1225                1230

Asp Gly Gly Asp Arg Thr Ala Asp Val Ser Ala Phe Thr Arg Glu
    1235                1240                1245

Leu Tyr Gly Ser Glu Ala Val Arg Thr Pro
    1250                1255

<210> SEQ ID NO 2
<211> LENGTH: 1256
<212> TYPE: PRT
<213> ORGANISM: Artificial sequence
<220> FEATURE:
<223> OTHER INFORMATION: EndoS-EndoH

<400> SEQUENCE: 2

Met Pro Ser Ile Asp Ser Leu His Tyr Leu Ser Glu Asn Ser Lys Lys
1               5                   10                  15

Glu Phe Lys Glu Glu Leu Ser Lys Ala Gly Gln Glu Ser Gln Lys Val
                20                  25                  30

Lys Glu Ile Leu Ala Lys Ala Gln Gln Ala Asp Lys Gln Ala Gln Glu
            35                  40                  45

Leu Ala Lys Met Lys Ile Pro Glu Lys Ile Pro Met Lys Pro Leu His
        50                  55                  60

Gly Pro Leu Tyr Gly Gly Tyr Phe Arg Thr Trp His Asp Lys Thr Ser
65              70                  75                  80

Asp Pro Thr Glu Lys Asp Lys Val Asn Ser Met Gly Glu Leu Pro Lys
                85                  90                  95

Glu Val Asp Leu Ala Phe Ile Phe His Asp Trp Thr Lys Asp Tyr Ser
            100                 105                 110

Leu Phe Trp Lys Glu Leu Ala Thr Lys His Val Pro Lys Leu Asn Lys
        115                 120                 125

Gln Gly Thr Arg Val Ile Arg Thr Ile Pro Trp Arg Phe Leu Ala Gly
    130                 135                 140

Gly Asp Asn Ser Gly Ile Ala Glu Asp Thr Ser Lys Tyr Pro Asn Thr
145                 150                 155                 160

Pro Glu Gly Asn Lys Ala Leu Ala Lys Ala Ile Val Asp Glu Tyr Val
                165                 170                 175
```

```
Tyr Lys Tyr Asn Leu Asp Gly Leu Asp Val Asp Val Glu His Asp Ser
            180                 185                 190

Ile Pro Lys Val Asp Lys Lys Glu Asp Thr Ala Gly Val Glu Arg Ser
        195                 200                 205

Ile Gln Val Phe Glu Glu Ile Gly Lys Leu Ile Gly Pro Lys Gly Val
    210                 215                 220

Asp Lys Ser Arg Leu Phe Ile Met Asp Ser Thr Tyr Met Ala Asp Lys
225                 230                 235                 240

Asn Pro Leu Ile Glu Arg Gly Ala Pro Tyr Ile Asn Leu Leu Leu Val
                245                 250                 255

Gln Val Tyr Gly Ser Gln Gly Lys Gly Trp Glu Pro Val Ser
            260                 265                 270

Asn Arg Pro Glu Lys Thr Met Glu Glu Arg Trp Gln Gly Tyr Ser Lys
        275                 280                 285

Tyr Ile Arg Pro Glu Gln Tyr Met Ile Gly Phe Ser Phe Tyr Glu Glu
    290                 295                 300

Asn Ala Gln Glu Gly Asn Leu Trp Tyr Asp Ile Asn Ser Arg Lys Asp
305                 310                 315                 320

Glu Asp Lys Ala Asn Gly Ile Asn Thr Asp Ile Thr Gly Thr Arg Ala
                325                 330                 335

Glu Arg Tyr Ala Arg Trp Gln Pro Lys Thr Gly Gly Val Lys Gly Gly
            340                 345                 350

Ile Phe Ser Tyr Ala Ile Asp Arg Asp Gly Val Ala His Gln Pro Lys
        355                 360                 365

Lys Tyr Ala Lys Gln Lys Glu Phe Lys Asp Ala Thr Asp Asn Ile Phe
    370                 375                 380

His Ser Asp Tyr Ser Val Ser Lys Ala Leu Lys Thr Val Met Leu Lys
385                 390                 395                 400

Asp Lys Ser Tyr Asp Leu Ile Asp Glu Lys Asp Phe Pro Asp Lys Ala
                405                 410                 415

Leu Arg Glu Ala Val Met Ala Gln Val Gly Thr Arg Lys Gly Asp Leu
            420                 425                 430

Glu Arg Phe Asn Gly Thr Leu Arg Leu Asp Asn Pro Ala Ile Gln Ser
        435                 440                 445

Leu Glu Gly Leu Asn Lys Phe Lys Lys Leu Ala Gln Leu Asp Leu Ile
    450                 455                 460

Gly Leu Ser Arg Ile Thr Lys Leu Asp Arg Ser Val Leu Pro Ala Asn
465                 470                 475                 480

Met Lys Pro Gly Lys Asp Thr Leu Glu Thr Val Leu Glu Thr Tyr Lys
                485                 490                 495

Lys Asp Asn Lys Glu Glu Pro Ala Thr Ile Pro Pro Val Ser Leu Lys
            500                 505                 510

Val Ser Gly Leu Thr Gly Leu Lys Glu Leu Asp Leu Ser Gly Phe Asp
        515                 520                 525

Arg Glu Thr Leu Ala Gly Leu Asp Ala Ala Thr Leu Thr Ser Leu Glu
    530                 535                 540

Lys Val Asp Ile Ser Gly Asn Lys Leu Asp Leu Ala Pro Gly Thr Glu
545                 550                 555                 560

Asn Arg Gln Ile Phe Asp Thr Met Leu Ser Thr Ile Ser Asn His Val
                565                 570                 575

Gly Ser Asn Glu Gln Thr Val Lys Phe Asp Lys Gln Lys Pro Thr Gly
            580                 585                 590
```

```
His Tyr Pro Asp Thr Tyr Gly Lys Thr Ser Leu Arg Leu Pro Val Ala
            595                 600                 605

Asn Glu Lys Val Asp Leu Gln Ser Gln Leu Leu Phe Gly Thr Val Thr
610                 615                 620

Asn Gln Gly Thr Leu Ile Asn Ser Glu Ala Asp Tyr Lys Ala Tyr Gln
625                 630                 635                 640

Asn His Lys Ile Ala Gly Arg Ser Phe Val Asp Ser Asn Tyr His Tyr
            645                 650                 655

Asn Asn Phe Lys Val Ser Tyr Glu Asn Tyr Thr Val Lys Val Thr Asp
            660                 665                 670

Ser Thr Leu Gly Thr Thr Thr Asp Lys Thr Leu Ala Thr Asp Lys Glu
            675                 680                 685

Glu Thr Tyr Lys Val Asp Phe Phe Ser Pro Ala Asp Lys Thr Lys Ala
            690                 695                 700

Val His Thr Ala Lys Val Ile Val Gly Asp Glu Lys Thr Met Met Val
705                 710                 715                 720

Asn Leu Ala Glu Gly Ala Thr Val Ile Gly Gly Ser Ala Asp Pro Val
                725                 730                 735

Asn Ala Arg Lys Val Phe Asp Gly Gln Leu Gly Ser Glu Thr Asp Asn
                740                 745                 750

Ile Ser Leu Gly Trp Asp Ser Lys Gln Ser Ile Ile Phe Lys Leu Lys
            755                 760                 765

Glu Asp Gly Leu Ile Lys His Trp Arg Phe Phe Asn Asp Ser Ala Arg
            770                 775                 780

Asn Pro Glu Thr Thr Asn Lys Pro Ile Gln Glu Ala Ser Leu Gln Ile
785                 790                 795                 800

Phe Asn Ile Lys Asp Tyr Asn Leu Asp Asn Leu Leu Glu Asn Pro Asn
                805                 810                 815

Lys Phe Asp Asp Glu Lys Tyr Trp Ile Thr Val Asp Thr Tyr Ser Ala
                820                 825                 830

Gln Gly Glu Arg Ala Thr Ala Phe Ser Asn Thr Leu Asn Asn Ile Thr
            835                 840                 845

Ser Lys Tyr Trp Arg Val Val Phe Asp Thr Lys Gly Asp Arg Tyr Ser
            850                 855                 860

Ser Pro Val Val Pro Glu Leu Gln Ile Leu Gly Tyr Pro Leu Pro Asn
865                 870                 875                 880

Ala Asp Thr Ile Met Lys Thr Val Thr Thr Ala Lys Glu Leu Ser Gln
                885                 890                 895

Gln Lys Asp Lys Phe Ser Gln Lys Met Leu Asp Glu Leu Lys Ile Lys
            900                 905                 910

Glu Met Ala Leu Glu Thr Ser Leu Asn Ser Lys Ile Phe Asp Val Thr
            915                 920                 925

Ala Ile Asn Ala Asn Ala Gly Val Leu Lys Asp Cys Ile Glu Lys Arg
            930                 935                 940

Gln Leu Leu Lys Lys Gly Gly Gly Ser Gly Gly Gly Ser Gly
945                 950                 955                 960

Gly Gly Gly Ser His His His His His Gly Gly Gly Ser Gly
            965                 970                 975

Gly Gly Gly Ser Gly Gly Gly Ser Ala Pro Ala Pro Val Lys Gln
            980                 985                 990

Gly Pro Thr Ser Val Ala Tyr Val  Glu Val Asn Asn Asn  Ser Met Leu
            995                 1000                1005
```

```
Asn Val Gly Lys Tyr Thr Leu Ala Asp Gly Gly Asn Ala Phe
    1010                1015                1020

Asp Val Ala Val Ile Phe Ala Ala Asn Ile Asn Tyr Asp Thr Gly
    1025                1030                1035

Thr Lys Thr Ala Tyr Leu His Phe Asn Glu Asn Val Gln Arg Val
    1040                1045                1050

Leu Asp Asn Ala Val Thr Gln Ile Arg Pro Leu Gln Gln Gln Gly
    1055                1060                1065

Ile Lys Val Leu Leu Ser Val Leu Gly Asn His Gln Gly Ala Gly
    1070                1075                1080

Phe Ala Asn Phe Pro Ser Gln Gln Ala Ala Ser Ala Phe Ala Lys
    1085                1090                1095

Gln Leu Ser Asp Ala Val Ala Lys Tyr Gly Leu Asp Gly Val Asp
    1100                1105                1110

Phe Asp Asp Glu Tyr Ala Glu Tyr Gly Asn Asn Gly Thr Ala Gln
    1115                1120                1125

Pro Asn Asp Ser Ser Phe Val His Leu Val Thr Ala Leu Arg Ala
    1130                1135                1140

Asn Met Pro Asp Lys Ile Ile Ser Leu Tyr Asn Ile Gly Pro Ala
    1145                1150                1155

Ala Ser Arg Leu Ser Tyr Gly Gly Val Asp Val Ser Asp Lys Phe
    1160                1165                1170

Asp Tyr Ala Trp Asn Pro Tyr Tyr Gly Thr Trp Gln Val Pro Gly
    1175                1180                1185

Ile Ala Leu Pro Lys Ala Gln Leu Ser Pro Ala Ala Val Glu Ile
    1190                1195                1200

Gly Arg Thr Ser Arg Ser Thr Val Ala Asp Leu Ala Arg Arg Thr
    1205                1210                1215

Val Asp Glu Gly Tyr Gly Val Tyr Leu Thr Tyr Asn Leu Asp Gly
    1220                1225                1230

Gly Asp Arg Thr Ala Asp Val Ser Ala Phe Thr Arg Glu Leu Tyr
    1235                1240                1245

Gly Ser Glu Ala Val Arg Thr Pro
    1250                1255

<210> SEQ ID NO 3
<211> LENGTH: 410
<212> TYPE: PRT
<213> ORGANISM: Artificial sequence
<220> FEATURE:
<223> OTHER INFORMATION: His-TnGalNAcT(33-421)

<400> SEQUENCE: 3

Met Gly Ser Ser His His His His His His Ser Ser Gly Leu Val Pro
1               5                   10                  15

Arg Gly Ser His Met Ser Pro Leu Arg Thr Tyr Leu Tyr Thr Pro Leu
                20                  25                  30

Tyr Asn Ala Thr Gln Pro Thr Leu Arg Asn Val Glu Arg Leu Ala Ala
        35                  40                  45

Asn Trp Pro Lys Lys Ile Pro Ser Asn Tyr Ile Glu Asp Ser Glu Glu
    50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95
```

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
        115                 120                 125

Thr Glu Asp Gly Val Lys Ala Glu Ala Val Val Thr Leu Pro Leu
    130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
        195                 200                 205

Asn His Met His Pro Phe Leu Met Lys Gln Gln Ile Glu Tyr Gly Ile
    210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
            260                 265                 270

Asn Leu Tyr Ser Cys Pro Arg Gln Pro Arg His Met Ser Ala Ser Ile
        275                 280                 285

Asp Lys Leu His Phe Lys Leu Pro Tyr Glu Asp Ile Phe Gly Gly Val
    290                 295                 300

Ser Ala Met Thr Leu Glu Gln Phe Thr Arg Val Asn Gly Phe Ser Asn
305                 310                 315                 320

Lys Tyr Trp Gly Trp Gly Gly Glu Asp Asp Asp Met Ser Tyr Arg Leu
                325                 330                 335

Lys Lys Ile Asn Tyr His Ile Ala Arg Tyr Lys Met Ser Ile Ala Arg
            340                 345                 350

Tyr Ala Met Leu Asp His Lys Lys Ser Thr Pro Asn Pro Lys Arg Tyr
        355                 360                 365

Gln Leu Leu Ser Gln Thr Ser Lys Thr Phe Gln Lys Asp Gly Leu Ser
    370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
                405                 410

<210> SEQ ID NO 4
<211> LENGTH: 949
<212> TYPE: PRT
<213> ORGANISM: Artificial sequence
<220> FEATURE:
<223> OTHER INFORMATION: EndoS

<400> SEQUENCE: 4

Met Pro Ser Ile Asp Ser Leu His Tyr Leu Ser Glu Asn Ser Lys Lys
1               5                   10                  15

Glu Phe Lys Glu Glu Leu Ser Lys Ala Gly Gln Glu Ser Gln Lys Val
            20                  25                  30

Lys Glu Ile Leu Ala Lys Ala Gln Gln Ala Asp Lys Gln Ala Gln Glu
        35                  40                  45

-continued

```
Leu Ala Lys Met Lys Ile Pro Glu Lys Ile Pro Met Lys Pro Leu His
    50                  55                  60

Gly Pro Leu Tyr Gly Tyr Phe Arg Thr Trp His Asp Lys Thr Ser
65                  70                  75                  80

Asp Pro Thr Glu Lys Asp Lys Val Asn Ser Met Gly Glu Leu Pro Lys
                85                  90                  95

Glu Val Asp Leu Ala Phe Ile Phe His Asp Trp Thr Lys Asp Tyr Ser
                100                 105                 110

Leu Phe Trp Lys Glu Leu Ala Thr Lys His Val Pro Lys Leu Asn Lys
            115                 120                 125

Gln Gly Thr Arg Val Ile Arg Thr Ile Pro Trp Arg Phe Leu Ala Gly
            130                 135                 140

Gly Asp Asn Ser Gly Ile Ala Glu Asp Thr Ser Lys Tyr Pro Asn Thr
145                 150                 155                 160

Pro Glu Gly Asn Lys Ala Leu Ala Lys Ala Ile Val Asp Glu Tyr Val
                165                 170                 175

Tyr Lys Tyr Asn Leu Asp Gly Leu Asp Val Asp Val Glu His Asp Ser
                180                 185                 190

Ile Pro Lys Val Asp Lys Glu Asp Thr Ala Gly Val Glu Arg Ser
            195                 200                 205

Ile Gln Val Phe Glu Glu Ile Gly Lys Leu Ile Gly Pro Lys Gly Val
    210                 215                 220

Asp Lys Ser Arg Leu Phe Ile Met Asp Ser Thr Tyr Met Ala Asp Lys
225                 230                 235                 240

Asn Pro Leu Ile Glu Arg Gly Ala Pro Tyr Ile Asn Leu Leu Leu Val
                245                 250                 255

Gln Val Tyr Gly Ser Gln Gly Leu Lys Gly Gly Trp Glu Pro Val Ser
                260                 265                 270

Asn Arg Pro Glu Lys Thr Met Glu Glu Arg Trp Gln Gly Tyr Ser Lys
            275                 280                 285

Tyr Ile Arg Pro Glu Gln Tyr Met Ile Gly Phe Ser Phe Tyr Glu Glu
    290                 295                 300

Asn Ala Gln Glu Gly Asn Leu Trp Tyr Asp Ile Asn Ser Arg Lys Asp
305                 310                 315                 320

Glu Asp Lys Ala Asn Gly Ile Asn Thr Asp Ile Thr Gly Thr Arg Ala
                325                 330                 335

Glu Arg Tyr Ala Arg Trp Gln Pro Lys Thr Gly Gly Val Lys Gly Gly
            340                 345                 350

Ile Phe Ser Tyr Ala Ile Asp Arg Asp Gly Val Ala His Gln Pro Lys
            355                 360                 365

Lys Tyr Ala Lys Gln Lys Glu Phe Lys Asp Ala Thr Asp Asn Ile Phe
    370                 375                 380

His Ser Asp Tyr Ser Val Ser Lys Ala Leu Lys Thr Val Met Leu Lys
385                 390                 395                 400

Asp Lys Ser Tyr Asp Leu Ile Asp Glu Lys Asp Phe Pro Asp Lys Ala
                405                 410                 415

Leu Arg Glu Ala Val Met Ala Gln Val Gly Thr Arg Lys Gly Asp Leu
            420                 425                 430

Glu Arg Phe Asn Gly Thr Leu Arg Leu Asp Asn Pro Ala Ile Gln Ser
            435                 440                 445

Leu Glu Gly Leu Asn Lys Phe Lys Lys Leu Ala Gln Leu Asp Leu Ile
    450                 455                 460
```

```
Gly Leu Ser Arg Ile Thr Lys Leu Asp Arg Ser Val Leu Pro Ala Asn
465                 470                 475                 480

Met Lys Pro Gly Lys Asp Thr Leu Glu Thr Val Leu Glu Thr Tyr Lys
            485                 490                 495

Lys Asp Asn Lys Glu Glu Pro Ala Thr Ile Pro Pro Val Ser Leu Lys
            500                 505                 510

Val Ser Gly Leu Thr Gly Leu Lys Glu Leu Asp Leu Ser Gly Phe Asp
        515                 520                 525

Arg Glu Thr Leu Ala Gly Leu Asp Ala Ala Thr Leu Thr Ser Leu Glu
        530                 535                 540

Lys Val Asp Ile Ser Gly Asn Lys Leu Asp Leu Ala Pro Gly Thr Glu
545                 550                 555                 560

Asn Arg Gln Ile Phe Asp Thr Met Leu Ser Thr Ile Ser Asn His Val
                565                 570                 575

Gly Ser Asn Glu Gln Thr Val Lys Phe Asp Lys Gln Lys Pro Thr Gly
            580                 585                 590

His Tyr Pro Asp Thr Tyr Gly Lys Thr Ser Leu Arg Leu Pro Val Ala
        595                 600                 605

Asn Glu Lys Val Asp Leu Gln Ser Gln Leu Leu Phe Gly Thr Val Thr
610                 615                 620

Asn Gln Gly Thr Leu Ile Asn Ser Glu Ala Asp Tyr Lys Ala Tyr Gln
625                 630                 635                 640

Asn His Lys Ile Ala Gly Arg Ser Phe Val Asp Ser Asn Tyr His Tyr
                645                 650                 655

Asn Asn Phe Lys Val Ser Tyr Glu Asn Tyr Thr Val Lys Val Thr Asp
            660                 665                 670

Ser Thr Leu Gly Thr Thr Thr Asp Lys Thr Leu Ala Thr Asp Lys Glu
        675                 680                 685

Glu Thr Tyr Lys Val Asp Phe Phe Ser Pro Ala Asp Lys Thr Lys Ala
        690                 695                 700

Val His Thr Ala Lys Val Ile Val Gly Asp Glu Lys Thr Met Met Val
705                 710                 715                 720

Asn Leu Ala Glu Gly Ala Thr Val Ile Gly Gly Ser Ala Asp Pro Val
                725                 730                 735

Asn Ala Arg Lys Val Phe Asp Gly Gln Leu Gly Ser Glu Thr Asp Asn
            740                 745                 750

Ile Ser Leu Gly Trp Asp Ser Lys Gln Ser Ile Ile Phe Lys Leu Lys
        755                 760                 765

Glu Asp Gly Leu Ile Lys His Trp Arg Phe Phe Asn Asp Ser Ala Arg
        770                 775                 780

Asn Pro Glu Thr Thr Asn Lys Pro Ile Gln Glu Ala Ser Leu Gln Ile
785                 790                 795                 800

Phe Asn Ile Lys Asp Tyr Asn Leu Asp Asn Leu Leu Glu Asn Pro Asn
                805                 810                 815

Lys Phe Asp Asp Glu Lys Tyr Trp Ile Thr Val Asp Thr Tyr Ser Ala
            820                 825                 830

Gln Gly Glu Arg Ala Thr Ala Phe Ser Asn Thr Leu Asn Asn Ile Thr
        835                 840                 845

Ser Lys Tyr Trp Arg Val Val Phe Asp Thr Lys Gly Asp Arg Tyr Ser
        850                 855                 860

Ser Pro Val Val Pro Glu Leu Gln Ile Leu Gly Tyr Pro Leu Pro Asn
865                 870                 875                 880
```

```
Ala Asp Thr Ile Met Lys Thr Val Thr Thr Ala Lys Glu Leu Ser Gln
            885                 890                 895

Gln Lys Asp Lys Phe Ser Gln Lys Met Leu Asp Glu Leu Lys Ile Lys
            900                 905                 910

Glu Met Ala Leu Glu Thr Ser Leu Asn Ser Lys Ile Phe Asp Val Thr
            915                 920                 925

Ala Ile Asn Ala Asn Ala Gly Val Leu Lys Asp Cys Ile Glu Lys Arg
            930                 935                 940

Gln Leu Leu Lys Lys
945

<210> SEQ ID NO 5
<211> LENGTH: 969
<212> TYPE: PRT
<213> ORGANISM: Artificial sequence
<220> FEATURE:
<223> OTHER INFORMATION: EndoS 2

<400> SEQUENCE: 5

Met Gly Ser Ser His His His His His His Ser Ser Gly Leu Val Pro
1               5                   10                  15

Arg Gly Ser His Met Pro Ser Ile Asp Ser Leu His Tyr Leu Ser Glu
            20                  25                  30

Asn Ser Lys Lys Glu Phe Lys Glu Glu Leu Ser Lys Ala Gly Gln Glu
            35                  40                  45

Ser Gln Lys Val Lys Glu Ile Leu Ala Lys Ala Gln Gln Ala Asp Lys
            50                  55                  60

Gln Ala Gln Glu Leu Ala Lys Met Lys Ile Pro Glu Lys Ile Pro Met
65                  70                  75                  80

Lys Pro Leu His Gly Pro Leu Tyr Gly Gly Tyr Phe Arg Thr Trp His
            85                  90                  95

Asp Lys Thr Ser Asp Pro Thr Glu Lys Asp Lys Val Asn Ser Met Gly
            100                 105                 110

Glu Leu Pro Lys Glu Val Asp Leu Ala Phe Ile Phe His Asp Trp Thr
            115                 120                 125

Lys Asp Tyr Ser Leu Phe Trp Lys Glu Leu Ala Thr Lys His Val Pro
            130                 135                 140

Lys Leu Asn Lys Gln Gly Thr Arg Val Ile Arg Thr Ile Pro Trp Arg
145                 150                 155                 160

Phe Leu Ala Gly Gly Asp Asn Ser Gly Ile Ala Glu Asp Thr Ser Lys
            165                 170                 175

Tyr Pro Asn Thr Pro Glu Gly Asn Lys Ala Leu Ala Lys Ala Ile Val
            180                 185                 190

Asp Glu Tyr Val Tyr Lys Tyr Asn Leu Asp Gly Leu Asp Val Asp Val
            195                 200                 205

Glu His Asp Ser Ile Pro Lys Val Asp Lys Glu Asp Thr Ala Gly
            210                 215                 220

Val Glu Arg Ser Ile Gln Val Phe Glu Glu Ile Gly Lys Leu Ile Gly
225                 230                 235                 240

Pro Lys Gly Val Asp Lys Ser Arg Leu Phe Ile Met Asp Ser Thr Tyr
            245                 250                 255

Met Ala Asp Lys Asn Pro Leu Ile Glu Arg Gly Ala Pro Tyr Ile Asn
            260                 265                 270

Leu Leu Leu Val Gln Val Tyr Gly Ser Gln Gly Glu Lys Gly Gly Trp
            275                 280                 285
```

```
Glu Pro Val Ser Asn Arg Pro Glu Lys Thr Met Glu Glu Arg Trp Gln
    290                 295                 300

Gly Tyr Ser Lys Tyr Ile Arg Pro Glu Gln Tyr Met Ile Gly Phe Ser
305                 310                 315                 320

Phe Tyr Glu Glu Asn Ala Gln Glu Gly Asn Leu Trp Tyr Asp Ile Asn
                325                 330                 335

Ser Arg Lys Asp Glu Asp Lys Ala Asn Gly Ile Asn Thr Asp Ile Thr
            340                 345                 350

Gly Thr Arg Ala Glu Arg Tyr Ala Arg Trp Gln Pro Lys Thr Gly Gly
        355                 360                 365

Val Lys Gly Gly Ile Phe Ser Tyr Ala Ile Asp Arg Asp Gly Val Ala
    370                 375                 380

His Gln Pro Lys Lys Tyr Ala Lys Gln Lys Glu Phe Lys Asp Ala Thr
385                 390                 395                 400

Asp Asn Ile Phe His Ser Asp Tyr Ser Val Ser Lys Ala Leu Lys Thr
                405                 410                 415

Val Met Leu Lys Asp Lys Ser Tyr Asp Leu Ile Asp Glu Lys Asp Phe
            420                 425                 430

Pro Asp Lys Ala Leu Arg Glu Ala Val Met Ala Gln Val Gly Thr Arg
        435                 440                 445

Lys Gly Asp Leu Glu Arg Phe Asn Gly Thr Leu Arg Leu Asp Asn Pro
    450                 455                 460

Ala Ile Gln Ser Leu Glu Gly Leu Asn Lys Phe Lys Lys Leu Ala Gln
465                 470                 475                 480

Leu Asp Leu Ile Gly Leu Ser Arg Ile Thr Lys Leu Asp Arg Ser Val
                485                 490                 495

Leu Pro Ala Asn Met Lys Pro Gly Lys Asp Thr Leu Glu Thr Val Leu
            500                 505                 510

Glu Thr Tyr Lys Lys Asp Asn Lys Glu Glu Pro Ala Thr Ile Pro Pro
        515                 520                 525

Val Ser Leu Lys Val Ser Gly Leu Thr Gly Leu Lys Glu Leu Asp Leu
    530                 535                 540

Ser Gly Phe Asp Arg Glu Thr Leu Ala Gly Leu Asp Ala Ala Thr Leu
545                 550                 555                 560

Thr Ser Leu Glu Lys Val Asp Ile Ser Gly Asn Lys Leu Asp Leu Ala
                565                 570                 575

Pro Gly Thr Glu Asn Arg Gln Ile Phe Asp Thr Met Leu Ser Thr Ile
            580                 585                 590

Ser Asn His Val Gly Ser Asn Glu Gln Thr Val Lys Phe Asp Lys Gln
        595                 600                 605

Lys Pro Thr Gly His Tyr Pro Asp Thr Tyr Gly Lys Thr Ser Leu Arg
    610                 615                 620

Leu Pro Val Ala Asn Glu Lys Val Asp Leu Gln Ser Gln Leu Leu Phe
625                 630                 635                 640

Gly Thr Val Thr Asn Gln Gly Thr Leu Ile Asn Ser Glu Ala Asp Tyr
                645                 650                 655

Lys Ala Tyr Gln Asn His Lys Ile Ala Gly Arg Ser Phe Val Asp Ser
            660                 665                 670

Asn Tyr His Tyr Asn Asn Phe Lys Val Ser Tyr Glu Asn Tyr Thr Val
        675                 680                 685

Lys Val Thr Asp Ser Thr Leu Gly Thr Thr Thr Asp Lys Thr Leu Ala
    690                 695                 700
```

Thr Asp Lys Glu Glu Thr Tyr Lys Val Asp Phe Ser Pro Ala Asp
705                 710                 715                 720

Lys Thr Lys Ala Val His Thr Ala Lys Val Ile Val Gly Asp Glu Lys
            725                 730                 735

Thr Met Met Val Asn Leu Ala Glu Gly Ala Thr Val Ile Gly Gly Ser
            740                 745                 750

Ala Asp Pro Val Asn Ala Arg Lys Val Phe Asp Gly Gln Leu Gly Ser
            755                 760                 765

Glu Thr Asp Asn Ile Ser Leu Gly Trp Asp Ser Lys Gln Ser Ile Ile
    770                 775                 780

Phe Lys Leu Lys Glu Asp Gly Leu Ile Lys His Trp Arg Phe Phe Asn
785                 790                 795                 800

Asp Ser Ala Arg Asn Pro Glu Thr Thr Asn Lys Pro Ile Gln Glu Ala
            805                 810                 815

Ser Leu Gln Ile Phe Asn Ile Lys Asp Tyr Asn Leu Asp Asn Leu Leu
            820                 825                 830

Glu Asn Pro Asn Lys Phe Asp Asp Glu Lys Tyr Trp Ile Thr Val Asp
            835                 840                 845

Thr Tyr Ser Ala Gln Gly Glu Arg Ala Thr Ala Phe Ser Asn Thr Leu
    850                 855                 860

Asn Asn Ile Thr Ser Lys Tyr Trp Arg Val Val Phe Asp Thr Lys Gly
865                 870                 875                 880

Asp Arg Tyr Ser Ser Pro Val Val Pro Glu Leu Gln Ile Leu Gly Tyr
            885                 890                 895

Pro Leu Pro Asn Ala Asp Thr Ile Met Lys Thr Val Thr Thr Ala Lys
            900                 905                 910

Glu Leu Ser Gln Gln Lys Asp Lys Phe Ser Gln Lys Met Leu Asp Glu
            915                 920                 925

Leu Lys Ile Lys Glu Met Ala Leu Glu Thr Ser Leu Asn Ser Lys Ile
    930                 935                 940

Phe Asp Val Thr Ala Ile Asn Ala Asn Ala Gly Val Leu Lys Asp Cys
945                 950                 955                 960

Ile Glu Lys Arg Gln Leu Leu Lys Lys
            965

<210> SEQ ID NO 6
<211> LENGTH: 271
<212> TYPE: PRT
<213> ORGANISM: Artificial sequence
<220> FEATURE:
<223> OTHER INFORMATION: EndoH

<400> SEQUENCE: 6

Ala Pro Ala Pro Val Lys Gln Gly Pro Thr Ser Val Ala Tyr Val Glu
1               5                   10                  15

Val Asn Asn Asn Ser Met Leu Asn Val Gly Lys Tyr Thr Leu Ala Asp
            20                  25                  30

Gly Gly Gly Asn Ala Phe Asp Val Ala Val Ile Phe Ala Ala Asn Ile
        35                  40                  45

Asn Tyr Asp Thr Gly Thr Lys Thr Ala Tyr Leu His Phe Asn Glu Asn
    50                  55                  60

Val Gln Arg Val Leu Asp Asn Ala Val Thr Gln Ile Arg Pro Leu Gln
65                  70                  75                  80

Gln Gln Gly Ile Lys Val Leu Leu Ser Val Leu Gly Asn His Gln Gly
            85                  90                  95

```
Ala Gly Phe Ala Asn Phe Pro Ser Gln Gln Ala Ala Ser Ala Phe Ala
            100                 105                 110

Lys Gln Leu Ser Asp Ala Val Ala Lys Tyr Gly Leu Asp Gly Val Asp
        115                 120                 125

Phe Asp Asp Glu Tyr Ala Glu Tyr Gly Asn Asn Gly Thr Ala Gln Pro
    130                 135                 140

Asn Asp Ser Ser Phe Val His Leu Val Thr Ala Leu Arg Ala Asn Met
145                 150                 155                 160

Pro Asp Lys Ile Ile Ser Leu Tyr Asn Ile Gly Pro Ala Ala Ser Arg
                165                 170                 175

Leu Ser Tyr Gly Gly Val Asp Val Ser Asp Lys Phe Asp Tyr Ala Trp
            180                 185                 190

Asn Pro Tyr Tyr Gly Thr Trp Gln Val Pro Gly Ile Ala Leu Pro Lys
        195                 200                 205

Ala Gln Leu Ser Pro Ala Ala Val Glu Ile Gly Arg Thr Ser Arg Ser
    210                 215                 220

Thr Val Ala Asp Leu Ala Arg Arg Thr Val Asp Glu Gly Tyr Gly Val
225                 230                 235                 240

Tyr Leu Thr Tyr Asn Leu Asp Gly Gly Asp Arg Thr Ala Asp Val Ser
                245                 250                 255

Ala Phe Thr Arg Glu Leu Tyr Gly Ser Glu Ala Val Arg Thr Pro
            260                 265                 270

<210> SEQ ID NO 7
<211> LENGTH: 289
<212> TYPE: PRT
<213> ORGANISM: Artificial sequence
<220> FEATURE:
<223> OTHER INFORMATION: EndoF1

<400> SEQUENCE: 7

Ala Val Thr Gly Thr Thr Lys Ala Asn Ile Lys Leu Phe Ser Phe Thr
1               5                   10                  15

Glu Val Asn Asp Thr Asn Pro Leu Asn Asn Leu Asn Phe Thr Leu Lys
            20                  25                  30

Asn Ser Gly Lys Pro Leu Val Asp Met Val Val Leu Phe Ser Ala Asn
        35                  40                  45

Ile Asn Tyr Asp Ala Ala Asn Asp Lys Val Phe Val Ser Asn Asn Pro
    50                  55                  60

Asn Val Gln His Leu Leu Thr Asn Arg Ala Lys Tyr Leu Lys Pro Leu
65                  70                  75                  80

Gln Asp Lys Gly Ile Lys Val Ile Leu Ser Ile Leu Gly Asn His Asp
                85                  90                  95

Arg Ser Gly Ile Ala Asn Leu Ser Thr Ala Arg Ala Lys Ala Phe Ala
            100                 105                 110

Gln Glu Leu Lys Asn Thr Cys Asp Leu Tyr Asn Leu Asp Gly Val Phe
        115                 120                 125

Phe Asp Asp Glu Tyr Ser Ala Tyr Gln Thr Pro Pro Ser Gly Phe
    130                 135                 140

Val Thr Pro Ser Asn Asn Ala Ala Ala Arg Leu Ala Tyr Glu Thr Lys
145                 150                 155                 160

Gln Ala Met Pro Asn Lys Leu Val Thr Val Tyr Val Tyr Ser Arg Thr
                165                 170                 175

Ser Ser Phe Pro Thr Ala Val Asp Gly Val Asn Ala Gly Ser Tyr Val
            180                 185                 190
```

-continued

```
Asp Tyr Ala Ile His Asp Tyr Gly Gly Ser Tyr Asp Leu Ala Thr Asn
            195                 200                 205
Tyr Pro Gly Leu Ala Lys Ser Gly Met Val Met Ser Ser Gln Glu Phe
    210                 215                 220
Asn Gln Gly Arg Tyr Ala Thr Ala Gln Ala Leu Arg Asn Ile Val Thr
225                 230                 235                 240
Lys Gly Tyr Gly Gly His Met Ile Phe Ala Met Asp Pro Asn Arg Ser
                245                 250                 255
Asn Phe Thr Ser Gly Gln Leu Pro Ala Leu Lys Leu Ile Ala Lys Glu
            260                 265                 270
Leu Tyr Gly Asp Glu Leu Val Tyr Ser Asn Thr Pro Tyr Ser Lys Asp
        275                 280                 285
Trp

<210> SEQ ID NO 8
<211> LENGTH: 291
<212> TYPE: PRT
<213> ORGANISM: Artificial sequence
<220> FEATURE:
<223> OTHER INFORMATION: EndoF2

<400> SEQUENCE: 8

Met Ala Val Asn Leu Ser Asn Leu Ile Ala Tyr Lys Asn Ser Asp His
1               5                   10                  15
Gln Ile Ser Ala Gly Tyr Tyr Arg Thr Trp Arg Asp Ser Ala Thr Ala
            20                  25                  30
Ser Gly Asn Leu Pro Ser Met Arg Trp Leu Pro Asp Ser Leu Asp Met
        35                  40                  45
Val Met Val Phe Pro Asp Tyr Thr Pro Pro Glu Asn Ala Tyr Trp Asn
    50                  55                  60
Thr Leu Lys Thr Asn Tyr Val Pro Tyr Leu His Lys Arg Gly Thr Lys
65                  70                  75                  80
Val Ile Ile Thr Leu Gly Asp Leu Asn Ser Ala Thr Thr Thr Gly Gly
                85                  90                  95
Gln Asp Ser Ile Gly Tyr Ser Ser Trp Ala Lys Gly Ile Tyr Asp Lys
            100                 105                 110
Trp Val Gly Glu Tyr Asn Leu Asp Gly Ile Asp Ile Asp Ile Glu Ser
        115                 120                 125
Ser Pro Ser Gly Ala Thr Leu Thr Lys Phe Val Ala Ala Thr Lys Ala
    130                 135                 140
Leu Ser Lys Tyr Phe Gly Pro Lys Ser Gly Thr Gly Lys Thr Phe Val
145                 150                 155                 160
Tyr Asp Thr Asn Gln Asn Pro Thr Asn Phe Phe Ile Gln Thr Ala Pro
                165                 170                 175
Arg Tyr Asn Tyr Val Phe Leu Gln Ala Tyr Gly Arg Ser Thr Thr Asn
            180                 185                 190
Leu Thr Thr Val Ser Gly Leu Tyr Ala Pro Tyr Ile Ser Met Lys Gln
        195                 200                 205
Phe Leu Pro Gly Phe Ser Phe Tyr Glu Glu Asn Gly Tyr Pro Gly Asn
    210                 215                 220
Tyr Trp Asn Asp Val Arg Tyr Pro Gln Asn Gly Thr Gly Arg Ala Tyr
225                 230                 235                 240
Asp Tyr Ala Arg Trp Gln Pro Ala Thr Gly Lys Lys Gly Gly Val Phe
                245                 250                 255
```

```
Ser Tyr Ala Ile Glu Arg Asp Ala Pro Leu Thr Ser Ser Asn Asp Asn
            260                 265                 270

Thr Leu Arg Ala Pro Asn Phe Arg Val Thr Lys Asp Leu Ile Lys Ile
            275                 280                 285

Met Asn Pro
    290

<210> SEQ ID NO 9
<211> LENGTH: 291
<212> TYPE: PRT
<213> ORGANISM: Artificial sequence
<220> FEATURE:
<223> OTHER INFORMATION: EndoF3

<400> SEQUENCE: 9

Met Ala Thr Ala Leu Ala Gly Ser Asn Gly Val Cys Ile Ala Tyr Tyr
1               5                   10                  15

Ile Thr Asp Gly Arg Asn Pro Thr Phe Lys Leu Lys Asp Ile Pro Asp
            20                  25                  30

Lys Val Asp Met Val Ile Leu Phe Gly Leu Lys Tyr Trp Ser Leu Gln
            35                  40                  45

Asp Thr Thr Lys Leu Pro Gly Gly Thr Gly Met Met Gly Ser Phe Lys
    50                  55                  60

Ser Tyr Lys Asp Leu Asp Thr Gln Ile Arg Ser Leu Gln Ser Arg Gly
65                  70                  75                  80

Ile Lys Val Leu Gln Asn Ile Asp Asp Val Ser Trp Gln Ser Ser
            85                  90                  95

Lys Pro Gly Gly Phe Ala Ser Ala Ala Tyr Gly Asp Ala Ile Lys
            100                 105                 110

Ser Ile Val Ile Asp Lys Trp Lys Leu Asp Gly Ile Ser Leu Asp Ile
            115                 120                 125

Glu His Ser Gly Ala Lys Pro Asn Pro Ile Pro Thr Phe Pro Gly Tyr
    130                 135                 140

Ala Ala Thr Gly Tyr Asn Gly Trp Tyr Ser Gly Ser Met Ala Ala Thr
145                 150                 155                 160

Pro Ala Phe Leu Asn Val Ile Ser Glu Leu Thr Lys Tyr Phe Gly Thr
            165                 170                 175

Thr Ala Pro Asn Asn Lys Gln Leu Gln Ile Ala Ser Gly Ile Asp Val
            180                 185                 190

Tyr Ala Trp Asn Lys Ile Met Glu Asn Phe Arg Asn Asn Phe Asn Tyr
            195                 200                 205

Ile Gln Leu Gln Ser Tyr Gly Ala Asn Val Ser Arg Thr Gln Leu Met
    210                 215                 220

Met Asn Tyr Ala Thr Gly Thr Asn Lys Ile Pro Ala Ser Lys Met Val
225                 230                 235                 240

Phe Gly Ala Tyr Ala Glu Gly Gly Thr Asn Gln Ala Asn Asp Val Glu
            245                 250                 255

Val Ala Lys Trp Thr Pro Thr Gln Gly Ala Lys Gly Gly Met Met Ile
            260                 265                 270

Tyr Thr Tyr Asn Ser Asn Val Ser Tyr Ala Asn Ala Val Arg Asp Ala
            275                 280                 285

Val Lys Asn
    290

<210> SEQ ID NO 10
```

```
<211> LENGTH: 273
<212> TYPE: PRT
<213> ORGANISM: Artificial sequence
<220> FEATURE:
<223> OTHER INFORMATION: EfEndo18A

<400> SEQUENCE: 10
```

Ala Ser Thr Val Thr Pro Lys Thr Val Met Tyr Val Glu Val Asn Asn
1               5                   10                  15

His Asp Phe Asn Asn Val Gly Lys Tyr Thr Leu Ala Gly Thr Asn Gln
            20                  25                  30

Pro Ala Phe Asp Met Gly Ile Ile Phe Ala Ala Asn Ile Asn Tyr Asp
        35                  40                  45

Thr Val Asn Lys Lys Pro Tyr Leu Tyr Leu Asn Glu Arg Val Gln Gln
    50                  55                  60

Thr Leu Asn Glu Ala Glu Thr Gln Ile Arg Pro Val Gln Ala Arg Gly
65                  70                  75                  80

Thr Lys Val Leu Leu Ser Ile Leu Gly Asn His Glu Gly Ala Gly Phe
                85                  90                  95

Ala Asn Phe Pro Thr Tyr Glu Ser Ala Asp Ala Phe Ala Ala Gln Leu
            100                 105                 110

Glu Gln Val Val Asn Thr Tyr His Leu Asp Gly Ile Asp Phe Asp Asp
        115                 120                 125

Glu Tyr Ala Glu Tyr Gly Lys Asn Gly Thr Pro Gln Pro Asn Asn Ser
    130                 135                 140

Ser Phe Ile Trp Leu Leu Gln Ala Leu Arg Asn Arg Leu Gly Asn Asp
145                 150                 155                 160

Lys Leu Ile Thr Phe Tyr Asn Ile Gly Pro Ala Ala Ala Asn Ser Ser
                165                 170                 175

Ala Asn Pro Gln Met Ser Ser Leu Ile Asp Tyr Ala Trp Asn Pro Tyr
            180                 185                 190

Tyr Ser Thr Trp Asn Pro Pro Gln Ile Ala Gly Met Pro Ala Ser Arg
        195                 200                 205

Leu Gly Ala Ser Ala Val Glu Val Gly Val Asn Gln Asn Leu Ala Ala
    210                 215                 220

Gln Tyr Ala Lys Arg Thr Lys Ala Glu Gln Tyr Gly Ile Tyr Leu Met
225                 230                 235                 240

Tyr Asn Leu Pro Gly Lys Asp Ser Ser Ala Tyr Ile Ser Ala Ala Thr
                245                 250                 255

Gln Glu Leu Tyr Gly Arg Lys Thr Asn Tyr Ser Pro Thr Val Pro Thr
            260                 265                 270

Pro

```
<210> SEQ ID NO 11
<211> LENGTH: 38
<212> TYPE: PRT
<213> ORGANISM: Artificial sequence
<220> FEATURE:
<223> OTHER INFORMATION: linker

<400> SEQUENCE: 11
```

Gly Gly Gly Gly Ser Gly Gly Gly Ser Gly Gly Gly Ser His
1               5                   10                  15

His His His His Glu Phe Gly Gly Gly Ser Gly Gly Gly Gly
            20                  25                  30

Ser Gly Gly Gly Gly Ser
        35

```
<210> SEQ ID NO 12
<211> LENGTH: 36
<212> TYPE: PRT
<213> ORGANISM: Artificial sequence
<220> FEATURE:
<223> OTHER INFORMATION: linker

<400> SEQUENCE: 12

Gly Gly Gly Gly Ser Gly Gly Gly Ser Gly Gly Gly Gly Ser His
1               5                   10                  15

His His His His His Gly Gly Gly Ser Gly Gly Gly Gly Ser Gly
                20                  25                  30

Gly Gly Gly Ser
            35

<210> SEQ ID NO 13
<211> LENGTH: 602
<212> TYPE: PRT
<213> ORGANISM: Artificial sequence
<220> FEATURE:
<223> OTHER INFORMATION: EndoF3-EfEndo18A

<400> SEQUENCE: 13

Met Ala Thr Ala Leu Ala Gly Ser Asn Gly Val Cys Ile Ala Tyr Tyr
1               5                   10                  15

Ile Thr Asp Gly Arg Asn Pro Thr Phe Lys Leu Lys Asp Ile Pro Asp
                20                  25                  30

Lys Val Asp Met Val Ile Leu Phe Gly Leu Lys Tyr Trp Ser Leu Gln
            35                  40                  45

Asp Thr Thr Lys Leu Pro Gly Gly Thr Gly Met Met Gly Ser Phe Lys
        50                  55                  60

Ser Tyr Lys Asp Leu Asp Thr Gln Ile Arg Ser Leu Gln Ser Arg Gly
65                  70                  75                  80

Ile Lys Val Leu Gln Asn Ile Asp Asp Val Ser Trp Gln Ser Ser
                85                  90                  95

Lys Pro Gly Gly Phe Ala Ser Ala Ala Ala Tyr Gly Asp Ala Ile Lys
            100                 105                 110

Ser Ile Val Ile Asp Lys Trp Lys Leu Asp Gly Ile Ser Leu Asp Ile
        115                 120                 125

Glu His Ser Gly Ala Lys Pro Asn Pro Ile Pro Thr Phe Pro Gly Tyr
    130                 135                 140

Ala Ala Thr Gly Tyr Asn Gly Trp Tyr Ser Gly Ser Met Ala Ala Thr
145                 150                 155                 160

Pro Ala Phe Leu Asn Val Ile Ser Glu Leu Thr Lys Tyr Phe Gly Thr
                165                 170                 175

Thr Ala Pro Asn Asn Lys Gln Leu Gln Ile Ala Ser Gly Ile Asp Val
            180                 185                 190

Tyr Ala Trp Asn Lys Ile Met Glu Asn Phe Arg Asn Asn Phe Asn Tyr
        195                 200                 205

Ile Gln Leu Gln Ser Tyr Gly Ala Asn Val Ser Arg Thr Gln Leu Met
    210                 215                 220

Met Asn Tyr Ala Thr Gly Thr Asn Lys Ile Pro Ala Ser Lys Met Val
225                 230                 235                 240

Phe Gly Ala Tyr Ala Glu Gly Gly Thr Asn Gln Ala Asn Asp Val Glu
                245                 250                 255
```

Val Ala Lys Trp Thr Pro Thr Gln Gly Ala Lys Gly Gly Met Met Ile
            260                 265                 270

Tyr Thr Tyr Asn Ser Asn Val Ser Tyr Ala Asn Ala Val Arg Asp Ala
            275                 280                 285

Val Lys Asn Gly Gly Gly Ser Gly Gly Gly Ser Gly Gly Gly
290                 295                 300

Gly Ser His His His His His His Glu Phe Gly Gly Gly Ser Gly
305                 310                 315                 320

Gly Gly Gly Ser Gly Gly Gly Ser Ala Ser Thr Val Thr Pro Lys
            325                 330                 335

Thr Val Met Tyr Val Glu Val Asn Asn His Asp Phe Asn Asn Val Gly
            340                 345                 350

Lys Tyr Thr Leu Ala Gly Thr Asn Gln Pro Ala Phe Asp Met Gly Ile
            355                 360                 365

Ile Phe Ala Ala Asn Ile Asn Tyr Asp Thr Val Asn Lys Lys Pro Tyr
            370                 375                 380

Leu Tyr Leu Asn Glu Arg Val Gln Gln Thr Leu Asn Glu Ala Glu Thr
385                 390                 395                 400

Gln Ile Arg Pro Val Gln Ala Arg Gly Thr Lys Val Leu Leu Ser Ile
            405                 410                 415

Leu Gly Asn His Glu Gly Ala Gly Phe Ala Asn Phe Pro Thr Tyr Glu
            420                 425                 430

Ser Ala Asp Ala Phe Ala Ala Gln Leu Glu Gln Val Val Asn Thr Tyr
            435                 440                 445

His Leu Asp Gly Ile Asp Phe Asp Asp Glu Tyr Ala Glu Tyr Gly Lys
    450                 455                 460

Asn Gly Thr Pro Gln Pro Asn Asn Ser Ser Phe Ile Trp Leu Leu Gln
465                 470                 475                 480

Ala Leu Arg Asn Arg Leu Gly Asn Asp Lys Leu Ile Thr Phe Tyr Asn
            485                 490                 495

Ile Gly Pro Ala Ala Ala Asn Ser Ser Ala Asn Pro Gln Met Ser Ser
            500                 505                 510

Leu Ile Asp Tyr Ala Trp Asn Pro Tyr Tyr Ser Thr Trp Asn Pro Pro
            515                 520                 525

Gln Ile Ala Gly Met Pro Ala Ser Arg Leu Gly Ala Ser Ala Val Glu
            530                 535                 540

Val Gly Val Asn Gln Asn Leu Ala Ala Gln Tyr Ala Lys Arg Thr Lys
545                 550                 555                 560

Ala Glu Gln Tyr Gly Ile Tyr Leu Met Tyr Asn Leu Pro Gly Lys Asp
            565                 570                 575

Ser Ser Ala Tyr Ile Ser Ala Ala Thr Gln Glu Leu Tyr Gly Arg Lys
            580                 585                 590

Thr Asn Tyr Ser Pro Thr Val Pro Thr Pro
            595                 600

<210> SEQ ID NO 14
<211> LENGTH: 602
<212> TYPE: PRT
<213> ORGANISM: Artificial sequence
<220> FEATURE:
<223> OTHER INFORMATION: EndoF2-EfEndo18A

<400> SEQUENCE: 14

Met Ala Val Asn Leu Ser Asn Leu Ile Ala Tyr Lys Asn Ser Asp His
1               5                   10                  15

-continued

```
Gln Ile Ser Ala Gly Tyr Tyr Arg Thr Trp Arg Asp Ser Ala Thr Ala
             20                  25                  30

Ser Gly Asn Leu Pro Ser Met Arg Trp Leu Pro Asp Ser Leu Asp Met
         35                  40                  45

Val Met Val Phe Pro Asp Tyr Thr Pro Pro Glu Asn Ala Tyr Trp Asn
 50                  55                  60

Thr Leu Lys Thr Asn Tyr Val Pro Tyr Leu His Lys Arg Gly Thr Lys
 65                  70                  75                  80

Val Ile Ile Thr Leu Gly Asp Leu Asn Ser Ala Thr Thr Gly Gly
             85                  90                  95

Gln Asp Ser Ile Gly Tyr Ser Ser Trp Ala Lys Gly Ile Tyr Asp Lys
             100                 105                 110

Trp Val Gly Glu Tyr Asn Leu Asp Gly Ile Asp Ile Asp Ile Glu Ser
             115                 120                 125

Ser Pro Ser Gly Ala Thr Leu Thr Lys Phe Val Ala Ala Thr Lys Ala
 130                 135                 140

Leu Ser Lys Tyr Phe Gly Pro Lys Ser Gly Thr Gly Lys Thr Phe Val
 145                 150                 155                 160

Tyr Asp Thr Asn Gln Asn Pro Thr Asn Phe Phe Ile Gln Thr Ala Pro
             165                 170                 175

Arg Tyr Asn Tyr Val Phe Leu Gln Ala Tyr Gly Arg Ser Thr Thr Asn
             180                 185                 190

Leu Thr Thr Val Ser Gly Leu Tyr Ala Pro Tyr Ile Ser Met Lys Gln
             195                 200                 205

Phe Leu Pro Gly Phe Ser Phe Tyr Glu Glu Asn Gly Tyr Pro Gly Asn
 210                 215                 220

Tyr Trp Asn Asp Val Arg Tyr Pro Gln Asn Gly Thr Gly Arg Ala Tyr
 225                 230                 235                 240

Asp Tyr Ala Arg Trp Gln Pro Ala Thr Gly Lys Lys Gly Gly Val Phe
             245                 250                 255

Ser Tyr Ala Ile Glu Arg Asp Ala Pro Leu Thr Ser Ser Asn Asp Asn
             260                 265                 270

Thr Leu Arg Ala Pro Asn Phe Arg Val Thr Lys Asp Leu Ile Lys Ile
             275                 280                 285

Met Asn Pro Gly Gly Gly Gly Ser Gly Gly Gly Gly Ser Gly Gly Gly
 290                 295                 300

Gly Ser His His His His His His Glu Phe Gly Gly Gly Ser Gly
 305                 310                 315                 320

Gly Gly Gly Ser Gly Gly Gly Ser Ala Ser Thr Val Thr Pro Lys
             325                 330                 335

Thr Val Met Tyr Val Glu Val Asn Asn His Asp Phe Asn Asn Val Gly
             340                 345                 350

Lys Tyr Thr Leu Ala Gly Thr Asn Gln Pro Ala Phe Asp Met Gly Ile
             355                 360                 365

Ile Phe Ala Ala Asn Ile Asn Tyr Asp Thr Val Asn Lys Lys Pro Tyr
             370                 375                 380

Leu Tyr Leu Asn Glu Arg Val Gln Gln Thr Leu Asn Glu Ala Glu Thr
 385                 390                 395                 400

Gln Ile Arg Pro Val Gln Ala Arg Gly Thr Lys Val Leu Leu Ser Ile
             405                 410                 415

Leu Gly Asn His Glu Gly Ala Gly Phe Ala Asn Phe Pro Thr Tyr Glu
             420                 425                 430
```

```
Ser Ala Asp Ala Phe Ala Ala Gln Leu Glu Gln Val Val Asn Thr Tyr
            435                 440                 445

His Leu Asp Gly Ile Asp Phe Asp Glu Tyr Ala Glu Tyr Gly Lys
    450                 455                 460

Asn Gly Thr Pro Gln Pro Asn Asn Ser Ser Phe Ile Trp Leu Leu Gln
465                 470                 475                 480

Ala Leu Arg Asn Arg Leu Gly Asn Asp Lys Leu Ile Thr Phe Tyr Asn
                485                 490                 495

Ile Gly Pro Ala Ala Asn Ser Ser Ala Asn Pro Gln Met Ser Ser
            500                 505                 510

Leu Ile Asp Tyr Ala Trp Asn Pro Tyr Ser Thr Trp Asn Pro Pro
    515                 520                 525

Gln Ile Ala Gly Met Pro Ala Ser Arg Leu Gly Ala Ser Ala Val Glu
530                 535                 540

Val Gly Val Asn Gln Asn Leu Ala Ala Gln Tyr Ala Lys Arg Thr Lys
545                 550                 555                 560

Ala Glu Gln Tyr Gly Ile Tyr Leu Met Tyr Asn Leu Pro Gly Lys Asp
                565                 570                 575

Ser Ser Ala Tyr Ile Ser Ala Ala Thr Gln Glu Leu Tyr Gly Arg Lys
            580                 585                 590

Thr Asn Tyr Ser Pro Thr Val Pro Thr Pro
    595                 600

<210> SEQ ID NO 15
<211> LENGTH: 1260
<212> TYPE: PRT
<213> ORGANISM: Artificial sequence
<220> FEATURE:
<223> OTHER INFORMATION: EndoS-EfEndo18A

<400> SEQUENCE: 15

Met Pro Ser Ile Asp Ser Leu His Tyr Leu Ser Glu Asn Ser Lys Lys
1               5                   10                  15

Glu Phe Lys Glu Glu Leu Ser Lys Ala Gly Gln Glu Ser Gln Lys Val
            20                  25                  30

Lys Glu Ile Leu Ala Lys Ala Gln Gln Ala Asp Lys Gln Ala Gln Glu
        35                  40                  45

Leu Ala Lys Met Lys Ile Pro Glu Lys Ile Pro Met Lys Pro Leu His
    50                  55                  60

Gly Pro Leu Tyr Gly Gly Tyr Phe Arg Thr Trp His Asp Lys Thr Ser
65              70                  75                  80

Asp Pro Thr Glu Lys Asp Lys Val Asn Ser Met Gly Glu Leu Pro Lys
                85                  90                  95

Glu Val Asp Leu Ala Phe Ile Phe His Asp Trp Thr Lys Asp Tyr Ser
            100                 105                 110

Leu Phe Trp Lys Glu Leu Ala Thr Lys His Val Pro Lys Leu Asn Lys
        115                 120                 125

Gln Gly Thr Arg Val Ile Arg Thr Ile Pro Trp Arg Phe Leu Ala Gly
    130                 135                 140

Gly Asp Asn Ser Gly Ile Ala Glu Asp Thr Ser Lys Tyr Pro Asn Thr
145                 150                 155                 160

Pro Glu Gly Asn Lys Ala Leu Ala Lys Ala Ile Val Asp Glu Tyr Val
                165                 170                 175

Tyr Lys Tyr Asn Leu Asp Gly Leu Asp Val Asp Val Glu His Asp Ser
            180                 185                 190
```

```
Ile Pro Lys Val Asp Lys Lys Glu Asp Thr Ala Gly Val Glu Arg Ser
            195                 200                 205

Ile Gln Val Phe Glu Glu Ile Gly Lys Leu Ile Gly Pro Lys Gly Val
        210                 215                 220

Asp Lys Ser Arg Leu Phe Ile Met Asp Ser Thr Tyr Met Ala Asp Lys
225                 230                 235                 240

Asn Pro Leu Ile Glu Arg Gly Ala Pro Tyr Ile Asn Leu Leu Leu Val
                245                 250                 255

Gln Val Tyr Gly Ser Gln Gly Glu Lys Gly Gly Trp Glu Pro Val Ser
            260                 265                 270

Asn Arg Pro Glu Lys Thr Met Glu Glu Arg Trp Gln Gly Tyr Ser Lys
        275                 280                 285

Tyr Ile Arg Pro Glu Gln Tyr Met Ile Gly Phe Ser Phe Tyr Glu Glu
    290                 295                 300

Asn Ala Gln Glu Gly Asn Leu Trp Tyr Asp Ile Asn Ser Arg Lys Asp
305                 310                 315                 320

Glu Asp Lys Ala Asn Gly Ile Asn Thr Asp Ile Thr Gly Thr Arg Ala
                325                 330                 335

Glu Arg Tyr Ala Arg Trp Gln Pro Lys Thr Gly Gly Val Lys Gly Gly
            340                 345                 350

Ile Phe Ser Tyr Ala Ile Asp Arg Asp Gly Val Ala His Gln Pro Lys
        355                 360                 365

Lys Tyr Ala Lys Gln Lys Glu Phe Lys Asp Ala Thr Asp Asn Ile Phe
    370                 375                 380

His Ser Asp Tyr Ser Val Ser Lys Ala Leu Lys Thr Val Met Leu Lys
385                 390                 395                 400

Asp Lys Ser Tyr Asp Leu Ile Asp Glu Lys Asp Phe Pro Asp Lys Ala
                405                 410                 415

Leu Arg Glu Ala Val Met Ala Gln Val Gly Thr Arg Lys Gly Asp Leu
            420                 425                 430

Glu Arg Phe Asn Gly Thr Leu Arg Leu Asp Asn Pro Ala Ile Gln Ser
        435                 440                 445

Leu Glu Gly Leu Asn Lys Phe Lys Lys Leu Ala Gln Leu Asp Leu Ile
    450                 455                 460

Gly Leu Ser Arg Ile Thr Lys Leu Asp Arg Ser Val Leu Pro Ala Asn
465                 470                 475                 480

Met Lys Pro Gly Lys Asp Thr Leu Glu Thr Val Leu Glu Thr Tyr Lys
                485                 490                 495

Lys Asp Asn Lys Glu Glu Pro Ala Thr Ile Pro Pro Val Ser Leu Lys
            500                 505                 510

Val Ser Gly Leu Thr Gly Leu Lys Glu Leu Asp Leu Ser Gly Phe Asp
        515                 520                 525

Arg Glu Thr Leu Ala Gly Leu Asp Ala Ala Thr Leu Thr Ser Leu Glu
    530                 535                 540

Lys Val Asp Ile Ser Gly Asn Lys Leu Asp Leu Ala Pro Gly Thr Glu
545                 550                 555                 560

Asn Arg Gln Ile Phe Asp Thr Met Leu Ser Thr Ile Ser Asn His Val
                565                 570                 575

Gly Ser Asn Glu Gln Thr Val Lys Phe Asp Lys Gln Lys Pro Thr Gly
            580                 585                 590

His Tyr Pro Asp Thr Tyr Gly Lys Thr Ser Leu Arg Leu Pro Val Ala
        595                 600                 605
```

```
Asn Glu Lys Val Asp Leu Gln Ser Gln Leu Phe Gly Thr Val Thr
    610             615                 620

Asn Gln Gly Thr Leu Ile Asn Ser Glu Ala Asp Tyr Lys Ala Tyr Gln
625             630                 635                 640

Asn His Lys Ile Ala Gly Arg Ser Phe Val Asp Ser Asn Tyr His Tyr
            645                 650                 655

Asn Asn Phe Lys Val Ser Tyr Glu Asn Tyr Thr Val Lys Val Thr Asp
                660                 665                 670

Ser Thr Leu Gly Thr Thr Thr Asp Lys Thr Leu Ala Thr Asp Lys Glu
            675                 680                 685

Glu Thr Tyr Lys Val Asp Phe Ser Pro Ala Asp Lys Thr Lys Ala
    690                 695                 700

Val His Thr Ala Lys Val Ile Val Gly Asp Glu Lys Thr Met Met Val
705                 710                 715                 720

Asn Leu Ala Glu Gly Ala Thr Val Ile Gly Gly Ser Ala Asp Pro Val
                725                 730                 735

Asn Ala Arg Lys Val Phe Asp Gly Gln Leu Gly Ser Glu Thr Asp Asn
            740                 745                 750

Ile Ser Leu Gly Trp Asp Ser Lys Gln Ser Ile Phe Lys Leu Lys
        755                 760                 765

Glu Asp Gly Leu Ile Lys His Trp Arg Phe Phe Asn Asp Ser Ala Arg
770                 775                 780

Asn Pro Glu Thr Thr Asn Lys Pro Ile Gln Glu Ala Ser Leu Gln Ile
785                 790                 795                 800

Phe Asn Ile Lys Asp Tyr Asn Leu Asp Asn Leu Leu Glu Asn Pro Asn
                805                 810                 815

Lys Phe Asp Asp Glu Lys Tyr Trp Ile Thr Val Asp Thr Tyr Ser Ala
                820                 825                 830

Gln Gly Glu Arg Ala Thr Ala Phe Ser Asn Thr Leu Asn Asn Ile Thr
            835                 840                 845

Ser Lys Tyr Trp Arg Val Val Phe Asp Thr Lys Gly Asp Arg Tyr Ser
    850                 855                 860

Ser Pro Val Val Pro Glu Leu Gln Ile Leu Gly Tyr Pro Leu Pro Asn
865                 870                 875                 880

Ala Asp Thr Ile Met Lys Thr Val Thr Thr Ala Lys Glu Leu Ser Gln
                885                 890                 895

Gln Lys Asp Lys Phe Ser Gln Lys Met Leu Asp Glu Leu Lys Ile Lys
            900                 905                 910

Glu Met Ala Leu Glu Thr Ser Leu Asn Ser Lys Ile Phe Asp Val Thr
    915                 920                 925

Ala Ile Asn Ala Asn Ala Gly Val Leu Lys Asp Cys Ile Glu Lys Arg
930                 935                 940

Gln Leu Leu Lys Lys Gly Gly Gly Ser Gly Gly Gly Ser Gly
945                 950                 955                 960

Gly Gly Gly Ser His His His His His Glu Phe Gly Gly Gly
                965                 970                 975

Ser Gly Gly Gly Gly Ser Gly Gly Gly Ser Ala Ser Thr Val Thr
            980                 985                 990

Pro Lys Thr Val Met Tyr Val Glu  Val Asn Asn His Asp  Phe Asn Asn
    995                 1000                1005

Val Gly Lys Tyr Thr Leu Ala  Gly Thr Asn Gln Pro  Ala Phe Asp
    1010                1015                1020
```

```
Met Gly Ile Ile Phe Ala Ala Asn Ile Asn Tyr Asp Thr Val Asn
    1025                1030                1035

Lys Lys Pro Tyr Leu Tyr Leu Asn Glu Arg Val Gln Gln Thr Leu
    1040                1045                1050

Asn Glu Ala Glu Thr Gln Ile Arg Pro Val Gln Ala Arg Gly Thr
    1055                1060                1065

Lys Val Leu Leu Ser Ile Leu Gly Asn His Glu Gly Ala Gly Phe
    1070                1075                1080

Ala Asn Phe Pro Thr Tyr Glu Ser Ala Asp Ala Phe Ala Ala Gln
    1085                1090                1095

Leu Glu Gln Val Val Asn Thr Tyr His Leu Asp Gly Ile Asp Phe
    1100                1105                1110

Asp Asp Glu Tyr Ala Glu Tyr Gly Lys Asn Gly Thr Pro Gln Pro
    1115                1120                1125

Asn Asn Ser Ser Phe Ile Trp Leu Leu Gln Ala Leu Arg Asn Arg
    1130                1135                1140

Leu Gly Asn Asp Lys Leu Ile Thr Phe Tyr Asn Ile Gly Pro Ala
    1145                1150                1155

Ala Ala Asn Ser Ser Ala Asn Pro Gln Met Ser Ser Leu Ile Asp
    1160                1165                1170

Tyr Ala Trp Asn Pro Tyr Tyr Ser Thr Trp Asn Pro Pro Gln Ile
    1175                1180                1185

Ala Gly Met Pro Ala Ser Arg Leu Gly Ala Ser Ala Val Glu Val
    1190                1195                1200

Gly Val Asn Gln Asn Leu Ala Ala Gln Tyr Ala Lys Arg Thr Lys
    1205                1210                1215

Ala Glu Gln Tyr Gly Ile Tyr Leu Met Tyr Asn Leu Pro Gly Lys
    1220                1225                1230

Asp Ser Ser Ala Tyr Ile Ser Ala Ala Thr Gln Glu Leu Tyr Gly
    1235                1240                1245

Arg Lys Thr Asn Tyr Ser Pro Thr Val Pro Thr Pro
    1250                1255                1260
```

<210> SEQ ID NO 16
<211> LENGTH: 618
<212> TYPE: PRT
<213> ORGANISM: Artificial sequence
<220> FEATURE:
<223> OTHER INFORMATION: EndoF3-EndoF1

<400> SEQUENCE: 16

```
Met Ala Thr Ala Leu Ala Gly Ser Asn Gly Val Cys Ile Ala Tyr Tyr
1               5                   10                  15

Ile Thr Asp Gly Arg Asn Pro Thr Phe Lys Leu Lys Asp Ile Pro Asp
                20                  25                  30

Lys Val Asp Met Val Ile Leu Phe Gly Leu Lys Tyr Trp Ser Leu Gln
            35                  40                  45

Asp Thr Thr Lys Leu Pro Gly Gly Thr Gly Met Met Gly Ser Phe Lys
        50                  55                  60

Ser Tyr Lys Asp Leu Asp Thr Gln Ile Arg Ser Leu Gln Ser Arg Gly
65                  70                  75                  80

Ile Lys Val Leu Gln Asn Ile Asp Asp Val Ser Trp Gln Ser Ser
                85                  90                  95

Lys Pro Gly Gly Phe Ala Ser Ala Ala Tyr Gly Asp Ala Ile Lys
            100                 105                 110
```

```
Ser Ile Val Ile Asp Lys Trp Lys Leu Asp Gly Ile Ser Leu Asp Ile
            115                 120                 125

Glu His Ser Gly Ala Lys Pro Asn Pro Ile Pro Thr Phe Pro Gly Tyr
            130                 135                 140

Ala Ala Thr Gly Tyr Asn Gly Trp Tyr Ser Gly Ser Met Ala Ala Thr
145                 150                 155                 160

Pro Ala Phe Leu Asn Val Ile Ser Glu Leu Thr Lys Tyr Phe Gly Thr
                165                 170                 175

Thr Ala Pro Asn Asn Lys Gln Leu Gln Ile Ala Ser Gly Ile Asp Val
            180                 185                 190

Tyr Ala Trp Asn Lys Ile Met Glu Asn Phe Arg Asn Asn Phe Asn Tyr
            195                 200                 205

Ile Gln Leu Gln Ser Tyr Gly Ala Asn Val Ser Arg Thr Gln Leu Met
            210                 215                 220

Met Asn Tyr Ala Thr Gly Thr Asn Lys Ile Pro Ala Ser Lys Met Val
225                 230                 235                 240

Phe Gly Ala Tyr Ala Glu Gly Gly Thr Asn Gln Ala Asn Asp Val Glu
                245                 250                 255

Val Ala Lys Trp Thr Pro Thr Gln Gly Ala Lys Gly Met Met Ile
            260                 265                 270

Tyr Thr Tyr Asn Ser Asn Val Ser Tyr Ala Asn Ala Val Arg Asp Ala
            275                 280                 285

Val Lys Asn Gly Gly Gly Ser Gly Gly Gly Ser Gly Gly
            290                 295                 300

Gly Ser His His His His His His Glu Phe Gly Gly Gly Ser Gly
305                 310                 315                 320

Gly Gly Gly Ser Gly Gly Gly Ser Ala Val Thr Gly Thr Thr Lys
                325                 330                 335

Ala Asn Ile Lys Leu Phe Ser Phe Thr Glu Val Asn Asp Thr Asn Pro
            340                 345                 350

Leu Asn Asn Leu Asn Phe Thr Leu Lys Asn Ser Gly Lys Pro Leu Val
            355                 360                 365

Asp Met Val Val Leu Phe Ser Ala Asn Ile Asn Tyr Asp Ala Ala Asn
            370                 375                 380

Asp Lys Val Phe Val Ser Asn Asn Pro Asn Val Gln His Leu Leu Thr
385                 390                 395                 400

Asn Arg Ala Lys Tyr Leu Lys Pro Leu Gln Asp Lys Gly Ile Lys Val
                405                 410                 415

Ile Leu Ser Ile Leu Gly Asn His Asp Arg Ser Gly Ile Ala Asn Leu
            420                 425                 430

Ser Thr Ala Arg Ala Lys Ala Phe Ala Gln Glu Leu Lys Asn Thr Cys
            435                 440                 445

Asp Leu Tyr Asn Leu Asp Gly Val Phe Phe Asp Glu Tyr Ser Ala
            450                 455                 460

Tyr Gln Thr Pro Pro Ser Gly Phe Val Thr Pro Ser Asn Asn Ala
465                 470                 475                 480

Ala Ala Arg Leu Ala Tyr Glu Thr Lys Gln Ala Met Pro Asn Lys Leu
                485                 490                 495

Val Thr Val Tyr Val Tyr Ser Arg Thr Ser Ser Phe Pro Thr Ala Val
            500                 505                 510

Asp Gly Val Asn Ala Gly Ser Tyr Val Asp Tyr Ala Ile His Asp Tyr
            515                 520                 525
```

```
Gly Gly Ser Tyr Asp Leu Ala Thr Asn Tyr Pro Gly Leu Ala Lys Ser
            530                 535                 540
Gly Met Val Met Ser Ser Gln Glu Phe Asn Gln Gly Arg Tyr Ala Thr
545                 550                 555                 560
Ala Gln Ala Leu Arg Asn Ile Val Thr Lys Gly Tyr Gly Gly His Met
                565                 570                 575
Ile Phe Ala Met Asp Pro Asn Arg Ser Asn Phe Thr Ser Gly Gln Leu
                580                 585                 590
Pro Ala Leu Lys Leu Ile Ala Lys Glu Leu Tyr Gly Asp Glu Leu Val
                595                 600                 605
Tyr Ser Asn Thr Pro Tyr Ser Lys Asp Trp
            610                 615

<210> SEQ ID NO 17
<211> LENGTH: 618
<212> TYPE: PRT
<213> ORGANISM: Artificial sequence
<220> FEATURE:
<223> OTHER INFORMATION: EndoF2-EndoF1

<400> SEQUENCE: 17

Met Ala Val Asn Leu Ser Asn Leu Ile Ala Tyr Lys Asn Ser Asp His
1               5                   10                  15
Gln Ile Ser Ala Gly Tyr Tyr Arg Thr Trp Arg Asp Ser Ala Thr Ala
            20                  25                  30
Ser Gly Asn Leu Pro Ser Met Arg Trp Leu Pro Asp Ser Leu Asp Met
        35                  40                  45
Val Met Val Phe Pro Asp Tyr Thr Pro Pro Glu Asn Ala Tyr Trp Asn
50                  55                  60
Thr Leu Lys Thr Asn Tyr Val Pro Tyr Leu His Lys Arg Gly Thr Lys
65                  70                  75                  80
Val Ile Ile Thr Leu Gly Asp Leu Asn Ser Ala Thr Thr Thr Gly Gly
                85                  90                  95
Gln Asp Ser Ile Gly Tyr Ser Ser Trp Ala Lys Gly Ile Tyr Asp Lys
            100                 105                 110
Trp Val Gly Glu Tyr Asn Leu Asp Gly Ile Asp Ile Asp Ile Glu Ser
        115                 120                 125
Ser Pro Ser Gly Ala Thr Leu Thr Lys Phe Val Ala Ala Thr Lys Ala
    130                 135                 140
Leu Ser Lys Tyr Phe Gly Pro Lys Ser Gly Thr Gly Lys Thr Phe Val
145                 150                 155                 160
Tyr Asp Thr Asn Gln Asn Pro Thr Asn Phe Phe Ile Gln Thr Ala Pro
                165                 170                 175
Arg Tyr Asn Tyr Val Phe Leu Gln Ala Tyr Gly Arg Ser Thr Thr Asn
            180                 185                 190
Leu Thr Thr Val Ser Gly Leu Tyr Ala Pro Tyr Ile Ser Met Lys Gln
        195                 200                 205
Phe Leu Pro Gly Phe Ser Phe Tyr Glu Glu Asn Gly Tyr Pro Gly Asn
    210                 215                 220
Tyr Trp Asn Asp Val Arg Tyr Pro Gln Asn Gly Thr Gly Arg Ala Tyr
225                 230                 235                 240
Asp Tyr Ala Arg Trp Gln Pro Ala Thr Gly Lys Lys Gly Gly Val Phe
                245                 250                 255
Ser Tyr Ala Ile Glu Arg Asp Ala Pro Leu Thr Ser Ser Asn Asp Asn
            260                 265                 270
```

Thr Leu Arg Ala Pro Asn Phe Arg Val Thr Lys Asp Leu Ile Lys Ile
            275                 280                 285

Met Asn Pro Gly Gly Gly Ser Gly Gly Gly Ser Gly Gly Gly
        290                 295                 300

Gly Ser His His His His His His Glu Phe Gly Gly Gly Ser Gly
305                 310                 315                 320

Gly Gly Ser Gly Gly Gly Ser Ala Val Thr Gly Thr Thr Lys
            325                 330                 335

Ala Asn Ile Lys Leu Phe Ser Phe Thr Glu Val Asn Asp Thr Asn Pro
            340                 345                 350

Leu Asn Asn Leu Asn Phe Thr Leu Lys Asn Ser Gly Lys Pro Leu Val
            355                 360                 365

Asp Met Val Val Leu Phe Ser Ala Asn Ile Asn Tyr Asp Ala Ala Asn
        370                 375                 380

Asp Lys Val Phe Val Ser Asn Asn Pro Asn Val Gln His Leu Leu Thr
385                 390                 395                 400

Asn Arg Ala Lys Tyr Leu Lys Pro Leu Gln Asp Lys Gly Ile Lys Val
            405                 410                 415

Ile Leu Ser Ile Leu Gly Asn His Asp Arg Ser Gly Ile Ala Asn Leu
            420                 425                 430

Ser Thr Ala Arg Ala Lys Ala Phe Ala Gln Glu Leu Lys Asn Thr Cys
            435                 440                 445

Asp Leu Tyr Asn Leu Asp Gly Val Phe Phe Asp Asp Glu Tyr Ser Ala
        450                 455                 460

Tyr Gln Thr Pro Pro Ser Gly Phe Val Thr Pro Ser Asn Asn Ala
465                 470                 475                 480

Ala Ala Arg Leu Ala Tyr Glu Thr Lys Gln Ala Met Pro Asn Lys Leu
            485                 490                 495

Val Thr Val Tyr Val Tyr Ser Arg Thr Ser Ser Phe Pro Thr Ala Val
            500                 505                 510

Asp Gly Val Asn Ala Gly Ser Tyr Val Asp Tyr Ala Ile His Asp Tyr
        515                 520                 525

Gly Gly Ser Tyr Asp Leu Ala Thr Asn Tyr Pro Gly Leu Ala Lys Ser
            530                 535                 540

Gly Met Val Met Ser Ser Gln Glu Phe Asn Gln Gly Arg Tyr Ala Thr
545                 550                 555                 560

Ala Gln Ala Leu Arg Asn Ile Val Thr Lys Gly Tyr Gly Gly His Met
            565                 570                 575

Ile Phe Ala Met Asp Pro Asn Arg Ser Asn Phe Thr Ser Gly Gln Leu
        580                 585                 590

Pro Ala Leu Lys Leu Ile Ala Lys Glu Leu Tyr Gly Asp Glu Leu Val
            595                 600                 605

Tyr Ser Asn Thr Pro Tyr Ser Lys Asp Trp
610                 615

<210> SEQ ID NO 18
<211> LENGTH: 1276
<212> TYPE: PRT
<213> ORGANISM: Artificial sequence
<220> FEATURE:
<223> OTHER INFORMATION: EndoS-EndoF1

<400> SEQUENCE: 18

Met Pro Ser Ile Asp Ser Leu His Tyr Leu Ser Glu Asn Ser Lys Lys
1               5                   10                  15

```
Glu Phe Lys Glu Glu Leu Ser Lys Ala Gly Gln Ser Gln Lys Val
                20                  25                  30

Lys Glu Ile Leu Ala Lys Ala Gln Gln Ala Asp Lys Gln Ala Gln Glu
     35                  40                  45

Leu Ala Lys Met Lys Ile Pro Glu Lys Ile Pro Met Lys Pro Leu His
 50                  55                  60

Gly Pro Leu Tyr Gly Gly Tyr Phe Arg Thr Trp His Asp Lys Thr Ser
65                   70                  75                  80

Asp Pro Thr Glu Lys Asp Lys Val Asn Ser Met Gly Glu Leu Pro Lys
             85                  90                  95

Glu Val Asp Leu Ala Phe Ile Phe His Asp Trp Thr Lys Asp Tyr Ser
                100                 105                 110

Leu Phe Trp Lys Glu Leu Ala Thr Lys His Val Pro Lys Leu Asn Lys
         115                 120                 125

Gln Gly Thr Arg Val Ile Arg Thr Ile Pro Trp Arg Phe Leu Ala Gly
     130                 135                 140

Gly Asp Asn Ser Gly Ile Ala Glu Asp Thr Ser Lys Tyr Pro Asn Thr
145                 150                 155                 160

Pro Glu Gly Asn Lys Ala Leu Ala Lys Ala Ile Val Asp Glu Tyr Val
                165                 170                 175

Tyr Lys Tyr Asn Leu Asp Gly Leu Asp Val Asp Val Glu His Asp Ser
            180                 185                 190

Ile Pro Lys Val Asp Lys Lys Glu Asp Thr Ala Gly Val Glu Arg Ser
        195                 200                 205

Ile Gln Val Phe Glu Glu Ile Gly Lys Leu Ile Gly Pro Lys Gly Val
    210                 215                 220

Asp Lys Ser Arg Leu Phe Ile Met Asp Ser Thr Tyr Met Ala Asp Lys
225                 230                 235                 240

Asn Pro Leu Ile Glu Arg Gly Ala Pro Tyr Ile Asn Leu Leu Leu Val
                245                 250                 255

Gln Val Tyr Gly Ser Gln Gly Glu Lys Gly Gly Trp Glu Pro Val Ser
            260                 265                 270

Asn Arg Pro Glu Lys Thr Met Glu Glu Arg Trp Gln Gly Tyr Ser Lys
        275                 280                 285

Tyr Ile Arg Pro Glu Gln Tyr Met Ile Gly Phe Ser Phe Tyr Glu Glu
    290                 295                 300

Asn Ala Gln Glu Gly Asn Leu Trp Tyr Asp Ile Asn Ser Arg Lys Asp
305                 310                 315                 320

Glu Asp Lys Ala Asn Gly Ile Asn Thr Asp Ile Thr Gly Thr Arg Ala
                325                 330                 335

Glu Arg Tyr Ala Arg Trp Gln Pro Lys Thr Gly Gly Val Lys Gly Gly
            340                 345                 350

Ile Phe Ser Tyr Ala Ile Asp Arg Asp Gly Val Ala His Gln Pro Lys
        355                 360                 365

Lys Tyr Ala Lys Gln Lys Glu Phe Lys Asp Ala Thr Asp Asn Ile Phe
    370                 375                 380

His Ser Asp Tyr Ser Val Ser Lys Ala Leu Lys Thr Val Met Leu Lys
385                 390                 395                 400

Asp Lys Ser Tyr Asp Leu Ile Asp Glu Lys Asp Phe Pro Asp Lys Ala
                405                 410                 415

Leu Arg Glu Ala Val Met Ala Gln Val Gly Thr Arg Lys Gly Asp Leu
            420                 425                 430
```

```
Glu Arg Phe Asn Gly Thr Leu Arg Leu Asp Asn Pro Ala Ile Gln Ser
            435                 440                 445

Leu Glu Gly Leu Asn Lys Phe Lys Lys Leu Ala Gln Leu Asp Leu Ile
450                 455                 460

Gly Leu Ser Arg Ile Thr Lys Leu Asp Arg Ser Val Leu Pro Ala Asn
465                 470                 475                 480

Met Lys Pro Gly Lys Asp Thr Leu Glu Thr Val Leu Glu Thr Tyr Lys
                485                 490                 495

Lys Asp Asn Lys Glu Glu Pro Ala Thr Ile Pro Pro Val Ser Leu Lys
                500                 505                 510

Val Ser Gly Leu Thr Gly Leu Lys Glu Leu Asp Leu Ser Gly Phe Asp
            515                 520                 525

Arg Glu Thr Leu Ala Gly Leu Asp Ala Ala Thr Leu Thr Ser Leu Glu
            530                 535                 540

Lys Val Asp Ile Ser Gly Asn Lys Leu Asp Leu Ala Pro Gly Thr Glu
545                 550                 555                 560

Asn Arg Gln Ile Phe Asp Thr Met Leu Ser Thr Ile Ser Asn His Val
                565                 570                 575

Gly Ser Asn Glu Gln Thr Val Lys Phe Asp Lys Gln Lys Pro Thr Gly
            580                 585                 590

His Tyr Pro Asp Thr Tyr Gly Lys Thr Ser Leu Arg Leu Pro Val Ala
            595                 600                 605

Asn Glu Lys Val Asp Leu Gln Ser Gln Leu Leu Phe Gly Thr Val Thr
            610                 615                 620

Asn Gln Gly Thr Leu Ile Asn Ser Glu Ala Asp Tyr Lys Ala Tyr Gln
625                 630                 635                 640

Asn His Lys Ile Ala Gly Arg Ser Phe Val Asp Ser Asn Tyr His Tyr
                645                 650                 655

Asn Asn Phe Lys Val Ser Tyr Glu Asn Tyr Thr Val Lys Val Thr Asp
                660                 665                 670

Ser Thr Leu Gly Thr Thr Thr Asp Lys Thr Leu Ala Thr Asp Lys Glu
            675                 680                 685

Glu Thr Tyr Lys Val Asp Phe Phe Ser Pro Ala Asp Lys Thr Lys Ala
            690                 695                 700

Val His Thr Ala Lys Val Ile Val Gly Asp Glu Lys Thr Met Met Val
705                 710                 715                 720

Asn Leu Ala Glu Gly Ala Thr Val Ile Gly Gly Ser Ala Asp Pro Val
                725                 730                 735

Asn Ala Arg Lys Val Phe Asp Gly Gln Leu Gly Ser Glu Thr Asp Asn
                740                 745                 750

Ile Ser Leu Gly Trp Asp Ser Lys Gln Ser Ile Ile Phe Lys Leu Lys
            755                 760                 765

Glu Asp Gly Leu Ile Lys His Trp Arg Phe Phe Asn Asp Ser Ala Arg
            770                 775                 780

Asn Pro Glu Thr Thr Asn Lys Pro Ile Gln Glu Ala Ser Leu Gln Ile
785                 790                 795                 800

Phe Asn Ile Lys Asp Tyr Asn Leu Asp Asn Leu Leu Glu Asn Pro Asn
                805                 810                 815

Lys Phe Asp Asp Glu Lys Tyr Trp Ile Thr Val Asp Thr Tyr Ser Ala
                820                 825                 830

Gln Gly Glu Arg Ala Thr Ala Phe Ser Asn Thr Leu Asn Asn Ile Thr
            835                 840                 845
```

```
Ser Lys Tyr Trp Arg Val Val Phe Asp Thr Lys Gly Asp Arg Tyr Ser
850                 855                 860

Ser Pro Val Val Pro Glu Leu Gln Ile Leu Gly Tyr Pro Leu Pro Asn
865                 870                 875                 880

Ala Asp Thr Ile Met Lys Thr Val Thr Thr Ala Lys Glu Leu Ser Gln
                885                 890                 895

Gln Lys Asp Lys Phe Ser Gln Lys Met Leu Asp Glu Leu Lys Ile Lys
            900                 905                 910

Glu Met Ala Leu Glu Thr Ser Leu Asn Ser Lys Ile Phe Asp Val Thr
        915                 920                 925

Ala Ile Asn Ala Asn Ala Gly Val Leu Lys Asp Cys Ile Glu Lys Arg
    930                 935                 940

Gln Leu Leu Lys Lys Gly Gly Gly Ser Gly Gly Gly Ser Gly
945                 950                 955                 960

Gly Gly Gly Ser His His His His His Glu Phe Gly Gly Gly
                965                 970                 975

Ser Gly Gly Gly Gly Ser Gly Gly Gly Ser Ala Val Thr Gly Thr
            980                 985                 990

Thr Lys Ala Asn Ile Lys Leu Phe Ser Phe Thr Glu Val Asn Asp Thr
        995                 1000                1005

Asn Pro Leu Asn Asn Leu Asn Phe Thr Leu Lys Asn Ser Gly Lys
    1010                1015                1020

Pro Leu Val Asp Met Val Val Leu Phe Ser Ala Asn Ile Asn Tyr
    1025                1030                1035

Asp Ala Ala Asn Asp Lys Val Phe Val Ser Asn Asn Pro Asn Val
    1040                1045                1050

Gln His Leu Leu Thr Asn Arg Ala Lys Tyr Leu Lys Pro Leu Gln
    1055                1060                1065

Asp Lys Gly Ile Lys Val Ile Leu Ser Ile Leu Gly Asn His Asp
    1070                1075                1080

Arg Ser Gly Ile Ala Asn Leu Ser Thr Ala Arg Ala Lys Ala Phe
    1085                1090                1095

Ala Gln Glu Leu Lys Asn Thr Cys Asp Leu Tyr Asn Leu Asp Gly
    1100                1105                1110

Val Phe Phe Asp Asp Glu Tyr Ser Ala Tyr Gln Thr Pro Pro Pro
    1115                1120                1125

Ser Gly Phe Val Thr Pro Ser Asn Asn Ala Ala Ala Arg Leu Ala
    1130                1135                1140

Tyr Glu Thr Lys Gln Ala Met Pro Asn Lys Leu Val Thr Val Tyr
    1145                1150                1155

Val Tyr Ser Arg Thr Ser Ser Phe Pro Thr Ala Val Asp Gly Val
    1160                1165                1170

Asn Ala Gly Ser Tyr Val Asp Tyr Ala Ile His Asp Tyr Gly Gly
    1175                1180                1185

Ser Tyr Asp Leu Ala Thr Asn Tyr Pro Gly Leu Ala Lys Ser Gly
    1190                1195                1200

Met Val Met Ser Ser Gln Glu Phe Asn Gln Gly Arg Tyr Ala Thr
    1205                1210                1215

Ala Gln Ala Leu Arg Asn Ile Val Thr Lys Gly Tyr Gly Gly His
    1220                1225                1230

Met Ile Phe Ala Met Asp Pro Asn Arg Ser Asn Phe Thr Ser Gly
    1235                1240                1245
```

-continued

Gln Leu Pro Ala Leu Lys Leu Ile Ala Lys Glu Leu Tyr Gly Asp
    1250                1255                1260

Glu Leu Val Tyr Ser Asn Thr Pro Tyr Ser Lys Asp Trp
    1265                1270                1275

<210> SEQ ID NO 19
<211> LENGTH: 600
<212> TYPE: PRT
<213> ORGANISM: Artificial sequence
<220> FEATURE:
<223> OTHER INFORMATION: EndoF3-EndoH

<400> SEQUENCE: 19

Met Ala Thr Ala Leu Ala Gly Ser Asn Gly Val Cys Ile Ala Tyr Tyr
1               5                   10                  15

Ile Thr Asp Gly Arg Asn Pro Thr Phe Lys Leu Lys Asp Ile Pro Asp
                20                  25                  30

Lys Val Asp Met Val Ile Leu Phe Gly Leu Lys Tyr Trp Ser Leu Gln
            35                  40                  45

Asp Thr Thr Lys Leu Pro Gly Gly Thr Gly Met Met Gly Ser Phe Lys
        50                  55                  60

Ser Tyr Lys Asp Leu Asp Thr Gln Ile Arg Ser Leu Gln Ser Arg Gly
65                  70                  75                  80

Ile Lys Val Leu Gln Asn Ile Asp Asp Val Ser Trp Gln Ser Ser
                85                  90                  95

Lys Pro Gly Gly Phe Ala Ser Ala Ala Ala Tyr Gly Asp Ala Ile Lys
            100                 105                 110

Ser Ile Val Ile Asp Lys Trp Lys Leu Asp Gly Ile Ser Leu Asp Ile
        115                 120                 125

Glu His Ser Gly Ala Lys Pro Asn Pro Ile Pro Thr Phe Pro Gly Tyr
130                 135                 140

Ala Ala Thr Gly Tyr Asn Gly Trp Tyr Ser Gly Ser Met Ala Ala Thr
145                 150                 155                 160

Pro Ala Phe Leu Asn Val Ile Ser Glu Leu Thr Lys Tyr Phe Gly Thr
                165                 170                 175

Thr Ala Pro Asn Asn Lys Gln Leu Gln Ile Ala Ser Gly Ile Asp Val
            180                 185                 190

Tyr Ala Trp Asn Lys Ile Met Glu Asn Phe Arg Asn Asn Phe Asn Tyr
        195                 200                 205

Ile Gln Leu Gln Ser Tyr Gly Ala Asn Val Ser Arg Thr Gln Leu Met
    210                 215                 220

Met Asn Tyr Ala Thr Gly Thr Asn Lys Ile Pro Ala Ser Lys Met Val
225                 230                 235                 240

Phe Gly Ala Tyr Ala Glu Gly Gly Thr Asn Gln Ala Asn Asp Val Glu
                245                 250                 255

Val Ala Lys Trp Thr Pro Thr Gln Gly Ala Lys Gly Met Met Ile
            260                 265                 270

Tyr Thr Tyr Asn Ser Asn Val Ser Tyr Ala Asn Ala Val Arg Asp Ala
        275                 280                 285

Val Lys Asn Gly Gly Gly Gly Ser Gly Gly Gly Ser Gly Gly Gly
    290                 295                 300

Gly Ser His His His His His Glu Phe Gly Gly Gly Ser Gly
305                 310                 315                 320

Gly Gly Gly Ser Gly Gly Gly Gly Ser Ala Pro Ala Pro Val Lys Gln
                325                 330                 335

```
Gly Pro Thr Ser Val Ala Tyr Val Glu Val Asn Asn Asn Ser Met Leu
                340                 345                 350

Asn Val Gly Lys Tyr Thr Leu Ala Asp Gly Gly Asn Ala Phe Asp
            355                 360                 365

Val Ala Val Ile Phe Ala Ala Asn Ile Asn Tyr Asp Thr Gly Thr Lys
        370                 375                 380

Thr Ala Tyr Leu His Phe Asn Glu Asn Val Gln Arg Val Leu Asp Asn
385                 390                 395                 400

Ala Val Thr Gln Ile Arg Pro Leu Gln Gln Gly Ile Lys Val Leu
                405                 410                 415

Leu Ser Val Leu Gly Asn His Gln Gly Ala Gly Phe Ala Asn Phe Pro
            420                 425                 430

Ser Gln Gln Ala Ala Ser Ala Phe Ala Lys Gln Leu Ser Asp Ala Val
        435                 440                 445

Ala Lys Tyr Gly Leu Asp Gly Val Asp Phe Asp Asp Glu Tyr Ala Glu
    450                 455                 460

Tyr Gly Asn Asn Gly Thr Ala Gln Pro Asn Asp Ser Ser Phe Val His
465                 470                 475                 480

Leu Val Thr Ala Leu Arg Ala Asn Met Pro Asp Lys Ile Ile Ser Leu
                485                 490                 495

Tyr Asn Ile Gly Pro Ala Ala Ser Arg Leu Ser Tyr Gly Gly Val Asp
            500                 505                 510

Val Ser Asp Lys Phe Asp Tyr Ala Trp Asn Pro Tyr Gly Thr Trp
        515                 520                 525

Gln Val Pro Gly Ile Ala Leu Pro Lys Ala Gln Leu Ser Pro Ala Ala
    530                 535                 540

Val Glu Ile Gly Arg Thr Ser Arg Ser Thr Val Ala Asp Leu Ala Arg
545                 550                 555                 560

Arg Thr Val Asp Glu Gly Tyr Gly Val Tyr Leu Thr Tyr Asn Leu Asp
                565                 570                 575

Gly Gly Asp Arg Thr Ala Asp Val Ser Ala Phe Thr Arg Glu Leu Tyr
            580                 585                 590

Gly Ser Glu Ala Val Arg Thr Pro
        595                 600

<210> SEQ ID NO 20
<211> LENGTH: 600
<212> TYPE: PRT
<213> ORGANISM: Artificial sequence
<220> FEATURE:
<223> OTHER INFORMATION: EndoF2-EndoH

<400> SEQUENCE: 20

Met Ala Val Asn Leu Ser Asn Leu Ile Ala Tyr Lys Asn Ser Asp His
1               5                   10                  15

Gln Ile Ser Ala Gly Tyr Tyr Arg Thr Trp Arg Asp Ser Ala Thr Ala
            20                  25                  30

Ser Gly Asn Leu Pro Ser Met Arg Trp Leu Pro Asp Ser Leu Asp Met
        35                  40                  45

Val Met Val Phe Pro Asp Tyr Thr Pro Pro Glu Asn Ala Tyr Trp Asn
    50                  55                  60

Thr Leu Lys Thr Asn Tyr Val Pro Tyr Leu His Lys Arg Gly Thr Lys
65              70                  75                  80

Val Ile Ile Thr Leu Gly Asp Leu Asn Ser Ala Thr Thr Gly Gly
                85                  90                  95
```

```
Gln Asp Ser Ile Gly Tyr Ser Ser Trp Ala Lys Gly Ile Tyr Asp Lys
                100                 105                 110

Trp Val Gly Glu Tyr Asn Leu Asp Gly Ile Asp Ile Asp Ile Glu Ser
        115                 120                 125

Ser Pro Ser Gly Ala Thr Leu Thr Lys Phe Val Ala Ala Thr Lys Ala
    130                 135                 140

Leu Ser Lys Tyr Phe Gly Pro Lys Ser Gly Thr Gly Lys Thr Phe Val
145                 150                 155                 160

Tyr Asp Thr Asn Gln Asn Pro Thr Asn Phe Phe Ile Gln Thr Ala Pro
                165                 170                 175

Arg Tyr Asn Tyr Val Phe Leu Gln Ala Tyr Gly Arg Ser Thr Thr Asn
            180                 185                 190

Leu Thr Thr Val Ser Gly Leu Tyr Ala Pro Tyr Ile Ser Met Lys Gln
        195                 200                 205

Phe Leu Pro Gly Phe Ser Phe Tyr Glu Glu Asn Gly Tyr Pro Gly Asn
    210                 215                 220

Tyr Trp Asn Asp Val Arg Tyr Pro Gln Asn Gly Thr Gly Arg Ala Tyr
225                 230                 235                 240

Asp Tyr Ala Arg Trp Gln Pro Ala Thr Gly Lys Lys Gly Gly Val Phe
                245                 250                 255

Ser Tyr Ala Ile Glu Arg Asp Ala Pro Leu Thr Ser Ser Asn Asp Asn
            260                 265                 270

Thr Leu Arg Ala Pro Asn Phe Arg Val Thr Lys Asp Leu Ile Lys Ile
        275                 280                 285

Met Asn Pro Gly Gly Gly Ser Gly Gly Gly Ser Gly Gly Gly
    290                 295                 300

Gly Ser His His His His His Glu Phe Gly Gly Gly Ser Gly
305                 310                 315                 320

Gly Gly Ser Gly Gly Gly Ser Ala Pro Ala Pro Val Lys Gln
                325                 330                 335

Gly Pro Thr Ser Val Ala Tyr Val Glu Val Asn Asn Asn Ser Met Leu
            340                 345                 350

Asn Val Gly Lys Tyr Thr Leu Ala Asp Gly Gly Asn Ala Phe Asp
        355                 360                 365

Val Ala Val Ile Phe Ala Ala Asn Ile Asn Tyr Asp Thr Gly Thr Lys
370                 375                 380

Thr Ala Tyr Leu His Phe Asn Glu Asn Val Gln Arg Val Leu Asp Asn
385                 390                 395                 400

Ala Val Thr Gln Ile Arg Pro Leu Gln Gln Gln Gly Ile Lys Val Leu
                405                 410                 415

Leu Ser Val Leu Gly Asn His Gln Gly Ala Gly Phe Ala Asn Phe Pro
            420                 425                 430

Ser Gln Gln Ala Ala Ser Ala Phe Ala Lys Gln Leu Ser Asp Ala Val
        435                 440                 445

Ala Lys Tyr Gly Leu Asp Gly Val Asp Phe Asp Asp Glu Tyr Ala Glu
    450                 455                 460

Tyr Gly Asn Asn Gly Thr Ala Gln Pro Asn Asp Ser Ser Phe Val His
465                 470                 475                 480

Leu Val Thr Ala Leu Arg Ala Asn Met Pro Asp Lys Ile Ile Ser Leu
                485                 490                 495

Tyr Asn Ile Gly Pro Ala Ala Ser Arg Leu Ser Tyr Gly Gly Val Asp
            500                 505                 510
```

```
Val Ser Asp Lys Phe Asp Tyr Ala Trp Asn Pro Tyr Tyr Gly Thr Trp
        515                 520                 525

Gln Val Pro Gly Ile Ala Leu Pro Lys Ala Gln Leu Ser Pro Ala Ala
        530                 535                 540

Val Glu Ile Gly Arg Thr Ser Arg Ser Thr Val Ala Asp Leu Ala Arg
545                 550                 555                 560

Arg Thr Val Asp Glu Gly Tyr Gly Val Tyr Leu Thr Tyr Asn Leu Asp
                565                 570                 575

Gly Gly Asp Arg Thr Ala Asp Val Ser Ala Phe Thr Arg Glu Leu Tyr
            580                 585                 590

Gly Ser Glu Ala Val Arg Thr Pro
        595                 600

<210> SEQ ID NO 21
<211> LENGTH: 1240
<212> TYPE: PRT
<213> ORGANISM: Artificial sequence
<220> FEATURE:
<223> OTHER INFORMATION: His6-EndoS-EndoH

<400> SEQUENCE: 21

Met Gly Ser Ser His His His His His His Ser Ser Gly Leu Val Pro
1               5                   10                  15

Arg Gly Ser His Met Pro Ser Ile Asp Ser Leu His Tyr Leu Ser Glu
            20                  25                  30

Asn Ser Lys Lys Glu Phe Lys Glu Glu Leu Ser Lys Ala Gly Gln Glu
        35                  40                  45

Ser Gln Lys Val Lys Glu Ile Leu Ala Lys Ala Gln Gln Ala Asp Lys
    50                  55                  60

Gln Ala Gln Glu Leu Ala Lys Met Lys Ile Pro Glu Lys Ile Pro Met
65                  70                  75                  80

Lys Pro Leu His Gly Pro Leu Tyr Gly Gly Tyr Phe Arg Thr Trp His
                85                  90                  95

Asp Lys Thr Ser Asp Pro Thr Glu Lys Asp Lys Val Asn Ser Met Gly
            100                 105                 110

Glu Leu Pro Lys Glu Val Asp Leu Ala Phe Ile Phe His Asp Trp Thr
        115                 120                 125

Lys Asp Tyr Ser Leu Phe Trp Lys Glu Leu Ala Thr Lys His Val Pro
    130                 135                 140

Lys Leu Asn Lys Gln Gly Thr Arg Val Ile Arg Thr Ile Pro Trp Arg
145                 150                 155                 160

Phe Leu Ala Gly Gly Asp Asn Ser Gly Ile Ala Glu Asp Thr Ser Lys
                165                 170                 175

Tyr Pro Asn Thr Pro Glu Gly Asn Lys Ala Leu Ala Lys Ala Ile Val
            180                 185                 190

Asp Glu Tyr Val Tyr Lys Tyr Asn Leu Asp Gly Leu Asp Val Asp Val
        195                 200                 205

Glu His Asp Ser Ile Pro Lys Val Asp Lys Lys Glu Asp Thr Ala Gly
    210                 215                 220

Val Glu Arg Ser Ile Gln Val Phe Glu Glu Ile Gly Lys Leu Ile Gly
225                 230                 235                 240

Pro Lys Gly Val Asp Lys Ser Arg Leu Phe Ile Met Asp Ser Thr Tyr
                245                 250                 255

Met Ala Asp Lys Asn Pro Leu Ile Glu Arg Gly Ala Pro Tyr Ile Asn
            260                 265                 270
```

```
Leu Leu Leu Val Gln Val Tyr Gly Ser Gln Gly Glu Lys Gly Gly Trp
            275                 280                 285

Glu Pro Val Ser Asn Arg Pro Glu Lys Thr Met Glu Glu Arg Trp Gln
    290                 295                 300

Gly Tyr Ser Lys Tyr Ile Arg Pro Glu Gln Tyr Met Ile Gly Phe Ser
305                 310                 315                 320

Phe Tyr Glu Glu Asn Ala Gln Glu Gly Asn Leu Trp Tyr Asp Ile Asn
                325                 330                 335

Ser Arg Lys Asp Glu Asp Lys Ala Asn Gly Ile Asn Thr Asp Ile Thr
                340                 345                 350

Gly Thr Arg Ala Glu Arg Tyr Ala Arg Trp Pro Lys Thr Gly Gly
                355                 360                 365

Val Lys Gly Gly Ile Phe Ser Tyr Ala Ile Asp Arg Asp Gly Val Ala
    370                 375                 380

His Gln Pro Lys Lys Tyr Ala Lys Gln Lys Glu Phe Lys Asp Ala Thr
385                 390                 395                 400

Asp Asn Ile Phe His Ser Asp Tyr Ser Val Ser Lys Ala Leu Lys Thr
                405                 410                 415

Val Met Leu Lys Asp Lys Ser Tyr Asp Leu Ile Asp Glu Lys Asp Phe
                420                 425                 430

Pro Asp Lys Ala Leu Arg Glu Ala Val Met Ala Gln Val Gly Thr Arg
            435                 440                 445

Lys Gly Asp Leu Glu Arg Phe Asn Gly Thr Leu Arg Leu Asp Asn Pro
            450                 455                 460

Ala Ile Gln Ser Leu Glu Gly Leu Asn Lys Phe Lys Lys Leu Ala Gln
465                 470                 475                 480

Leu Asp Leu Ile Gly Leu Ser Arg Ile Thr Lys Leu Asp Arg Ser Val
                485                 490                 495

Leu Pro Ala Asn Met Lys Pro Gly Lys Asp Thr Leu Glu Thr Val Leu
                500                 505                 510

Glu Thr Tyr Lys Lys Asp Asn Lys Glu Glu Pro Ala Thr Ile Pro Pro
            515                 520                 525

Val Ser Leu Lys Val Ser Gly Leu Thr Gly Leu Lys Glu Leu Asp Leu
    530                 535                 540

Ser Gly Phe Asp Arg Glu Thr Leu Ala Gly Leu Asp Ala Ala Thr Leu
545                 550                 555                 560

Thr Ser Leu Glu Lys Val Asp Ile Ser Gly Asn Lys Leu Asp Leu Ala
                565                 570                 575

Pro Gly Thr Glu Asn Arg Gln Ile Phe Asp Thr Met Leu Ser Thr Ile
                580                 585                 590

Ser Asn His Val Gly Ser Asn Glu Gln Thr Val Lys Phe Asp Lys Gln
            595                 600                 605

Lys Pro Thr Gly His Tyr Pro Asp Thr Tyr Gly Lys Thr Ser Leu Arg
    610                 615                 620

Leu Pro Val Ala Asn Glu Lys Val Asp Leu Gln Ser Gln Leu Leu Phe
625                 630                 635                 640

Gly Thr Val Thr Asn Gln Gly Thr Leu Ile Asn Ser Glu Ala Asp Tyr
                645                 650                 655

Lys Ala Tyr Gln Asn His Lys Ile Ala Gly Arg Ser Phe Val Asp Ser
                660                 665                 670

Asn Tyr His Tyr Asn Asn Phe Lys Val Ser Tyr Glu Asn Tyr Thr Val
                675                 680                 685
```

```
Lys Val Thr Asp Ser Thr Leu Gly Thr Thr Thr Asp Lys Thr Leu Ala
    690             695                 700

Thr Asp Lys Glu Glu Thr Tyr Lys Val Asp Phe Phe Ser Pro Ala Asp
705             710                 715                 720

Lys Thr Lys Ala Val His Thr Ala Lys Val Ile Val Gly Asp Glu Lys
                725                 730                 735

Thr Met Met Val Asn Leu Ala Glu Gly Ala Thr Val Ile Gly Gly Ser
            740                 745                 750

Ala Asp Pro Val Asn Ala Arg Lys Val Phe Asp Gly Gln Leu Gly Ser
        755                 760                 765

Glu Thr Asp Asn Ile Ser Leu Gly Trp Asp Ser Lys Gln Ser Ile Ile
770                 775                 780

Phe Lys Leu Lys Glu Asp Gly Leu Ile Lys His Trp Arg Phe Phe Asn
785                 790                 795                 800

Asp Ser Ala Arg Asn Pro Glu Thr Thr Asn Lys Pro Ile Gln Glu Ala
                805                 810                 815

Ser Leu Gln Ile Phe Asn Ile Lys Asp Tyr Asn Leu Asp Asn Leu Leu
            820                 825                 830

Glu Asn Pro Asn Lys Phe Asp Asp Glu Lys Tyr Trp Ile Thr Val Asp
        835                 840                 845

Thr Tyr Ser Ala Gln Gly Glu Arg Ala Thr Ala Phe Ser Asn Thr Leu
850                 855                 860

Asn Asn Ile Thr Ser Lys Tyr Trp Arg Val Val Phe Asp Thr Lys Gly
865                 870                 875                 880

Asp Arg Tyr Ser Ser Pro Val Val Pro Glu Leu Gln Ile Leu Gly Tyr
                885                 890                 895

Pro Leu Pro Asn Ala Asp Thr Ile Met Lys Thr Val Thr Thr Ala Lys
            900                 905                 910

Glu Leu Ser Gln Gln Lys Asp Lys Phe Ser Gln Lys Met Leu Asp Glu
        915                 920                 925

Leu Lys Ile Lys Glu Met Ala Leu Glu Thr Ser Leu Asn Ser Lys Ile
930                 935                 940

Phe Asp Val Thr Ala Ile Asn Ala Asn Ala Gly Val Leu Lys Asp Cys
945                 950                 955                 960

Ile Glu Lys Arg Gln Leu Leu Lys Lys Ala Pro Ala Pro Val Lys Gln
                965                 970                 975

Gly Pro Thr Ser Val Ala Tyr Val Glu Val Asn Asn Ser Met Leu
            980                 985                 990

Asn Val Gly Lys Tyr Thr Leu Ala Asp Gly Gly Gly Asn Ala Phe Asp
        995                 1000                1005

Val Ala Val Ile Phe Ala Ala Asn Ile Asn Tyr Asp Thr Gly Thr
    1010            1015                1020

Lys Thr Ala Tyr Leu His Phe Asn Glu Asn Val Gln Arg Val Leu
    1025            1030                1035

Asp Asn Ala Val Thr Gln Ile Arg Pro Leu Gln Gln Gln Gly Ile
    1040            1045                1050

Lys Val Leu Leu Ser Val Leu Gly Asn His Gln Gly Ala Gly Phe
    1055            1060                1065

Ala Asn Phe Pro Ser Gln Gln Ala Ala Ser Ala Phe Ala Lys Gln
    1070            1075                1080

Leu Ser Asp Ala Val Ala Lys Tyr Gly Leu Asp Gly Val Asp Phe
    1085            1090                1095
```

| | | | | | | | | | | |
|---|---|---|---|---|---|---|---|---|---|---|
| Asp | Asp | Glu | Tyr | Ala | Glu | Tyr | Gly | Asn | Asn | Gly | Thr | Ala | Gln | Pro |
| | 1100 | | | | 1105 | | | | 1110 | |

Asn Asp Ser Ser Phe Val His Leu Val Thr Ala Leu Arg Ala Asn
    1115                 1120                 1125

Met Pro Asp Lys Ile Ile Ser Leu Tyr Asn Ile Gly Pro Ala Ala
    1130                 1135                 1140

Ser Arg Leu Ser Tyr Gly Gly Val Asp Val Ser Asp Lys Phe Asp
    1145                 1150                 1155

Tyr Ala Trp Asn Pro Tyr Tyr Gly Thr Trp Gln Val Pro Gly Ile
    1160                 1165                 1170

Ala Leu Pro Lys Ala Gln Leu Ser Pro Ala Ala Val Glu Ile Gly
    1175                 1180                 1185

Arg Thr Ser Arg Ser Thr Val Ala Asp Leu Ala Arg Arg Thr Val
    1190                 1195                 1200

Asp Glu Gly Tyr Gly Val Tyr Leu Thr Tyr Asn Leu Asp Gly Gly
    1205                 1210                 1215

Asp Arg Thr Ala Asp Val Ser Ala Phe Thr Arg Glu Leu Tyr Gly
    1220                 1225                 1230

Ser Glu Ala Val Arg Thr Pro
    1235                 1240

<210> SEQ ID NO 22
<211> LENGTH: 1812
<212> TYPE: DNA
<213> ORGANISM: Artificial sequence
<220> FEATURE:
<223> OTHER INFORMATION: synthetic DNA encoding fusion protein EndoF3-
      EfEndo18A

<400> SEQUENCE: 22

```
atggctacag cgctggctgg ttctaacggg gtctgcatcg cgtattacat caccgatggg      60
cgtaatccga cgttcaaatt gaaagacatc ccggataaag tagacatggt aattcttttt     120
ggtcttaagt attggtcatt gcaggataca accaaattgc aggggggtac tggtatgatg     180
ggttcgttta atcctacaag gaccctggac acccagattc gtagtcttca aagccgtgga     240
atcaaagtgt tgcagaacat tgacgacgac gtctcatggc agtcctcgaa gccgggtggg     300
ttcgcttccg ccgctgctta cggggatgct attaagagta tcgtaattga taagtggaag     360
ctggacggga ttagcttgga tattgagcat tcgggggcta aacccaaccc tatcccaact     420
tttcctggat atgccgcgac aggatataat ggctggtatt caggatctat ggcagccacg     480
cctgcctttc ttaatgttat ctcagagctt actaaatact ttggtacaac ggcaccgaat     540
aataagcaac ttcagattgc ttcgggtatt gacgtatatg cctggaataa atcatggag     600
aactttcgta taacttcaa ctacatccaa ttacagtcat acggagctaa tgtctctcgt     660
actcaactta tgatgaatta cgcaacggga actaataaaa ttcccgcctc taaaatggtt     720
ttcggcgcct acgcagaggg tggcactaac caggcaaatg acgtggaggt cgccaagtgg     780
acacctacgc agggcgcaaa gggcggtatg atgatctata cttacaattc gaacgtgagc     840
tatgcaaatg cggttcgcga cgcagtgaaa aatggcggcg cggctctgg cggcggcggc     900
tctggcggcg gcggctctca ccaccaccac caccgaat cggcggcgg cggctctggc     960
ggcggcggct ctggcggcgg cggtctgct tcaaccgtaa cccctaaaac ggttatgtac    1020
gtagaagtaa ataaccacga tttcaacaat gtcgggaat acactcttgc cggtactaat    1080
cagccggcgt tcgatatggg tattattttt gccgccaaca tcaattatga caccgtcaat    1140
```

```
aagaaaccat acctgtactt gaacgagcgc gtacagcaaa cactgaatga agcggagacg    1200
cagatccgtc cggtccaggc acgtggaacg aaggttttgc tttccatctt gggtaatcac    1260
gaaggcgcag gatttgccaa ttttcctacg tatgagtcgg cggacgcttt cgccgcgcaa    1320
cttgagcagg ttgtcaatac gtaccattta gacgggattg atttcgatga tgagtacgcc    1380
gagtacggaa aaaacgggac ccctcagccg aacaactcat ccttcatctg gttactgcaa    1440
gctcttcgca accgtctggg aaatgataaa cttatcactt tctacaacat ggcccggca    1500 gccgctaaca gcagcgcaaa ccctcaaatg tcatctttga ttgactatgc ctggaatccc    1560
tattattcga catggaaccc cccacaaatt gcaggtatgc ctgcctcccg cctgggggct    1620
tctgcggttg aagtgggcgt taaccagaat cttgcagcac agtatgccaa gcgtactaag    1680
gctgagcagt atggaatcta tctgatgtac aatctgccag gaaaagattc tagcgcttat    1740
atctcagcag cgactcagga gctgtatggg cgcaagacga actatagccc cacggtcccg    1800
actccgtgat aa                                                        1812
```

<210> SEQ ID NO 23
<211> LENGTH: 1812
<212> TYPE: DNA
<213> ORGANISM: Artificial sequence
<220> FEATURE:
<223> OTHER INFORMATION: synthetic DNA encoding fusion protein EndoF2-
      EfEndo18A

<400> SEQUENCE: 23

```
atggcggtaa accttagtaa tcttatcgct tataaaaata gtgaccatca gatcagtgcg     60
ggatattacc gtacatggcg tgacagcgcc acagccagtg gtaatcttcc tagtatgcgt    120
tggttgccag actcattgga catggtaatg gtattcccag actatactcc tccggaaaat    180
gcgtattgga acacactgaa gactaactac gtaccatacc tgcataagcg tggcacgaaa    240
gttattatca cattggggga ccttaactct gcaacgacca cgggagggca agattctatt    300
gggtattcat cgtgggccaa aggaatctat gataaatggg tgggcgagta taatcttgat    360
ggaatcgata ttgacatcga atcgtcaccg tccggtgcga ccttaacgaa gtttgttgcg    420
gcaacaaaag cgttgtcaaa gtatttttgga ccaaagagtg ggacaggcaa gacctttgta    480
tacgatacca atcagaatcc gactaatttc tttatccaaa ctgccccacg ctacaactac    540
gtatttcttc aagcatacgg gcgctcgacc actaatctga cgacggtctc tggattatac    600 gcccccctata tttcaatgaa acaatttctg cccggcttct cttttacga agaaaacggt     660 tacccaggta attattggaa tgatgtgcgt taccccagaa acgtacagg ccgtgcctac     720 gactacgcgc gctggcagcc cgccacggga aaaaaaggag gggtgttcag ttatgccatc    780
gagcgcgacg cccctcttac atcgtcaaac gacaatacc tgcgtgcgcc taactttcgt    840
gtaacgaagg acttaatcaa aattatgaat cctggcggcg gcggctctgg cggcggcggc    900
tctggcggcg gcggctctca ccaccaccac caccgaat cggcggcgg cggctctggc    960 ggcggcggct ctggcggcgg cggctctgct tcaaccgtaa cccctaaaac ggttatgtac   1020
gtagaagtaa ataaccacga tttcaacaat gtcgggaaat acactcttgc cggtactaat   1080
cagccggcgt tcgatatggg tattattttt gccgccaaca tcaattatga caccgtcaat   1140
aagaaaccat acctgtactt gaacgagcgc gtacagcaaa cactgaatga agcggagacg   1200
cagatccgtc cggtccaggc acgtggaacg aaggttttgc tttccatctt gggtaatcac   1260
gaaggcgcag gatttgccaa ttttcctacg tatgagtcgg cggacgcttt cgccgcgcaa   1320
```

```
cttgagcagg ttgtcaatac gtaccattta gacgggattg atttcgatga tgagtacgcc    1380
gagtacggaa aaaacgggac ccctcagccg aacaactcat ccttcatctg gttactgcaa    1440
gctcttcgca accgtctggg aaatgataaa cttatcactt tctacaacat tggcccggca    1500
gccgctaaca gcagcgcaaa ccctcaaatg tcatctttga ttgactatgc ctggaatccc    1560
tattattcga catggaaccc cccacaaatt gcaggtatgc ctgcctcccg cctgggggct    1620
tctgcggttg aagtgggcgt taaccagaat cttgcagcac agtatgccaa gcgtactaag    1680
gctgagcagt atggaatcta tctgatgtac aatctgccag aaaagattc tagcgcttat    1740 atctcagcag cgactcagga gctgtatggg cgcaagacga actatagccc cacggtcccg    1800
actccgtgat aa                                                         1812

<210> SEQ ID NO 24
<211> LENGTH: 3786
<212> TYPE: DNA
<213> ORGANISM: Artificial sequence
<220> FEATURE:
<223> OTHER INFORMATION: synthetic DNA encoding fusion protein EndoS-
      EfEndo18A

<400> SEQUENCE: 24
atgccgtcaa tcgattcgct gcattatctg agcgaaaact ctaaaaaaga atttaaagaa     60
gaactgagca agcgggcca ggaatctcaa aaagttaaag aaatcctggc aaaagctcag    120
caagccgata acaggcaca agaactggct aaaatgaaaa ttccggaaaa aatcccgatg    180
aaaccgctgc atggtccgct gtacggcggt tatttccgta cctggcacga taaaacgtca    240
gacccgaccg aaaaagacaa agtcaactcg atgggcgaac tgccgaaaga gtggatctg    300 gctttttattt tccatgattg gaccaaagac tactctctgt tttggaaaga actggcaacg    360
aaacacgttc cgaaactgaa caaacagggt acgcgtgtca ttcgtaccat tccgtggcgc    420
ttcctggctg gcgtgataaa ttcaggcatc gcggaagaca cctcgaaata tccgaacacg    480
ccggaaggta ataaagcgct ggccaaagca atcgtcgatg aatacgtgta caaatacaat    540
ctggacggcc tggatgtgga cgttgaacat gattcaattc cgaaagtgga taaaaaagaa    600
gacaccgccg gcgtggaacg ttcgatccag ttttttgaag aaattggtaa actgatcggc    660
ccgaaaggtt tgataaaag ccgtctgttc atcatggatt ctacctatat ggccgacaaa    720
aatccgctga ttgaacgcgg tgcaccgtac atcaacctgc tgctggtcca ggtgtatggc    780
agccaaggtg aaaaaggcgg ttgggaaccg gtgtctaacc gtccggaaaa accatggaa    840 gaacgctggc agggctactc aaaatatatt cgtccggaac aatacatgat cggctttcg    900 ttctatgaag aaaacgcgca ggaagtaat ctgtggtacg atattaatag tcgcaaagat    960
gaagacaaag ccaacggcat taataccgat atcacgggta cccgtgcgga cgctatgcc   1020 cgttggcagc cgaaaaccgg cggtgttaaa ggcggtattt ttagctacgc gatcgatcgt   1080
gacggtgtcg cccatcagcc gaaaaaatac gcaaaacaaa aagagttcaa agatgctacc   1140
gacaacatct ccacagcga ttacagtgtc tccaaagcgc tgaaaaccgt gatgctgaaa   1200
gataaatctt acgatctgat cgacgaaaaa gattttccgg acaaagcgct gcgcgaagcc   1260
gttatggcac aggtcggcac ccgcaaaggt gacctggaac gttttaatgg cacgctgcgc   1320
ctggataacc cggccattca gagcctggaa ggtctgaata aattcaaaaa actggcacaa   1380
ctggacctga ttggcctgag ccgtatcacc aaactggatc gctctgtgct gccggccaac   1440
atgaaaccgg gtaaagacac gctggaaacc gttctggaaa cctacaaaaa agataacaaa   1500
```

```
gaagaaccgg caacgatccc gccggtgtct ctgaaagttt ccggcctgac cggtctgaaa    1560
gaactggatc tgagcggctt tgaccgtgaa acgctggcag gtctggatgc ggccacgctg    1620
accagtctgg aaaaagttga tatttccggc aataaactgg acctggcgcc gggtaccgaa    1680
aaccgccaga tttttgatac gatgctgagt accatctcca accatgttgg cagcaatgaa    1740
cagaccgtca aattcgacaa acaaaaaccg acgggccact acccggatac gtatggtaaa    1800
accagcctgc gtctgccggt cgccaacgaa aaagtggatc tgcagtctca actgctgttt    1860
ggcacggtta ccaatcaggg taccctgatt aacagcgaag cagattacaa ggcttaccaa    1920
aaccataaaa tcgcgggtcg ctcatttgtg gattcgaact accactacaa caacttcaaa    1980
gttagttacg aaaactacac cgttaaagtc acggattcca ccctgggcac cacgaccgat    2040
aaaacgctgg ccaccgacaa agaagaaacc tacaaagtcg atttctttag cccggcagac    2100
aaaacgaaag cggtgcatac cgccaaagtg attgttggcg atgaaaaaac catgatggtg    2160
aacctggctg aaggtgcgac ggttatcggc ggttccgcag acccggttaa cgctcgcaaa    2220
gtctttgatg ccagctgggt agtgaaaccc gataatattt ccctgggttg ggactcaaaa    2280
cagtcgatta tcttcaaact gaaagaagac ggcctgatca acactggcg tttctttaac    2340 gatagtgccc gcaatccgga aacgaccaac aaaccgattc aggaagcatc cctgcaaatc    2400
ttcaacatca aagattacaa cctggacaat ctgctggaaa acccgaataa attcgatgac    2460
gaaaaatact ggatcacggt ggataccat agcgcgcagg gcgaacgtgc tacggcgttt    2520
agtaacaccc tgaacaatat tacgtccaaa tactggcgtg tggttttcga taccaaaggt    2580
gaccgctata gctctccggt cgtgccggaa ctgcagattc tgggctatcc gctgccgaat    2640
gctgatacga tcatgaaaac cgtgacgacc gcgaaagaac tgtcacagca aaaagataaa    2700
ttctcgcaga aaatgctgga cgaactgaaa attaaagaaa tggctctgga aaccagcctg    2760
aacagtaaaa ttttcgatgt tacggcgatc aatgctaacg ctggtgtgct gaaagactgt    2820
attgaaaaac gccaactgct gaaaaaaggc ggcggcggct ctggcggcgg cggctctggc    2880
ggcggcggct ctcaccacca ccaccaccac gaattcggcg gcggcggctc tggcggcggc    2940
ggctctggcg gcggcggctc tgcttcaacc gtaaccccta aaacggttat gtacgtagaa    3000
gtaaataacc acgatttcaa caatgtcggg aaatacactc ttgccggtac taatcagccg    3060
gcgttcgata tgggtattat ttttgccgcc aacatcaatt atgacaccgt caataagaaa    3120
ccatacctgt acttgaacga gcgcgtacag caaacactga atgaagcgga gacgcagatc    3180
cgtccggtcc aggcacgtgg aacgaaggtt ttgctttcca tcttgggtaa tcacgaaggc    3240
gcaggatttg ccaattttcc tacgtatgag tcggcggacg ctttcgccgc gcaacttgag    3300
caggttgtca atacgtacca tttagacggg attgatttcg atgatgagta cgccgagtac    3360
ggaaaaaacg ggaccccctca gccgaacaac tcatccttca tctggttact gcaagctctt    3420
cgcaaccgtc tgggaaatga taaacttatc actttctaca acattggccc ggcagccgct    3480
aacagcagcg caaaccctca aatgtcatct tgattgact atgcctggaa tccctattat    3540
tcgacatgga accccccaca aattgcaggt atgcctgcct cccgcctggg ggcttctgcg    3600
gttgaagtgg gcgttaacca gaatcttgca gcacagtatg ccaagcgtac taaggctgag    3660
cagtatggaa tctatctgat gtacaatctg ccaggaaaag attctagcgc ttatatctca    3720
gcagcgactc aggagctgta tgggcgcaag acgaactata gccccacggt cccgactccg    3780
tgataa                                                              3786
```

<210> SEQ ID NO 25
<211> LENGTH: 1860
<212> TYPE: DNA
<213> ORGANISM: Artificial sequence
<220> FEATURE:
<223> OTHER INFORMATION: synthetic DNA encoding fusion protein EndoF3-
      EndoF1

<400> SEQUENCE: 25

```
atggctacag cgctggctgg ttctaacggg gtctgcatcg cgtattacat caccgatggg     60
cgtaatccga cgttcaaatt gaaagacatc ccggataaag tagacatggt aattctttttt    120 ggtcttaagt attggtcatt gcaggataca accaaattgc caggggggtac tggtatgatg    180 ggttcgttta atcctacaa ggacctggac acccagattc gtagtcttca aagccgtgga     240
atcaaagtgt tgcagaacat tgacgacgac gtctcatggc agtcctcgaa gccgggtggg    300
ttcgcttccg ccgctgctta cggggatgct attaagagta tcgtaattga taagtggaag    360
ctggacggga ttagcttgga tattgagcat tcgggggcta aacccaaccc tatcccaact    420
tttcctggat atgccgcgac aggatataat ggctggtatt caggatctat ggcagccacg    480
cctgcctttc ttaatgttat ctcagagctt actaaatact ttggtacaac ggcaccgaat    540
aataagcaac ttcagattgc ttcgggtatt gacgtatatg cctggaataa aatcatggag    600
aactttcgta taacttcaa ctacatccaa ttacagtcat acggagctaa tgtctctcgt    660
actcaactta tgatgaatta cgcaacggga actaataaaa ttcccgcctc taaaatggtt    720
ttcggcgcct acgcagaggg tggcactaac caggcaaatg acgtggaggt cgccaagtgg    780
acacctacgc agggcgcaaa gggcggtatg atgatctata cttacaattc gaacgtgagc    840
tatgcaaatg cggttcgcga cgcagtgaaa aatggcggcg gcggctctgg cggcggcggc    900
tctggcggcg gcggctctca ccaccaccac caccacgaat cggcggcgg cggctctggc    960 ggcggcggct ctggcggcgg cggctctgcg gtaaccggga caacgaaggc taacatcaaa    1020
ctttttagtt ttacagaggt aaacgacact aatccgttga caatctgaa ctttaccta     1080 aaaaactcgg gaaacccctt agtagatatg gtagtgttat tttccgcgaa cattaactat    1140
gacgcggcca acgataaggt cttcgtatcg aataatccga acgtacagca tcttttgacc    1200
aatcgtgcga agtaccttaa gccgttacaa gacaagggga tcaaggtgat tttgtcaatc    1260
ttagggaacc atgatcgctc cgggatcgcc aatttgagta cggctcgtgc gaaggcattt    1320
gctcaggaac tgaagaatac ttgcgatttg tataatttag acggggtatt ctttgatgat    1380
gagtactctg cttaccaaac gccaccgccg agcggcttcg tgacacccag taataacgcc    1440
gcagctcgcc ttgcttatga aacaaagcag gctatgccaa acaagctggt cacggtgtac    1500
gtctattccc gcacttcgag tttttcccaca gcggtagacg gggtcaacgc cgggtcctac    1560
gtagactatg cgattcatga ctacggtggc tcatacgact tggctactaa ttatccgggg    1620
ttggctaagt ctgggatggt gatgtctagt caggagttta accagggccg ttacgcgact    1680
gcacaagcat tgcgcaacat tgtgaccaag ggctatggag gccacatgat ctttgccatg    1740
gaccccaatc gttctaattt cacgtcaggg caactgcccg cactgaagct gattgccaag    1800
gagctttacg gggatgagct tgtgtacagc aacactcctt acagtaagga ttggtgataa    1860
```

<210> SEQ ID NO 26
<211> LENGTH: 1860
<212> TYPE: DNA
<213> ORGANISM: Artificial sequence
<220> FEATURE:

<223> OTHER INFORMATION: DNA encoding fusion protein EndoF2-EndoF1

<400> SEQUENCE: 26

| | | | | | |
|---|---|---|---|---|---|
| atggcggtaa | accttagtaa | tcttatcgct | tataaaaata | gtgaccatca | gatcagtgcg | 60 |
| ggatattacc | gtacatggcg | tgacagcgcc | acagccagtg | gtaatcttcc | tagtatgcgt | 120 |
| tggttgccag | actcattgga | catggtaatg | gtattcccag | actatactcc | tccggaaaat | 180 |
| gcgtattgga | acacactgaa | gactaactac | gtaccatacc | tgcataagcg | tggcacgaaa | 240 |
| gttattatca | cattggggga | ccttaactct | gcaacgacca | cgggagggca | agattctatt | 300 |
| gggtattcat | cgtgggccaa | aggaatctat | gataaatggg | tgggcgagta | taatcttgat | 360 |
| ggaatcgata | ttgacatcga | atcgtcaccg | tccggtgcga | ccttaacgaa | gtttgttgcg | 420 |
| gcaacaaaag | cgttgtcaaa | gtattttgga | ccaaagagtg | ggacaggcaa | gacctttgta | 480 |
| tacgatacca | atcagaatcc | gactaatttc | tttatccaaa | ctgccccacg | ctacaactac | 540 |
| gtatttcttc | aagcatacgg | gcgctcgacc | actaatctga | cgacggtctc | tggattatac | 600 |
| gcccccctata | tttcaatgaa | acaatttctg | cccggcttct | cttttttacga | agaaaacggt | 660 |
| tacccaggta | attattggaa | tgatgtgcgt | taccccagaa | acggtacagg | ccgtgcctac | 720 |
| gactacgcgc | gctggcagcc | cgccacggga | aaaaaggag | gggtgttcag | ttatgccatc | 780 |
| gagcgcgacg | cccctcttac | atcgtcaaac | gacaataccc | tgcgtgcgcc | taactttcgt | 840 |
| gtaacgaagg | acttaatcaa | aattatgaat | cctggcggcg | gcggctctgg | cggcggcggc | 900 |
| tctggcggcg | gcggctctca | ccaccaccac | caccacgaat | tcggcggcgg | cggctctggc | 960 |
| ggcggcggct | ctggcggcgg | cggctctgcg | gtaaccggga | caacgaaggc | taacatcaaa | 1020 |
| cttttttagtt | ttacagaggt | aaacgacact | aatccgttga | acaatctgaa | ctttaccta | 1080 |
| aaaaactcgg | gaaaaccctt | agtagatatg | gtagtgttat | tttccgcgaa | cattaactat | 1140 |
| gacgcggcca | acgataaggt | cttcgtatcg | aataatccga | acgtacagca | tcttttgacc | 1200 |
| aatcgtgcga | gtaccttaa | gccgttacaa | gacaaggga | tcaaggtgat | tttgtcaatc | 1260 |
| ttagggaacc | atgatcgctc | cgggatcgcc | aatttgagta | cggctcgtgc | gaaggcattt | 1320 |
| gctcaggaac | tgaagaatac | ttgcgatttg | tataatttag | acggggtatt | ctttgatgat | 1380 |
| gagtactctg | cttaccaaac | gccaccgccg | agcggcttcg | tgacacccag | taataacgcc | 1440 |
| gcagctcgcc | ttgcttatga | aacaaagcag | gctatgccaa | caagctggt | cacggtgtac | 1500 |
| gtctattccc | gcacttcgag | ttttcccaca | gcggtagacg | gggtcaacgc | cgggtcctac | 1560 |
| gtagactatg | cgattcatga | ctacggtggc | tcatacgact | tggctactaa | ttatccgggg | 1620 |
| ttggctaagt | ctgggatggt | gatgtctagt | caggagttta | accagggccg | ttacgcgact | 1680 |
| gcacaagcat | tgcgcaacat | tgtgaccaag | ggctatggag | ccacatgat | ctttgccatg | 1740 |
| gaccccaatc | gttctaattt | cacgtcaggg | caactgcccg | cactgaagct | gattgccaag | 1800 |
| gagctttacg | gggatgagct | tgtgtacagc | aacactcctt | acagtaagga | ttggtgataa | 1860 |

<210> SEQ ID NO 27
<211> LENGTH: 3834
<212> TYPE: DNA
<213> ORGANISM: Artificial sequence
<220> FEATURE:
<223> OTHER INFORMATION: synthetic DNA encoding fusion protein EndoS-
EndoF1

<400> SEQUENCE: 27

```
atgccgtcaa tcgattcgct gcattatctg agcgaaaact ctaaaaaaga atttaaagaa    60
gaactgagca aagcgggcca ggaatctcaa aaagttaaag aaatcctggc aaaagctcag   120
caagccgata acaggcaca agaactggct aaaatgaaaa ttccggaaaa atcccgatg    180
aaaccgctgc atggtccgct gtacggcggt tatttccgta cctggcacga taaaacgtca   240
gacccgaccg aaaagacaa agtcaactcg atgggcgaac tgccaaaaga agtggatctg   300
gcttttattt tccatgattg gaccaaagac tactctctgt tttggaaaga actggcaacg   360
aaacacgttc cgaaactgaa caaacagggt acgcgtgtca ttcgtaccat tccgtggcgc   420
ttcctggctg gcggtgataa ttcaggcatc gcggaagaca cctcgaaata tccgaacacg   480
ccggaaggta taaagcgct ggccaaagca atcgtcgatg aatacgtgta caaatacaat   540
ctggacggcc tggatgtgga cgttgaacat gattcaattc cgaaagtgga taaaaaagaa   600
gacaccgccg cgctggaacg ttcgatccag gttttttgaag aaattggtaa actgatcggc   660
ccgaaaggtg ttgataaaag ccgtctgttc atcatggatt ctacctatat ggccgacaaa   720
aatccgctga ttgaacgcgg tgcaccgtac atcaacctgc tgctggtcca ggtgtatggc   780
agccaaggtg aaaaaggcgg ttgggaaccg gtgtctaacc gtccggaaaa aaccatggaa   840
gaacgctggc agggctactc aaaatatatt cgtccggaac aatacatgat cggcttttcg   900
ttctatgaag aaaacgcgca ggaaggtaat ctgtggtacg atattaatag tcgcaaagat   960
gaagacaaag ccaacggcat taataccgat atcacgggta cccgtgcgga acgctatgcc  1020
cgttggcagc cgaaaaccgg cggtgttaaa ggcggtattt ttagctacgc gatcgatcgt  1080
gacggtgtcg cccatcagcc gaaaaaatac gcaaaacaaa aagagttcaa agatgctacc  1140
gacaacatct tccacagcga ttacagtgtc tccaaagcgc tgaaaaccgt gatgctgaaa  1200
gataaatctt acgatctgat cgacgaaaaa gatttttccgg acaaagcgct gcgcgaagcc  1260
gttatggcac aggtcggcac ccgcaaaggt gacctggaac gttttaatgg cacgctgcgc  1320
ctggataacc cggccattca gagcctggaa ggtctgaata aattcaaaaa actggcacaa  1380
ctggacctga ttggcctgag ccgtatcacc aaactggatc gctctgtgct gccggccaac  1440
atgaaaccgg taaagacac gctggaaacc gttctggaaa cctacaaaaa agataacaaa  1500
gaagaaccgg caacgatccc gccggtgtct ctgaaagttt ccggcctgac cggtctgaaa  1560
gaactggatc tgagcggctt tgaccgtgaa acgctggcag gtctggatgc ggccacgctg  1620
accagtctgg aaaagttga tatttccggc aataaactgg acctggcgcc gggtaccgaa  1680
aaccgccaga ttttttgatac gatgctgagt accatctcca accatgttgg cagcaatgaa  1740
cagaccgtca aattcgacaa acaaaaaccg acgggccact acccggatac gtatggtaaa  1800
accagcctgc gtctgccggt cgccaacgaa aaagtggatc tgcagtctca actgctgttt  1860
ggcacggtta ccaatcaggg taccctgatt aacagcgaag cagattacaa ggcttaccaa  1920
aaccataaaa tcgcgggtcg ctcatttgtg gattcgaact accactacaa caacttcaaa  1980
gttagttacg aaaactacac cgttaaagtc acggattcca ccctgggcac cacgaccgat  2040
aaaacgctgg ccaccgacaa agaagaaacc tacaaagtcg atttctttag cccggcagac  2100
aaaacgaaag cggtgcatac cgccaaagtg attgttggcg atgaaaaaac catgatggtg  2160
aacctggctg aaggtgcgac ggttatcggc ggttccgcag acccggttaa cgctcgcaaa  2220
gtctttgatg ccagctgggg tagtgaaacc gataatattt ccctgggttg ggactcaaaa  2280
```

| | |
|---|---:|
| cagtcgatta tcttcaaact gaaagaagac ggcctgatca aacactggcg tttctttaac | 2340 |
| gatagtgccc gcaatccgga aacgaccaac aaaccgattc aggaagcatc cctgcaaatc | 2400 |
| ttcaacatca aagattacaa cctggacaat ctgctggaaa acccgaataa attcgatgac | 2460 |
| gaaaaatact ggatcacggt ggatacctat agcgcgcagg gcgaacgtgc tacggcgttt | 2520 |
| agtaacaccc tgaacaatat tacgtccaaa tactggcgtg tggttttcga taccaaaggt | 2580 |
| gaccgctata gctctccggt cgtgccggaa ctgcagattc tgggctatcc gctgccgaat | 2640 |
| gctgatacga tcatgaaaac cgtgacgacc gcgaaagaac tgtcacagca aaaagataaa | 2700 |
| ttctcgcaga aaatgctgga cgaactgaaa attaaagaaa tggctctgga aaccagcctg | 2760 |
| aacagtaaaa ttttcgatgt tacggcgatc aatgctaacg ctggtgtgct gaaagactgt | 2820 |
| attgaaaaac gccaactgct gaaaaaaggc ggcggcggct ctggcggcgg cggctctggc | 2880 |
| ggcggcggct ctcaccacca ccaccaccac gaattcggcg gcggcggctc tggcggcggc | 2940 |
| ggctctggcg gcggcggctc tgcggtaacc gggacaacga aggctaacat caaacttttt | 3000 |
| agttttacag aggtaaacga cactaatccg ttgaacaatc tgaactttac cttaaaaaac | 3060 |
| tcggaaaaac ccttagtaga tatggtagtg ttattttccg cgaacattaa ctatgacgcg | 3120 |
| gccaacgata aggtcttcgt atcgaataat ccgaacgtac agcatctttt gaccaatcgt | 3180 |
| gcgaagtacc ttaagccgtt acaagacaag gggatcaagg tgattttgtc aatcttaggg | 3240 |
| aaccatgatc gctccgggat cgccaatttg agtacggctc gtgcgaaggc atttgctcag | 3300 |
| gaactgaaga atacttgcga tttgtataat ttagacgggg tattctttga tgatgagtac | 3360 |
| tctgcttacc aaacgccacc gccgagcggc ttcgtgacac ccagtaataa cgccgcagct | 3420 |
| cgccttgctt atgaaacaaa gcaggctatg ccaaacaagc tggtcacggt gtacgtctat | 3480 |
| tccgcactt cgagttttcc cacagcgta gacggggtca acgccgggtc ctacgtagac | 3540 |
| tatgcgattc atgactacgg tggctcatac gacttggcta ctaattatcc ggggttggct | 3600 |
| aagtctggga tggtgatgtc tagtcaggag ттттaaccagg gccgttacgc gactgcacaa | 3660 |
| gcattgcgca acattgtgac caagggctat ggaggccaca tgatctttgc catggacccc | 3720 |
| aatcgttcta atttcacgtc agggcaactg cccgcactga agctgattgc caaggagctt | 3780 |
| tacggggatg agcttgtgta cagcaacact ccttacagta aggattggtg ataa | 3834 |

<210> SEQ ID NO 28
<211> LENGTH: 1806
<212> TYPE: DNA
<213> ORGANISM: Artificial sequence
<220> FEATURE:
<223> OTHER INFORMATION: synthetic DNA encoding fusion protein EndoF3-EndoH

<400> SEQUENCE: 28

| | |
|---|---:|
| atggctacag cgctggctgg ttctaacggg gtctgcatcg cgtattacat caccgatggg | 60 |
| cgtaatccga cgttcaaatt gaaagacatc ccggataaag tagacatggt aattctttt | 120 |
| ggtcttaagt attggtcatt gcaggataca accaaattgc cagggggtac tggtatgatg | 180 |
| ggttcgttta atcctacaa ggacctggac acccagattc gtagtcttca aagccgtgga | 240 |
| atcaaagtgt gcagaacat tgacgacgac gtctcatggc agtcctcgaa gccgggtggg | 300 |
| ttcgcttccg ccgctgctta cggggatgct attaagagta tcgtaattga taagtggaag | 360 |
| ctggacggga ttagcttgga tattgagcat тcggggggcтa aacccaaccc tadcccaact | 420 |
| tttcctggat atgccgcgac aggatataat ggctggtatt caggatctat ggcagccacg | 480 |

```
cctgcctttc ttaatgttat ctcagagctt actaaatact ttggtacaac ggcaccgaat    540
aataagcaac ttcagattgc ttcgggtatt gacgtatatg cctggaataa aatcatggag    600
aactttcgta ataacttcaa ctacatccaa ttacagtcat acggagctaa tgtctctcgt    660
actcaactta tgatgaatta cgcaacggga actaataaaa ttcccgcctc taaaatggtt    720
ttcggcgcct acgcagaggg tggcactaac caggcaaatg acgtggaggt cgccaagtgg    780
acacctacgc agggcgcaaa gggcggtatg atgatctata cttacaattc gaacgtgagc    840
tatgcaaatg cggttcgcga cgcagtgaaa aatggcggcg cgggtctgg  cggcggcggc    900
tctggcggcg gcggctctca ccaccaccac caccacgaat cggcggcgg  cggctctggc    960
ggcggcggct ctggcggcgg cggctctgcc ccggccccgg tgaagcaggg gccgacctcg   1020
gtggcctacg tcgaggtgaa caacaacagc atgctcaacg tcgcaagta  caccctggcg   1080
gacgaggcg  gcaacgcctt cgacgtagcc gtgatcttcg cggcgaacat caactacgac   1140
accggcacga agacgcccta cctgcacttc aacgagaacg tgcagcgcgt ccttgacaac   1200
gctgtcacgc agatacggcc gttgcagcaa caggcatca  aggtcctcct ctcggtgctc   1260
ggcaaccacc agggcgccgg gttcgcgaac ttcccctcac agcaggcggc ttcggcgttc   1320
gcgaagcagc tctcggacgc cgtggcgaag tacgccctcg acgcgtcga  cttcgacgac   1380
gaatacgccg agtacggcaa caacggcacc gcgcagccca cgacagttc  gttcgtgcac   1440
ctggtgacgg cactgcgcgc gaacatgccc gacaagatca tcagcctcta caacatcggc   1500
ccggccgcgt cccgcctgtc gtacggcggt gtcgacgtct ccgacaagtt cgactacgcc   1560
tggaatccct actacggcac ctggcaggtc cccggcatcg cactgcccaa ggcgcagctg   1620
tcgccggcgg ccgtcgagat cggccggacc tcacggagca ccgtcgccga cctcgcccgt   1680
cgcaccgtcg acgaggggta cggcgtctat ctgacgtaca acctcgacgg cggcgatcgc   1740
accgccgacg tctccgcgtt caccagggag ctgtacggca gcgaggcggt ccggacgccg   1800
tgataa                                                              1806
```

<210> SEQ ID NO 29
<211> LENGTH: 1806
<212> TYPE: DNA
<213> ORGANISM: Artificial sequence
<220> FEATURE:
<223> OTHER INFORMATION: synthetic DNA encoding fusion protein EndoF2-
      EndoH

<400> SEQUENCE: 29

```
atggcggtaa accttagtaa tcttatcgct tataaaaata gtgaccatca gatcagtgcg     60
ggatattacc gtacatggcg tgacagcgcc acagccagtg gtaatcttcc tagtatgcgt    120
tggttgccag actcattgga catggtaatg gtattcccag actatactcc tccggaaaat    180
gcgtattgga acacactgaa gactaactac gtaccatacc tgcataagcg tggcacgaaa    240
gttattatca cattgggga  ccttaactct gcaacgacca cggagggca  agattctatt    300
gggtattcat cgtgggccaa aggaatctat gataaatggg tggcgagta  taatcttgat    360
ggaatcgata ttgacatcga atcgtcaccg tccggtgcga ccttaacgaa gtttgttgcg    420
gcaacaaaag cgttgtcaaa gtattttgga ccaaagagtg ggacaggcaa gacctttgta    480
tacgatacca atcagaatcc gactaatttc tttatccaaa ctgccccacg ctacaactac    540
gtatttcttc aagcatacgg cgctcgacc  actaatctga cgacggtctc tggattatac    600
gcccctata  tttcaatgaa acaatttctg cccggcttct cttttacga  agaaaacggt    660
```

```
tacccaggta attattggaa tgatgtgcgt tacccccaga acggtacagg ccgtgcctac    720
gactacgcgc gctggcagcc cgccacggga aaaaaggag gggtgttcag ttatgccatc    780
gagcgcgacg cccctcttac atcgtcaaac gacaataccc tgcgtgcgcc taactttcgt    840
gtaacgaagg acttaatcaa aattatgaat cctggcggcg gcggctctgg cggcggcggc    900
tctggcggcg gcggctctca ccaccaccac caccacgaat cggcggcgg cggctctggc    960
ggcggcggct ctggcggcgg cggctctgcc ccggccccgg tgaagcaggg gccgacctcg   1020
gtggcctacg tcgaggtgaa caacaacagc atgctcaacg tcggcaagta caccctggcg   1080
gacgagggcg gcaacgcctt cgacgtagcc gtgatcttcg cggcgaacat caactacgac   1140
accggcacga agacggccta cctgcacttc aacgagaacg tgcagcgcgt ccttgacaac   1200
gctgtcacgc agatacggcc gttgcagcaa caggggcatca aggtcctcct ctcggtgctc   1260
ggcaaccacc agggcgccgg gttcgcgaac ttcccctcac agcaggcggc ttcggcgttc   1320
gcgaagcagc tctcggacgc cgtggcgaag tacggcctcg acggcgtcga cttcgacgac   1380
gaatacgccg agtacggcaa caacggcacc gcgcagccca cgacagttc gttcgtgcac   1440
ctggtgacgg cactcgcgc gaacatgccc gacaagatca tcagcctcta caacatcggc   1500
ccggccgcgt cccgcctgtc gtacggcggt gtcgacgtct ccgacaagtt cgactacgcc   1560
tggaatccct actacggcac ctggcaggtc cccggcatcg cactgcccaa ggcgcagctg   1620
tcgccggcgg ccgtcgagat cggccggacc tcacggagca ccgtcgccga cctcgcccgt   1680
cgcaccgtcg acgaggggta cggcgtctat ctgacgtaca acctcgacgg cggcgatcgc   1740
accgccgacg tctccgcgtt caccagggag ctgtacggca gcgaggcggt ccggacgccg   1800
tgataa                                                               1806

<210> SEQ ID NO 30
<211> LENGTH: 3780
<212> TYPE: DNA
<213> ORGANISM: Artificial sequence
<220> FEATURE:
<223> OTHER INFORMATION: synthetic DNA encoding fusion protein EndoS-
      EndoH (or EndoSH)

<400> SEQUENCE: 30
atgccgtcaa tcgattcgct gcattatctg agcgaaaaact ctaaaaaaga atttaaagaa     60
gaactgagca aagcgggcca ggaatctcaa aaagttaaag aaatcctggc aaaagctcag    120
caagccgata acaggcaca agaactggct aaaatgaaaa ttccggaaaa aatcccgatg    180
aaaccgctgc atggtccgct gtacggcggt tatttccgta cctggcacga taaaacgtca    240
gaccccgaccg aaaaagacaa agtcaactcg atgggcgaac tgccgaaaga agtggatctg    300
gcttttattt tccatgattg gaccaaagac tactctctgt tttggaaaga actggcaacg    360
aaacacgttc gaaactgaa caaacagggt acgcgtgtca ttcgtaccat tccgtggcgc    420
ttcctggctg gcggtgataa ttcaggcatc gcggaagaca cctcgaaata tccgaacacg    480
ccggaaggta ataaagcgct ggccaaagca atcgtcgatg aatacgtgta caaatacaat    540
ctggacggcc tggatgtgga cgttgaacat gattcaattc cgaaagtgga taaaaagaa    600
gacaccgccg gcgtggaacg ttcgatccag gttttgaag aaattggtaa actgatcggc    660
ccgaaaggtg ttgataaaag ccgtctgttc atcatggatt ctacctatat ggccgacaaa    720
aatccgctga ttaacgcggg tgcaccgtac atcaacctgc tgctggtcca ggtgtatggc    780
agccaaggtg aaaaaggcgg ttgggaaccg gtgtctaacc gtccggaaaa aaccatggaa    840
```

```
gaacgctggc agggctactc aaaatatatt cgtccggaac aatacatgat cggcttttcg    900
ttctatgaag aaaacgcgca ggaaggtaat ctgtggtacg atattaatag tcgcaaagat    960
gaagacaaag ccaacggcat taataccgat atcacgggta cccgtgcgga acgctatgcc   1020
cgttggcagc cgaaaaccgg cggtgttaaa ggcggtattt ttagctacgc gatcgatcgt   1080
gacggtgtcg cccatcagcc gaaaaaatac gcaaaacaaa aagagttcaa agatgctacc   1140
gacaacatct tccacagcga ttacagtgtc tccaaagcgc tgaaaaccgt gatgctgaaa   1200
gataaatctt acgatctgat cgacgaaaaa gattttccgg acaaagcgct gcgcgaagcc   1260
gttatggcac aggtcggcac ccgcaaaggt gacctggaac gttttaatgg cacgctgcgc   1320
ctggataacc cggccattca gagcctggaa ggtctgaata aattcaaaaa actggcacaa   1380
ctggacctga ttggcctgag ccgtatcacc aaactggatc gctctgtgct gccgcccaac   1440
atgaaaccgg gtaaagacac gctggaaacc gttctggaaa cctacaaaaa agataacaaa   1500
gaagaaccgg caacgatccc gccggtgtct ctgaaagttt ccggcctgac cggtctgaaa   1560
gaactggatc tgagcggctt tgaccgtgaa acgctggcag gtctggatgc ggccacgctg   1620
accagtctgg aaaaagttga tatttccggc aataaactgg acctggcgcc gggtaccgaa   1680
aaccgccaga tttttgatac gatgctgagt accatctcca accatgttgg cagcaatgaa   1740
cagaccgtca aattcgacaa acaaaaaccg acgggccact acccggatac gtatggtaaa   1800
accagcctgc gtctgccggt cgccaacgaa aaagtggatc tgcagtctca actgctgttt   1860
ggcacggtta ccaatcaggg taccctgatt aacagcgaag cagattacaa ggcttaccaa   1920
aaccataaaa tcgcgggtcg ctcatttgtg gattcgaact accactacaa caacttcaaa   1980
gttagttacg aaaactacac cgttaaagtc acggattcca ccctgggcac cacgaccgat   2040
aaaacgctgg ccaccgacaa agaagaaacc tacaaagtcg atttctttag cccggcagac   2100
aaaacgaaag cggtgcatac cgccaaagtg attgttggcg atgaaaaaac catgatggtg   2160
aacctggctg aagtgcgac ggttatcggc ggttccgcag acccggttaa cgctcgcaaa   2220
gtctttgatg gccagctggg tagtgaaacc gataatattt ccctgggttg ggactcaaaa   2280
cagtcgatta tcttcaaact gaaagaagac ggcctgatca acactggcg tttcttttaac   2340
gatagtgccc gcaatccgga aacgaccaac aaaccgattc aggaagcatc cctgcaaatc   2400
ttcaacatca agattacaa cctggacaat ctgctggaaa acccgaataa attcgatgac   2460
gaaaaatact ggatcacggt ggataccatat agcgcgcagg gcgaacgtgc tacggcgtttt   2520
agtaacaccc tgaacaatat tacgtccaaa tactggcgtg tggttttcga taccaaaggt   2580
gaccgctata gctctccggt cgtgccggaa ctgcagattc tgggctatcc gctgccgaat   2640
gctgatacga tcatgaaaac cgtgacgacc gcgaaagaac tgtcacagca aaaagataaa   2700
ttctcgcaga aaatgctgga cgaactgaaa attaaagaaa tggctctgga accagcctg    2760
aacagtaaaa ttttcgatgt tacggcgatc aatgctaacg ctggtgtgct gaaagactgt   2820
attgaaaaac gccaactgct gaaaaaaggc ggcggcggct ctggcggcgg cggctctggc   2880
ggcggcggct ctcaccacca ccaccaccac gaattcggcg gcggcggctc tggcggcggc   2940
ggctctggcg gcggcggctc tgccccgcc ccggtgaagc aggggccgac ctcggtggcc   3000
tacgtcgagg tgaacaacaa cagcatgctc aacgtcggca gtacacccct ggcggacgga   3060
ggcggcaacg ccttcgacgt agccgtgatc ttcgcggcga acatcaacta cgacaccggc   3120
acgaagacgg cctacctgca cttcaacgag aacgtcagcg cgtccttga caacgctgtc   3180
acgcagatac ggccgttgca gcaacagggc atcaaggtcc tcctctcggt gctcggcaac   3240
```

```
caccagggcg ccgggttcgc gaacttcccc tcacagcagg cggcttcggc gttcgcgaag    3300
cagctctcgg acgccgtggc gaagtacggc ctcgacggcg tcgacttcga cgacgaatac    3360
gccgagtacg gcaacaacgg caccgcgcag cccaacgaca gttcgttcgt gcacctggtg    3420
acggcactgc gcgcgaacat gcccgacaag atcatcagcc tctacaacat cggcccggcc    3480
gcgtcccgcc tgtcgtacgg cggtgtcgac gtctccgaca gttcgacta cgcctggaat    3540 ccctactacg gcacctggca ggtccccggc atcgcactgc ccaaggcgca gctgtcgccg    3600
gcggccgtcg agatcggccg gacctcacgg agcaccgtcg ccgacctcgc ccgtcgcacc    3660
gtcgacgagg ggtacggcgt ctatctgacg tacaacctcg acggcggcga tcgcaccgcc    3720
gacgtctccg cgttcaccag ggagctgtac ggcagcgagg cggtccggac gccgtgataa    3780
```

<210> SEQ ID NO 31
<211> LENGTH: 3726
<212> TYPE: DNA
<213> ORGANISM: Artificial sequence
<220> FEATURE:
<223> OTHER INFORMATION: synthetic DNA encoding fusion protein His6-
      EndoS-EndoH (EndoS-EndoH without GS-linker)

<400> SEQUENCE: 31

```
atgggcagca gccatcatca tcatcatcac agcagcggcc tggtgccgcg cggcagccat     60
atgccgtcaa tcgattcgct gcattatctg agcgaaaact ctaaaaaaga atttaaagaa    120
gaactgagca agcgggcca ggaatctcaa aaagttaaag aaatcctggc aaaagctcag    180
caagccgata acaggcaca gaactggct aaaatgaaaa ttccggaaaa atcccgatg    240 aaaccgctgc atggtccgct gtacggcggt tatttccgta cctggcacga taaaacgtca    300
gacccgaccg aaaagacaa agtcaactcg atgggcgaac tgccgaaaga gtggatctg    360 gctttatt tccatgattg gaccaaagac tactctctgt tttggaaaga actggcaacg    420
aaacacgttc cgaaactgaa caaacagggt acgcgtgtca ttcgtaccat tccgtggcgc    480
ttcctggctg gcgtgataa ttcaggcatc gcggaagaca cctcgaaata tccgaacacg    540
ccggaaggta taaagcgct ggccaaagca atcgtcgatg aatacgtgta caaatacaat    600
ctggacggcc tggatgtgga cgttgaacat gattcaattc gaaagtgga taaaaaagaa    660 gacaccgccg gcgtggaacg ttcgatccag gttttttgaag aaattggtaa actgatcggc    720
ccgaaaggtg ttgataaaag ccgtctgttc atcatggatt ctacctatat ggccgacaaa    780
aatccgctga ttgaacgcgg tgcaccgtac atcaacctgc tgctggtcca ggtgtatggc    840
agccaaggtg aaaaggcgg ttgggaaccg gtgtctaacc gtccggaaaa accatggaa    900 gaacgctggc agggctactc aaaatatatt cgtccggaac aatacatgat cggctttcg    960 ttctatgaag aaaacgcgca ggaaggtaat ctgtggtacg atattaatag tcgcaaagat    1020
gaagacaaag ccaacggcat taatacccgat atcacgggta cccgtgcgga acgctatgcc    1080
cgttggcagc cgaaaaccgg cggtgttaaa ggcggtattt ttagctacgc gatcgatcgt    1140
gacggtgtcg cccatcagcc gaaaaaatac gcaaaacaaa aagagttcaa agatgctacc    1200
gacaacatct tccacagcga ttacagtgtc tccaaagcgc tgaaaaccgt gatgctgaaa    1260
gataaatctt acgatctgat cgacgaaaaa gattttccgg acaaagcgct gcgcgaagcc    1320
gttatggcac aggtcggcac ccgcaaaggt gacctggaac gttttaatgg cacgctgcgc    1380
ctggataacc cggccattca gagcctggaa ggtctgaata aattcaaaaa actggcacaa    1440 ctggaccctga ttggcctgag ccgtatcacc aaactggatc gctctgtgct gccggccaac    1500
```

```
atgaaaccgg gtaaagacac gctggaaacc gttctggaaa cctacaaaaa agataacaaa      1560
gaagaaccgg caacgatccc gccggtgtct ctgaaagttt ccggcctgac cggtctgaaa      1620
gaactggatc tgagcggctt tgaccgtgaa acgctggcag gtctggatgc ggccacgctg      1680
accagtctgg aaaaagttga tatttccggc aataaactgg acctggcgcc gggtaccgaa      1740
aaccgccaga tttttgatac gatgctgagt accatctcca accatgttgg cagcaatgaa      1800
cagaccgtca aattcgacaa acaaaaaccg acgggccact acccggatac gtatggtaaa      1860
accagcctgc gtctgccggt cgccaacgaa aaagtggatc tgcagtctca actgctgttt      1920
ggcacggtta ccaatcaggg taccctgatt aacagcgaag cagattacaa ggcttaccaa      1980
aaccataaaa tcgcgggtcg ctcatttgtg gattcgaact accactacaa caacttcaaa      2040
gttagttacg aaaactacac cgttaaagtc acggattcca ccctgggcac cacgaccgat      2100
aaaacgctgg ccaccgacaa agaagaaacc tacaaagtcg atttctttag cccggcagac      2160
aaaacgaaag cggtgcatac cgccaaagtg attgttggcg atgaaaaaac catgatggtg      2220
aacctggctg aaggtgcgac ggttatcggc ggttccgcag acccggttaa cgctcgcaaa      2280
gtctttgatg ccagctgggt agtgaaaccc gataatattt ccctgggttg ggactcaaaa      2340
cagtcgatta tcttcaaact gaaagaagac ggcctgatca aacactggcg tttctttaac      2400
gatagtgccc gcaatccgga aacgaccaac aaaccgattc aggaagcatc cctgcaaatc      2460
ttcaacatca agattacaa cctggacaat ctgctggaaa cccgaataa attcgatgac      2520 gaaaaatact ggatcacggt ggataccttat agcgcgcagg gcgaacgtgc tacggcgttt      2580
agtaacaccc tgaacaatat tacgtccaaa tactggcgtg tggttttcga taccaaaggt      2640
gaccgctata gctctccggt cgtgccggaa ctgcagattc tgggctatcc gctgccgaat      2700
gctgatacga tcatgaaaac cgtgacgacc gcgaaagaac tgtcacagca aaaagataaa      2760
ttctcgcaga aaatgctgga cgaactgaaa attaaagaaa tggctctgga aaccagcctg      2820
aacagtaaaa ttttcgatgt tacggcgatc aatgctaacg ctggtgtgct gaaagactgt      2880
attgaaaaac gccaactgct gaaaaaagcc ccggccccgg tgaagcaggg gccgacctcg      2940
gtggcctacg tcgaggtgaa caacaacagc atgctcaact cggcaagta cccctggcg      3000 gacggaggcg gcaacgcctt cgacgtagcc gtgatcttcg cggcgaacat caactacgac      3060
accggcacga agacggccta cctgcacttc aacgagaacg tgcagcgcgt ccttgacaac      3120
gctgtcacgc agatacggcc gttgcagcaa cagggcatca aggtcctcct ctcggtgctc      3180
ggcaaccacc agggcgccgg gttcgcgaac ttcccctcac agcaggcggc ttcggcgttc      3240
gcgaagcagc tctcggacgc cgtggcgaag tacggcctcg acggcgtcga cttcgacgac      3300
gaatacgccg agtacggcaa caacggcacc gcgcagccca acgacagttc gttcgtgcac      3360
ctggtgacgg cactgcgcgc gaacatgccc gacaagatca tcagcctcta caacatcggc      3420
ccggccgcgt cccgcctgtc gtacggcggt gtcgacgtct ccgacaagtt cgactacgcc      3480
tggaatccct actacggcac ctggcaggtc cccggcatcg cactgcccaa ggcgcagctg      3540
tcgccggcgg ccgtcgagat cggccggacc tcacggagca ccgtcgccga cctcgcccgt      3600
cgcaccgtcg acgaggggta cggcgtctat ctgacgtaca acctcgacgg cggcgatcgc      3660
accgccgacg tctccgcgtt caccagggag ctgtacggca gcgaggcggt ccggacgccg      3720
tgataa                                                                3726
```

<210> SEQ ID NO 32

<211> LENGTH: 1248
<212> TYPE: DNA
<213> ORGANISM: Artificial sequence
<220> FEATURE:
<223> OTHER INFORMATION: synthetic DNA encoding His6-TnGalNAcT(33-421)
<220> FEATURE:
<221> NAME/KEY: sig_peptide
<222> LOCATION: (4)..(57)

<400> SEQUENCE: 32

```
atgaattttg gactgaggct gattttcctg gtgctgaccc tgaaaggcgt ccagtgtcat      60
caccatcacc atcactcccc gcttcgcaca tatctttaca ctccattata caatgccacc     120
cagcccacac tcagaaacgt cgagaggctg cagctaact ggccaaagaa gatccctagt     180
aattatatag aagatagcga agagtatagc atcaagaata tttctttgag caaccacaca     240
actagagcat ctgtggtaca tcctccttcc tctatcaccg aaacggcaag caaactggat     300
aagaatatga ccatccaaga cggcgccttt gctatgatta gcccgacgcc cttgcttatc     360
accaaattga tggatagcat caaatcttat gttactaccg aggatggggt taagaaagcc     420
gaagccgtcg taactctccc cctctgtgat agcatgcctc ctgaccttgg tcctattact     480
cttaacaaaa ccgagctcga gctcgaatgg gttgagaaaa agttccctga ggtcgagtgg     540
ggtggacgtt atagtccccc caactgcaca gctaggcatc gcgtagcaat catagtcccg     600
taccgagaca dacagcaaca cctggcaatc ttcttaaatc acatgcaccc cttcctgatg     660
aaacagcaga tcgaatatgg catctttatc gtggagcagg aaggaaacaa ggactttaac     720
cgtgcgaaac ttatgaacgt cggctttgtt gaaagtcaaa aactcgttgc cgagggatgg     780
cagtgtttcg tttttcatga catagacctg ctcccactgg acactagaaa cctctatagc     840
tgcccgagac agccacgcca catgagcgct tccattgaca aacttcactt taagctgcct     900
tacgaagaca tcttcggtgg cgtgtcagcc atgactctgg aacagttcac ccgagtgaat     960
ggattttcaa ataaatactg gggatggggg ggagaggacg acgatatgag ttatcggctt    1020
aagaaaatca actaccatat tgcaagatat aaaatgtcca tcgcccgata cgccatgttg    1080
gaccacaaga agtcaacacc caatcctaag cggtaccaat tactctcaca gacctcaaag    1140
acattccaga aagacgggct gagcaccctg gaatatgagc tggtgcaagt cgttcaatat    1200
catctgtata ctcacatcct ggttaatatt gacgagaggt cctgataa              1248
```

<210> SEQ ID NO 33
<211> LENGTH: 395
<212> TYPE: PRT
<213> ORGANISM: Artificial sequence
<220> FEATURE:
<223> OTHER INFORMATION: His6-TnGalNAcT(33-421)

<400> SEQUENCE: 33

```
His His His His His His Ser Pro Leu Arg Thr Tyr Leu Tyr Thr Pro
1               5                  10                  15

Leu Tyr Asn Ala Thr Gln Pro Thr Leu Arg Asn Val Glu Arg Leu Ala
            20                  25                  30

Ala Asn Trp Pro Lys Lys Ile Pro Ser Asn Tyr Ile Glu Asp Ser Glu
        35                  40                  45

Glu Tyr Ser Ile Lys Asn Ile Ser Leu Ser Asn His Thr Thr Arg Ala
    50                  55                  60

Ser Val Val His Pro Pro Ser Ser Ile Thr Glu Thr Ala Ser Lys Leu
65                  70                  75                  80
```

```
Asp Lys Asn Met Thr Ile Gln Asp Gly Ala Phe Ala Met Ile Ser Pro
            85                  90                  95

Thr Pro Leu Leu Ile Thr Lys Leu Met Asp Ser Ile Lys Ser Tyr Val
            100                 105                 110

Thr Thr Glu Asp Gly Val Lys Lys Ala Glu Ala Val Val Thr Leu Pro
            115                 120                 125

Leu Cys Asp Ser Met Pro Pro Asp Leu Gly Pro Ile Thr Leu Asn Lys
    130                 135                 140

Thr Glu Leu Glu Leu Glu Trp Val Glu Lys Lys Phe Pro Glu Val Glu
145                 150                 155                 160

Trp Gly Gly Arg Tyr Ser Pro Pro Asn Cys Thr Ala Arg His Arg Val
                165                 170                 175

Ala Ile Ile Val Pro Tyr Arg Asp Arg Gln Gln His Leu Ala Ile Phe
                180                 185                 190

Leu Asn His Met His Pro Phe Leu Met Lys Gln Gln Ile Glu Tyr Gly
            195                 200                 205

Ile Phe Ile Val Glu Gln Glu Gly Asn Lys Asp Phe Asn Arg Ala Lys
    210                 215                 220

Leu Met Asn Val Gly Phe Val Glu Ser Gln Lys Leu Val Ala Glu Gly
225                 230                 235                 240

Trp Gln Cys Phe Val Phe His Asp Ile Asp Leu Leu Pro Leu Asp Thr
                245                 250                 255

Arg Asn Leu Tyr Ser Cys Pro Arg Gln Pro Arg His Met Ser Ala Ser
            260                 265                 270

Ile Asp Lys Leu His Phe Lys Leu Pro Tyr Glu Asp Ile Phe Gly Gly
    275                 280                 285

Val Ser Ala Met Thr Leu Glu Gln Phe Thr Arg Val Asn Gly Phe Ser
    290                 295                 300

Asn Lys Tyr Trp Gly Trp Gly Gly Glu Asp Asp Asp Met Ser Tyr Arg
305                 310                 315                 320

Leu Lys Lys Ile Asn Tyr His Ile Ala Arg Tyr Lys Met Ser Ile Ala
            325                 330                 335

Arg Tyr Ala Met Leu Asp His His Lys Lys Ser Thr Pro Asn Pro Lys Arg
            340                 345                 350

Tyr Gln Leu Leu Ser Gln Thr Ser Lys Thr Phe Gln Lys Asp Gly Leu
    355                 360                 365

Ser Thr Leu Glu Tyr Glu Leu Val Gln Val Val Gln Tyr His Leu Tyr
    370                 375                 380

Thr His Ile Leu Val Asn Ile Asp Glu Arg Ser
385                 390                 395
```